(12) United States Patent
Askew, Jr. et al.

(10) Patent No.: US 7,662,811 B2
(45) Date of Patent: Feb. 16, 2010

(54) 1,2,3,4-TETRAHYDROPYRAZIN-2-YL ACETAMIDES AND METHODS OF USE

(75) Inventors: Benny C. Askew, Jr., Marshfield, MA (US); Toshihiro Aya, Thousand Oaks, CA (US); Kaustav Biswas, Calabasas, CA (US); Guolin Cai, Thousand Oaks, CA (US); Jian J. Chen, Newbury Park, CA (US); Nianhe Han, Thousand Oaks, CA (US); Qingyian Liu, Camarillo, CA (US); Thomas Nguyen, Thousand Oaks, CA (US); Nobuko Nishimura, West Hills, CA (US); Rana Nomak, Westlake Village, CA (US); Tanya Peterkin, Woodland Hills, CA (US); Wenyuan Qian, Camarillo, CA (US); Kevin Yang, San Gabriel, CA (US); Chester Chenguang Yuan, Newbury Park, CA (US); Jiawang Zhu, Thousand Oaks, CA (US); Derin C. D'Amico, Newbury Park, CA (US); Jason B. Human, Calabasas, CA (US); Qi Huang, Moorpark, CA (US)

(73) Assignee: Amgen Inc., Thousand Oaks, CA (US)

( * ) Notice: Subject to any disclaimer, the term of this patent is extended or adjusted under 35 U.S.C. 154(b) by 413 days.

(21) Appl. No.: 11/182,216

(22) Filed: Jul. 15, 2005

(65) Prior Publication Data

US 2006/0025400 A1 Feb. 2, 2006

Related U.S. Application Data

(60) Provisional application No. 60/588,904, filed on Jul. 15, 2004.

(51) Int. Cl.
| | | |
|---|---|---|
| *A01N 43/00* | (2006.01) | |
| *A61K 31/00* | (2006.01) | |
| *A61K 31/55* | (2006.01) | |
| *A61K 31/4965* | (2006.01) | |
| *C07D 401/00* | (2006.01) | |
| *C07D 403/00* | (2006.01) | |
| *C07D 405/00* | (2006.01) | |
| *C07D 409/00* | (2006.01) | |
| *C07D 411/00* | (2006.01) | |
| *C07D 413/00* | (2006.01) | |
| *C07D 417/00* | (2006.01) | |
| *C07D 419/00* | (2006.01) | |

(52) U.S. Cl. .............................. 514/210.2; 514/217.05; 514/255.05; 544/405

(58) Field of Classification Search ....................... None
See application file for complete search history.

(56) References Cited

U.S. PATENT DOCUMENTS

2005/0014749 A1   1/2005   Chen et al.

FOREIGN PATENT DOCUMENTS

| WO | WO 03/007958 A1 | 1/2003 |
|---|---|---|
| WO | WO 03/093245 A1 | 11/2003 |
| WO | WO 2004/033436 A1 | 4/2004 |
| WO | 2004/054854 | 7/2004 |
| WO | 2004/083173 | 9/2004 |
| WO | WO 2005/061467 A2 | 7/2005 |

OTHER PUBLICATIONS

Dorwald F. A. Side Reactions in Organic Synthesis, 2005, Wiley: VCH, Weinheim p. IX of Preface.*

* cited by examiner

*Primary Examiner*—James O Wilson
*Assistant Examiner*—Jeffrey H Murray
(74) *Attorney, Agent, or Firm*—Rekha P. Bansal

(57) ABSTRACT

Selected compounds are effective for treatment of pain and diseases, such as inflammation mediated diseases. The invention encompasses novel compounds, analogs, prodrugs and pharmaceutically acceptable derivatives thereof, pharmaceutical compositions and methods for prophylaxis and treatment of diseases and other maladies or conditions involving pain, inflammation, and the like. The subject invention also relates to processes for making such compounds as well as to intermediates useful in such processes.

13 Claims, No Drawings

1,2,3,4-TETRAHYDROPYRAZIN-2-YL ACETAMIDES AND METHODS OF USE

This application claims the benefit of U.S. Provisional Application No. 60/588,904, filed Jul. 15, 2004, which is hereby incorporated by reference.

FIELD OF THE INVENTION

This invention is in the field of pharmaceutical agents and specifically relates to compounds, compositions, uses and methods for treating inflammation-related disorders, including pain.

BACKGROUND OF THE INVENTION

More than two million people in the United States alone are incapacitated by chronic pain on any given day (T. Jessell & D. Kelly, Pain and Analgesia in PRINCIPLES OF NEURAL SCIENCE, third edition (E. Kandel, J. Schwartz, T. Jessell, eds., (1991)). Unfortunately, current treatments for pain are only partially effective, and many cause lifestyle altering, debilitating, and/or dangerous side effects. For example, non-steroidal anti-inflammatory drugs ("NSAIDs") such as aspirin, ibuprofen, and indomethacin are moderately effective against inflammatory pain but they are also renally toxic, and high doses tend to cause gastrointestinal irritation, ulceration, bleeding, increased cardiovascular risk, and confusion. Patients treated with opioids frequently experience confusion and constipation, and long-term opioid use is associated with tolerance and dependence. Local anesthetics such as lidocaine and mixelitine simultaneously inhibit pain and cause loss of normal sensation. In addition, when used systemically, local anesthetics are associated with adverse cardiovascular effects. Thus, there is currently an unmet need in the treatment of chronic pain.

Pain is a perception based on signals received from the environment and transmitted and interpreted by the nervous system (for review, see M. Millan, Prog. Neurobiol. 57:1-164 (1999)). Noxious stimuli such as heat and touch cause specialized sensory receptors in the skin to send signals to the central nervous system ("CNS"). This process is called nociception, and the peripheral sensory neurons that mediate it are nociceptors. Depending on the strength of the signal from the nociceptor(s) and the abstraction and elaboration of that signal by the CNS, a person may or may not experience a noxious stimulus as painful. When one's perception of pain is properly calibrated to the intensity of the stimulus, pain serves its intended protective function. However, certain types of tissue damage cause a phenomenon, known as hyperalgesia or pronociception, in which relatively innocuous stimuli are perceived as intensely painful because the person's pain thresholds have been lowered. Both inflammation and nerve damage can induce hyperalgesia. Thus, persons afflicted with inflammatory conditions, such as sunburn, osteoarthritis, colitis, carditis, dermatitis, myositis, neuritis, inflammatory bowel disease, collagen vascular diseases (which include rheumatoid arthritis and lupus) and the like, often experience enhanced sensations of pain. Similarly, trauma, surgery, amputation, abscess, causalgia, collagen vascular diseases, demyelinating diseases, trigeminal neuralgia, cancer, chronic alcoholism, stroke, thalamic pain syndrome, diabetes, herpes infections, acquired immune deficiency syndrome ("AIDS"), toxins and chemotherapy cause nerve injuries that result in pain.

As the mechanisms by which nociceptors transduce external signals under normal and hyperalgesic conditions become better understood, processes implicated in hyperalgesia can be targeted to inhibit the lowering of the pain threshold and thereby lessen the amount of pain experienced.

Bradykinin (BK) and the related peptide, kallidin (Lys-BK) mediate the physiological actions of kinins on the cardiovascular and renal systems. However, the active peptides, BK and kallidin, are quickly degraded by peptidases in the plasma and other biological fluids and by those released from a variety of cells, so that the half-life of BK in plasma is reported to be approximately 17 seconds (1). BK and kallidin are rapidly metabolized in the body by carboxypeptidase N, which removes the carboxyterminal arginine residue to generate des-Arg BK or des-Arg kallidin. Des-Arg-kallidin is among the predominant kinins in man and mediate the pathophysiological actions of kinins in man. In addition to being a very potent proinflammatory peptide, des-Arg-BK or des-Arg-kallidin is known to induce vasodilation, vascular permeability, and bronchoconstriction (for review, see Regoli and Barabe, Pharmacological Rev, 32(1), 1-46 (1980)). In addition, des-Arg-BK and des-Arg-kallidin appear to be particularly important mediators of inflammation and inflammatory pain as well as being involved in the maintenance thereof. There is also a considerable body of evidence implicating the overproduction of des-Arg-kallidin in conditions in which pain is a prominent feature such as septic shock, arthritis, angina, and migraine.

The membrane receptors that mediate the pleiotropic actions of kinins are of two distinct classes, designated B1 and B2. Both classes of receptors have been cloned and sequenced from a variety of species, including man (Menke, et al, J. Biol. Chem. 269, 21583-21586 (1994); Hess et al, Biochem. Biophys. Res. Commun. 184, 260-268 (1992)). They are typical G protein coupled receptors having seven putative membrane spanning regions. In various tissues, BK receptors are coupled to every known second messenger. B2 receptors, which have a higher affinity for BK, appear to be the most prevalent form of bradykinin receptor. Essentially all normal physiological responses and many pathophysio-logical responses to bradykinin are mediated by B2 receptors.

B1 receptors, on the other hand, have a higher affinity for des-Arg-BK compared with BK, whereas des-Arg-BK is inactive at B2 receptors. In addition, B1 receptors are not normally expressed in most tissues. Their expression is induced upon injury or tissue damage as well as in certain kinds of chronic inflammation or systemic insult (F. Marceau, et al., Immunopharmacology, 30, 1-26 (1995)). Furthermore, responses mediated by B1 receptors are up-regulated from a null level following administration of bacterial lipopolysaccharide (LPS) or inflammatory cytokines in rabbits, rats, and pigs.

The pain-inducing properties of kinins coupled with the inducible expression of B1 receptors make the B1 receptor an interesting target in the development of anti-inflammatory, antinociceptive, antihyperalgesic and analgesic agents that may be directed specifically at injured tissues with minimal actions in normal tissues.

Certain compounds have been described as bradykinin antagonists. WO 03/07958, published 30 Jan. 2003, describes tetrahydroquinoxalines. Dihydroquinoxalinones are described in a JACS communication.

Piperazine-2,3,5-triones are described in Tet. Lett., 40, 7557-7560 (1999). European application 641779, published 8 Mar. 1995, describes 3,6-dioxopiperazines as platelet aggregation inhibitors.

Clearly, there is a need for new, safe and effective treatments for inflammation and pain. Such agents are provided in the present invention.

DETAILED DESCRIPTION OF THE INVENTION

One aspect of the present invention relates to a class of compounds useful in treating inflammation and pain is defined by Formula I

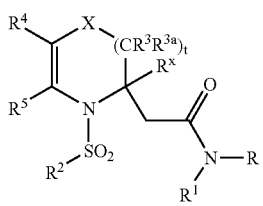

wherein:

t is 0, 1 or 2;

X is selected from NH, S, O and $NR^a$; wherein $R^a$ is selected form alkyl, substituted alkyl, $-C(O)R^8$, $-CO_2R^8$, $-C(O)NR^8R^{8'}$, $-SO_2R^8$ and $-SO_2NR^8R^{8'}$; provided $R^3$ and $R^{3a}$ together do not form oxo if $R^a$ is $-C(O)R^8$, $-CO_2R^8$, $-C(O)NR^8R^{8'}$, $-SO_2R^8$ or $-SO_2NR^8R^{8'}$;

R is selected from
  a) 9-, 10-, or 11-membered fused bicyclic carbocyclic or heterocyclic ring substituted by 1, 2 or 3 basic moieties, and substituted by 0, 1, 2 or 3 groups independently selected from halo, hydroxyl, cyano, oxo, nitro, $(C_1-C_6)$alkoxy, $(C_2-C_6)$alkenyl, $(C_2-C_6)$alkynyl, $-C(O)R^8$, $-COOR^8$, $-C(O)NR^8R^{8'}$, $-NR^8C(O)R^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
  b) 3-, 4-, 5-, 6- or 7-membered carbocyclic ring substituted by 0, 1, 2 or 3 basic moieties, and substituted by 0, 1, 2 or 3 groups independently selected from halo, hydroxyl, cyano, $(C_1-C_6)$alkoxy, $(C_2-C_6)$alkenyl, $(C_2-C_6)$alkynyl, $-C(O)R^8$, $-COOR^8$, $-C(O)NR^8R^{8'}$, $-NR^8C(O)R^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
  c) 4-, 5-, 6- or 7-membered heterocyclic ring substituted by 1, 2 or 3 basic moieties, and substituted by 0, 1, 2 or 3 groups independently selected from halo, hydroxyl, cyano, oxo, $(C_1-C_6)$alkoxy, $(C_2-C_6)$alkenyl, $(C_2-C_6)$alkynyl, $-C(O)R^8$, $-COOR^8$, $-C(O)NR^8R^{8'}$, $-NR^8C(O)R^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
  d) aralkyl substituted by 0, 1, 2 or 3 basic moieties, and substituted by 0, 1, 2 or 3 groups independently selected from halo, hydroxyl, cyano, $(C_1-C_6)$alkoxy, $(C_2-C_6)$alkenyl, $(C_2-C_6)$alkynyl, $-C(O)R^8$, $-COOR^8$, $-C(O)NR^8R^{8'}$, $-NR^8C(O)R^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
  e) 5- or 6-membered heterocyclylalkyl substituted by 1, 2 or 3 basic moieties, and substituted by 0, 1, 2 or 3 groups independently selected from halo, hydroxyl, cyano, oxo, $(C_1-C_6)$alkoxy, $(C_2-C_6)$alkenyl, $(C_2-C_6)$alkynyl, $-C(O)R^8$, $-COOR^8$, $-C(O)NR^8R^{8'}$, $-NR^8C(O)R^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
  f) 4-, 5-, 6- or 7-membered carbocyclic or heterocyclic ring substituted by 0, 1, 2 or 3 groups independently selected from halo, hydroxyl, cyano, oxo, $(C_1-C_6)$alkoxy, $(C_2-C_6)$alkenyl, $(C_2-C_6)$alkynyl, $-C(O)R^8$, $-COOR^8$, $-C(O)NR^8R^{8'}$, $-NR^8C(O)R^{8'}$, $(C_1-C_6)$alkyl, substituted $(C_1-C_6)$alkyl, aralkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
  g) $-(C_1-C_8)$alkyl-$R^8$, wherein the alkyl is substituted by 0, 1 or 2 groups selected from a basic moiety, phenyl, benzyl, $OR^8$ and $NR^8R^{8'}$;
  h) 9-, 10-, or 11-membered fused bicyclic carbocyclic or heterocyclic ring substituted by 0, 1, 2, 3 or 4 groups independently selected from halo, cyano, oxo, $(C_1-C_6)$alkoxy, $(C_2-C_6)$alkenyl, $(C_2-C_6)$alkynyl, $-C(O)R^8$, $-COOR^8$, $-C(O)NR^8R^{8'}$, $-NR^8C(O)R^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; and
  i) 12-, 13-, 14-, or 15-membered fused tricyclic carbocyclic or heterocyclic ring substituted by 0, 1, 2 or 3 basic moieties, and substituted by 0, 1, 2 or 3 groups independently selected from halo, hydroxyl, cyano, oxo, $(C_1-C_6)$alkoxy, $(C_2-C_6)$alkenyl, $(C_2-C_6)$alkynyl, $-C(O)R^8$, $-COOR^8$, $-C(O)NR^8R^{8'}$, $-NR^8C(O)R^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

$R^1$ is selected from H, $C_{1-4}$-alkyl, substituted $C_{1-4}$-alkyl, aryl and substituted aryl;

alternatively R and $R^1$ together with the nitrogen atom to which they are attached form a 4-10 membered mono- or bicyclic heterocyclyl ring, optionally containing 1-2 additional heteroatoms, optionally fused with 1 or 2 phenyl or $(C_5-C_7)$cycloalkyl groups or optionally substituted with one aryl, heteroaryl or aralkyl group, wherein the heterocyclyl ring and aryl, heteroaryl or aralkyl groups are further optionally substituted with a basic moiety and further substituted by 0, 1, 2 or 3 groups independently selected from halo, cyano, oxo, $(C_1-C_6)$alkoxy, $(C_2-C_6)$alkenyl, $(C_2-C_6)$alkynyl, $-C(O)R^8$, $-COOR^8$, $-C(O)NR^8R^{8'}$, $-NR^8C(O)R^{8'}$, $-Oaralkyl$, $-OR^8$, $(C_1-C_6)$alkyl, and substituted $(C_1-C_6)$alkyl;

$R^2$ is selected from arylalkenyl, aryl, and heterocyclyl selected from thienyl, quinolinyl, isoquinolinyl, 3-pyridyl, thiazol-4-yl, 4-imidazolyl, benzofuryl, benzoxadiazolyl, benzothiadiazolyl, benzothiazolyl, 1H-pyrazolyl, isoxazolthienyl, benzothienyl, thieno[3,2-c]pyridinyl, and tetrahydroisoquinolinyl, wherein $R^2$ is optionally substituted with one to five groups independently selected from halo, $-NH_2$, hydroxyl, cyano, $(C_1-C_6)$alkylamino, oxo, $(C_1-$ $C_6$)alkoxy, ($C_2$-$C_6$)alkenyl, ($C_2$-$C_6$)alkynyl, di($C_1$-$C_6$)alkylamino, —C(O)R$^8$, —COOR$^8$, —C(O)NR$^8$R$^{8'}$, —NR$^8$C(O)R$^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

R$^3$, R$^{3a}$, R$^4$ and R$^5$ are independently selected from H, $C_{1-3}$ alkyl and substituted $C_{1-3}$ alkyl;

or R$^3$ and R$^{3a}$ together form oxo;

R$^8$ and R$^{8'}$ independently in each instance are H or selected from lower alkyl, aryl heterocyclyl and heteroaryl, each of which is optionally substituted with one, two or three groups independently selected from lower alkyl, halogen, lower alkoxy, hydroxy, amino, mono- or dialkylamino, and trifluoromethyl;

R$^x$ is selected from H, ($C_1$-$C_3$)haloalkyl, and ($C_1$-$C_3$)alkyl; and wherein each substituted alkyl, substituted aryl, substituted heteroaryl, substituted cycloalkyl and substituted saturated or partially saturated heterocyclyl is substituted by 1, 2 or 3 groups independently selected from halo, —NH$_2$, hydroxyl, cyano, ($C_1$-$C_6$)alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)R$^8$, —COOR$^8$, —C(O)NR$^8$R$^{8'}$, and —NR$^8$C(O)R$^{8'}$, and pharmaceutically acceptable derivatives thereof In conjunction with any of the above or below embodiments, X is NH.

In conjunction with any of the above or below embodiments, X is NR$^a$; wherein R$^a$ is selected from alkyl and substituted alkyl.

In conjunction with any of the above or below embodiments, R is selected from a 9-, 10-, or 11-membered fused bicyclic carbocyclic or heterocyclic ring substituted by 1, 2 or 3 basic moieties, and substituted by 0, 1, 2 or 3 groups independently selected from halo, hydroxyl, cyano, oxo, nitro, ($C_1$-$C_6$)alkoxy, ($C_2$-$C_6$)alkenyl, ($C_2$-$C_6$)alkynyl, —C(O)R$^8$, —COOR$^8$, —C(O)NR$^8$R$^{8'}$, —NR$^8$C(O)R$^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

In conjunction with any of the above or below embodiments, R is selected from a 3-, 4-, 5-, 6- or 7-membered carbocyclic ring substituted by 0, 1, 2 or 3 basic moieties, and substituted by 0, 1, 2 or 3 groups independently selected from halo, hydroxyl, cyano, ($C_1$-$C_6$)alkoxy, ($C_2$-$C_6$)alkenyl, ($C_2$-$C_6$)alkynyl, —C(O)R$^8$, —COOR$^8$, —C(O)NR$^8$R$^{8'}$, —NR$^8$C(O)R$^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

In conjunction with any of the above or below embodiments, R is selected from a 4-, 5-, 6- or 7-membered heterocyclic ring substituted by 1, 2 or 3 basic moieties, and substituted by 0, 1, 2 or 3 groups independently selected from halo, hydroxyl, cyano, oxo, ($C_1$-$C_6$)alkoxy, ($C_2$-$C_6$)alkenyl, ($C_2$-$C_6$)alkynyl, —C(O)R$^8$, —COOR$^8$, —C(O)NR$^8$R$^{8'}$, —NR$^8$C(O)R$^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

In conjunction with any of the above or below embodiments, R is selected from an aralkyl substituted by 0, 1, 2 or 3 basic moieties, and substituted by 0, 1, 2 or 3 groups independently selected from halo, hydroxyl, cyano, ($C_1$-$C_6$)alkoxy, ($C_2$-$C_6$)alkenyl, ($C_2$-$C_6$)alkynyl, —C(O)R$^8$, —COOR$^8$, —C(O)NR$^8$R$^{8'}$, —NR$^8$C(O)R$^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

In conjunction with any of the above or below embodiments, R is selected from a 5- or 6-membered heterocyclylalkyl substituted by 1, 2 or 3 basic moieties, and substituted by 0, 1, 2 or 3 groups independently selected from halo, hydroxyl, cyano, oxo, ($C_1$-$C_6$)alkoxy, ($C_2$-$C_6$)alkenyl, ($C_2$-$C_6$)alkynyl, —C(O)R$^8$, —COOR$^8$, —C(O)NR$^8$R$^{8'}$, —NR$^8$C(O)R$^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

In conjunction with any of the above or below embodiments, R is selected from a 4-, 5-, 6- or 7-membered carbocyclic or heterocyclic ring substituted by 0, 1, 2 or 3 groups independently selected from halo, hydroxyl, cyano, oxo, ($C_1$-$C_6$)alkoxy, ($C_2$-$C_6$)alkenyl, ($C_2$-$C_6$)alkynyl, —C(O)R$^8$, —COOR$^8$, —C(O)NR$^8$R$^{8'}$, —NR$^8$C(O)R$^{8'}$, ($C_1$-$C_6$)alkyl, substituted ($C_1$-$C_6$)alkyl, aralkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

In conjunction with any of the above or below embodiments, R is —($C_1$-$C_8$)alkyl-R$^8$, wherein the alkyl is substituted by 0, 1 or 2 groups selected from a basic moiety, phenyl, benzyl, OR$^8$ and NR$^8$R$^{8'}$.

In conjunction with any of the above or below embodiments, R is a 9-, 10-, or 11-membered fused bicyclic carbocyclic or heterocyclic ring substituted by 0, 1, 2, 3 or 4 groups independently selected from halo, cyano, oxo, ($C_1$-$C_6$)alkoxy, ($C_2$-$C_6$)alkenyl, ($C_2$-$C_6$)alkynyl, —C(O)R$^8$, —COOR$^8$, —C(O)NR$^8$R$^{8'}$, —NR$^8$C(O)R$^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

In conjunction with any of the above or below embodiments, R is a 12-, 13-, 14-, or 15-membered fused tricyclic carbocyclic or heterocyclic ring substituted by 0, 1, 2 or 3 basic moieties, and substituted by 0, 1, 2 or 3 groups independently selected from halo, hydroxyl, cyano, oxo, ($C_1$-$C_6$)alkoxy, ($C_2$-$C_6$)alkenyl, ($C_2$-$C_6$)alkynyl, —C(O)R$^8$, —COOR$^8$, —C(O)NR$^8$R$^{8'}$, —NR$^8$C(O)R$^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

In conjunction with any of the above or below embodiments, R$^2$ is selected from arylalkenyl optionally substituted with one to five groups independently selected from halo, —NH$_2$, hydroxyl, cyano, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)R$^8$, —COOR$^8$, —C(O)NR$^8$R$^{8'}$, —NR$^8$C(O)R$^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

In conjunction with any of the above or below embodiments, $R^2$ is heterocyclyl selected from thienyl, quinolinyl, isoquinolinyl, 3-pyridyl, thiazol-4-yl, 4-imidazolyl, benzofuryl, benzoxadiazolyl, benzothiadiazolyl, benzothiazolyl, 1H-pyrazolyl, isoxazolthienyl, benzothienyl, thieno[3,2-c]pyridinyl, and tetrahydroisoquinolinyl, wherein the heterocyclyl is optionally substituted with one to five groups independently selected from halo, —$NH_2$, hydroxyl, cyano, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —$C(O)R^8$, —$COOR^8$, —$C(O)NR^8R^{8'}$, —$NR^8C(O)R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

In conjunction with any of the above or below embodiments, $R^2$ is selected from aryl optionally substituted with 1, 2, 3, 4 or 5 groups independently selected from halo, —$NH_2$, hydroxyl, cyano, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —$C(O)R^8$, —$COOR^8$, —$C(O)NR^8R^{8'}$, —$NR^8C(O)R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

In conjunction with any of the above or below embodiments, $R^2$ is selected from aryl substituted with 1, 2, 3, 4 or 5 groups independently selected from halo, —$NH_2$, hydroxyl, cyano, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —$C(O)R^8$, —$COOR^8$, —$C(O)NR^8R^{8'}$, —$NR^8C(O)R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

In conjunction with any of the above or below embodiments, the basic moiety is independently selected from cycloalkylamino($C_1$-$C_6$)alkyl, cycloalkyl($C_1$-$C_6$)alkylamino($C_1$-$C_6$)alkyl, heterocyclylamino($C_1$-$C_6$)alkyl, heterocyclyl($C_1$-$C_6$)alkylamino($C_1$-$C_6$)alkyl, arylamino($C_1$-$C_6$)alkyl, aryl($C_1$-$C_6$)alkylamino($C_1$-$C_6$)alkyl, ($C_1$-$C_6$)alkyl amino ($C_1$-$C_6$)alkoxy, ($C_1$-$C_6$)alkylamino($C_1$-$C_6$)alkoxy($C_1$-$C_6$)alkoxy, amino($C_1$-$C_6$)alkoxy, amino($C_1$-$C_6$)alkyl, ($C_1$-$C_6$)alkylamino($C_1$-$C_6$)alkyl, ($C_1$-$C_4$)alkylamino-($C_2$-$C_6$)alkenyl, 4-8-membered nitrogen-containing heterocyclyl($C_2$-$C_6$)alkenyl, 4-8-membered nitrogen-containing heterocyclyl($C_1$-$C_6$)alkyl, [4-8-membered nitrogen-containing heterocyclyl]-[4-8-membered nitrogen-containing heterocyclyl], 7-12-membered bicyclic nitrogen-containing heterocyclyl($C_1$-$C_6$)alkyl, heterocyclyl($C_1$-$C_6$)alkylamino($C_2$-$C_6$)alkyl, 5-6 membered heterocyclyloxy, 5-6 membered nitrogen-containing heterocyclyl and 5-7 membered nitrogen-containing heterocyclyl-alkyl; more specifically amino, cycloalkylamino($C_1$-$C_6$)alkyl, cycloalkyl($C_1$-$C_6$) alkylamino($C_1$-$C_6$)alkyl, heterocyclylamino($C_1$-$C_6$)alkyl, heterocyclyl($C_1$-$C_6$)alkylamino($C_1$-$C_6$)alkyl, arylamino($C_1$-$C_6$) alkyl, aryl($C_1$-$C_6$)alkylamino($C_1$-$C_6$)alkyl, ($C_1$-$C_6$)alkyl amino($C_1$-$C_6$)alkoxy, ($C_1$-$C_6$)alkylamino($C_1$-$C_6$)alkoxy($C_1$-$C_6$)alkoxy, amino($C_1$-$C_6$)alkoxy, amino($C_1$-$C_6$)alkyl, ($C_1$-$C_6$)alkylamino($C_1$-$C_6$)alkyl, ($C_1$-$C_4$)alkylamino-($C_2$-$C_6$)alkenyl, 5-8-membered nitrogen-containing heterocyclyl($C_2$-$C_6$)alkenyl, heterocyclyl($C_1$-$C_6$)amino($C_2$-$C_6$)alkyl, 5-6 membered heterocyclyloxy, 5-6 membered nitrogen-containing heterocyclyl and 5-7 membered nitrogen-containing heterocyclyl($C_1$-$C_6$)alkyl; and more specifically, amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl. Each basic moiety can be substituted by 0, 1, 2 or 3 groups independently selected from halo, —$NH_2$, —OH, —CN, —$CF_3$, ($C_1$-$C_6$)alkylamino, haloalkyl, oxo, ($C_1$-$C_6$)alkoxy, ($C_1$-$C_6$)alkoxyalkyl, ($C_2$-$C_6$)alkenyl, ($C_2$-$C_6$)alkynyl, di($C_1$-$C_6$)alkylamino, —$C(O)R^8$, —$COOR^8$, —$C(O)NR^8R^{8'}$, —$NR^8C(O)R^{8'}$, =NCN; and ($C_1$-$C_6$)alkyl, aryl, heteroaryl, cycloalkyl and heterocyclyl, each of which is substituted by 0, 1, 2 or 3 groups independently selected from halo, —$NH_2$, —OH, —CN, —$CF_3$, ($C_1$-$C_6$)alkylamino, haloalkyl, oxo, ($C_1$-$C_6$)alkoxy, ($C_1$-$C_6$)alkoxyalkyl, ($C_1$-$C_6$)alkyl, ($C_2$-$C_6$)alkenyl, ($C_2$-$C_6$)alkynyl, di($C_1$-$C_6$)alkylamino, —$C(O)R^8$, —$COOR^8$, —$C(O)NR^8R^{8'}$, and —$NR^8C(O)R^{8'}$. In one embodiment, the basic moiety is selected from cycloalkylamino($C_1$-$C_6$)alkyl, cycloalkyl($C_1$-$C_6$)alkylamino($C_1$-$C_6$) alkyl, heterocyclylamino($C_1$-$C_6$)alkyl, heterocyclyl($C_1$-$C_6$) alkylamino($C_1$-$C_6$)alkyl, arylamino($C_1$-$C_6$)alkyl, aryl($C_1$-$C_6$)alkylamino($C_1$-$C_6$)alkyl, ($C_1$-$C_6$)alkyl amino($C_1$-$C_6$)alkoxy, ($C_1$-$C_6$)alkylamino($C_1$-$C_6$)alkoxy($C_1$-$C_6$)alkoxy, amino($C_1$-$C_6$)alkoxy, amino($C_1$-$C_6$)alkyl, ($C_1$-$C_6$)alkylamino($C_1$-$C_6$)alkyl, ($C_1$-$C_4$)alkylamino-($C_2$-$C_6$)alkenyl, 4-8-membered nitrogen-containing heterocyclyl($C_2$-$C_6$)alkenyl, heterocyclyl($C_1$-$C_6$)amino($C_2$-$C_6$)alkyl, 5-6 membered heterocyclyloxy, 5-6 membered nitrogen-containing heterocyclyl and 5-7 membered nitrogen-containing heterocyclylalkyl. In another embodiment, the basic moiety is selected from cycloalkylamino($C_1$-$C_6$)alkyl, cycloalkyl($C_1$-$C_6$) alkylamino($C_1$-$C_6$)alkyl, heterocyclylamino($C_1$-$C_6$)alkyl, heterocyclyl($C_1$-$C_6$)alkylamino($C_1$-$C_6$)alkyl, arylamino($C_1$-$C_6$) alkyl, aryl($C_1$-$C_6$)alkylamino($C_1$-$C_6$)alkyl, ($C_1$-$C_6$)alkyl amino($C_1$-$C_6$)alkoxy, ($C_1$-$C_6$)alkylamino($C_1$-$C_6$)alkoxy($C_1$-$C_6$)alkoxy, amino($C_1$-$C_6$)alkoxy, amino($C_1$-$C_6$)alkyl, ($C_1$-$C_6$)alkylamino($C_1$-$C_6$)alkyl, ($C_1$-$C_4$)alkylamino-($C_2$-$C_6$)alkenyl, 4-8-membered nitrogen-containing heterocyclyl($C_2$-$C_6$)alkenyl, heterocyclyl($C_1$-$C_6$)amino($C_2$-$C_6$)alkyl, 5-6 membered heterocyclyloxy, 5-6 membered nitrogen-containing heterocyclyl and 5-7 membered nitrogen-containing heterocyclyl-alkyl any of which are substituted by $COOR_8$, halo, $C_{1-6}$alkyl or cycloalkyl.

In another aspect of the invention, the compounds are defined by Formula I

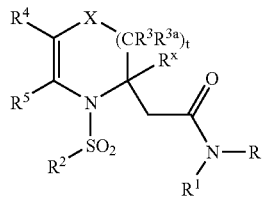

wherein:

t is 0-2;

X is selected from NH, S, O and NR$^a$; wherein R$^a$ is selected form alkyl, substituted alkyl, —C(O)R$^8$, —CO$_2$R$^8$, —C(O)NR$^8$R$^{8'}$, —SO$_2$R$^8$ and —SO$_2$NR$^8$R$^{8'}$; provided R$^3$ and R$^{3a}$ together do not form oxo if R$^a$ is —C(O)R$^8$, —CO$_2$R$^8$, —C(O)NR$^8$R$^{8'}$, —SO$_2$R$^8$ or —SO$_2$NR$^8$R$^{8'}$;

R is selected from
  a) 9-, 10-, or 11-membered fused bicyclic carbocyclic or heterocyclic ring substituted by 1, 2 or 3 basic moieties, and substituted by 0, 1, 2 or 3 groups independently selected from halo, hydroxyl, cyano, oxo, (C$_1$-C$_6$)alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
  b) 4-, 5-, 6- or 7-membered carbocyclic ring substituted by 0, 1, 2 or 3 basic moieties, and substituted by 0, 1, 2 or 3 groups independently selected from halo, hydroxyl, cyano, (C$_1$-C$_6$)alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
  c) 4-, 5-, 6- or 7-membered heterocyclic ring substituted by 1, 2 or 3 basic moieties, and substituted by 0, 1, 2 or 3 groups independently selected from halo, hydroxyl, cyano, oxo, (C$_1$-C$_6$)alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
  d) arylalkyl substituted by 0, 1, 2 or 3 basic moieties, and substituted by 0, 1, 2 or 3 groups independently selected from halo, hydroxyl, cyano, (C$_1$-C$_6$)alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
  e) 5- or 6-membered heterocyclylalkyl substituted by 1, 2 or 3 basic moieties, and substituted by 0, 1, 2 or 3 groups independently selected from halo, hydroxyl, cyano, oxo, (C$_1$-C$_6$)alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
  f) 5-, 6-, or 7-membered cycloalkyl;
  g) 4-, 5-, 6- or 7-membered carbocyclic or heterocyclic ring substituted by 0, 1, 2 or 3 groups independently selected from halo, hydroxyl, cyano, oxo, (C$_1$-C$_6$)alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
  h) diphenylmethyl;
  i) 9-, 10-, or 11-membered fused bicyclic carbocyclic or heterocyclic ring substituted by 0, 1, 2 or 3 groups independently selected from halo, cyano, oxo, (C$_1$-C$_6$)alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; and
  j) 12-, 13-, 14-, or 15-membered fused tricyclic carbocyclic or heterocyclic ring substituted by 0, 1, 2 or 3 basic moieties, and substituted by 0, 1, 2 or 3 groups independently selected from halo, hydroxyl, cyano, oxo, (C$_1$-C$_6$)alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

R$^1$ is selected from H, C$_{1-4}$-alkyl, substituted C$_{1-4}$ alkyl, aryl and substituted aryl;

alternatively R and R$^1$ together with the nitrogen atom to which they are attached form a 5-8 membered heterocyclyl ring, optionally containing 1-2 additional heteroatoms, optionally fused with a phenyl group or substituted with one aryl, heteroaryl or aralkyl group, wherein the heterocyclyl ring and aryl, heteroaryl or aralkyl groups are further optionally substituted with a basic moiety and further substituted by 0, 1, 2 or 3 groups independently selected from halo, cyano, oxo, (C$_1$-C$_6$)alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$)alkyl, and substituted (C$_1$-C$_6$)alkyl;

R$^2$ is selected from arylalkenyl, aryl, and heterocyclyl selected from thienyl, quinolinyl, isoquinolinyl, 3-pyridyl, thiazol-4-yl, 4-imidazolyl, benzofuryl, benzoxadiazolyl, benzothiadiazolyl, benzothiazolyl, 1H-pyrazolyl, isoxazolthienyl, benzothienyl, thieno[3,2-c]pyridinyl, and tetrahydroisoquinolinyl, wherein R$^2$ is optionally substituted with one to five groups independently selected from halo, —NH$_2$, hydroxyl, cyano, (C$_1$-C$_6$)alkylamino, oxo, (C$_1$-C$_6$)alkoxy, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

$R^3$, $R^{3a}$, $R^4$ and $R^5$ are independently selected from H, $C_{1-3}$ alkyl and substituted $C_{1-3}$ alkyl;

or $R^3$ and $R^{3a}$ together form oxo;

$R^8$ and $R^{8'}$ independently are H or selected from lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

$R^x$ is selected from H, $(C_1-C_3)$haloalkyl, and $(C_1-C_3)$alkyl; and wherein each substituted alkyl, substituted aryl, heteroaryl, substituted heteroaryl, substituted cycloalkyl and substituted saturated or partially saturated heterocyclyl is substituted by 1, 2 or 3 groups independently selected from halo, —$NH_2$, hydroxyl, cyano, $(C_1-C_6)$alkylamino, $(C_1-C_6)$haloalkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —$C(O)R^8$, —$COOR^8$, —$C(O)NR^8R^{8'}$, and —$NR^8C(O)R^{8'}$, and pharmaceutically acceptable derivatives thereof.

The invention also relates to compounds of Formula I wherein X is selected from NH and $NR^a$; and wherein $R^a$ is $(C_{1-3})$alkyl, in conjunction with any of the above or below embodiments.

The invention also relates to compounds of Formula I wherein X is NH, in conjunction with any of the above or below embodiments.

The invention also relates to compounds of Formula I wherein R is selected from 9-, 10-, or 11-membered fused bicyclic carbocyclic or heterocyclic ring substituted with zero to two basic moieties, and substituted by 0, 1, 2 or 3 groups independently selected from halo, hydroxyl, cyano, oxo, $(C_1-C_6)$alkoxy, $(C_2-C_6)$alkenyl, $(C_2-C_6)$alkynyl, —$C(O)R^8$, —$COOR^8$, —$C(O)NR^8R^{8'}$, —$NR^8C(O)R^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, in conjunction with any of the above or below embodiments.

The invention also relates to compounds of Formula I wherein R is a partially unsaturated carbocyclic ring, such as 1,2,3,4-tetrahydronaphthyl or indanyl, substituted with a basic moiety, optionally substituted with chloro, in conjunction with any of the above or below embodiments.

The invention also relates to compounds of Formula I wherein R is selected from 1,2,3,4-tetrahydronaphth-1-yl, 1,2,3,4-tetrahydronaphth-2-yl, indan-1-yl and indan-2-yl, substituted with a basic moiety, optionally substituted with chloro, in conjunction with any of the above or below embodiments.

The invention also relates to compounds of Formula I wherein R is partially unsaturated heterocyclyl, such as chroman and 2,2-dioxo-3,4-dihydro-1H-2,1-benzothiazinyl, substituted with a basic moiety, optionally substituted with chloro, in conjunction with any of the above or below embodiments.

The invention also relates to compounds of Formula I wherein R is chroman-4-yl, or 2,2-dioxo-3,4-dihydro-1H-2,1-benzothiazin-4-yl, substituted with a basic moiety, optionally substituted with chloro, in conjunction with any of the above or below embodiments.

The invention also relates to compounds of Formula I wherein R is selected from phenyl and 5-6 membered heteroaryl; wherein R is substituted with one to two basic moieties, and substituted by 0, 1, 2 or 3 groups independently selected from halo, hydroxyl, cyano, oxo, $(C_1-C_6)$alkoxy, —$C(O)R^8$, —$COOR^8$, —$C(O)NR^8R^{8'}$, —$NR^8C(O)R^{8'}$, $(C_1$-$C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, in conjunction with any of the above or below embodiments.

The invention also relates to compounds of Formula I wherein R is phenyl substituted with a basic moiety selected from $(C_1-C_6)$alkylamino$(C_1-C_6)$alkyl, $C_{1-4}$-alkylamino-$C_{2-6}$-alkenyl, 5-8 membered nitrogen-containing heterocyclyl-$C_{2-6}$-alkenyl, and heterocyclyl-$(C_1-C_6)$alkylamino$(C_2$-$C_6)$alkyl, in conjunction with any of the above or below embodiments.

The invention also relates to compounds of Formula I wherein R is selected from 3-((piperidin-1-ylethyl)aminomethyl)phenyl and 4-imidazolin-2-ylphenyl, in conjunction with any of the above or below embodiments.

The invention also relates to compounds of Formula I wherein R is phenyl-$(C_{1-3})$-alkyl substituted with a basic moiety, such as 4-(imidazolin-2-yl)phenylmethyl, 4-(imidazolin-2-yl)phenylethyl and 4-(imidazolin-2-yl)phenylpropyl, in conjunction with any of the above or below embodiments.

The invention also relates to compounds of Formula I wherein $R^1$ is H or methyl, in conjunction with any of the above or below embodiments.

The invention also relates to compounds of Formula I wherein $R^2$ is selected from phenyl-$(C_{2-4})$-alkenyl, phenyl, naphthyl, 5-membered nitrogen containing heteroaryl, 5-membered sulfur containing heteroaryl, 6-membered nitrogen containing heteroaryl, 9-membered heterocyclyl, and 10-membered heterocyclyl; in conjunction with any of the above or below embodiments.

The invention also relates to compounds of Formula I wherein $R^2$ is selected from phenyl-CH=CH—, tetrahydronaphthyl, naphtho[2.3-d]dioxolyl, benzofuranyl, benzoxadiazolyl, benzothiadiazolyl, benzothiazolyl, 2-thienyl, isoxazolthienyl, benzothienyl, thieno[3,2-c]pyridinyl, naphthyl, phenyl, 3-pyridinyl, tetrahydroisoquinolinyl, quinolinyl and isoquinolinyl; wherein $R^2$ is optionally substituted with one to five groups independently selected from halo, —$NH_2$, hydroxyl, cyano, $(C_1-C_6)$alkylamino, oxo, $(C_1-C_6)$alkoxy, $(C_2-C_6)$alkenyl, $(C_2-C_6)$alkynyl, di$(C_1-C_6)$alkylamino, —$C(O)R^8$, —$COOR^8$, —$C(O)NR^8R^{8'}$, —$NR^8C(O)R^{8'}$, $(C_1$-$C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted $(C_1-C_6)$alkyl, substituted aryl substituted heteroaryl and substituted saturated or partially saturated heterocyclyl is substituted by 0, 1, 2 or 3 groups independently selected from halo, —$NH_2$, hydroxyl, cyano, $(C_1-C_4)$alkylamino, $(C_1-C_4)$haloalkyl, oxo, $(C_1-C_4)$alkoxy, $(C_1-C_4)$alkoxy$(C_1-C_4)$alkyl, $(C_1-C_4)$alkyl, $(C_2-C_4)$alkenyl, $(C_2-C_4)$alkynyl, di$(C_1-C_4)$alkylamino, —$C(O)R^8$, —$COOR^8$, —$C(O)NR^8R^{8'}$, and —$NR^8C(O)R^{8'}$; in conjunction with any of the above or below embodiments.

The invention also relates to compounds of Formula I wherein $R^2$ is selected from phenyl-CH=CH—, tetrahydronaphthyl, 2,1,3-benzoxadiazol-4-yl, thien-2-yl, 2-naphthyl, phenyl, 3-pyridyl, 8-quinolyl and 5-isoquinolyl; and wherein $R^2$ is optionally substituted; preferably with one or two groups independently selected from methyl, chloro, methoxy, —$OCF_3$ or —$CF_3$; such as 2,4,6-trimethylphenyl, 3,4-dichlorophenyl, 3-chloro-4-methylphenyl, 4-chloro-3-methylphenyl, 3-trifluoromethylphenyl, 4-trifluoromethylphenyl, 4-trifluoromethoxyphenyl, 4-methoxyphenyl, 4-methylphenyl, 4-chlorophenyl and 4-tert-butylphenyl; in conjunction with any of the above or below embodiments.

The invention also relates to compounds of Formula I wherein the basic moieties on R are independently selected from amino, cycloalkylamino($C_1$-$C_6$)alkyl, cycloalkyl($C_1$-$C_6$)alkylamino($C_1$-$C_6$)alkyl, heterocyclylamino($C_1$-$C_6$)alkyl, heterocyclyl($C_1$-$C_6$)alkylamino($C_1$-$C_6$)alkyl, arylamino($C_1$-$C_6$)alkyl, aryl($C_1$-$C_6$)alkylamino($C_1$-$C_6$)alkyl, $C_{1-6}$-alkylamino-$C_{1-6}$-alkoxy, $C_{1-6}$-alkylamino-$C_{1-6}$-alkoxy-$C_{1-6}$-alkoxy, amino($C_1$-$C_6$)alkoxy, amino($C_1$-$C_6$)alkyl, ($C_1$-$C_6$)alkylamino($C_1$-$C_6$)alkyl, $C_{1-4}$-alkylamino-$C_{2-6}$-alkenyl, 5-8 membered nitrogen-containing heterocyclyl-$C_{2-6}$-alkenyl, heterocyclyl-($C_1$-$C_6$)alkylamino($C_2$-$C_6$)alkyl, 5-6 membered heterocyclyloxy, 4-6 membered nitrogen-containing heterocyclyl and 5-7 membered nitrogen-containing heterocyclyl-alkyl; and wherein each of said basic moieties is substituted by 0, 1, 2 or 3 groups independently selected from halo, —$NH_2$, hydroxyl, cyano, —$CF_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted ($C_1$-$C_6$)alkyl, substituted aryl substituted heteroaryl and substituted saturated or partially saturated heterocyclyl is substituted by 0, 1, 2 or 3 groups independently selected from halo, —$NH_2$, hydroxyl, cyano, ($C_1$-$C_6$)alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^8$, in conjunction with any of the above or below embodiments.

The invention also relates to compounds of Formula I wherein the basic moieties on R are independently selected from amino, mono-$C_{1-4}$-alkylamino-$C_{1-4}$-alkyl, di-$C_{1-4}$-alkylamino-$C_{1-4}$-alkyl, mono-$C_{1-4}$-alkylamino-$C_{2-4}$-alkenyl, di-$C_{1-4}$-alkylamino-$C_{2-4}$-alkenyl, 5-8 membered nitrogen-containing heterocyclyl-$C_{2-4}$-alkenyl, optionally substituted 5-6 membered nitrogen-containing heterocyclyl and 5-8 membered nitrogen-containing heterocyclyl-$C_{1-4}$-alkyl, in conjunction with any of the above or below embodiments.

The invention also relates to compounds of Formula I wherein the basic moieties on R are independently selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylaminomethyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl, in conjunction with any of the above or below embodiments.

The invention also relates to compounds of Formula I wherein $R^3$ and $R^{3a}$ together form oxo; wherein $R^4$ is selected from H and $C_{1-3}$ alkyl; and wherein $R^5$ is H, in conjunction with any of the above or below embodiments.

Alternatively, the invention also relates to compounds wherein $R^3$ and $R^{3a}$ together form oxo; wherein $R^4$ is selected from H and methyl; and wherein $R^5$ is H, in conjunction with any of the above or below embodiments.

The invention also relates to compounds wherein $R^8$ and $R^{8'}$ independently are H or selected from lower alkyl, aryl and heteroaryl, each of which is optionally substituted with one, two or three groups independently selected from lower alkyl, halogen, lower alkoxy, hydroxy, amino, mono-alkylamino, dialkylamino, and trifluoromethyl; in conjunction with any of the above or below embodiments.

The invention also relates to compounds of Formula I $R^x$ is H, methyl or trifluoromethyl, such as H; in conjunction with any of the above or below embodiments.

The invention also relates to compounds of Formula II

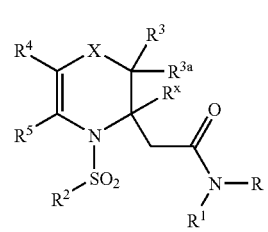

II wherein:
X is selected from NH, S, O and N$R^a$;
$R^a$ is selected form alkyl, substituted alkyl, —C(O)$R^8$, —$CO_2R^8$, —C(O)N$R^8R^{8'}$, —$SO_2R^8$ and —$SO_2NR^8R^{8'}$; provided $R^3$ and $R^{3a}$ do not form oxo if $R^a$ is —C(O)$R^8$, —$CO_2R^8$, —C(O)N$R^8R^{8'}$, —$SO_2R^8$ or —$SO_2NR^8R^{8'}$;
R is selected from
a) 9-, 10-, or 11-membered fused bicyclic carbocyclic or heterocyclic ring substituted by 1, 2 or 3 basic moieties, and substituted by 0, 1, 2 or 3 groups independently selected from halo, hydroxyl, cyano, oxo, ($C_1$-$C_6$)alkoxy, ($C_2$-$C_6$)alkenyl, ($C_2$-$C_6$)alkynyl, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
b) 4-, 5-, 6- or 7-membered carbocyclic ring substituted by 0, 1, 2 or 3 basic moieties, and substituted by 0, 1, 2 or 3 groups independently selected from halo, hydroxyl, cyano, ($C_1$-$C_6$)alkoxy, ($C_2$-$C_6$)alkenyl, ($C_2$-$C_6$)alkynyl, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
c) 4-, 5-, 6- or 7-membered heterocyclic ring substituted by 1, 2 or 3 basic moieties, and substituted by 0, 1, 2 or 3 groups independently selected from halo, hydroxyl, cyano, oxo, ($C_1$-$C_6$)alkoxy, ($C_2$-$C_6$)alkenyl, ($C_2$-$C_6$)alkynyl, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
  d) arylalkyl substituted by 0, 1, 2 or 3 basic moieties, and substituted by 0, 1, 2 or 3 groups independently selected from halo, hydroxyl, cyano, ($C_1$-$C_6$)alkoxy, ($C_2$-$C_6$)alkenyl, ($C_2$-$C_6$)alkynyl, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; and
  e) 5- or 6-membered heterocyclylalkyl substituted by 1, 2 or 3 basic moieties, and substituted by 0, 1, 2 or 3 groups independently selected from halo, hydroxyl, cyano, oxo, ($C_1$-$C_6$)alkoxy, ($C_2$-$C_6$)alkenyl, ($C_2$-$C_6$)alkynyl, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

$R^1$ is selected from H, $C_{1-4}$-alkyl, substituted $C_{1-4}$-alkyl, aryl and substituted aryl; alternatively R and $R^1$ together with the nitrogen atom to which they are attached form a 5-8 membered heterocyclyl ring, optionally containing 1-2 additional heteroatoms, optionally fused with a phenyl group or substituted with one aryl, heteroaryl or aralkyl group, wherein the heterocyclyl ring and aryl, heteroaryl or aralkyl groups are further optionally substituted with a basic moiety and further substituted by 0, 1, 2 or 3 groups independently selected from halo, cyano, oxo, ($C_1$-$C_6$)alkoxy, ($C_2$-$C_6$)alkenyl, ($C_2$-$C_6$)alkynyl, —C(O)$R^8$, —COO$R^8$, —C(O)N$R^8R^{8'}$, —N$R^8$C(O)$R^8$, ($C_1$-$C_6$)alkyl, and substituted ($C_1$-$C_6$)alkyl;

$R^2$ is selected from arylalkenyl, aryl, and heterocyclyl selected from thienyl, quinolinyl, isoquinolinyl, 3-pyridyl, thiazol-4-yl, 4-imidazolyl, benzofuryl, benzoxadiazolyl, benzothiadiazolyl, benzothiazolyl, 1H-pyrazolyl, isoxazolthienyl, benzothienyl, thieno[3,2-c]pyridinyl, and tetrahydroisoquinolinyl, wherein $R^2$ is optionally substituted with one to five groups independently selected from halo, —$NH_2$, hydroxyl, cyano, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

$R^3$, $R^{3a}$, $R^4$ and $R^5$ are independently selected from H, $C_{1-3}$ alkyl, and substituted alkyl;

or wherein $R^3$ and $R^{3a}$ together form oxo;

$R^8$ and $R^{8'}$ independently are H or selected from lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

$R^x$ is selected from H, ($C_1$-$C_3$)haloalkyl, and ($C_1$-$C_3$)alkyl; and wherein each substituted alkyl, substituted aryl, heteroaryl, substituted heteroaryl, substituted cycloalkyl and substituted saturated or partially saturated heterocyclyl is substituted by 1, 2 or 3 groups independently selected from halo, —$NH_2$, hydroxyl, cyano, ($C_1$-$C_6$)alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$, and pharmaceutically acceptable derivatives thereof; provided the basic substituent is not 2-pyridyl, 3-pyridyl or 2-oxo-piperazinyl-4-ylmethyl.

The invention also relates to compounds of Formula II wherein X is selected from NH and N$R^a$; and wherein $R^a$ is ($C_{1-3}$)alkyl or Boc; in conjunction with any of the above or below embodiments.

The invention also relates to compounds of Formula II wherein X is NH; in conjunction with any of the above or below embodiments.

The invention also relates to compounds of Formula II wherein R is selected from 9-, 10-, or 11-membered fused bicyclic carbocyclic or heterocyclic ring substituted with one to two basic moieties, and substituted by 0, 1, 2 or 3 groups independently selected from halo, hydroxyl, cyano, oxo, ($C_1$-$C_6$)alkoxy, ($C_2$-$C_6$)alkenyl, ($C_2$-$C_6$)alkynyl, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; in conjunction with any of the above or below embodiments.

The invention also relates to compounds of Formula II wherein R is a partially unsaturated carbocyclic ring, such as 1,2,3,4-tetrahydronaphthyl or indanyl; substituted with a basic moiety, optionally substituted with chloro; in conjunction with any of the above or below embodiments.

The invention also relates to compounds of Formula II wherein R is selected from 1,2,3,4-tetrahydronaphth-1-yl, 1,2,3,4-tetrahydronaphth-2-yl, indan-1-yl and indan-2-yl; substituted with a basic moiety, optionally substituted with chloro; in conjunction with any of the above or below embodiments.

The invention also relates to compounds of Formula II wherein R is partially unsaturated heterocyclyl, such as chroman and 2,2-dioxo-3,4-dihydro-1H-2,1-benzothiazinyl; substituted with a basic moiety, optionally substituted with chloro; in conjunction with any of the above or below embodiments.

The invention also relates to compounds of Formula II wherein R is chroman-4-yl, or 2,2-dioxo-3,4-dihydro-1H-2, 1-benzothiazin-4-yl; substituted with a basic moiety, optionally substituted with chloro; in conjunction with any of the above or below embodiments.

The invention also relates to compounds of Formula II wherein R is selected from phenyl and 5-6 membered heteroaryl; wherein R is substituted with one to two basic moieties, and substituted by 0, 1, 2 or 3 groups independently selected from halo, hydroxyl, cyano, oxo, ($C_1$-$C_6$)alkoxy, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; in conjunction with any of the above or below embodiments.

The invention also relates to compounds of Formula II wherein R is phenyl substituted with a basic moiety selected from ($C_1$-$C_6$)alkylamino($C_1$-$C_6$)alkyl, $C_{1-4}$-alkylamino- $C_{2-6}$-alkenyl, 5-8 membered nitrogen-containing heterocyclyl-$C_{2-6}$-alkenyl, and heterocyclyl-($C_1$-$C_6$)alkylamino($C_2$-$C_6$)alkyl; in conjunction with any of the above or below embodiments.

The invention also relates to compounds of Formula II wherein R is selected from 3-((piperidin-1-ylethyl) aminomethyl)phenyl and 4-imidazolin-2-ylphenyl; in conjunction with any of the above or below embodiments.

The invention also relates to compounds of Formula II wherein R is phenyl-($C_{1-3}$)-alkyl substituted with a basic moiety, such as 4-(imidazolin-2-yl)phenylmethyl, 4-(imidazolin-2-yl)phenylethyl and 4-(imidazolin-2-yl)phenylpropyl; in conjunction with any of the above or below embodiments.

The invention also relates to compounds of Formula II wherein $R^1$ is H or methyl; in conjunction with any of the above or below embodiments.

The invention also relates to compounds of Formula I wherein $R^2$ is selected from phenyl-($C_{2-4}$)-alkenyl, phenyl, naphthyl, 5-membered nitrogen containing heteroaryl, 5-membered sulfur containing heteroaryl, 6-membered nitrogen containing heteroaryl, 9-membered heterocyclyl, and 10-membered heterocyclyl; in conjunction with any of the above or below embodiments.

The invention also relates to compounds of Formula I wherein $R^2$ is selected from phenyl-CH=CH—, tetrahydronaphthyl, naphtho[2.3-d]dioxolyl, benzofuranyl, benzoxadiazolyl, benzothiadiazolyl, benzothiazolyl, 2-thienyl, isoxazolthienyl, benzothienyl, thieno[3,2-c]pyridinyl, naphthyl, phenyl, 3-pyridinyl, tetrahydroisoquinolinyl, quinolinyl and isoquinolinyl; wherein $R^2$ is optionally substituted with one to five groups independently selected from halo, —$NH_2$, hydroxyl, cyano, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted ($C_1$-$C_6$)alkyl, substituted aryl substituted heteroaryl and substituted saturated or partially saturated heterocyclyl is substituted by 0, 1, 2 or 3 groups independently selected from halo, —$NH_2$, hydroxyl, cyano, ($C_1$-$C_4$)alkylamino, ($C_1$-$C_4$)haloalkyl, oxo, ($C_1$-$C_4$)alkoxy, ($C_1$-$C_4$)alkoxy($C_1$-$C_4$)alkyl, ($C_1$-$C_4$)alkyl, ($C_2$-$C_4$)alkenyl, ($C_2$-$C_4$)alkynyl, di($C_1$-$C_4$)alkylamino, —C(O)$R^8$, —COO$R^8$, —C(O)N$R^8R^{8'}$, and —N$R^8$C(O)$R^{8'}$; in conjunction with any of the above or below embodiments.

The invention also relates to compounds of Formula I wherein $R^2$ is selected from phenyl-CH=CH—, tetrahydronaphthyl, 2,1,3-benzoxadiazol-4-yl, thien-2-yl, 2-naphthyl, phenyl, 3-pyridyl, 8-quinolyl and 5-isoquinolyl; and wherein $R^2$ is optionally substituted; preferably with one or two groups independently selected from methyl, chloro, methoxy, —OCF$_3$ or —CF$_3$; such as 2,4,6-trimethylphenyl, 3,4-dichlorophenyl, 3-chloro-4-methylphenyl, 4-chloro-3-methylphenyl, 3-trifluoromethylphenyl, 4-trifluoromethylphenyl, 4-trifluoromethoxyphenyl, 4-methoxyphenyl, 4-methylphenyl, 4-chlorophenyl and 4-tert-butylphenyl; in conjunction with any of the above or below embodiments.

The invention also relates to compounds of Formula II wherein the basic moieties on R are independently selected from amino, cycloalkylamino($C_1$-$C_6$)alkyl, cycloalkyl($C_1$-$C_6$)alkylamino($C_1$-$C_6$)alkyl, heterocyclylamino($C_1$-$C_6$)alkyl, heterocyclyl($C_1$-$C_6$)alkylamino($C_1$-$C_6$)alkyl, arylamino($C_1$-$C_6$)alkyl, aryl($C_1$-$C_6$)alkylamino($C_1$-$C_6$)alkyl, $C_{1-6}$-alkylamino-$C_{1-6}$-alkoxy, $C_{1-6}$-alkylamino-$C_{1-6}$-alkoxy-$C_{1-6}$-alkoxy, amino($C_1$-$C_6$)alkoxy, amino($C_1$-$C_6$)alkyl, ($C_1$-$C_6$)alkylamino($C_1$-$C_6$)alkyl, $C_{1-4}$-alkylamino-$C_{2-6}$-alkenyl, 5-8 membered nitrogen-containing heterocyclyl-$C_{2-6}$-alkenyl, heterocyclyl-($C_1$-$C_6$)alkylamino ($C_2$-$C_6$)alkyl, 5-6 membered heterocyclyloxy, 5-6 membered nitrogen-containing heterocyclyl and 5-7 membered nitrogen-containing heterocyclyl-alkyl; and wherein each of said basic moieties is substituted by 0, 1, 2 or 3 groups independently selected from halo, —$NH_2$, hydroxyl, cyano, —CF$_3$, ($C_1$-$C_6$)alkylamino, oxo, ($C_1$-$C_6$)alkoxy, ($C_2$-$C_6$)alkenyl, ($C_2$-$C_6$)alkynyl di($C_1$-$C_6$)alkylamino, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted ($C_1$-$C_6$)alkyl, substituted aryl substituted heteroaryl and substituted saturated or partially saturated heterocyclyl is substituted by 0, 1, 2 or 3 groups independently selected from halo, —$NH_2$, hydroxyl, cyano, ($C_1$-$C_6$)alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^8$; in conjunction with any of the above or below embodiments.

The invention also relates to compounds of Formula II wherein the basic moieties on R are independently selected from amino, mono-$C_{1-4}$-alkylamino-$C_{1-4}$-alkyl, di-$C_{1-4}$-alkylamino-$C_{1-4}$-alkyl, mono-$C_{1-4}$-alkylamino-$C_{2-4}$-alkenyl, di-$C_{1-4}$-alkylamino-$C_{2-4}$-alkenyl, 5-8 membered nitrogen-containing heterocyclyl-$C_{2-4}$-alkenyl, optionally substituted 5-6 membered nitrogen-containing heterocyclyl and 5-8 membered nitrogen-containing heterocyclyl-$C_{1-4}$-alkyl; in conjunction with any of the above or below embodiments.

The invention also relates to compounds of Formula II wherein the basic moieties on R are independently selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylaminomethyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl; in conjunction with any of the above or below embodiments.

The invention also relates to compounds wherein $R^8$ and $R^{8'}$ independently are H or selected from lower alkyl, aryl and heteroaryl, each of which is optionally substituted with one, two or three groups independently selected from lower alkyl, halogen, lower alkoxy, hydroxy, amino, mono-alkylamino, dialkylamino, and trifluoromethyl; in conjunction with any of the above or below embodiments.

The invention also relates to compounds of Formula II $R^x$ is H, methyl or trifluoromethyl, such as H; in conjunction with any of the above or below embodiments.

The invention also relates to compounds of Formula III

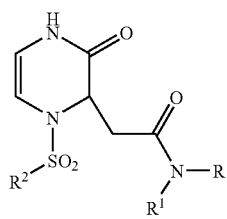

III wherein

R is a 9-, 10-, or 11-membered fused bicyclic carbocyclic or heterocyclic ring substituted with one to two basic moieties, and substituted by 0, 1, 2 or 3 groups independently selected from halo, —$NH_2$, hydroxyl, cyano, oxo, $(C_1-C_6)$ alkoxy, $(C_2-C_6)$alkenyl, $(C_2-C_6)$alkynyl, —$C(O)R^8$, —$COOR^8$, —$C(O)NR^8R^{8'}$, —$NR^8C(O)R^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; wherein each substituted $(C_1-C_6)$alkyl, substituted aryl, substituted heteroaryl, substituted cycloalkyl and substituted saturated or partially saturated heterocyclyl is substituted by 1, 2 or 3 groups independently selected from halo, —$NH_2$, hydroxyl, cyano, $(C_1-C_6)$alkylamino, $(C_1-C_6)$haloalkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$ alkylamino, —$C(O)R^8$, —$COOR^8$, —$C(O)NR^8R^{8'}$, and —$NR^8C(O)R^{8'}$;

$R^1$ is selected from H, and $C_{1-2}$-alkyl;

$R^2$ is selected from arylalkenyl, aryl, and heterocyclyl selected from thienyl, quinolinyl, isoquinolinyl, 3-pyridyl, thiazol-4-yl, 4-imidazolyl, benzofuryl, benzoxadiazolyl, benzothiadiazolyl, benzothiazolyl, 1H-pyrazolyl, isoxazolthienyl, benzothienyl, thieno[3,2-c]pyridinyl, and tetrahydroisoquinolinyl, wherein $R^2$ is optionally substituted with one to five groups independently selected from halo, —$NH_2$, hydroxyl, cyano, $(C_1-C_6)$alkylamino, oxo, $(C_1-C_6)$alkoxy, $(C_2-C_6)$alkenyl, $(C_2-C_6)$alkynyl, di$(C_1-C_6)$ alkylamino, —$C(O)R^8$, —$COOR^8$, —$C(O)NR^8R^{8'}$, —$NR^8C(O)R^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted $(C_1-C_6)$alkyl, substituted aryl substituted heteroaryl and substituted saturated or partially saturated heterocyclyl is substituted by 0, 1, 2 or 3 groups independently selected from halo, —$NH_2$, hydroxyl, cyano, $(C_1-C_6)$alkylamino, $(C_1-C_6)$haloalkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —$C(O)R^8$, —$COOR^8$, —$C(O)NR^8R^{8'}$, and —$NR^8C(O)R^{8'}$; and $R^8$ and $R^{8'}$ independently are H or selected from lower alkyl, aryl and heteroaryl, each of which is optionally substituted with one, two or three groups independently selected from lower alkyl, halogen, lower alkoxy, hydroxy, amino, mono- or dialkylamino, and trifluoromethyl; and pharmaceutically acceptable derivatives thereof; provided the basic substituent is not 2-pyridyl, 3-pyridyl or 2-oxo-piperazinyl-4-ylmethyl.

The invention also relates to compounds of Formula III R is a partially unsaturated carbocyclic ring, such as 1,2,3,4-tetrahydronaphthyl or indanyl.

The invention also relates to compounds of Formula III R is selected from 1,2,3,4-tetrahydronaphth-1-yl, 1,2,3,4-tetrahydronaphth-2-yl, indan-1-yl and indan-2-yl.

The invention also relates to compounds of Formula III wherein R is partially unsaturated heterocyclyl, such as chroman and 2,2-dioxo-3,4-dihydro-1H-2,1-benzothiazinyl; substituted with a basic moiety, optionally substituted with chloro; in conjunction with any of the above or below embodiments.

The invention also relates to compounds of Formula III wherein R is chroman-4-yl, or 2,2-dioxo-3,4-dihydro-1H-2,1-benzothiazin-4-yl; substituted with a basic moiety, optionally substituted with chloro; in conjunction with any of the above or below embodiments.

The invention also relates to compounds wherein each $R^2$ is selected from phenyl-CH=CH—, tetrahydronaphthyl, naphtho[2.3-d] dioxolyl, benzofuranyl, benzoxadiazolyl, benzothiadiazolyl, benzothiazolyl, 1H-pyrazolyl, thienyl, isoxazolthienyl, benzothienyl, thieno[3,2-c]pyridinyl, naphthyl, phenyl, pyridinyl, tetrahydroisoquinolinyl, quinolinyl and isoquinolinyl; wherein $R^2$ is optionally substituted with one to five groups independently selected from halo, —$NH_2$, hydroxyl, cyano, —$CF_3$, $(C_1-C_6)$alkylamino, oxo, $(C_1-C_6)$ alkoxy, $(C_2-C_6)$alkenyl, $(C_2-C_6)$alkynyl, di$(C_1-C_6)$alkylamino, —$C(O)R^8$, —$COOR^8$, —$C(O)NR R^{8'}$, —$NR^8C(O)$ $R^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; wherein each substituted $(C_1-C_6)$alkyl, substituted aryl, substituted heteroaryl, substituted cycloalkyl and substituted saturated or partially saturated heterocyclyl is substituted by 1, 2 or 3 groups independently selected from halo, —$NH_2$, hydroxyl, cyano, $(C_1-C_6)$alkylamino, halo$(C_1-C_6)$alkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkyl, di$(C_1-C_6)$alkylamino, —$C(O)R^8$, —$COOR^8$, —$C(O)NR^8R^{8'}$, and —$NR^8C$ $(O)R^{8'}$; wherein $R^1$ is selected from H and $C_{1-2}$-alkyl; wherein the basic substituent on R is selected from amino, cycloalkylamino$(C_1-C_6)$alkyl, cycloalkyl$(C_1-C_6)$alkylamino$(C_1-C_6)$ alkyl, heterocyclylamino$(C_1-C_6)$alkyl, heterocyclyl$(C_1-C_6)$ alkyl amino $(C_1-C_6)$alkyl, arylamino$(C_1-C_6)$alkyl, aryl$(C_1-C_6)$alkylamino$(C_1-C_6)$alkyl, $C_{1-6}$-alkylamino-$C_{1-6}$-alkoxy, $C_{1-6}$-alkylamino-$C_{1-6}$-alkoxy-$C_{1-6}$-alkoxy, amino$(C_1-C_6)$ alkoxy, amino $(C_1-C_6)$alkyl, $(C_1-C_6)$alkylamino$(C_1-C_6)$ alkyl, $C_{1-4}$-alkylamino-$C_{2-6}$-alkenyl, 5-8 membered nitrogen-containing heterocyclyl-$C_{2-6}$-alkenyl, heterocyclyl-$(C_1-C_6)$alkylamino$(C_2-C_6)$alkyl, 5-6 membered heterocyclyloxy, 5-6 membered nitrogen-containing heterocyclyl and 5-7 membered nitrogen-containing heterocyclyl-alkyl; and wherein each of said basic moieties is substituted by 0, 1, 2 or 3 groups independently selected from halo, —$NH_2$, hydroxyl, cyano, —$CF_3$, $(C_1-C_6)$alkylamino, oxo, $(C_1-C_6)$ alkoxy, $(C_2-C_6)$alkenyl, $(C_2-C_6)$alkynyl, di$(C_1-C_6)$alkylamino, —$C(O)R^8$, —$COOR^8$, —$C(O)NR^8R^{8'}$, —$NR^8C(O)$ $R^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted ($C_1$-$C_6$)alkyl, substituted aryl substituted heteroaryl and substituted saturated or partially saturated heterocyclyl is substituted by 0, 1, 2 or 3 groups independently selected from halo, —$NH_2$, hydroxyl, cyano, ($C_1$-$C_4$)alkylamino, ($C_1$-$C_4$)haloalkyl, oxo, ($C_1$-$C_4$)alkoxy, ($C_1$-$C_4$)alkoxy($C_1$-$C_4$)alkyl, ($C_1$-$C_4$)alkyl, ($C_2$-$C_4$)alkenyl, ($C_2$-$C_4$)alkynyl, di($C_1$-$C_4$)alkylamino, —C(O)$R^8$, —$COOR^8$, —C(O)$NR^8R^{8'}$, and —$NR^8C(O)R^{8'}$; in conjunction with any of the above or below embodiments.

The invention also relates to compounds wherein $R^2$ is selected from phenyl-CH=CH—, tetrahydronaphthyl, 2,1,3-benzoxadiazol-4-yl, thien-2-yl, 2-naphthyl, phenyl, 3-pyridyl, 8-quinolyl and 5-isoquinolyl; wherein each $R^2$ is said optionally substituted; wherein $R^a$ is H; and wherein the basic substituent on R is selected from amino, mono-$C_{1-4}$-alkylamino-$C_{1-4}$-alkyl, di-$C_{1-4}$-alkylamino-$C_{1-4}$-alkyl, mono-$C_{1-4}$-alkylamino-$C_{2-4}$-alkenyl, di-$C_{1-4}$-alkylamino-$C_{2-4}$-alkenyl, 5-8 membered nitrogen-containing heterocyclyl-$C_{2-4}$-alkenyl, optionally substituted 5-6 membered nitrogen-containing heterocyclyl and 5-8 membered nitrogen-containing heterocyclyl-$C_{1-4}$-alkyl; in conjunction with any of the above or below embodiments.

The invention also relates to compounds of Formula III wherein the basic moieties on R are independently selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylaminomethyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl; in conjunction with any of the above or below embodiments.

The invention also relates to compounds of Formula IV

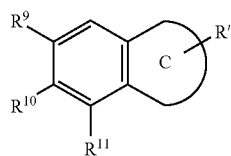

IV wherein the C ring is a 4- to 7-membered saturated carbocyclic or heterocyclic moiety; optionally substituted with halo, —$NH_2$, hydroxyl, cyano, oxo, ($C_1$-$C_6$)alkoxy, ($C_2$-$C_6$)alkenyl, ($C_2$-$C_6$)alkynyl, —C(O)$R^8$, —$COOR^8$, —C(O)$NR^8R^{8'}$, —$NR^8C(O)R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, saturated or partially saturated heterocyclyl and unsubstituted saturated or partially saturated heterocyclyl;

wherein R' is

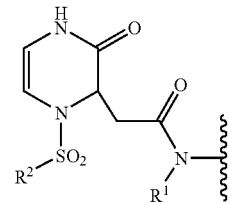

wherein:

$R^1$ is independently selected from H and $C_{1-2}$-alkyl;

$R^2$ is selected from arylalkenyl, aryl, and heterocyclyl selected from thienyl, quinolinyl, isoquinolinyl, 3-pyridyl, thiazol-4-yl, 4-imidazolyl, benzofuryl, benzoxadiazolyl, benzothiadiazolyl, benzothiazolyl, 1H-pyrazolyl, isoxazolthienyl, benzothienyl, thieno[3,2-c]pyridinyl, and tetrahydroisoquinolinyl, wherein $R^2$ is optionally substituted with one to five groups independently selected from halo, —$NH_2$, hydroxyl, cyano, —$CF_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —$COOR^8$, —C(O)$NR^8R^{8'}$, —$NR^8C(O)R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

wherein each substituted ($C_1$-$C_6$)alkyl, substituted aryl, substituted heteroaryl, substituted cycloalkyl and substituted saturated or partially saturated heterocyclyl is substituted by 1, 2 or 3 groups independently selected from halo, —$NH_2$, hydroxyl, cyano, ($C_1$-$C_6$)alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —$COOR^8$, —C(O)$NR^8R^{8'}$, and —$NR^8C(O)R^{8'}$;

$R^8$ and $R^{8'}$ independently are H or selected from lower alkyl, aryl and heteroaryl, each of which is optionally substituted with one, two or three groups independently selected from lower alkyl, halogen, lower alkoxy, hydroxy, amino, mono- or dialkylamino, and trifluoromethyl; and $R^9$, $R^{10}$ and $R^{11}$ are the same or different and represent H, halo, —$NH_2$, hydroxyl, cyano, —$CF_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —$COOR^8$, —C(O)$NR^8R^{8'}$, —$NR^8C(O)R^{8'}$, a basic moiety, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

wherein each substituted ($C_1$-$C_6$)alkyl, substituted aryl, substituted heteroaryl, substituted cycloalkyl and substituted saturated or partially saturated heterocyclyl is substituted by 1, 2 or 3 groups independently selected from halo, —$NH_2$, hydroxyl, cyano, ($C_1$-$C_6$)alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$) alkylamino, —C(O)$R^8$, —COO$R^8$, —C(O)N$R^8R^{8'}$, and —N$R^8$C(O)$R^{8'}$;

provided at least one of $R^9$, $R^{10}$ and $R^{11}$ is a basic moiety; further provided the basic substituent is not 2-pyridyl, 3-pyridyl or 2-oxo-piperazinyl-4-ylmethyl; and pharmaceutically acceptable derivatives thereof.

The invention also relates to compounds of Formula IV wherein $R^9$ and $R^{11}$ are H; and wherein $R^{10}$ is selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl) propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl.

The invention also relates to compounds of Formula IV wherein $R^{10}$ and $R^{11}$ are H; and wherein $R^9$ is selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl) propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl; in conjunction with any of the above or below embodiments.

The invention also relates to compounds of Formula IV wherein $R^9$ and $R^{10}$ are H; and wherein $R^{11}$ is selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl) propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl; in conjunction with any of the above or below embodiments.

The invention also relates to compounds of Formula IV wherein the C ring is selected from

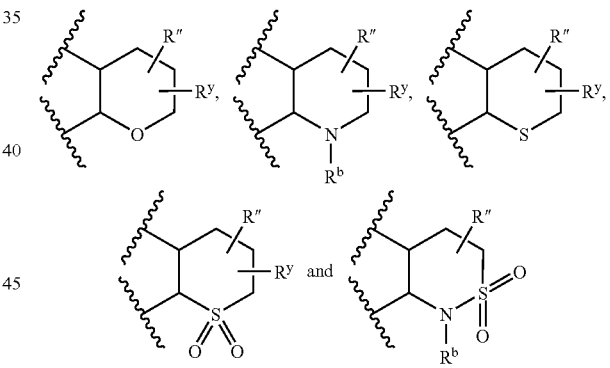

wherein $R^b$ is independently selected from R', H and $C_{1-2}$-alkyl; wherein $R^y$ is selected from halo, hydroxyl, cyano, oxo, ($C_1$-$C_4$)alkoxy, ($C_2$-$C_4$)alkenyl, ($C_2$-$C_4$)alkynyl, —C(O)$R^8$, —COO$R^8$, —C(O)N$R^8R^{8'}$, —N$R^8$C(O)$R^{8'}$, ($C_1$-$C_4$)alkyl, substituted ($C_1$-$C_4$)alkyl, phenyl, substituted phenyl, 5-6 membered heteroaryl, substituted 5-6 membered heteroaryl, $C_{3-6}$-cycloalkyl, substituted $C_{3-6}$-cycloalkyl, substituted saturated or partially saturated 5-6 membered heterocyclyl and unsubstituted saturated or partially saturated 5-6 membered heterocyclyl; and wherein R" is R' when $R^b$ is hydrogen or $C_{1-2}$alkyl, or R" is hydrogen when $R^b$ is R'; in conjunction with any of the above or below embodiments.

The invention also relates to compounds of Formula IV wherein $R^2$ is selected from phenyl-CH═CH—, tetrahydronaphthyl, naphtho[2.3-d]dioxol-6-yl, 1-benzofur-2-yl, 2,1,3-benzoxadiazol-4-yl, 2,1,3-benzothiadiazol-4-yl, 1,3-benzothiazol-2-yl, 1H-pyrazol-4-yl, thien-2-yl, 5-isoxazolthien-2-yl, benzothien-2-yl, thieno[3,2-c]pyridin-2-yl, 2-naphthyl, phenyl, 3-pyridyl, tetrahydroisoquinolyl, 8-quinolyl and 5-isoquinolyl; wherein $R^2$ is selected from phenyl-CH=CH—, tetrahydronaphthyl, 2,1,3-benzoxadiazol-4-yl, thien-2-yl, 2-naphthyl, phenyl, 3-pyridyl, 8-quinolyl and 5-isoquinolyl; wherein each $R^2$ is optionally substituted with one to five groups independently selected from halo, —$NH_2$, hydroxyl, cyano, —$CF_3$, ($C_1$-$C_6$)alkylamino, oxo, ($C_1$-$C_6$) alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C(O) $R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; wherein each substituted ($C_1$-$C_6$)alkyl, substituted aryl, substituted heteroaryl, substituted cycloalkyl and substituted saturated or partially saturated heterocyclyl is substituted by 1, 2 or 3 groups independently selected from halo, —$NH_2$, hydroxyl, cyano, ($C_1$-$C_6$)alkylamino, ($C_1$-$C_6$) haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$) alkylamino, —C(O)$R^8$, —COO$R^8$, —C(O)N$R^8R^{8'}$, and —N$R^8$C(O)$R^{8'}$; in conjunction with any of the above or below embodiments.

The invention also relates to compounds of Formula IV wherein $R^2$ is selected from 2-naphthyl, 1-naphthyl, phenyl, 3-chlorophenyl, 4-chlorophenyl, 3,5-dichlorophenyl, 3,4-dichlorophenyl, 2,4,6-trichlorophenyl, 3-fluorophenyl, 3-methoxyphenyl, 4-methoxyphenyl, 3-biphenyl, 3-chloro-4-methylphenyl, 4-chloro-3-methylphenyl, 3-trifluoromethylphenyl, 4-trifluoromethylphenyl, 4-trifluoromethoxyphenyl, 3-methylphenyl, 2,1,3-benzoxadiazol-4-yl, thien-2-yl, 3-pyridyl, 8-quinolyl and 5-isoquinolyl; in conjunction with any of the above or below embodiments.

The invention also relates to compounds of Formula IV wherein $R^1$ is H; in conjunction with any of the above or below embodiments.

The invention also relates to compounds of Formula IV wherein $R^2$ is 2-naphthyl; in conjunction with any of the above or below embodiments.

The invention also relates to compounds of Formula IV wherein $R^2$ is 3,4-dichlorophenyl; in conjunction with any of the above or below embodiments.

The invention also relates to compounds of Formula IV wherein $R^2$ is 3-trifluoromethylphenyl; in conjunction with any of the above or below embodiments.

The invention also relates to compounds of Formula V

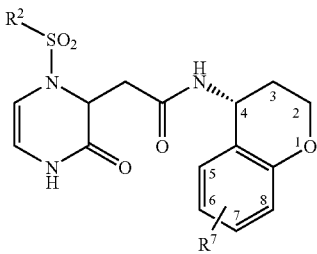

V wherein:
$R^2$ is selected from naphthyl, phenyl, thienyl, heterocyclyl selected from thienyl, benzoxadiazolyl, quinolinyl and isoquinolinyl, and wherein each is substituted by 0, 1, 2 or 3 substituents selected from chloro, fluoro, methoxy, methyl, trifluoromethyl and phenyl;

$R^7$ is selected from amino-($CH_2$)$_p$—, mono($C_{1-4}$)alkylamino-($CH_2$)$_p$—, di($C_{1-4}$)alkylamino-($CH_2$)$_p$—, amino-($C_{2-4}$)-alkenyl, ($C_{1-4}$)alkylamino-($C_{2-4}$)-alkenyl, di($C_{1-4}$)alkylamino-($C_{2-4}$)-alkenyl, 5-7 membered nitrogen-containing heterocyclyl-($C_{2-4}$)-alkenyl, 5-7 membered nitrogen-containing heterocyclyl and 5-7 membered nitrogen-containing heterocyclyl-($CH_2$)$_p$— substituted by 0, 1, 2 or 3 groups independently selected from halo, —$NH_2$, hydroxyl, cyano, —$CF_3$, ($C_1$-$C_6$)alkylamino, oxo, ($C_1$-$C_6$) alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C (O)$R^{8'}$, =NCN, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; wherein each substituted ($C_1$-$C_6$)alkyl, substituted aryl, substituted heteroaryl, substituted cycloalkyl and substituted saturated or partially saturated heterocyclyl is substituted by 1, 2 or 3 groups independently selected from halo, —$NH_2$, hydroxyl, cyano, ($C_1$-$C_6$)alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$) alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$;

p is 0-2;
$R^7$ is at position 6, 7 or 8; and
$R^8$ and $R^{8'}$ independently are H or selected from lower alkyl, aryl and heteroaryl, each of which is optionally substituted with one, two or three groups independently selected from lower alkyl, halogen, lower alkoxy, hydroxy, amino, mono- or dialkylamino, and trifluoromethyl; and pharmaceutically acceptable derivatives thereof;
provided $R^7$ is not 2-pyridyl, 3-pyridyl or 2-oxo-piperazinyl-4-ylmethyl.

The invention also relates to compounds of Formula V wherein $R^7$ is selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl; in conjunction with any of the above or below embodiments.

The invention also relates to compounds of Formula V wherein $R^7$ is at position 7; in conjunction with any of the above or below embodiments.

The invention also relates to compounds of Formula V wherein R² is 2-naphthyl, 3,4-dichlorophenyl or 3-trifluoromethylphenyl; in conjunction with any of the above or below embodiments.

The invention also relates to compounds wherein each R² is selected from phenyl-CH=CH—, tetrahydronaphthyl, naphtho[2.3-d]dioxolyl, benzofuranyl, benzoxadiazolyl, benzothiadiazolyl, benzothiazolyl, 1H-pyrazolyl, thienyl, isoxazolthienyl, benzothienyl, thieno[3,2-c]pyridinyl, naphthyl, phenyl, pyridinyl, tetrahydroisoquinolinyl, quinolinyl and isoquinolinyl; wherein R² is optionally substituted with one to five groups independently selected from halo, —NH₂, hydroxyl, cyano, —CF₃, ($C_1$-$C_6$)alkylamino, oxo, ($C_1$-$C_6$) alkoxy, ($C_2$-$C_6$)alkenyl, ($C_2$-$C_6$)alkynyl, di($C_1$-$C_6$)alkylamino, —C(O)R⁸, —COOR⁸, —C(O)NR⁸R⁸', —NR⁸C(O) R⁸', ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; wherein each substituted ($C_1$-$C_6$)alkyl, substituted aryl, substituted heteroaryl, substituted cycloalkyl and substituted saturated or partially saturated heterocyclyl is substituted by 1, 2 or 3 groups independently selected from halo, —NH₂, hydroxyl, cyano, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$) alkylamino, —C(O)R⁸, —COOR⁸, —C(O)NR⁸R⁸', and —NR⁸C(O)R⁸'; wherein R¹ is selected from H and $C_{1-2}$-alkyl; wherein the basic substituent on R is selected from amino, cycloalkylamino($C_1$-$C_6$)alkyl, cycloalkyl($C_1$-$C_6$) alkylamino($C_1$-$C_6$)alkyl, heterocyclylamino($C_1$-$C_6$)alkyl, heterocyclyl($C_1$-$C_6$)alkylamino($C_1$-$C_6$)alkyl, arylamino($C_1$-$C_6$)alkyl, aryl($C_1$-$C_6$)alkylamino($C_1$-$C_6$)alkyl, $C_{1-6}$-alkylamino-$C_{1-6}$-alkoxy, $C_{1-6}$-alkylamino-$C_{1-6}$-alkoxy-$C_{1-6}$-alkoxy, amino($C_1$-$C_6$)alkoxy, amino($C_1$-$C_6$)alkyl, ($C_1$-$C_6$) alkylamino($C_1$-$C_6$)alkyl, $C_{1-4}$-alkylamino-$C_{2-6}$-alkenyl, 5-8 membered nitrogen-containing heterocyclyl-$C_{2-6}$-alkenyl, heterocyclyl-($C_1$-$C_6$)alkylamino($C_2$-$C_6$)alkyl, 5-6 membered heterocyclyloxy, 5-6 membered nitrogen-containing heterocyclyl and 5-7 membered nitrogen-containing heterocyclyl-alkyl; and wherein each of said basic moieties is substituted by 0, 1, 2 or 3 groups independently selected from halo, —NH₂, hydroxyl, cyano, —CF₃, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)R⁸, —COOR⁸, —C(O)NR⁸R⁸', —NR⁸C(O)R⁸', ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted ($C_1$-$C_6$)alkyl, substituted aryl substituted heteroaryl and substituted saturated or partially saturated heterocyclyl is substituted by 0, 1, 2 or 3 groups independently selected from halo, —NH₂, hydroxyl, cyano, ($C_1$-$C_4$)alkylamino, ($C_1$-$C_4$)haloalkyl, oxo, ($C_1$-$C_4$)alkoxy, ($C_1$-$C_4$)alkoxy($C_1$-$C_4$)alkyl, ($C_1$-$C_4$)alkyl, ($C_2$-$C_4$)alkenyl, ($C_2$-$C_4$)alkynyl, di($C_1$-$C_4$) alkylamino, —C(O)R⁸, —COOR⁸, —C(O)NR⁸R⁸', and —NR⁸C(O)R⁸'; in conjunction with any of the above or below embodiments.

The invention also relates to compounds wherein R² is selected from phenyl-CH=CH—, tetrahydronaphthyl, 2,1,3-benzoxadiazol-4-yl, thien-2-yl, 2-naphthyl, phenyl, 3-pyridyl, 8-quinolyl and 5-isoquinolyl; wherein each R² is said optionally substituted; wherein Rᵃ is H; and wherein the basic substituent on R is selected from amino, mono-$C_{1-4}$-alkylamino-$C_{1-4}$-alkyl, di-$C_{1-4}$-alkylamino-$C_{1-4}$-alkyl, mono-$C_{1-4}$-alkylamino-$C_{2-4}$-alkenyl, di-$C_{1-4}$-alkylamino-$C_{2-4}$-alkenyl, 5-8 membered nitrogen-containing heterocyclyl-$C_{2-4}$-alkenyl, optionally substituted 5-6 membered nitrogen-containing heterocyclyl and 5-8 membered nitrogen-containing heterocyclyl-$C_{1-4}$-alkyl; in conjunction with any of the above or below embodiments.

The invention also relates to compounds of Formula VI wherein the basic moieties on R are independently selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylaminomethyl)-vinyl, 1-(piperidin-1-ylmethyl)-vinyl, N-isobutylaminomethyl, N-isobutyl-aminoethyl, (2,2-dimethyl) propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-yl-methyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl; in conjunction with any of the above or below embodiments.

A family of specific compounds of particular interest within Formula I consists of compounds and pharmaceutically-acceptable salts thereof as follows:

(3R)-3-(2-(4-(2-hydroxyethyl)-1-piperazinyl)-2-oxoethyl)-4-((4-methylphenyl)sulfonyl)-3,4-dihydro-2(1H)-pyrazinone;

(3R)-4-((3,4-dichlorophenyl)sulfonyl)-3-(2-oxo-2-(4-(2-pyridinyl)-1-piperazinyl)ethyl)-3,4-dihydro-2(1H)-pyrazinone;

(4-(((2S)-1-((3,4-dichlorophenyl)sulfonyl)-3-oxo-1,2,3,4-tetrahydro-2-pyrazinyl)acetyl)-1-piperazinyl)acetonitrile;

1,1-dimethylethyl (1R)-6-(((((2R)-1-((4-methylphenyl)sulfonyl)-3-oxo-1,2,3,4-tetrahydro-2-pyrazinyl)acetyl) amino)methyl)-1,2,3,4-tetrahydro-1-naphthalenylcarbamate;

2-((2R)-1-((2,3-dichlorophenyl)sulfonyl)-3-oxo-1,2,3,4-tetrahydro-2-pyrazinyl)-N-((4-(1-piperidinylmethyl)phenyl) methyl)acetamide;

2-((2R)-1-((2,3-dichlorophenyl)sulfonyl)-3-oxo-1,2,3,4-tetrahydro-2-pyrazinyl)-N-((1R)-1-(4-fluorophenyl)ethyl) acetamide;

2-((2R)-1-((2,3-dichlorophenyl)sulfonyl)-3-oxo-1,2,3,4-tetrahydro-2-pyrazinyl)-N-(3-pyridinylmethyl)acetamide;

2-((2R)-1-((2,3-dichlorophenyl)sulfonyl)-3-oxo-1,2,3,4-tetrahydro-2-pyrazinyl)-N-((2-(2-thienyl)-1,3-thiazol-4-yl) methyl)acetamide;

2-((2R)-1-((2,3-dichlorophenyl)sulfonyl)-3-oxo-1,2,3,4-tetrahydro-2-pyrazinyl)-N-((1R)-1-phenylethyl)acetamide;

2-((2R)-1-((2,3-dichlorophenyl)sulfonyl)-3-oxo-1,2,3,4-tetrahydro-2-pyrazinyl)-N-((1S)-1-(3,3'-difluoro-2'-(3-methyl-1,2,4-oxadiazol-5-yl)-1,1'-biphenyl-4-yl)ethyl)acetamide;

2-((2R)-1-((2,3-dichlorophenyl)sulfonyl)-3-oxo-1,2,3,4-tetrahydro-2-pyrazinyl)-N-(4-pyridinylmethyl)acetamide;

2-((2R)-1-((2,3-dichlorophenyl)sulfonyl)-3-oxo-1,2,3,4-tetrahydro-2-pyrazinyl)-N-(2-pyridinylmethyl)acetamide;

2-((2R)-1-((2,3-dichlorophenyl)sulfonyl)-3-oxo-1,2,3,4-tetrahydro-2-pyrazinyl)-N-(phenylmethyl)acetamide;

2-((2R)-1-((2,3-dichlorophenyl)sulfonyl)-3-oxo-1,2,3,4-tetrahydro-2-pyrazinyl)-N-((1R)-6-(1-piperidinylmethyl)-1,2,3,4-tetrahydro-1-naphthalenyl)acetamide;

2-((2R)-1-((2,3-dichlorophenyl)sulfonyl)-3-oxo-1,2,3,4-tetrahydro-2-pyrazinyl)-N-((3-fluorophenyl)methyl)acetamide;

2-((2R)-1-((3,4-dichlorophenyl)sulfonyl)-3-oxo-1,2,3,4-tetrahydro-2-pyrazinyl)-N-((1R)-1,2,3,4-tetrahydro-1-naphthalenyl)acetamide;

2-((2R)-1-((3,4-dichlorophenyl)sulfonyl)-3-oxo-1,2,3,4-tetrahydro-2-pyrazinyl)-N-((1R)-6-(hydroxymethyl)-1,2,3,4-tetrahydro-1-naphthalenyl)acetamide;

2-((2R)-1-((3,4-dichlorophenyl)sulfonyl)-3-oxo-1,2,3,4-tetrahydro-2-pyrazinyl)-N-((4R)-7-(hydroxymethyl)-3,4-dihydro-2H-chromen-4-yl)acetamide;

2-((2R)-1-((3,4-dichlorophenyl)sulfonyl)-3-oxo-1,2,3,4-tetrahydro-2-pyrazinyl)-N-((1R)-6-(((1-methylethyl)amino)methyl)-1,2,3,4-tetrahydro-1-naphthalenyl)acetamide;

2-((2R)-1-((3,4-dichlorophenyl)sulfonyl)-3-oxo-1,2,3,4-tetrahydro-2-pyrazinyl)-N-((4R)-7-(((1-methylethyl)amino)methyl)-3,4-dihydro-2H-chromen-4-yl)acetamide;

2-((2R)-1-((3,4-dichlorophenyl)sulfonyl)-3-oxo-1,2,3,4-tetrahydro-2-pyrazinyl)-N-((5R)-5,6,7,8-tetrahydro-5-quinolinyl)acetamide;

2-((2R)-1-((3,4-dichlorophenyl)sulfonyl)-3-oxo-1,2,3,4-tetrahydro-2-pyrazinyl)-N-(1-naphthalenyl)acetamide;

2-((2R)-1-((3,4-dichlorophenyl)sulfonyl)-3-oxo-1,2,3,4-tetrahydro-2-pyrazinyl)-N-((4-(1-piperidinylmethyl)phenyl)methyl)acetamide;

2-((2R)-1-((3,4-dichlorophenyl)sulfonyl)-3-oxo-1,2,3,4-tetrahydro-2-pyrazinyl)-N-((1R)-6-(1-piperidinylmethyl)-1,2,3,4-tetrahydro-1-naphthalenyl)acetamide;

2-((2R)-1-((3,4-dichlorophenyl)sulfonyl)-3-oxo-1,2,3,4-tetrahydro-2-pyrazinyl)-N-((1R)-6-(2-(1-piperidinyl)ethyl)-1,2,3,4-tetrahydro-1-naphthalenyl)acetamide;

2-((2R)-1-((3,4-dichlorophenyl)sulfonyl)-3-oxo-1,2,3,4-tetrahydro-2-pyrazinyl)-N-((1R)-6-(((1,1-dimethylethyl)amino)methyl)-1,2,3,4-tetrahydro-1-naphthalenyl)acetamide;

2-((2R)-1-((4-chloro-2,5-dimethylphenyl)sulfonyl)-3-oxo-1,2,3,4-tetrahydro-2-pyrazinyl)-N-((4R)-7-(hydroxymethyl)-3,4-dihydro-2H-chromen-4-yl)acetamide;

2-((2R)-1-((4-chloro-2,5-dimethylphenyl)sulfonyl)-3-oxo-1,2,3,4-tetrahydro-2-pyrazinyl)-N-((1R)-6-(hydroxymethyl)-1,2,3,4-tetrahydro-1-naphthalenyl)acetamide;

2-((2R)-1-((4-chloro-2,5-dimethylphenyl)sulfonyl)-3-oxo-1,2,3,4-tetrahydro-2-pyrazinyl)-N-((1R)-1,2,3,4-tetrahydro-1-naphthalenyl)acetamide;

2-((2R)-1-((4-chloro-2,5-dimethylphenyl)sulfonyl)-3-oxo-1,2,3,4-tetrahydro-2-pyrazinyl)-N-((1R)-1-phenylethyl)acetamide;

2-((2R)-1-((4-chloro-2,5-dimethylphenyl)sulfonyl)-3-oxo-1,2,3,4-tetrahydro-2-pyrazinyl)-N-((4R)-7-((cyclopentylamino)methyl)-3,4-dihydro-2H-chromen-4-yl)acetamide;

2-((2R)-1-((4-chloro-2,5-dimethylphenyl)sulfonyl)-3-oxo-1,2,3,4-tetrahydro-2-pyrazinyl)-N-((1R)-6-((cyclopentylamino)methyl)-1,2,3,4-tetrahydro-1-naphthalenyl)acetamide;

2-((2R)-1-((4-chloro-2,5-dimethylphenyl)sulfonyl)-3-oxo-1,2,3,4-tetrahydro-2-pyrazinyl)-N-((1R)-6-(((1,1-dimethylethyl)amino)methyl)-1,2,3,4-tetrahydro-1-naphthalenyl)acetamide;

2-((2R)-1-((4-chloro-2,5-dimethylphenyl)sulfonyl)-3-oxo-1,2,3,4-tetrahydro-2-pyrazinyl)-N-((4R)-7-(((1,1-dimethylethyl)amino)methyl)-3,4-dihydro-2H-chromen-4-yl)acetamide;

2-((2R)-1-((4-chloro-2,5-dimethylphenyl)sulfonyl)-3-oxo-1,2,3,4-tetrahydro-2-pyrazinyl)-N-((1R)-6-(((2,2-dimethylpropyl)amino)methyl)-1,2,3,4-tetrahydro-1-naphthalenyl)acetamide;

2-((2R)-1-((4-chloro-2,5-dimethylphenyl)sulfonyl)-3-oxo-1,2,3,4-tetrahydro-2-pyrazinyl)-N-((4-(1-piperidinylmethyl)phenyl)methyl)acetamide;

2-((2R)-1-((4-chloro-2,5-dimethylphenyl)sulfonyl)-3-oxo-1,2,3,4-tetrahydro-2-pyrazinyl)-N-((1R)-6-(1-piperidinylmethyl)-1,2,3,4-tetrahydro-1-naphthalenyl)acetamide;

2-((2R)-1-((4-chloro-2,5-dimethylphenyl)sulfonyl)-3-oxo-1,2,3,4-tetrahydro-2-pyrazinyl)-N-((4R)-7-(1-piperidinylmethyl)-3,4-dihydro-2H-chromen-4-yl)acetamide;

2-((2R)-1-((4-chlorophenyl)sulfonyl)-3-oxo-1,2,3,4-tetrahydro-2-pyrazinyl)-N-((1R)-6-(2-(1-piperidinyl)ethyl)-1,2,3,4-tetrahydro-1-naphthalenyl)acetamide;

2-((2R)-1-((4-chlorophenyl)sulfonyl)-3-oxo-1,2,3,4-tetrahydro-2-pyrazinyl)-N-((1R)-6-((cyclopropylamino)methyl)-1,2,3,4-tetrahydro-1-naphthalenyl)acetamide;

2-((2R)-1-((4-chlorophenyl)sulfonyl)-3-oxo-1,2,3,4-tetrahydro-2-pyrazinyl)-N-((1R)-6-(((3R)-3-hydroxy-1-piperidinyl)methyl)-1,2,3,4-tetrahydro-1-naphthalenyl)acetamide;

2-((2R)-1-((4-chlorophenyl)sulfonyl)-3-oxo-1,2,3,4-tetrahydro-2-pyrazinyl)-N-((1R)-6-(((2-(methyloxy)ethyl)amino)methyl)-1,2,3,4-tetrahydro-1-naphthalenyl)acetamide;

2-((2R)-1-((4-chlorophenyl)sulfonyl)-3-oxo-1,2,3,4-tetrahydro-2-pyrazinyl)-N-((1R)-6-(((2-hydroxyethyl)amino)methyl)-1,2,3,4-tetrahydro-1-naphthalenyl)acetamide;

2-((2R)-1-((4-chlorophenyl)sulfonyl)-3-oxo-1,2,3,4-tetrahydro-2-pyrazinyl)-N-((1R)-1-phenylethyl)acetamide;

2-((2R)-1-((4-methylphenyl)sulfonyl)-3-oxo-1,2,3,4-tetrahydro-2-pyrazinyl)-N-((1R)-6-(1-(1-piperidinylmethyl)ethenyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((1R)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((1R)-6-(1-piperidinylmethyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((5S)-2-(2-(1-piperidinyl)ethyl)-5,6,7,8-tetrahydro-5-quinazolinyl)acetamide;

2-((2R)-1-((4-methylphenyl)sulfonyl)-3-oxo-1,2,3,4-tetrahydro-2-pyrazinyl)-N-(4-(3-(1-piperidinyl)propyl)phenyl)acetamide;

2-((2R)-1-((4-methylphenyl)sulfonyl)-3-oxo-1,2,3,4-tetrahydro-2-pyrazinyl)-N-(4-(3-(4-methyl-1-piperazinyl)propyl)phenyl)acetamide;

2-((2R)-1-((4-methylphenyl)sulfonyl)-3-oxo-1,2,3,4-tetrahydro-2-pyrazinyl)-N-((1R)-6-((1S)-1-((2-methylpropyl)amino)ethyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((1R)-6-(2-(1-piperidinyl)ethyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((1R)-5-(1-piperidinylmethyl)-2,3-dihydro-1H-inden-1-yl)acetamide;

2-((2R)-1-((4-methylphenyl)sulfonyl)-3-oxo-1,2,3,4-tetrahydro-2-pyrazinyl)-N-(4-(2-(4-morpholinyl)ethyl)phenyl)acetamide;

2-((2R)-1-((4-methylphenyl)sulfonyl)-3-oxo-1,2,3,4-tetrahydro-2-pyrazinyl)-N-(2-(4-(1-piperidinylmethyl)phenyl)ethyl)acetamide;

2-((2R)-1-((4-methylphenyl)sulfonyl)-3-oxo-1,2,3,4-tetrahydro-2-pyrazinyl)-N-(3-(1-pyrrolidinyl)propyl)acetamide;

2-((2R)-1-((4-methylphenyl)sulfonyl)-3-oxo-1,2,3,4-tetrahydro-2-pyrazinyl)-N-(4-(2-(1-pyrrolidinyl)ethyl)phenyl)acetamide;

2-((2R)-1-((4-methylphenyl)sulfonyl)-3-oxo-1,2,3,4-tetrahydro-2-pyrazinyl)-N-((1R)-1-methyl-2-(3-(1-piperidinylmethyl)phenyl)ethyl)acetamide;

2-((2R)-1-((4-methylphenyl)sulfonyl)-3-oxo-1,2,3,4-tetrahydro-2-pyrazinyl)-N-((1R)-1-(4-(1-piperidinylmethyl)phenyl)ethyl)acetamide;

2-((2R)-1-((4-methylphenyl)sulfonyl)-3-oxo-1,2,3,4-tetrahydro-2-pyrazinyl)-N-(4-(1-piperidinyl)butyl)acetamide;

2-((2R)-1-((4-methylphenyl)sulfonyl)-3-oxo-1,2,3,4-tetrahydro-2-pyrazinyl)-N-(4-(1-pyrrolidinyl)butyl)acetamide;

2-((2R)-1-((4-methylphenyl)sulfonyl)-3-oxo-1,2,3,4-tetrahydro-2-pyrazinyl)-N-(5-(1-piperidinyl)pentyl)acetamide;

2-((2R)-1-((4-methylphenyl)sulfonyl)-3-oxo-1,2,3,4-tetrahydro-2-pyrazinyl)-N-(5-(1-pyrrolidinyl)pentyl)acetamide;

2-((2R)-1-((4-methylphenyl)sulfonyl)-3-oxo-1,2,3,4-tetrahydro-2-pyrazinyl)-N-((1R)-1-phenylethyl)acetamide;

2-((2R)-1-((4-methylphenyl)sulfonyl)-3-oxo-1,2,3,4-tetrahydro-2-pyrazinyl)-N-((4S)-1-(2-(1-piperidinyl)ethyl)-4,5,6,7-tetrahydro-1H-indazol-4-yl)acetamide;

2-((2R)-1-((4-methylphenyl)sulfonyl)-3-oxo-1,2,3,4-tetrahydro-2-pyrazinyl)-N-(3-(3-(1-piperidinyl)propyl)phenyl)acetamide;

2-((2R)-1-((4-methylphenyl)sulfonyl)-3-oxo-1,2,3,4-tetrahydro-2-pyrazinyl)-N-(3-(3-(1-pyrrolidinyl)propyl)phenyl)acetamide;

2-((2R)-1-((4-methylphenyl)sulfonyl)-3-oxo-1,2,3,4-tetrahydro-2-pyrazinyl)-N-(3-(3-((2-methylpropyl)amino)propyl)phenyl)acetamide;

2-((2R)-1-((4-methylphenyl)sulfonyl)-3-oxo-1,2,3,4-tetrahydro-2-pyrazinyl)-N-((1R)-6-((4-(2-pyridinyl)-1-piperazinyl)methyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-(2-(4-((4-methyl-1-piperazinyl)methyl)phenyl)ethyl)acetamide;

2-((2R)-1-((4-methylphenyl)sulfonyl)-3-oxo-1,2,3,4-tetrahydro-2-pyrazinyl)-N-(2-(4-(((2-methylpropyl)amino)methyl)phenyl)ethyl)acetamide;

2-((2R)-1-((4-methylphenyl)sulfonyl)-3-oxo-1,2,3,4-tetrahydro-2-pyrazinyl)-N-((4R)-7-(1-pyrrolidinylmethyl)-3,4-dihydro-2H-chromen-4-yl)acetamide;

2-((2R)-1-((4-methylphenyl)sulfonyl)-3-oxo-1,2,3,4-tetrahydro-2-pyrazinyl)-N-((4-(1-piperidinylmethyl)phenyl)methyl)acetamide;

2-((2R)-1-((4-methylphenyl)sulfonyl)-3-oxo-1,2,3,4-tetrahydro-2-pyrazinyl)-N-((1R)-6-(1-pyrrolidinylmethyl)-1,2,3,4-tetrahydro-1-naphthalenyl)acetamide;

2-((2R)-1-(cyclopropylsulfonyl)-3-oxo-1,2,3,4-tetrahydro-2-pyrazinyl)-N-((1R)-6-(1-piperidinylmethyl)-1,2,3,4-tetrahydro-1-naphthalenyl)acetamide;

2-((2R)-3-oxo-1-(phenylsulfonyl)-1,2,3,4-tetrahydro-2-pyrazinyl)-N-((1R)-6-(1-piperidinylmethyl)-1,2,3,4-tetrahydro-1-naphthalenyl)acetamide;

2-((2R)-3-oxo-1-(phenylsulfonyl)-1,2,3,4-tetrahydro-2-pyrazinyl)-N-(phenylmethyl)acetamide;

2-((2R)-3-oxo-1-(phenylsulfonyl)-1,2,3,4-tetrahydro-2-pyrazinyl)-N-((4R)-7-(1-piperidinylmethyl)-3,4-dihydro-2H-chromen-4-yl)acetamide;

2-((2R)-3-oxo-1-(phenylsulfonyl)-1,2,3,4-tetrahydro-2-pyrazinyl)-N-((1R)-1-phenylethyl)acetamide;

2-((2R)-3-oxo-1-(phenylsulfonyl)-1,2,3,4-tetrahydro-2-pyrazinyl)-N-((1S)-1-phenylethyl)acetamide;

2-((2R)-3-oxo-1-(phenylsulfonyl)-1,2,3,4-tetrahydro-2-pyrazinyl)-N-((1R)-1,2,3,4-tetrahydro-1-naphthalenyl)acetamide;

2-((2S)-1-((4-methylphenyl)sulfonyl)-3-oxo-1,2,3,4-tetrahydro-2-pyrazinyl)-N-((1R)-6-(1-piperidinylmethyl)-1,2,3,4-tetrahydro-1-naphthalenyl)acetamide;

2-((4S)-4-((2-((2R)-1-((4-methylphenyl)sulfonyl)-3-oxo-1,2,3,4-tetrahydro-2-pyrazinyl)acetyl)amino)-4,5,6,7-tetrahydro-1H-indazol-1-yl)ethyl methanesulfonate;

2-((5R)-5-((2-((2S)-1-((4-methylphenyl)sulfonyl)-3-oxo-1,2,3,4-tetrahydro-2-pyrazinyl)acetyl)amino)-5,6,7,8-tetrahydro-2-quinazolinyl)ethyl methanesulfonate;

N-(((5R)-5-((1-methylethyl)amino)-5,6,7,8-tetrahydro-2-naphthalenyl)methyl)-2-((2R)-1-((4-methylphenyl)sulfonyl)-3-oxo-1,2,3,4-tetrahydro-2-pyrazinyl)acetamide;

N-(((5R)-5-amino-5,6,7,8-tetrahydro-2-naphthalenyl)methyl)-2-((2R)-1-((4-methylphenyl)sulfonyl)-3-oxo-1,2,3,4-tetrahydro-2-pyrazinyl)acetamide;

N-((1R)-1-(3,3'-difluoro-2'-(3-methyl-1,2,4-oxadiazol-5-yl)-1,1'-biphenyl-4-yl)ethyl)-2-((2R)-1-((4-methylphenyl)sulfonyl)-3-oxo-1,2,3,4-tetrahydro-2-pyrazinyl)acetamide;

N-((1R)-1-(4-(hydroxymethyl)phenyl)ethyl)-2-((2R)-1-((4-methylphenyl)sulfonyl)-3-oxo-1,2,3,4-tetrahydro-2-pyrazinyl)acetamide;

N-((1R)-5-(hydroxymethyl)-2,3-dihydro-1H-inden-1-yl)-2-((2R)-1-((4-methylphenyl)sulfonyl)-3-oxo-1,2,3,4-tetrahydro-2-pyrazinyl)acetamide;

N-((1R)-6-(((2,2-dimethylpropyl)amino)methyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-(((2,2-dimethylpropyl)amino)methyl)-1,2,3,4-tetrahydro-1-naphthalenyl)-2-((2R)-3-oxo-1-(phenylsulfonyl)-1,2,3,4-tetrahydro-2-pyrazinyl)acetamide;

N-((1R)-6-(((cyclopropylmethyl)(propyl)amino)methyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-((1S)-1-(cyclobutylamino)ethyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-((1S)-1-(cyclopentylamino)ethyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-((1S)-1-(cyclopropylamino)ethyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-((4-fluoro-1-piperidinyl)methyl)-1,2,3,4-tetrahydro-1-naphthalenyl)-2-((2R)-3-oxo-1-(phenylsulfonyl)-1,2,3,4-tetrahydro-2-pyrazinyl)acetamide;
N-((1R)-6-((cyclopentylamino)methyl)-1,2,3,4-tetrahydro-1-naphthalenyl)-2-((2R)-1-((3,4-dichlorophenyl)sulfonyl)-3-oxo-1,2,3,4-tetrahydro-2-pyrazinyl)acetamide;
N-((1R)-6-((cyclopentylamino)methyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;
N-((1R)-6-((cyclopentylamino)methyl)-1,2,3,4-tetrahydro-1-naphthalenyl)-2-((2R)-3-oxo-1-(phenylsulfonyl)-1,2,3,4-tetrahydro-2-pyrazinyl)acetamide;
N-((1R)-6-((cyclopropylamino)methyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;
N-((1R)-6-((dimethylamino)methyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;
N-((1R)-6-(1-azepanylmethyl)-1,2,3,4-tetrahydro-1-naphthalenyl)-2-((2R)-1-((4-chlorophenyl)sulfonyl)-3-oxo-1,2,3,4-tetrahydro-2-pyrazinyl)acetamide;
N-((1R)-6-(aminomethyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;
N-((1R)-6-(hydroxymethyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;
N-((1R)-6-acetyl-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;
N-((1S)-2-(3-(hydroxymethyl)phenyl)-1-methylethyl)-2-((2R)-1-((4-methylphenyl)sulfonyl)-3-oxo-1,2,3,4-tetrahydro-2-pyrazinyl)acetamide;
N-((2-fluorophenyl)methyl)-2-((2R)-3-oxo-1-(phenylsulfonyl)-1,2,3,4-tetrahydro-2-pyrazinyl)acetamide;
N-((2R)-6-bromo-1,2,3,4-tetrahydro-2-naphthalenyl)-2-((2R)-1-((4-methylphenyl)sulfonyl)-3-oxo-1,2,3,4-tetrahydro-2-pyrazinyl)acetamide;
N-((2S)-6-bromo-1,2,3,4-tetrahydro-2-naphthalenyl)-2-((2R)-1-((4-methylphenyl)sulfonyl)-3-oxo-1,2,3,4-tetrahydro-2-pyrazinyl)acetamide;
N-((3-fluorophenyl)methyl)-2-((2R)-3-oxo-1-(phenylsulfonyl)-1,2,3,4-tetrahydro-2-pyrazinyl)acetamide;
N-((4-cyanophenyl)methyl)-2-((2R)-1-((4-methylphenyl)sulfonyl)-3-oxo-1,2,3,4-tetrahydro-2-pyrazinyl)acetamide;
N-((4-fluorophenyl)methyl)-2-((2R)-3-oxo-1-(phenylsulfonyl)-1,2,3,4-tetrahydro-2-pyrazinyl)acetamide;
N-((4R)-6-chloro-7-methyl-3,4-dihydro-2H-chromen-4-yl)-2-((2R)-1-((3,4-dichlorophenyl)sulfonyl)-3-oxo-1,2,3,4-tetrahydro-2-pyrazinyl)acetamide;
N-((4R)-7-(((2,2-dimethylpropyl)amino)methyl)-3,4-dihydro-2H-chromen-4-yl)-2-((2R)-1-((4-methylphenyl)sulfonyl)-3-oxo-1,2,3,4-tetrahydro-2-pyrazinyl)acetamide;
N-((4R)-7-(((2,2-dimethylpropyl)amino)methyl)-3,4-dihydro-2H-chromen-4-yl)-2-((2R)-3-oxo-1-(phenylsulfonyl)-1,2,3,4-tetrahydro-2-pyrazinyl)acetamide;
N-((4R)-7-((cyclopentylamino)methyl)-3,4-dihydro-2H-chromen-4-yl)-2-((2R)-1-((4-methylphenyl)sulfonyl)-3-oxo-1,2,3,4-tetrahydro-2-pyrazinyl)acetamide;
N-((4R)-7-((cyclopentylamino)methyl)-3,4-dihydro-2H-chromen-4-yl)-2-((2R)-1-((3,4-dichlorophenyl)sulfonyl)-3-oxo-1,2,3,4-tetrahydro-2-pyrazinyl)acetamide;
N-((4R)-7-((cyclopentylamino)methyl)-3,4-dihydro-2H-chromen-4-yl)-2-((2R)-3-oxo-1-(phenylsulfonyl)-1,2,3,4-tetrahydro-2-pyrazinyl)acetamide;
N-((4R)-7-((cyclopropylamino)methyl)-3,4-dihydro-2H-chromen-4-yl)-2-((2R)-1-((4-methylphenyl)sulfonyl)-3-oxo-1,2,3,4-tetrahydro-2-pyrazinyl)acetamide;
N-((4R)-7-(hydroxymethyl)-3,4-dihydro-2H-chromen-4-yl)-2-((2R)-1-((4-methylphenyl)sulfonyl)-3-oxo-1,2,3,4-tetrahydro-2-pyrazinyl)acetamide;
N-((4S)-1-(2-(((1,1-dimethylethyl)(dimethyl)silyl)oxy)ethyl)-4,5,6,7-tetrahydro-1H-indazol-4-yl)-2-((2R)-1-((4-methylphenyl)sulfonyl)-3-oxo-1,2,3,4-tetrahydro-2-pyrazinyl)acetamide;
N-((4S)-1-(2-((2,2-dimethylpropyl)amino)ethyl)-4,5,6,7-tetrahydro-1H-indazol-4-yl)-2-((2R)-1-((4-methylphenyl)sulfonyl)-3-oxo-1,2,3,4-tetrahydro-2-pyrazinyl)acetamide;
N-((4S)-1-(2-(cyclopropylamino)ethyl)-4,5,6,7-tetrahydro-1H-indazol-4-yl)-2-((2R)-1-((4-methylphenyl)sulfonyl)-3-oxo-1,2,3,4-tetrahydro-2-pyrazinyl)acetamide;
N-((4S)-1-(2-hydroxyethyl)-4,5,6,7-tetrahydro-1H-indazol-4-yl)-2-((2R)-1-((4-methylphenyl)sulfonyl)-3-oxo-1,2,3,4-tetrahydro-2-pyrazinyl)acetamide;
N-((5S)-2-(2-hydroxyethyl)-5,6,7,8-tetrahydro-5-quinazolinyl)-2-((2R)-1-((4-methylphenyl)sulfonyl)-3-oxo-1,2,3,4-tetrahydro-2-pyrazinyl)acetamide;
N-(2-(3-formylphenyl)propyl)-2-((2R)-1-((4-methylphenyl)sulfonyl)-3-oxo-1,2,3,4-tetrahydro-2-pyrazinyl)acetamide;
N-(2-(4-((cyclopentylamino)methyl)phenyl)ethyl)-2-((2R)-1-((4-methylphenyl)sulfonyl)-3-oxo-1,2,3,4-tetrahydro-2-pyrazinyl)acetamide;
N-(2-(4-((cyclopropylamino)methyl)phenyl)ethyl)-2-((2R)-1-((4-methylphenyl)sulfonyl)-3-oxo-1,2,3,4-tetrahydro-2-pyrazinyl)acetamide;
N-(2-(4-(hydroxymethyl)phenyl)ethyl)-2-((2R)-1-((4-methylphenyl)sulfonyl)-3-oxo-1,2,3,4-tetrahydro-2-pyrazinyl)acetamide;
N-(2-(4-aminophenyl)ethyl)-2-((2R)-1-((4-methylphenyl)sulfonyl)-3-oxo-1,2,3,4-tetrahydro-2-pyrazinyl)acetamide;
N-(3-(3-hydroxypropyl)phenyl)-2-((2R)-1-((4-methyl-2,4-cyclohexadien-1-yl)sulfonyl)-3-oxo-1,2,3,4-tetrahydro-2-pyrazinyl)acetamide;
N-(3-(cyclohexylamino)propyl)-2-((2R)-1-((4-methylphenyl)sulfonyl)-3-oxo-1,2,3,4-tetrahydro-2-pyrazinyl)acetamide;
N-(4-(2-(dimethylamino)ethyl)phenyl)-2-((2R)-1-((4-methylphenyl)sulfonyl)-3-oxo-1,2,3,4-tetrahydro-2-pyrazinyl)acetamide;
N-(4-(3-hydroxypropyl)phenyl)-2-((2R)-1-((4-methylphenyl)sulfonyl)-3-oxo-1,2,3,4-tetrahydro-2-pyrazinyl)acetamide;
N-(4-hydroxybutyl)-2-((2R)-1-((4-methylphenyl)sulfonyl)-3-oxo-1,2,3,4-tetrahydro-2-pyrazinyl)acetamide;
N-(5-hydroxypentyl)-2-((2R)-1-((4-methylphenyl)sulfonyl)-3-oxo-1,2,3,4-tetrahydro-2-pyrazinyl)acetamide; and
N-cycloheptyl-2-((2R)-1-((3,4-dichlorophenyl)sulfonyl)-3-oxo-1,2,3,4-tetrahydro-2-pyrazinyl)acetamide.

INDICATIONS

The present invention also provides methods of using the compounds in for the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

The invention also provides for the use of the compounds of the present invention for the prevention or for the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

Accordingly, the present invention also relates to the use of one or more of the compounds of the present invention in the manufacture of a medicament for the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

The compounds of this invention may also act as inhibitors of other receptors or kinases, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

DEFINITIONS

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective pain therapeutic agents relieve the pain sensation of the patient. Alternatively, effective therapeutic agents for the treatment of inflammation minimize the damage from the inflammation, and the like.

The term "treatment" includes therapeutic treatment as well as prophylactic treatment (either preventing the onset of disorders altogether or delaying the onset of a pre-clinically evident stage of disorders in individuals).

The term "H" denotes a single hydrogen atom. This radical may be attached, for example, to an oxygen atom to form a hydroxyl radical.

Where the term "alkyl" is used, either alone or within other terms such as "haloalkyl", "cyanoalkyl" and "alkylamino", it embraces linear or branched radicals having one to about twenty carbon atoms or, preferably, one to about twelve carbon atoms, or as otherwise indicated. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Even more preferred are lower alkyl radicals having one to four carbon atoms. The term "alkyl" also includes divalent radicals such as methylenyl and ethyleneyl.

The term "alkenyl" embraces linear or branched radicals having at least one carbon-carbon double bond of two to about twenty carbon atoms or, preferably, two to about twelve carbon atoms, or as otherwise indicated. More preferred alkenyl radicals are "lower alkenyl" radicals having two to about four carbon atoms. Examples of alkenyl radicals include ethenyl, 2-propenyl, allyl, butenyl and 4-methylbutenyl. The terms "alkenyl" and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms, or as otherwise indicated. More preferred alkynyl radicals are "lower alkynyl" radicals having two to about four carbon atoms. Examples of alkynyl radicals include ethynyl, 2-propynyl, and 4-methylbutynyl.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. The "alkoxy" radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy, and fluoropropoxy.

The term "alkoxyalkyl" embraces linear or branched alkyl radicals having one to about ten carbon atoms any one of which may be substituted with one or more alkoxyl radicals. More preferred alkoxyalkyl radicals are "lower alkoxyalkyl" radicals respectively having one to six carbon atoms. Examples of such radicals include methoxymethyl, methoxyethyl, and the like. Even more preferred are lower alkoxyalkyl radicals respectively having one to three carbon atoms alkyl radicals.

The term "aryl", alone or in combination, means a carbocyclic aromatic system containing one or two rings wherein such rings may be attached together in a pendent manner or may be fused. The term "aryl" embraces aromatic radicals such as phenyl, naphthyl, tetrahydronaphthyl, indane and biphenyl. More preferred aryl is phenyl. Said "aryl" group may have 1 to 3 substituents such as lower alkyl, hydroxyl, halo, haloalkyl, nitro, cyano, alkoxy, and lower alkylamino. Benzodioxolyl is considered aryl.

The term "heterocyclyl" embraces saturated, partially saturated and unsaturated heteroatom-containing ring radicals, where the heteroatoms may be selected from nitrogen, sulfur and oxygen. It does not include rings containing —O—O— or —S—S— portions. Said "heterocyclyl" group may have 1 to 3 substituents such as hydroxyl, halo, haloalkyl, cyano, lower alkyl, lower aralkyl, oxo, lower alkoxy, amino, and lower alkylamino.

Examples of saturated heterocyclic radicals include saturated 3 to 8-membered heteromonocyclic group containing 1 to 4 nitrogen atoms [e.g. pyrrolidinyl, imidazolidinyl, piperidino, piperazinyl]; saturated 3 to 8-membered heteromonocyclic group containing 1 to 2 oxygen atoms and 1 to 3 nitrogen atoms [e.g. morpholinyl]; saturated 3 to 8-membered heteromonocyclic group containing 1 to 2 sulfur atoms and 1 to 3 nitrogen atoms [e.g., thiazolidinyl]. Examples of partially saturated heterocyclyl radicals include dihydrothiophene, dihydropyran, dihydrofuran and dihydrothiazole.

Examples of unsaturated heterocyclic radicals, also termed "heteroaryl" radicals, include unsaturated 5 to 6 membered heteromonocyclyl groups containing 1 to 4 nitrogen atoms, for example, pyrrolyl, pyrrolinyl, imidazolyl, pyrazolyl, 2-pyridinyl, 3-pyridinyl, 4-pyridinyl, pyrimidinyl, pyrazinyl, pyridazinyl, triazolyl [e.g., 4H-1,2,4-triazolyl, 1H-1,2,3-triazolyl, 2H-1,2,3-triazolyl]; unsaturated 3 to 6-membered heteromonocyclic group containing an oxygen atom, for example, pyranyl, 2-furyanl, 3-furyanl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolinyl, isoindolinyl, indolizinyl, benzimidazolyl, quinolinyl, isoquinolinyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl].

The term also includes bridged, spiro and oxo-containing heterocyclic rings, such as 1,4-dioxa-8-aza-spiro[4.5]decyl, phthalimidyl, 1,4-dioxa-8-aza-spiro[4.5]decyl, and (1-azabicyclo[2.2.2]oct-3-yl).

Preferred heterocyclic radicals include five to ten membered fused or unfused radicals. More preferred examples of heteroaryl radicals include quinolinyl, isoquinolinyl, imidazolyl, pyridinyl, thienyl, thiazolyl, oxazolyl, furanyl, and pyrazinyl. Even more preferred heteroaryl radicals are 5- or 6-membered heteroaryl, containing one or two heteroatoms selected from sulfur, nitrogen and oxygen, selected from thienyl, furanyl, pyrrolyl, thiazolyl, oxazolyl, imidazolyl, pyrazolyl, isoxazolyl, isothiazolyl, pyridinyl, piperidinyl and pyrazinyl.

The term "sulfonyl", whether used alone or linked to other terms such as alkylsulfonyl, denotes respectively divalent radicals —$SO_2$—.

The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—$SO_2NH_2$).

The term "cycloalkylaminoalkyl" includes "N-cycloalkylaminoalkyl" and "N,N-dicycloalkylaminoalkyl" where alkyl radicals are independently substituted, respectively, with one cycloalkyl radical, or two cycloalkyl radicals. More preferred cycloalkylaminoalkyl radicals are "lower cycloalkylaminoalkyl" radicals having alkyl radicals with one to six carbon atoms. Even more preferred are lower cycloalkylaminoalkyl radicals having alkyl radicals with one to three carbon atoms. Examples of such lower alkylaminosulfonyl radicals include N-cyclohexylaminomethyl, and N-cyclopentylaminoethyl.

The term "cycloalkyl-alkylaminoalkyl" embraces cycloalkyl radicals as described above, attached to an alkylaminoalkyl radical. More preferred are lower cycloalkyl-alkylaminoalkyl radicals independently having alkyl radicals of one to three carbon atoms.

The term "N-arylaminoalkyl" denotes alkyl radicals substituted with an aryl radical. More preferred arylaminoalkyl radicals are "lower N-arylaminoalkyl" radicals having alkyl radicals of one to six carbon atoms. Even more preferred are phenylaminoalkyl radicals having one to three carbon atoms. Examples of such radicals include N-phenylaminomethyl and N-phenylaminoethyl.

The term "aralkylaminoalkyl" embraces aralkyl radicals as described above, attached to an aminoalkyl radical. More preferred are lower arylalkylaminoalkyl radicals independently having alkyl radicals of one to three carbon atoms.

The term "heterocyclylaminoalkyl" embraces heterocyclyl radicals as described above, attached to an aminoalkyl radical.

The term "heteroarylalkylaminoalkyl" embraces heteroarylalkyl radicals as described above, attached to an aminoalkyl radical. More preferred are lower heteroarylalkylaminoalkyl radicals having, independently, alkyl radicals of one to three carbon atoms.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—.

The terms "alkylcarbonyl" denotes carbonyl radicals which have been substituted with an alkyl radical. More preferred are "lower alkylcarbonyl" having lower alkyl radicals as described above attached to a carbonyl radical.

The terms "arylcarbonyl" denotes carbonyl radicals substituted with an aryl radical. More preferred are "optionally substituted phenylcarbonyl" radicals.

The terms "cycloalkylcarbonyl" denotes carbonyl radicals substituted with an cycloalkyl radical. More preferred are "optionally substituted cycloalkylcarbonyl" radicals, even more preferably containing $C_{3-6}$ cycloalkyl.

The terms "heterocyclylcarbonyl" denotes carbonyl radicals substituted with an heterocyclyl radical. More preferred are "optionally substituted 5-6 membered heterocyclylcarbonyl" radicals.

The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula $H_2NC$(=O)—.

The terms "N-alkylaminocarbonyl" and "N,N-dialkylaminocarbonyl" denote aminocarbonyl radicals which have been substituted with one alkyl radical and independently with two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces aminoalkyl radicals having the nitrogen atom independently substituted with an alkyl radical. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "heterocyclylalkyl" embraces heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkyl radicals having alkyl portions of one to three carbon atoms. Examples include such radicals as pyridinylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are lower aralkyl radicals phenyl attached to alkyl portions having one to three carbon atoms. Examples of such radicals include benzyl, diphenylmethyl and phenylethyl. The aryl in said aralkyl may be additionally substituted with halo, alkyl, alkoxy, haloalkyl and haloalkoxy.

The term "arylalkenyl" embraces aryl-substituted alkenyl radicals. Preferable arylalkenyl radicals are "lower arylalkenyl" radicals having aryl radicals attached to alkenyl radicals having two to six carbon atoms. Examples of such radicals include phenylethenyl. The aryl in said arylalkenyl may be additionally substituted with halo, alkyl, alkoxy, haloalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylsulfinyl" embraces radicals containing a linear or branched alkyl radical, of one to ten carbon atoms, attached to a divalent —S(=O)— atom. More preferred are lower alkylsulfinyl radicals having one to three carbon atoms.

The term "arylsulfinyl" embraces radicals containing an aryl radical, attached to a divalent —S(=O)— atom. Even more preferred are optionally substituted phenylsulfinyl radicals.

The term "haloalkylsulfinyl" embraces radicals containing a haloalkyl radical, of one to ten carbon atoms, attached to a divalent —S(=O)— atom. Even more preferred are lower haloalkylsulfinyl radicals having one to three carbon atoms.

The term "alkylamino" denotes amino groups which have been substituted with one alkyl radical and with two alkyl radicals, including terms "N-alkylamino" and "N,N-dialkylamino". More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable "alkylamino" may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The "arylamino" radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-$C_1$-$C_3$-alkylamino radicals, such as N-benzylamino. The "aralkylamino" radicals may be further substituted on the aryl ring portion of the radical.

The term "alkylaminoalkylamino" denotes alkylamino groups which have been substituted with one or two alkylamino radicals. More preferred are $C_1$-$C_3$-alkylamino-$C_1$-$C_3$-alkylamino radicals.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals independently having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminoethoxymethoxy, N,N-dimethylaminoethoxymethoxy, N,N-diethylaminomethoxymethoxy, and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "aminoalkoxy" embraces alkoxy radicals substituted with an amino radical. More preferred aminoalkoxy radicals are "lower aminoalkoxy" radicals having alkoxy radicals of one to six carbon atoms. Suitable aminoalkoxy radicals may be aminoethoxy, aminomethoxy, aminopropoxy and the like.

The terms "N-aralkyl-N-alkylamino" and "N-alkyl-N-arylamino" denote amino groups which have been substituted with one aralkyl and one alkyl radical, or one aryl and one alkyl radical, respectively, to an amino group.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heterocyclyloxy" embraces optionally substituted heterocyclyl radicals, as defined above, attached to an oxygen atom. Examples of such radicals include piperidyloxy.

The term "heterocyclylalkoxy" embraces oxy-containing heterocyclylalkyl radicals attached through an oxygen atom to other radicals. More preferred heterocyclylalkoxy radicals are "lower heteroarylalkoxy" radicals having optionally substituted heteroaryl radicals attached to lower alkoxy radical as described above.

The term "heterocyclyloxyalkyl" embraces heteroaryl radicals attached through an ether oxygen atom to an alkyl radical. More preferred heterocyclyloxyalkyl radicals are "lower heteroaryloxyalkyl" radicals having optionally substituted heteroaryl radicals attached to an —O—$C_{1-6}$ alkyl radical.

The term "cycloalkyl" includes saturated carbocyclic groups and spiro groups. Preferred cycloalkyl groups include $C_3$-$C_6$ rings. More preferred compounds include cyclopentyl, cyclopropyl, and cyclohexyl.

The term "cycloalkenyl" includes carbocyclic groups have one or more carbon-carbon double bonds. "Cycloalkenyl" and "cycloalkyldienyl" compounds are included. Preferred cycloalkenyl groups include $C_3$-$C_6$ rings. More preferred compounds include, for example, cyclopentenyl, cyclopentadienyl, cyclohexenyl and cycloheptadienyl.

The term "basic moiety" or "basic moieties" means a chemical moiety that has a measured or calculated $pK_a$ of from about 7 to about 13. The term also can include a chemical moiety that is protonable, to some extent, between a pH range of from about 7 to about 10. In one embodiment, a basic moiety comprises 5, 6, 7, 8, 9, 10, 11, 12, 13 or 14 carbon atoms and 1, 2 or 3 nitrogen atoms, and 0 or 1 oxygen atoms, not including the substituents outlined herein.

Examples of basic moieties include, but are not limited to, amino, cycloalkylamino($C_1$-$C_6$)alkyl, cycloalkyl($C_1$-$C_6$) alkylamino($C_1$-$C_6$)alkyl, heterocyclylamino($C_1$-$C_6$)alkyl, heterocyclyl($C_1$-$C_6$)alkylamino($C_1$-$C_6$)alkyl, arylamino($C_1$-$C_6$)alkyl, aryl($C_1$-$C_6$)alkylamino($C_1$-$C_6$)alkyl, ($C_1$-$C_6$)alkyl amino($C_1$-$C_6$)alkoxy, ($C_1$-$C_6$)alkylamino($C_1$-$C_6$)alkoxy($C_1$-$C_6$)alkoxy, amino($C_1$-$C_6$)alkoxy, amino($C_1$-$C_6$)alkyl, ($C_1$-$C_6$)alkylamino($C_1$-$C_6$)alkyl, ($C_1$-$C_4$)alkylamino-($C_2$-$C_6$)alkenyl, 4-8-membered nitrogen-containing heterocyclyl($C_2$-$C_6$)alkenyl, 4-8-membered nitrogen-containing heterocyclyl ($C_1$-$C_6$)alkyl, [4-8-membered nitrogen-containing heterocyclyl]-[4-8-membered nitrogen-containing heterocyclyl], 7-12-membered bicyclic nitrogen-containing heterocyclyl($C_1$-$C_6$)alkyl, heterocyclyl($C_1$-$C_6$)alkylamino($C_2$-$C_6$) alkyl, 5-6 membered heterocyclyloxy, 5-6 membered nitrogen-containing heterocyclyl and 5-7 membered nitrogen-containing heterocyclyl-alkyl; more specifically amino, cycloalkylamino($C_1$-$C_6$)alkyl, cycloalkyl($C_1$-$C_6$) alkylamino($C_1$-$C_6$)alkyl, heterocyclylamino($C_1$-$C_6$)alkyl, heterocyclyl($C_1$-$C_6$)alkylamino($C_1$-$C_6$)alkyl, arylamino($C_1$-$C_6$) alkyl, aryl($C_1$-$C_6$)alkylamino($C_1$-$C_6$)alkyl, ($C_1$-$C_6$)alkyl amino($C_1$-$C_6$)alkoxy, ($C_1$-$C_6$)alkylamino($C_1$-$C_6$)alkoxy($C_1$-$C_6$)alkoxy, amino($C_1$-$C_6$)alkoxy, amino($C_1$-$C_6$)alkyl, ($C_1$-$C_6$)alkylamino($C_1$-$C_6$)alkyl, ($C_1$-$C_4$)alkylamino-($C_2$-$C_6$)alkenyl, 5-8-membered nitrogen-containing heterocyclyl($C_2$-$C_6$)alkenyl, heterocyclyl($C_1$-$C_6$)amino($C_2$-$C_6$)alkyl, 5-6 membered heterocyclyloxy, 5-6 membered nitrogen-containing heterocyclyl and 5-7 membered nitrogen-containing heterocyclyl($C_1$-$C_6$)alkyl; and more specifically, amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl. Each basic moiety can be substituted by 0, 1, 2 or 3 groups independently selected from halo, —$NH_2$, —OH, —CN, —$CF_3$, ($C_1$-$C_6$)alkylamino, haloalkyl, oxo, ($C_1$-$C_6$)alkoxy, ($C_1$-$C_6$)alkoxyalkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —$NR^8$C(O)$R^{8'}$, =NCN; and ($C_1$-$C_6$)alkyl, aryl, heteroaryl, cycloalkyl and heterocyclyl, each of which is substituted by 0, 1, 2 or 3 groups independently selected from halo, —$NH_2$, —OH, —CN, —$CF_3$, ($C_1$-$C_6$)alkylamino, haloalkyl, oxo, ($C_1$-$C_6$)alkoxy, ($C_1$-$C_6$)alkoxyalkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —$NR^8$C(O)$R^{8'}$. In one embodiment, the basic moiety is selected from cycloalkylamino($C_1$-$C_6$)alkyl, cycloalkyl($C_1$-$C_6$) alkylamino($C_1$-$C_6$) alkyl, heterocyclylamino($C_1$-$C_6$)alkyl, heterocyclyl($C_1$-$C_6$) alkylamino($C_1$-$C_6$)alkyl, arylamino($C_1$-$C_6$)alkyl, aryl($C_1$-$C_6$)alkylamino($C_1$-$C_6$)alkyl, ($C_1$-$C_6$)alkyl amino($C_1$-$C_6$) alkoxy, ($C_1$-$C_6$)alkylamino($C_1$-$C_6$)alkoxy($C_1$-$C_6$)alkoxy, amino($C_1$-$C_6$)alkoxy, amino($C_1$-$C_6$)alkyl, ($C_1$-$C_6$)alkylamino($C_1$-$C_6$)alkyl, ($C_1$-$C_4$)alkylamino-($C_2$-$C_6$)alkenyl, 4-8-membered nitrogen-containing heterocyclyl($C_2$-$C_6$)alkenyl, heterocyclyl($C_1$-$C_6$)amino($C_2$-$C_6$)alkyl, 5-6 membered heterocyclyloxy, 5-6 membered nitrogen-containing heterocyclyl and 5-7 membered nitrogen-containing heterocyclylalkyl. In another embodiment, the basic moiety is selected from cycloalkylamino($C_1$-$C_6$)alkyl, cycloalkyl($C_1$-$C_6$) alkylamino($C_1$-$C_6$)alkyl, heterocyclylamino($C_1$-$C_6$)alkyl, heterocyclyl($C_1$-$C_6$)alkylamino($C_1$-$C_6$)alkyl, arylamino($C_1$-$C_6$) alkyl, aryl($C_1$-$C_6$)alkylamino($C_1$-$C_6$)alkyl, ($C_1$-$C_6$)alkyl amino($C_1$-$C_6$)alkoxy, ($C_1$-$C_6$)alkylamino($C_1$-$C_6$)alkoxy($C_1$-$C_6$)alkoxy, amino($C_1$-$C_6$)alkoxy, amino($C_1$-$C_6$)alkyl, ($C_1$-$C_6$)alkylamino($C_1$-$C_6$)alkyl, ($C_1$-$C_4$)alkylamino-($C_2$-$C_6$)alkenyl, 4-8-membered nitrogen-containing heterocyclyl($C_2$-$C_6$)alkenyl, heterocyclyl($C_1$-$C_6$)amino($C_2$-$C_6$)alkyl, 5-6 membered heterocyclyloxy, 5-6 membered nitrogen-containing heterocyclyl and 5-7 membered nitrogen-containing heterocyclyl-alkyl any of which are substituted by COO$R_8$, halo, $C_{1-6}$alkyl or cycloalkyl.

The term "comprising" is meant to be open ended, including the indicated component but not excluding other elements.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups from the genus.

The present invention preferably includes compounds that antagonize bradykinin 1.

The present invention also comprises the use of a compound of the invention, or pharmaceutically acceptable salt thereof, in the manufacture of a medicament for the treatment either acutely or chronically of pain or an inflammation mediated disease state, including those described previously. The compounds of the present invention are also useful in the manufacture of an anti-inflammatory medicament. The compounds of the present invention are also useful in the manufacture of a medicament to attenuate or prevent disorders through inhibition of bradykinin 1. The compounds of the present invention are also useful in the manufacture of a medicament to treat pain.

The present invention comprises a pharmaceutical composition comprising a therapeutically-effective amount of a compound of Formulas I-VI in association with at least one pharmaceutically-acceptable carrier, adjuvant or diluent.

COMBINATIONS

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

The present compounds may also be used in combination therapies with opioids and other anti-pain analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists, COX-2 inhibitors such as celecoxib, rofecoxib, valdecoxib, parecoxib, and darecoxib, NSAID's, and sodium channel blockers, among others. More preferred would be combinations with compounds selected from morphine, meperidine, codeine, pentazocine, buprenorphine, butorphanol, dezocine, meptazinol, hydrocodone, oxycodone, methadone, tetrahydrocannibinol, pregabalin, Tramadol [(+) enantiomer], DuP 747, Dynorphine A, Enadoline, RP-60180, HN-11608, E-2078, ICI-204448, acetominophen (paracetamol), propoxyphene, nalbuphine, E-4018, filenadol, mirtentanil, amitriptyline, DuP631, Tramadol [(−) enantiomer], GP-531, acadesine, AKI-1, AKI-2, GP-1683, GP-3269, 4030W92, tramadol racemate, Dynorphine A, E-2078, AXC3742, SNX-111, ADL2-1294, ICI-204448, CT-3, CP-99,994, and CP-99,994.

Alternatively, the present compounds may also be used in co-therapies with other treatments for inflammation, e.g. steroids, NSAIDs, iNOS inhibitors, p38 inhibitors, TNF inhibitors, 5-lipoxygenase inhibitors, $LTB_4$ receptor antagonists and $LTA_4$ hydrolase inhibitors.

The present invention comprises a process for the preparation of a compound of Formula I-VI.

Compounds of the present invention can possess, in general, one or more asymmetric carbon atoms and are thus capable of existing in the form of optical isomers as well as in the form of racemic or non-racemic mixtures thereof. Unless otherwise indicated, the compounds of the present invention, as depicted or named, may exist as the racemate, a single enantiomer, or any uneven (i.e. non 50/50) mixture of enantiomers, and are all included in the family of compounds in Formula I-VI. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column, such as, for example, a CHIRAL-AGP column, optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. Preferred compounds of the invention have an R configuration at the amide bond for example

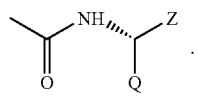

Compounds of the present invention can possess, in general, tautomeric forms, including any enolate anions, which are included in the family of compounds in Formula I-VI.

Also included in the family of compounds of Formula I-VI are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I-VI may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I-VI include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethylmorpholine, piperazine, piperidine, triethylamine, trimethylamine. All of these salts may be prepared by conventional means from the corresponding compound of the invention by reacting, for example, the appropriate acid or base with the compound of Formula I-VI.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as HCl, $H_2SO_4$ and $H_3PO_4$ and such organic acids as oxalic acid, maleic acid, succinic acid and citric acid. Other examples include salts with alkali metals or alkaline earth metals, such as sodium, potassium, calcium or magnesium or with organic bases.

General Synthetic Procedures

The compounds of the invention can be synthesized according to the following procedures of Schemes 1-9, wherein the substituents are as defined for Formulas I-V, above, except where further noted.

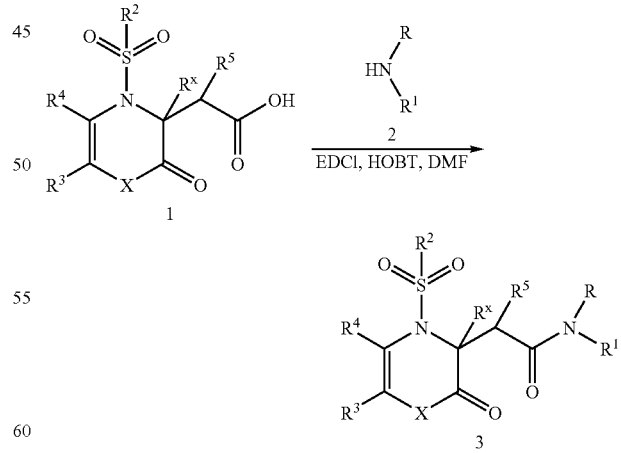

Compounds of Formula I may be prepared in a convergent manner as described in Scheme 1. Acids 1 are coupled with the substituted amine 2 using standard peptide coupling conditions, such as with HOBT, and EDC in a solvent, such as DMF or $CH_2Cl_2$, and reacted at RT, to afford the substituted amide 3. The acids 1 are prepared according to Scheme 2. Similarly, substituted amine 2 are either commercially available, can be prepared via literature methods, or may be prepared following literature methods described for analogous compounds. Some of these methods are illustrated in the subsequent schemes.

the amine 7 using standard peptide coupling conditions, such as with HOBT, and EDC in a solvent, such as DMF, and reacted at RT, to afford the substituted amide 8. The reaction is kept at a temperature above about 0° C., preferably at about RT. The amide 8 undergoes cyclization in the presence of catalytic amount of acid such as TsOH under elevated tem-

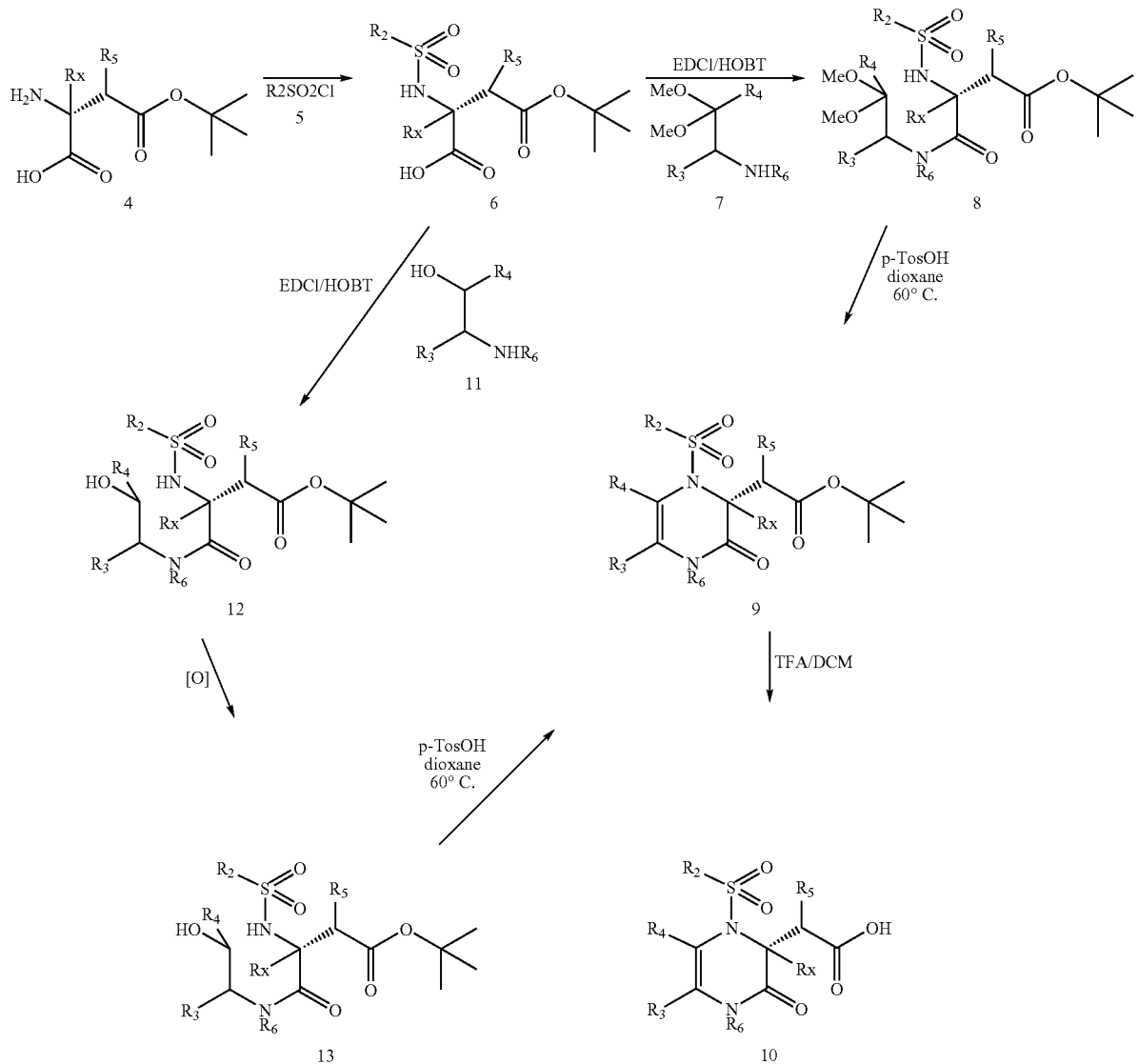

The acid 1 may be prepared as described in Scheme 2. The amino acids 4 either commercially available such as (R)-2-amino-4-tert-butoxy-4-oxobutanoic acid from a number of vendors including Chem-Impex international, Inc.) or prepared according to literature procedures (Schabbert, S.; Pierschbacher, M. D.; Mattern, R.; Goodman, M. Bioorg. Med. Chem. 2002, 10, 3331-7; Bold, G.; Duthaler, R. O.; Riediker, M'Angew. Chem. 1989, 101, 491-3.) are coupled with an active sulfonyl compound, such as a substituted sulfonyl chloride 5, in the presence of base, preferably a inorganic base such as sodium carbonate, in solvents such as dioxane and water to form the substituted sulfonyl ester 6. It is reacted with perature such as at 60° C. The tert-butyl ester 9 obtained is hydrolyzed with acid such as TFA in DCM to yield the acid 10. Alternatively, the sulfonylated acid 6 can coupled to the amino alcohol 11 using standard peptide coupling conditions, such as with HOBT, and EDC in a solvent, such as DMF, and reacted at RT, to afford the substituted amide 12. The alcohol 12 can be oxidized to the corresponding carbonyl compounds 13 using various standard methods such as Dess-Martin periodinane (see J. Org. Chem. 1983, 48,4155). The carbonyl compound 13 undergoes cyclization in the presence of catalytic amount of acid such as TsOH under elevated temperature such as at 60° C. to give the same cyclized compound 9.

Scheme 3

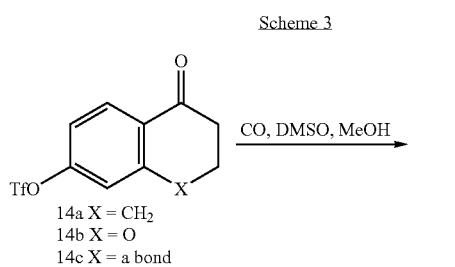
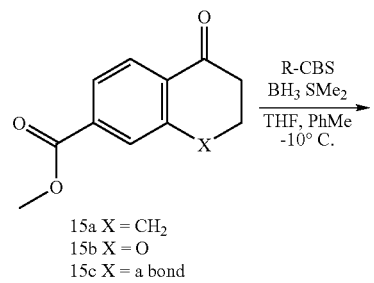
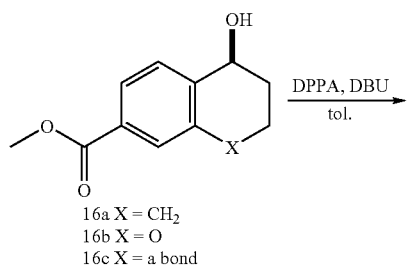
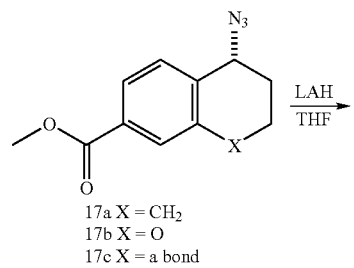
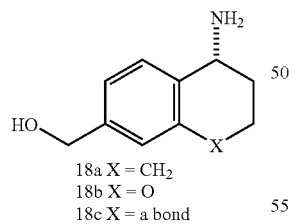

In addition compounds of Formula I can be prepared in diasteromerically pure forms using the method described in Scheme 3. Keto-trifalates 14a-c are subjected to Pd mediated carbonylation in a mixture of DMSO and MeOH to afford the ketoesters 15a-c. Enantioselective reduction of the ketone moieties, e.g. using either the CBS (E. J. Corey et al., J. Am. Chem. Soc. 109, 5551 (1987)) or Noyori (T. Noyori, et al., *J. Am. Chem. Soc.*, 1995, 117, 2675-2676) protocols affords either enantiomer of the alcohols with an enantiomeric excess of >99%. Either the R or S enantiomer of the amine may be prepared by using either of the enantioselective reduction protocols. Azidation of the resulting secondary alcohol using a method described by Thompson et al. (Journal of Org. Chem. (1993), 58(22), 5886-8.) and LAH reduction affords the enantiopure amino alcohols 18a-c in high yield The resulting amino alcohols further elaborated into compounds of Formula I as depicted in Scheme 4. The acid 10 is coupled with the amino alcohols such as 18 using standard peptide coupling conditions, such as with HOBT, and EDC in a solvent, such as DMF, and reacted at RT, to afford the substituted amide 19. The alcohol 19 is oxidized with $MnO_2$ in DCM at RT to yield the aldehyde 20. Reductive amination of the aldehyde 20 with various amines under normal reductive amination conditions such as sodium triacetoxyborohydride in DCE or a stepwise procedure involving imine formation in DCE followed by reduction with $NaBH_4$ (see: Abdel-Magid, A.; Carson, K. C.; Harris, B. D.; Maryanoff, C. A.; Shah, R. J. Org. Chem. 1996, 61, 3,849.) gives the final amine 21.

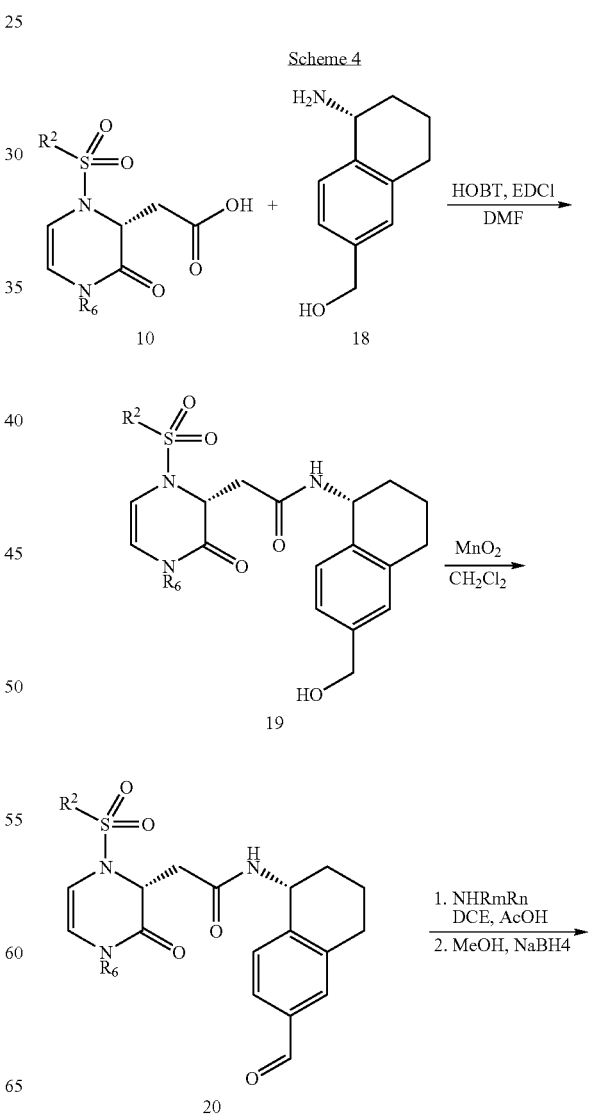

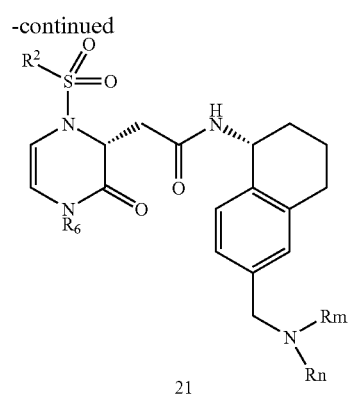

21

Analogs of compounds of Formula II may be prepared as illustrated in Schemes 12-14. Following Boc protection, amino alcohol 18 is converted to its methyl ketone 25 by the three step procedure depicted in scheme 5. Protected 1-amino-6-hydroxymethyl-1,2,3,4-tetrahydro-naphthalene 22 is oxidized, such as with $MnO_2$ in an organic solvent, such as $CH_2Cl_2$, preferably at a temperature of about RT, to form the aldehyde 23. The aldehyde is alkylated, such as with a Grignard reagent in a solvent such as THF, at a temperature initially below RT, preferably about −30° C. and more preferably at about −78° C., then at about RT, to form the alcohol 24. The alcohol 24 is oxidized, such as with $MnO_2$ as previously described, to form the protected ketone 25. The resulting ketone 25 is deprotected such as with HCl, and converted to compound 26 similar to the method described in Scheme 4.

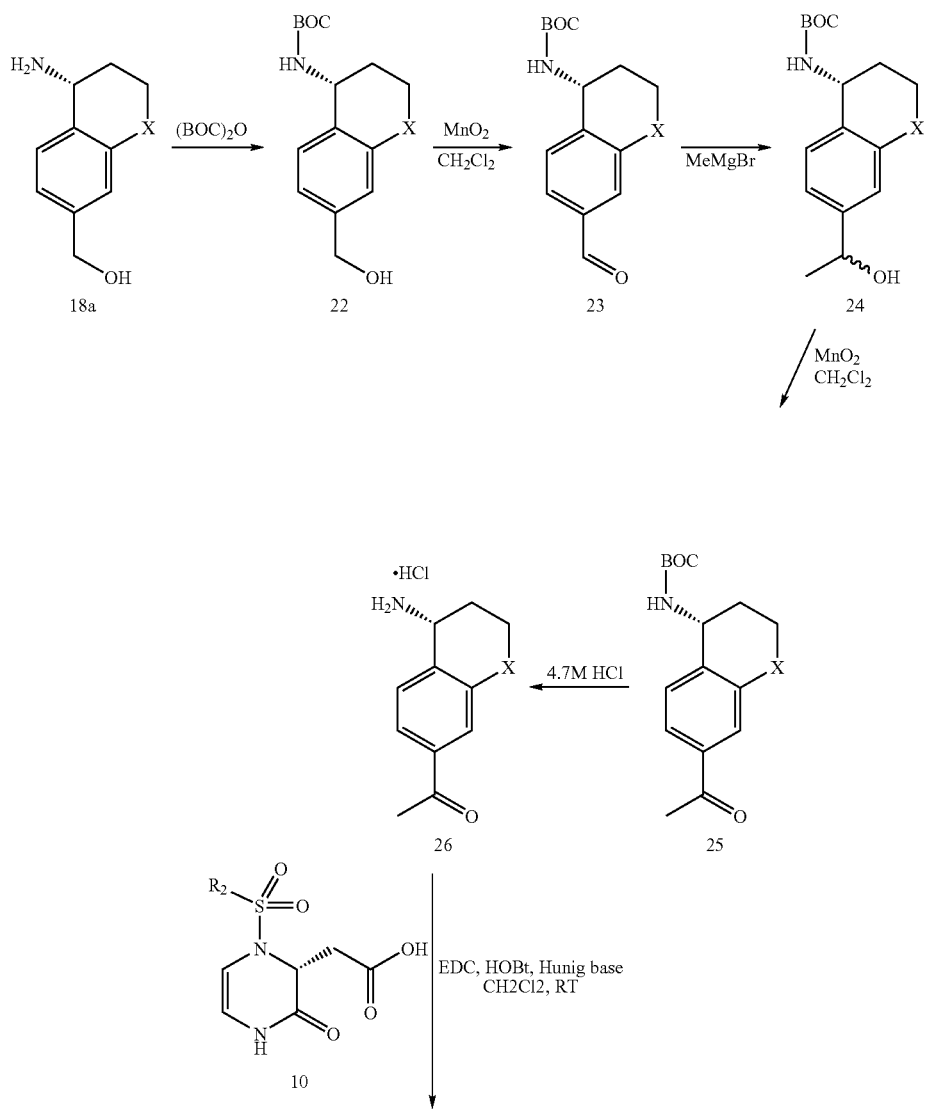

Scheme 5

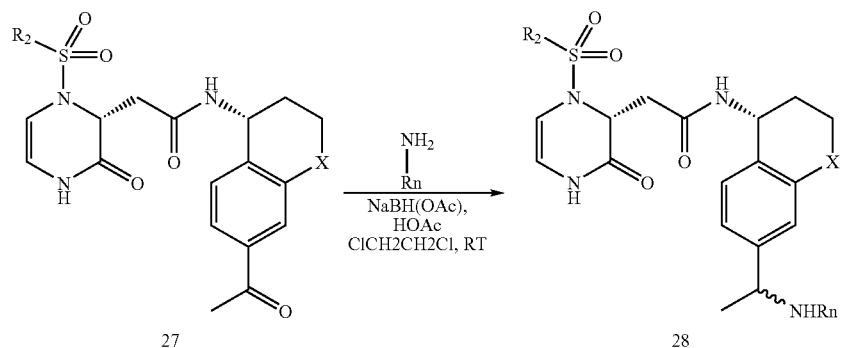
Scheme 6
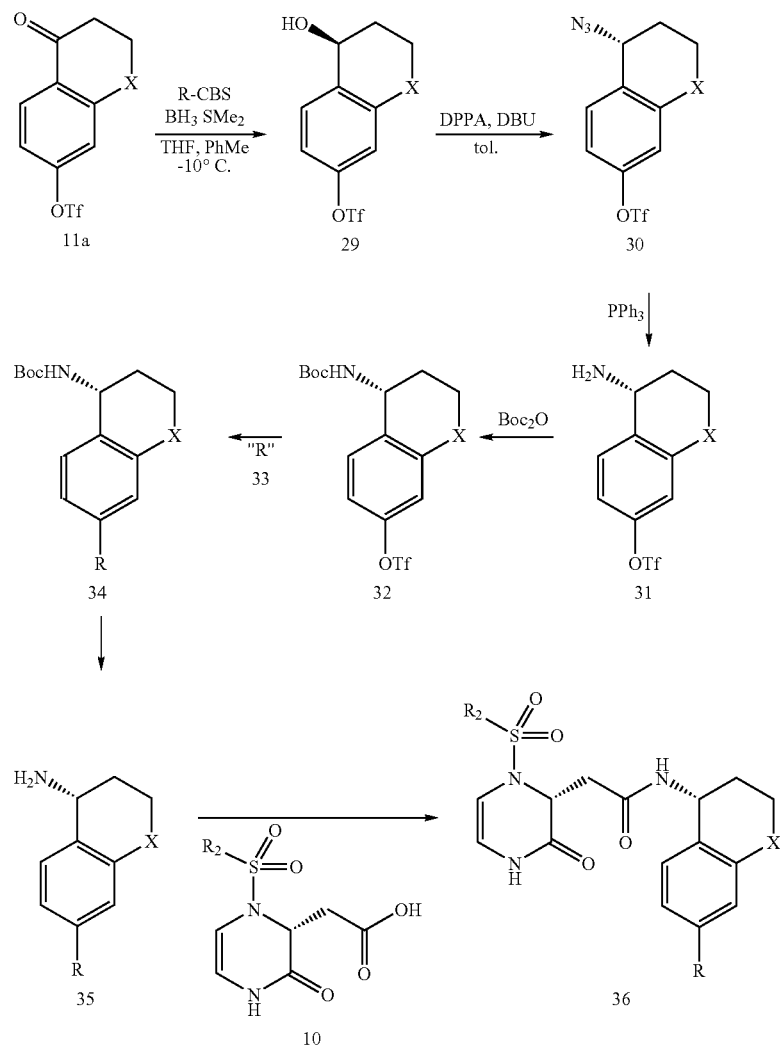
R: 2, 3, or 4-Py; Ar; NR1R2
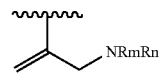

The substituted bicyclic amine derivatives of compounds of Formula 36 and 43 may be prepared by the methods illustrated in Scheme 6-7. The triflate 11a is converted to the azide 30 similar to methods described in Scheme 3. Addition of PPh₃ to the azide 30 provides the amine 31, which is Boc protected to give 32. The triflate can be substituted with various R group using organometallic mediated reactions such as Heck coupling with the olefins (palladium(II)acetate, dppf, base (e.g. Et₃N) at a temperature above RT, preferably between about 50° C. and about 100° C., more preferably at about 80° C.), Suzuki couplings (Chem. Rev. 1995, 95, 2457), or cross couplings (e.g. see Org. Lett. 2002, 4, 3517) provides the substituted tetralin 34. The Boc deprotection of 34 followed by coupling to the acid 10 gives the amide 36.

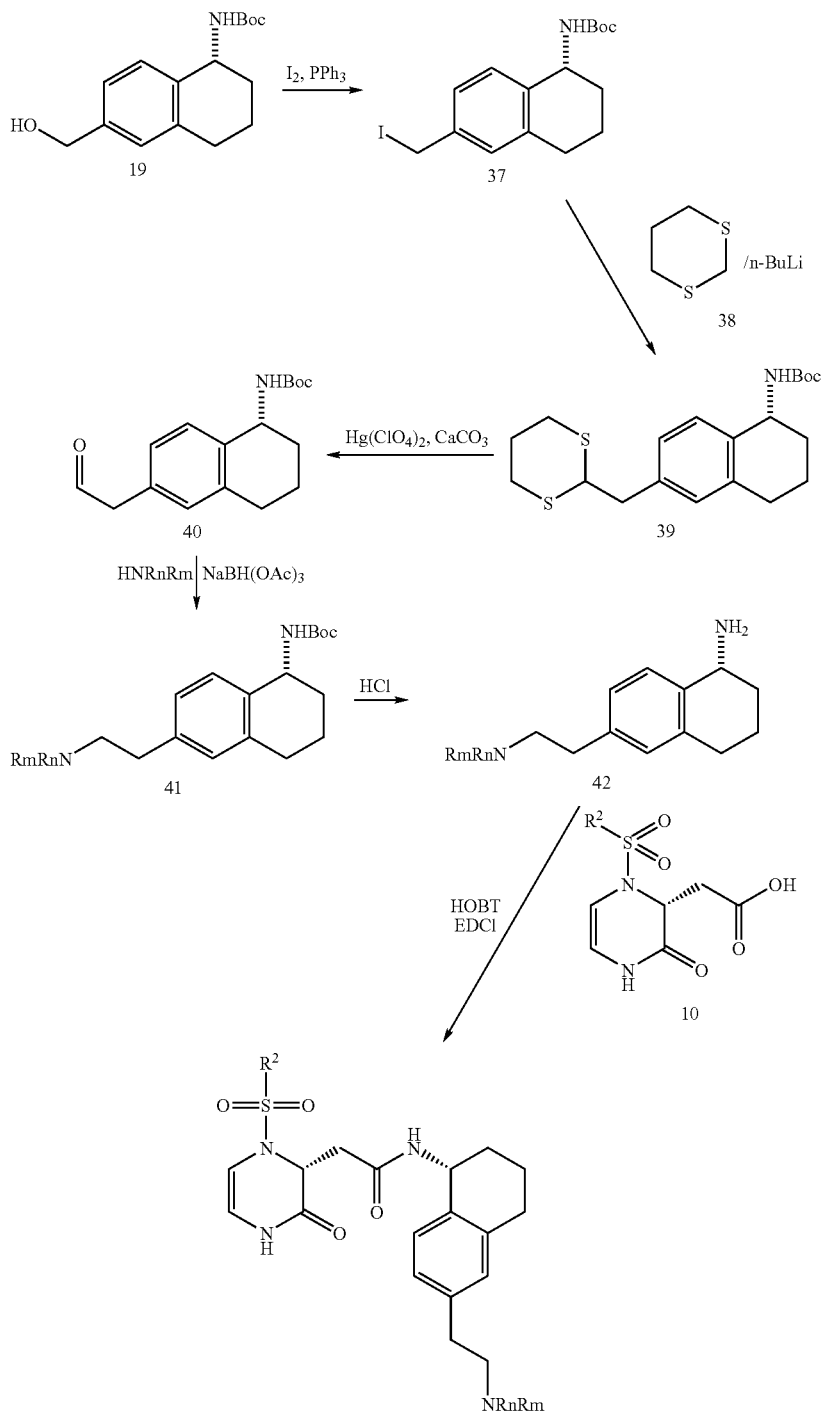

In scheme 7 the alcohol 22 is converted to the iodide with iodine and triphenyl phosphine. The iodide 37 is reacted with lithiated 1,3-dithiane to give compound 39. The dithiane is converted to the aldehyde 40 which is then reductively aminated to give the amine 41. After Boc deprotection the amine 42 is coupled with the acid 10 to give the amide 43.

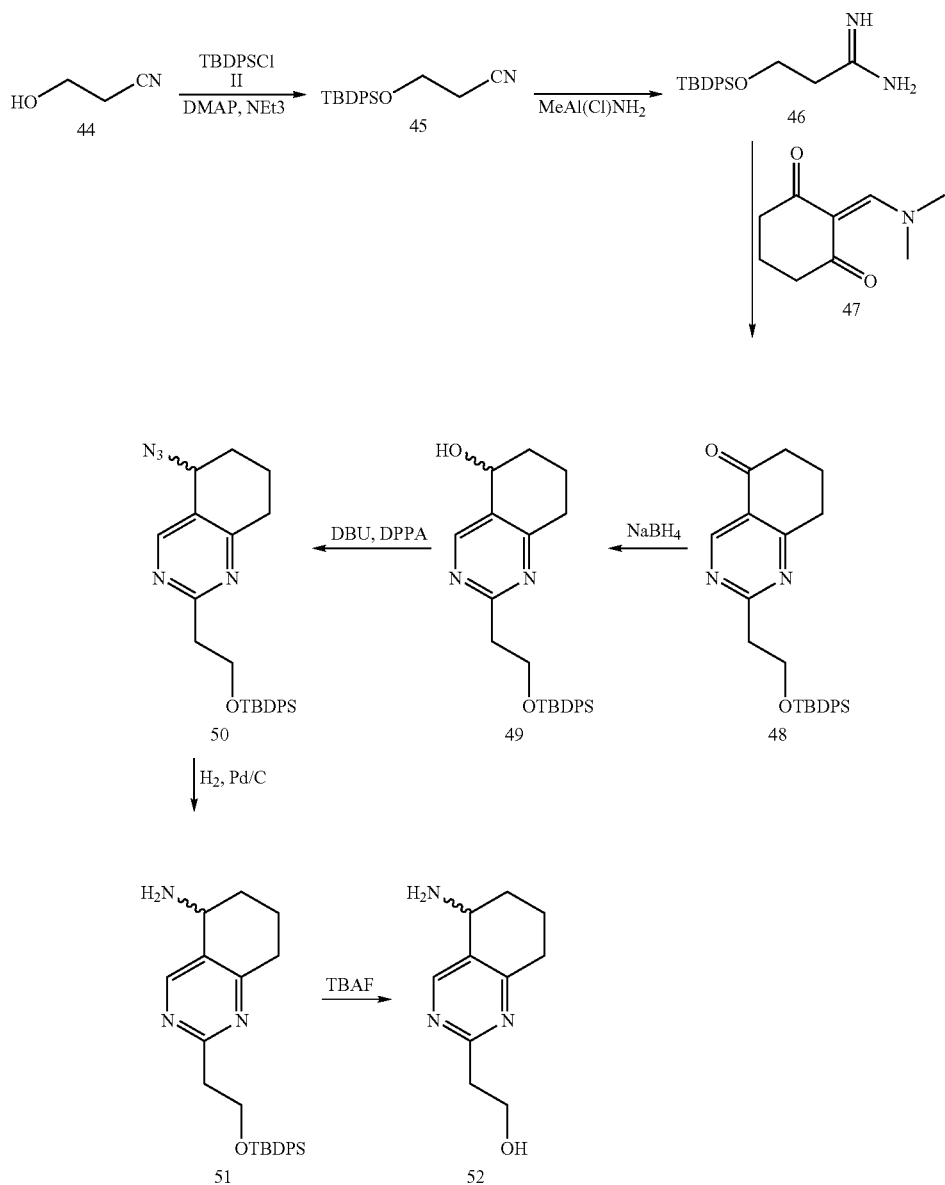

Methods for preparing additional compounds of formulas I and II are illustrated in scheme 8. The cyano alcohol 44 can be treated with DMAP, base (e.g. NEt₃), and PBDPSCl to form the protected alcohol 45. The protected alcohol 45 is aminated, such as with Me₃Al, at a temperature below RT and preferably at about 0° C., to yield the amidine 46. Formation of the 5,6,7,8-tetrahydro-quinazolone 48 is achieved such as by reaction of amidine 46 and 2-dimethylaminomethylene-cyclohexane-1,3-dione 47 at a temperature above RT, preferably above about 50° C. and more preferably at about 80° C. 5,6,7,8-tetrahydro-quinazolone 48 is reduced such as with NaBH₄ to give the alcohol 49. The alcohol 49 is treated with DPPA and DBU to form the azide derivative which is reduced to form the amine 51. The amine 51 is deprotected, such as with TBAF to form the desired intermediate 52.

Scheme 9

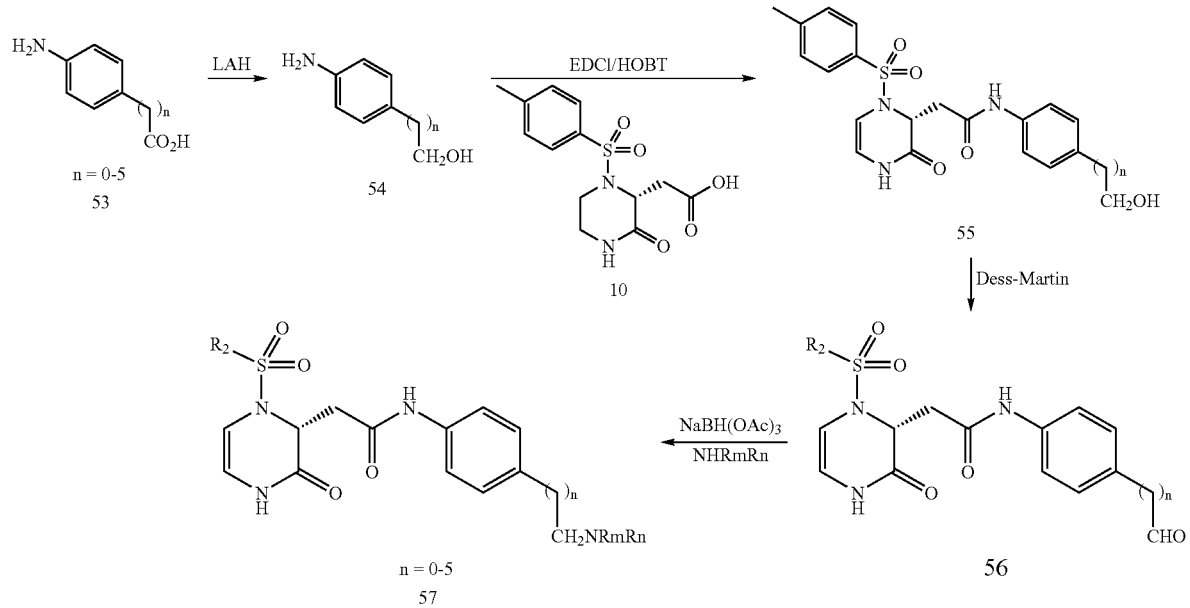

Compounds of formula 57 can be prepared as described in Scheme 9. The aminoalcohol 54, either commercially available or obtained from the reduction of the corresponding amino acid 53 with LAH, is coupled to the acid 10 to give the amide 55. Dess-Martin oxidation of 55 yields the aldehyde 56. Reductive amination of 56 with piperidine gives the amine 57.

Additional analogs of any of the templates in described in Schemes 1-9 may be prepared using the procedures analogous to those described for above and illustrated in the examples below. In addition elaboration of all intermediates in the above schemes to compounds of Formula I may be accomplished using known by those skilled in the arts of organic and medicinal chemistry.

If one or more other functional groups, for example carboxy, hydroxy, amino, or mercapto, are or need to be protected in a compound of Formulas I-VI, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. McOmie, "Protective Groups in Organic Chemistry", Plenum Press, London and New York (1973); in T. Greene, "Protective Groups in Organic Synthesis", Wiley, New York (1981); in "The Peptides", Volume 3 (eds: E. Gross and J. Meienhofer), Academic Press, London and New York (1981); in "Methoden der organischen Chemie" (Methods of organic chemistry), Houben Weyl, 4th edition, Volume 15/1, Georg Thieme Verlag, Stuttgart (1974); in H. Jakubke and H. Jescheit, "Aminosäuren, Peptide, Proteine" (Amino acids, peptides, proteins), Verlag Chemie, Weinheim, Deerfield Beach, and Basel (1982); and in Jochen Lehmann, "Chemie der Kohlenhydrate: Monosaccharide und Derivate" (Chemistry of carbohydrates: monosaccharides and derivatives), Georg Thieme Verlag, Stuttgart (1974).

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of Formula I with a salt-forming group may be prepared in a manner known per se. Acid addition salts of compounds of Formula I may thus be obtained by treatment with an acid or with a suitable anion exchange reagent. A salt with two acid molecules (for example a dihalogenide of a compound of Formula I) may also be converted into a salt with one acid molecule per compound (for example a monohalogenide); this may be done by heating to a melt, or for example by heating as a solid under a high vacuum at elevated temperature, for example from 130-170° C., one molecule of the acid being expelled per molecule of a compound of Formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H+ form, depending on the type of reaction and/or reactants at reduced, normal, or elevated temperature, for example in the range from about −100° C. to about 190° C., preferably from about −80° C. to about 150° C., for example at about −80° C. to about 60° C., at RT, at about −20° C. to about 40° C. or at the boiling point of the solvent used, under atmospheric pressure or in a closed vessel, where appropriate under pressure, and/or in an inert atmosphere, for example, under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include, for example, $H_2O$, esters, typically lower alkyl-lower alkanoates, e.g. EtOAc, ethers, typically aliphatic ethers, e.g. $Et_2O$, or cyclic ethers, e.g. THF, liquid aromatic hydrocarbons, typically benzene or toluene, alcohols, typically MeOH, EtOH or 1-propanol, IPA, nitriles, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g. HOAc, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of Formula I-VI, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

The following examples contain detailed descriptions of the methods of preparation of compounds of Formulas I-VI. These detailed descriptions fall within the scope, and serve to exemplify, the above-described General Synthetic Procedures which form part of the invention. These detailed descriptions are presented for illustrative purposes only and are not intended as a restriction on the scope of the invention.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention. The compounds of this invention may also be represented in multiple tautomeric forms, for example, as illustrated below:

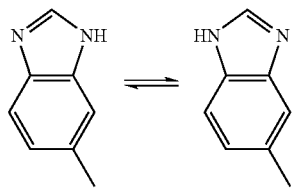

The invention expressly includes all tautomeric forms of the compounds described herein. The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. Greene and P. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Unless otherwise noted, all materials were obtained from commercial suppliers and used without further purification. All parts are by weight and temperatures are in Degrees centigrade unless otherwise indicated. All compounds showed NMR spectra consistent with their assigned structures.

In order that the invention described herein may be more readily understood, the following examples are set forth. It should be understood that these examples are for illustrative purposes only and are not to be construed as limiting this invention in any manner.

The following examples contain detailed descriptions of the methods of preparation of compounds of Formulas I-V. These detailed descriptions fall within the scope, and serve to exemplify, the above-described General Synthetic Procedures which form part of the invention. These detailed descriptions are presented for illustrative purposes only and are not intended as a restriction on the scope of the invention.

The following abbreviations are used:
AcOH, HOAc—acetic acid
CH₃CN—acetonitrile
NH₃—ammonia
NH₄Cl—ammonium chloride
NH₄OH—ammonium hydroxide
HATU—O-(7-Azabenzotriazol-1-yl)-N,N,N',N'-tetramethyluronium hexafluorophosphate
AIBN—2,2'-azobisisobutyronitrile
(PPh₃)₂NiBr₂ bis(triphenylphosphine)nickel(II) bromide
BH₃—borane
BH₃ SMe₂—borane-methyl sulfide complex
Br₂—bromine
NBS—N-bromosuccinimide
CCl₄—carbon tetrachloride
CHCl₃—chloroform
DBU—1,8-diazabicyclo[5.4.0]undec-7-ene
CH₂Cl₂—dichloromethane
Et₂O—diethyl ether
Ip₂NEt, DIEA diisopropylethylamine
Me₂NH—dimethylamine
EDC—(3-dimethylamino-propyl)-ethyl-carbodiimide-HCl salt
DMAP—4-(dimethylamino)pyridine
DMF—dimethylformamide
DMSO—dimethyl sulfoxide (also known as methyl sulfoxide)
DPPA—diphenylphosphoryl azide
EtOH—ethanol
EtOAc—ethyl acetate
HCO₂H—formic acid
g—gram
h—h
HCl—hydrochloric acid
H₂—hydrogen
HOAt—1-hydroxy-7-azabenzotriazole
HOBt—1-hydroxybenzotriazole
IPA—isopropanol
iPrOH—isopropanol
LAH—lithium aluminum hydride
LDA—lithium diisopropylamide
LiOH—lithium hydroxide
MgSO₄—magnesium sulfate
MeOH—methanol
NMM—N-methylmorpholine
NMP—1-methyl-2-pyrrolidone
mL—milliliter
min—minutes
N₂—nitrogen
Pd/C—palladium on carbon
Pd(OH)₂—palladium hydroxide
H₃PO₄—phosphoric acid
K₂CO₃—potassium carbonate
KCN—potassium cyanide
KOH—potassium hydroxide
RT—room temperature
SiO₂—silica
NaOAc—sodium acetate
NaN₃—sodium azide
NaRCO₃—sodium bicarbonate
NaBH₄—sodium borohydride
NaOH—sodium hydroxide
NaBH(OAc)₃—sodium triacetoxyborohydride
H₂SO₄—sulfuric acid
SOCl₂—thionyl chloride
THF—tetrahydrofuran
TsCl—p-tosyl chloride
TsOH—p-toluene sulfonic acid
TEA, Et₃N—triethylamine
TFA—trifluoroacetic acid
PPh₃—triphenylphosphine
H₂O—water Unless otherwise noted, all materials were obtained from commercial suppliers and used without further purification. All parts are by weight unless otherwise indicated. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chomatography. Unless otherwise stated, reactions were run at RT.

EXAMPLE 1

(R)-2-(3-oxo-1-tosyl-1,2,3,4-tetrahydropyrazin-2-yl) acetic acid

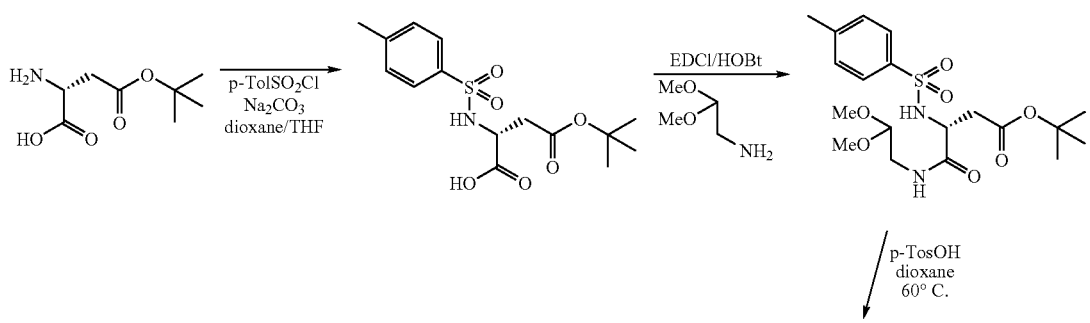

-continued

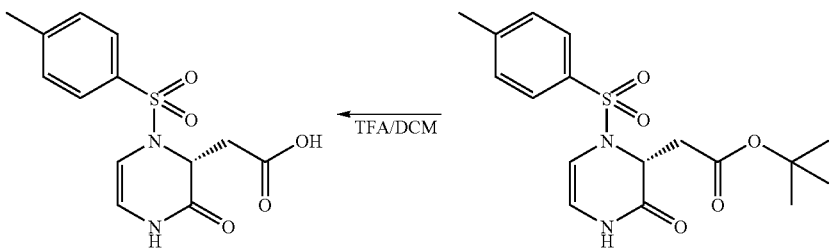

Step 1: To (D)-Aspartic acid β-tert-butyl ester (Chemimpex, 29.5 g, 0.142 mol) in 500 mL of dioxane and 500 mL of water was added at room temperature sodium carbonate (38.7 g) followed portionwise by p-tolunesulfonyl chloride (28 g, 0.146 mol). The mixture was stirred overnight. It was carefully acidified with 10% HCl and 800 mL of brine. The mixture was extracted with EtOAc (3×600 mL). The combined organic layer was washed with brine (3×500 mL), dried, and evaporated to give the desired product.

Step 2: The above compound (60 g, 0.124 mol) was dissolved in anhydrous DMF (400 mL). HOBt (Aldrich, 19.2 g) and aminoacetaldhyde dimethyl acetal (Aldrich, 16 mL) were added followed by EDCI (Aldrich, 30 g). The mixture was stirred at room temperature overnight. EtOAc (1000 mL) and water (1000 mL) were added. The EtOAc layer was washed with brine (2×500 mL), diluted HCl/brine, and 10% sodium carbonate/brine (3×300 mL), dried, and evaporated to give the desired product.

Step 3: The above compound (54 g) was dissolved in anhydrous dioxane (1L). p-Tolune sulfonic acid (6.6 g) was added. The mixture was heated at 60° C. for 17 h until LC/MS indicated that the starting material was consumed. The solution was cooled to RT and concentrated to above 100 mL. EtOAc (1L) was added and washed with sodium bicarbonate solution/brine (2×400 mL), dried and evaporated. Column chomatograph (20-50% EtAOAc/hexanes, silica gel) gave the pure product.

Step 4: The above product (33.5 g) was dissolved in DCM (400 mL) and TFA (160 mL) was added. The mixture was stirred at RT until TLC (50% EtOAc/hexanes) indicated the reaction was complete. The mixture was evaporated. DCM (200 mL) was added and evaporated again. The resulting residue was stirred with ether (500 mL) for 1 h. The solids were filtered and washed with ether to give the desired product (R)-2-(3-oxo-1-tosyl-1,2,3,4-tetrahydropyrazin-2-yl) acetic acid. Similarly the following acids were prepared: (R)-2-(3-oxo-1-(phenylsulfonyl)-1,2,3,4-tetrahydropyrazin-2-yl)acetic acid, (R)-2-(1-(2-methylphenylsulfonyl)-3-oxo-1,2,3,4-tetrahydropyrazin-2-yl)acetic acid, (R)-2-(1-(3-methylphenylsulfonyl)-3-oxo-1,2,3,4-tetrahydropyrazin-2-yl)acetic acid, (R)-2-(1-(3-chlorophenyl-sulfonyl)-3-oxo-1,2,3,4-tetrahydropyrazin-2-yl)acetic acid, (R)-2-(1-(4-chlorophenylsulfonyl)-3-oxo-1,2,3,4-tetrahydropyrazin-2-yl) acetic acid, (R)-2-(1-(4-methoxyphenylsulfonyl)-3-oxo-1,2,3,4-tetrahydropyrazin-2-yl)acetic acid, (R)-2-(1-(3-trifluorophenylsulfonyl)-3-oxo-1,2,3,4-tetrahydropyrazin-2-yl)acetic acid, (R)-2-(1-(3-trifluoromethoxyphenylsulfonyl)-3-oxo-1,2,3,4-tetrahydropyrazin-2-yl)acetic acid, (R)-2-(1-(3,4-dichlorophenylsulfonyl)-3-oxo-1,2,3,4-tetrahydropyrazin-2-yl)acetic acid, (R)-2-(1-(2,3-dichlorophenylsulfonyl)-3-oxo-1,2,3,4-tetrahydropyrazin-2-yl)acetic acid, (R)-2-(1-(4-chloro-2,5-dimethylphenylsulfonyl)-3-oxo-1,2,3,4-tetrahydropyrazin-2-yl)acetic acid, (R)-2-(1-(cyclopropyl-sulfonyl)-3-oxo-1,2,3,4-tetrahydropyrazin-2-yl)acetic acid, and (R)-2-(4-methyl-3-oxo-1-tosyl-1,2,3,4-tetrahydropyrazin-2-yl)acetic acid.

EXAMPLE 2

(5(R)-Amino-5,6,7,8-tetrahydro-naphthalen-2-yl)-methanol

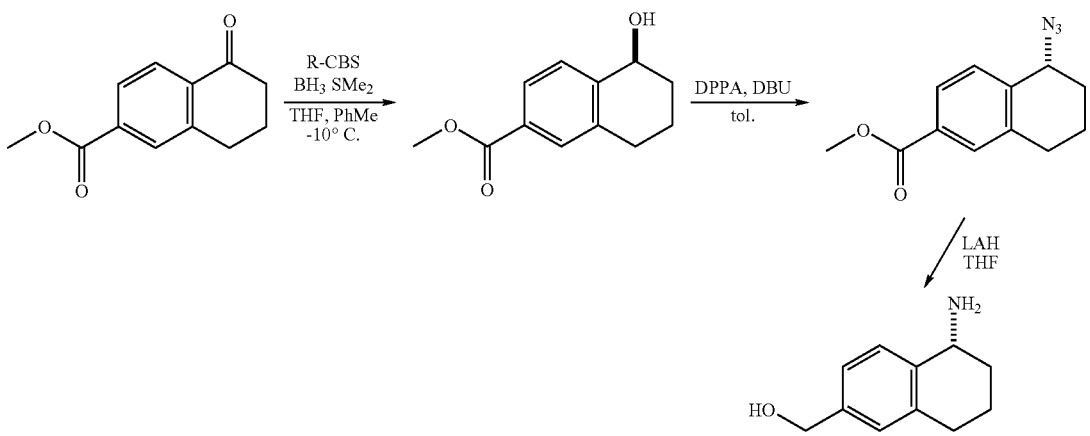

Preparation 5(S)-Hydroxy-5,6,7,8-tetrahydro-naphthalene-2-carboxylic acid methyl ester: To an oven-dried 2 L round-bottomed flask equipped with an argon inlet/outlet and magnetic stirring was added (R)-2-methyl-CBS-oxazaborolidine (7.4 mL of a 1M soln in toluene, 7.4 mmol, Aldrich). Toluene 190 mL was added and the reaction was cooled in an ice-salt bath (bath temp. =−10° C.). $BH_3$—$SMe_2$ was added (17 mL, 180 mmol, Aldrich), then 5-oxo-5,6,7,8-tetrahydro-naphth-alene-2-carboxylic acid methyl ester (30 g, 150 mmol, Albany Molecular) in 200 mL of THF was added over 5 h using a syringe pump. After the addition was complete, the mixture was stirred for an additional 1 h. The mixture was poured into an addition funnel, and the mixture was added to 200 mL of MeOH, cooled in a ice-salt bath, over 30 min at such a rate that the internal temp. was kept below 0° C. The mixture was concentrated in vacuo. $Et_2O$ (1 L) was added, and the mixture was washed with 1M $H_3PO_4$ (3×), satd $NaHCO_3$, and brine (ca. 400 mL each wash). The organic layer was dried over $MgSO_4$, filtered and concentrated in vacuo. The residue was dissolved in $Et_2O$ again (500 mL), and the mixture was washed with 1M $H_3PO_4$ (3×200 mL), satd $NaHCO_3$, and brine. After drying the organic layer over $MgSO_4$, the mixture was filtered and concentrated in vacuo, which gave the title compound as a white-yellow solid. MS (+ion ESI) m/z=207 ($MH^+$), 189 ($MH^+$—$H_2O$).

Preparation of 5(R)-azido-5,6,7,8-tetrahydro-naphthalene-2-carboxylic acid methyl ester: To a 500 mL thee-neck round-bottomed flask equipped with argon inlet/outlet, thermometer, and magnetic stirring was added 5(S)-hydroxy-5,6,7,8-tetrahydro-naphthalene-2-carboxylic acid methyl ester (29 g, 140 mmol) in 280 mL of toluene. The reaction was cooled in a ice-salt bath, and DPPA (36 mL, 170 mmol, Aldrich) was added (internal temp.=−4° C.). DBU (25 mL, 170 mmol, Aldrich) was added over 10 min at such a rate that the internal temp was kept below 1° C. The ice in the bath was allowed to melt, and the reaction continued for 12 h during which time the mixture stopped stirring because a precipitate had formed. Stirring was resumed, and the mixture was stirred at RT for another 11 h. The reaction contents were poured into a 2 L sep funnel, and the lower dark-brown layer was removed. Water (250 mL) was added to the remaining top layer, and the mixture was extracted with $Et_2O$ (3×250 mL). The combined organic layers were washed with 1M $H_3PO_4$, water, satd $NaHCO_3$, and brine. The organic layer was dried over $MgSO_4$, filtered and concentrated in vacuo. Purification by silica gel chomatography (330 g Isco Redisep® column, 1:1 hexane-$CH_2Cl_2$) of the crude material provided the title compound. MS (+ion ESI) m/z=232 ($MH^+$).

Preparation (5(R)-Amino-5,6,7,8-tetrahydro-naphthalen-2-yl)-methanol: To an oven-dried, 3-neck, 2 L round-bottomed flask equipped with argon inlet/outlet, addition funnel, thermometer, and overhead stirring was added 700 mL of THF and LAH (470 mL of a 1M soln in THF, 470 mmol, Aldrich). The reaction was cooled in a ice-salt bath, and 5-azido-5,6,7,8-tetrahydro-naphthalene-2-carboxylic acid methyl ester (27 g, 120 mmol) in 100 mL of THF was added over ca. 30 min. The mixture was warmed to RT overnight, then cooled in an ice-salt bath the next morning. Water (18 mL) in THF (20 mL) was added to the reaction mixture over 4 h. Vigorous gas evolution occurred. 5M NaOH (18 mL) was added over 30 min followed by 54 mL of water. After stirring for an additional 1 h, the mixture was filtered, and the filtrate was concentrated in vacuo. The residue was reconstituted in MeOH and $CH_3CN$, and concentrated in vacuo again to provide the title compound as light-brown solid. MS (+ ion ESI) m/z=161 (M-$NH_3$).

Similarly (4-(R)-amino-choman-7-yl)-methanol and (1-(R)-amino-indan-5-yl)-methanol, and [4-(1(R)-Amino-ethyl)-phenyl]-methanol, (R)-6,7,8,9-tetrahydro-5H-benzo[7]annulen-5-amine, (R)-6-chloro-1,2,3,4-tetrahydro naphthalen-1-amine, (R)-6-methoxy-1,2,3,4-tetrahydronaphthalen-1-amine, (R)-6-fluoro-1,2,3,4-tetrahydronaphthalen-1-amine, (R)-6-acetylamino-1,2,3,4-tetrahydronaphthalen-1-amine, (R)-7-methoxy-1,2,3,4-tetrahydronaphthalen-1-amine, (R)-7-amino-1,2,3,4-tetrahydronaphthalen-1-amine, (R)-7-chloro-3,4-dihydro-2H-chomen-4-amine, (R)-7-fluoro-3,4-dihydro-2H-chomen-4-amine, (R)-7-methoxy-3,4-dihydro-2H-chomen-4-amine, and (R)-6-fluoro-3,4-dihydro-2H-chomen-4-amine (in some cases the reduction of the azide to amine was accomplished using $SnCl_2$ or $PPh_3$) were prepared.

EXAMPLE 3

Preparation of 4-(R)-amino-3,4-tetrahydro-1-benzothiopyran-1,1(2H)-dione

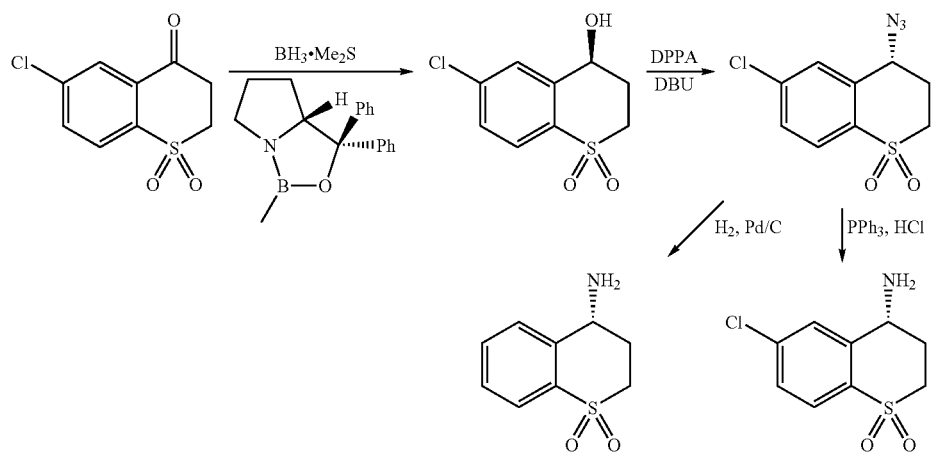

69

Preparation of 6-chloro-4-(R)-amino-3,4-tetrahydro-1-benzothiopyran-1,1(2H)-dione: To 6-chloro-4-(R)-azido-3,4-tetrahydro-1-benzothiopyran-1,1(2H)-dione (prepared according to procedures similar to Example 2) in 15 mL of dry THF at 0° C. was added triphenylphosphine. After triphenylphosphine was completely dissolved, 2 mL of 2N HCl solution was added dropwise. The reaction was stirred at 0° C. for 0.5 h and then at room temperature overnight. It was then quenched with Sat. $Na_2CO_3$ solution, extracted with EtOAc, dried over $Na_2SO_4$, filtered, and evaporated to dryness. Flash chomatography ($SiO_2$, DCM to DCM/MeOH=100:5 to 10:1 to 5:1) afforded the amine.

Preparation of 4-(R)-amino-3,4-tetrahydro-1-benzothiopyran-1,1 (2H)-dione: To a solution of 6-chloro-4-(R)-azido-3,4-tetrahydro-1-benzothiopyran-1,1(2H)-dione (230 mg, 893 µmol) in 20 mL of EtOAc was added palladium 10% on carbon (30 mg, 282 µmol) and the resulting solution was stirred under $H_2$ atmosphere at RT for 30 h. The solvent was evaporated and the residue was submitted to CC ($SiO_2$, EtOAc to EtOAc/MeOH=10:1 to 10:3) to give the desired product as a sticky oil. It became white solid upon standing.

EXAMPLE 4

Preparation of 2,2-dimethyl-3,4-dihydro-2H-chomen-4-amine and 2,2-dimethyl-2,3-dihydrochomen-4-one: A solution of 1-(2-hydroxyphenyl)ethanone (4.1 g, 30 mmol), propan-2-one (2.6 g, 45 mmol), and pyrrolidine (3.2 g, 45 mmol) in 100 mL of MeOH was stirred at RT overnight. The solution was concentrated to give a red oil. Water was added and the solution was adjusted to pH 1 with 5N HCl. The product was extracted with ether. The organic layer was washed with brine, dried over $Na_2SO_4$, filtered, and evaporated to give 2,2-dimethyl-2,3-dihydrochomen-4-one as a white solid.

Preparation of 2,2-dimethyl-3,4-dihydro-2H-chomen-4-ol: To a solution of 2,2-dimethyl-2,3-dihydrochomen-4-one (2.80 g, 15.9 mmol) in 60 mL of MeOH was added sodium borohydride (0.560 ml, 15.9 mmol) and the resulting solution was stirred at RT for 1 h. 20 mL of Sat. $NH_4Cl$ was added and the MeOH was evaporated. The residue was diluted with water, extracted with EtOAc, washed with water, dried over $Na_2SO_4$, filtered, and evaporated to give 2,2-dimethyl-3,4-dihydro-2H-chomen-4-ol as a sticky oil.

Preparation of 2,2-dimethyl-3,4-dihydro-2H-chomen-4-amine: To a solution of 4-azido-2,2-dimethyl-3,4-dihydro-2H-chomene (700 mg, 3444 µmol) in 15 mL of MeOH was added Tin(II) chloride dihydrate (1243 mg, 5511 µmol) and the resulting solution was stirred at RT for 14 h. The solvent was evaporated and the residue was treated with Sat. $NaHCO_3$, filtered though Celite with EtOAc. The filtrate was evaporated and submitted to CC ($SiO_2$, EtOAc to EtOAc/MeOH=10:1 to 10:3) to give 2,2-dimethyl-3,4-dihydro-2H-chomen-4-amine as a white solid.

Similarly, 7-fluoro-2,2-dimethyl-3,4-dihydro-2H-chomen-4-amine, 7-methoxy-2,2-dimethyl-3,4-dihydro-2H-chomen-4-amine, 6-methoxy-2,2-dimethyl-3,4-dihydro-2H-chomen-4-amine, 5-methoxy-2,2-dimethyl-3,4-dihydro-2H-chomen-4-amine, 8-methoxy-2,2-dimethyl-3,4-dihydro-2H-chomen-4-amine, 7-chloro-2,2-dimethyl-3,4-dihydro-2H-chomen-4-amine, 7-bromo-2,2-dimethyl-3,4-dihydro-2H-chomen-4-amine, and 6,8-dichloro-2,2-dimethyl-3,4-dihydro-2H-chomen-4-amine were prepared.

70

EXAMPLE 5

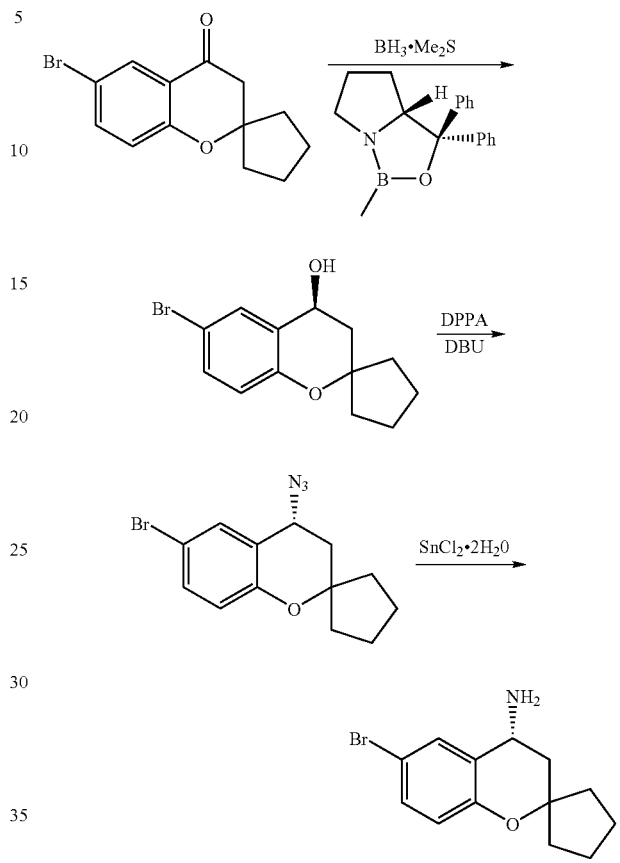

$BH_3.SMe_2$ (1.34 mL, 14.1 mmol) was added dropwise to a solution of CBS (0.6 mL, 1M solution in toluene) in dry toluene (12 mL) at −10° C. Then a solution of the ketone in 20 mL of dry THF was added dropwise over 0.5 h at the same temperature. After stirring at −10° C. to RT for 2 h, the reaction solution was cooled to −10° C. and quenched with 4 mL of MeOH (a lot of gas was generated during the quenching). The quenched reaction solution was evaporated to dryness and was directly submitted to column chomatography ($SiO_2$, hexane to DCM) to give the alcohol as a white solid.

Step 2: To a solution of the alcohol (3.18 g, 11.24 mmol) in toluene (30 mL) at −10° C. was added DPPA (2.92 mL, 13.5 mmol). To this stirred solution was then added DBU (2.02 mL, 13.5 mmol) dropwise while keeping the temperature below 0° C. After stirring at room temperature for 16 h, the reaction was evaporated to dryness and directly submitted to flash chomatography ($SiO_2$, hexane/EtOAc=10:1) to afford the azide as a white solid.

Step 3: To a solution of the azide (100 mg, 0.325 mmol) in 5 mL of MeOH at RT was added Tin(II) chloride. The reaction was stirred at RT for 4 h. It was then quenched with Sat. $Na_2CO_3$ solution, filtered though celite with EtOAc, dried over $Na_2SO_4$, filtered, and evaporated to dryness. Flash chomatography ($SiO_2$, EtOAc to EtOAc/2M $NH_3$ in MeOH=100:10 to 1100:20 to 100:30) afforded the desired amine as a white solid.

EXAMPLE 6

Preparation of (R)-3-isobutyl-1,2,3,4,7,8,9,10-octahydrobenzo[f]isoquinolin-7-amine

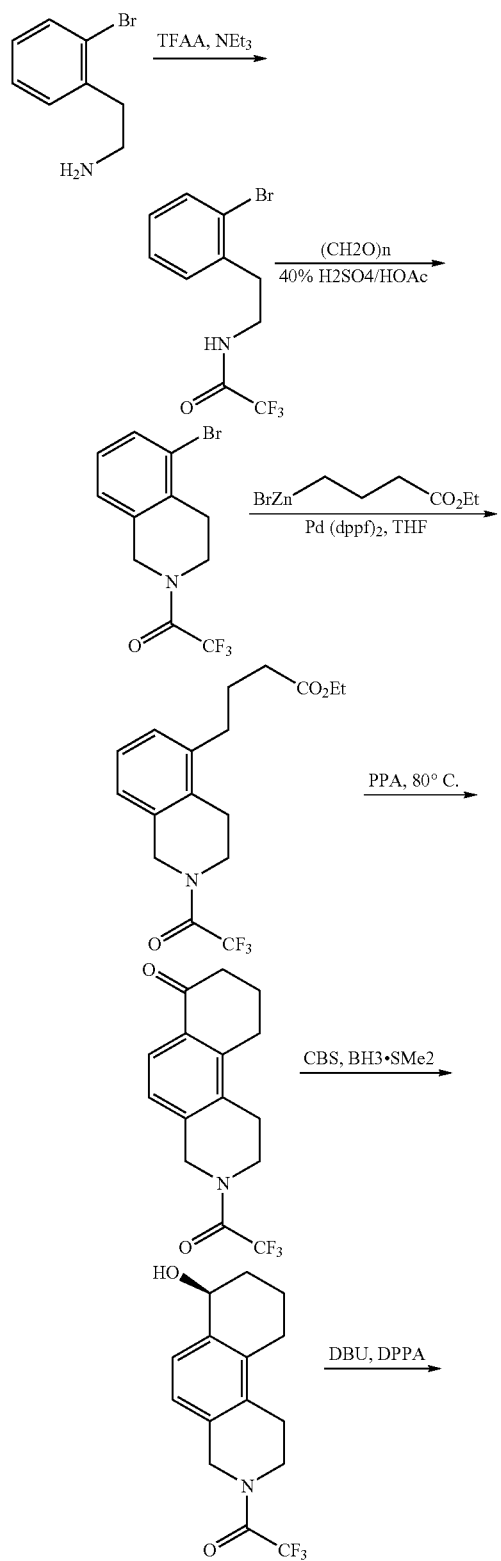

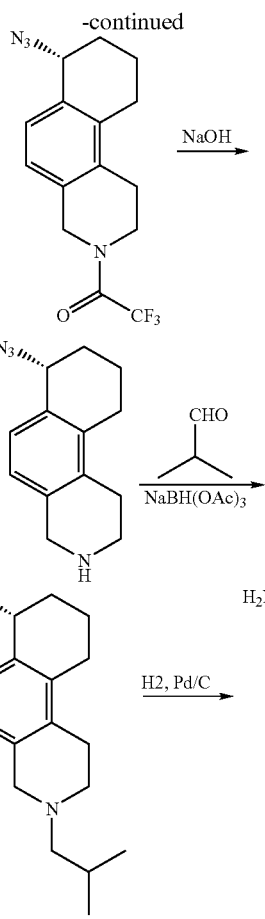

Preparation of 2-(2-bromophenyl)ethanamine: To a solution of 2-(2-bromophenyl)-ethanamine (10 g, 50 mmol) and NEt3 (13.9 mL, 100 mmol) in 50 mL of dry THF at room temperature was slowly added TFAA (7.76 mL, 55 mmol). After stirring at room temperature for 1 h, the reaction mixture was quenched with Sat. $NaHCO_3$ solution, extracted with EtOAc, washed with brine, dried over $Na_2SO_4$, and evaporated in vacuo to give of N-(2-bromophenethyl)-2,2,2-trifluoroacetamide as a white solid.

Preparation of 1-(5-bromo-3,4-dihydroisoquinolin-2(1H)-yl)-2,2,2-trifluoro-ethanone: To a suspension of N-(2-bromophenethyl)-2,2,2-trifluoroacetamide (8.88 g, 30 mmol) and paraformaldehyde (13.5 g, 0.45 mol) in 45 mL of glacial acetic acid at room temperature was slowly added 30 mL of sulfuric acid (96.6%). After stirring at room temperature overnight, the reaction mixture was quenched with ice water and extracted with EtOAc, washed with brine and Sat. $NaHCO_3$ and dried over $Na_2SO_4$. After concentration, flash chomatography ($SiO_2$, hexane/DCM=1:1) gave of 1-(5-bromo-3,4-dihydroisoquinolin-2(1H)-yl)-2,2,2-trifluoroethanone as a white solid.

Preparation of ethyl 4-(2-(2,2,2-trifluoroacetyl)-1,2,3,4-tetrahydroisoquinolin-5-yl)butanoate: A mixture of 1-(5-bromo-3,4-dihydroisoquinolin-2(1H)-yl)-2,2,2-trifluoroethanone (4.0 g, 13 mmol) and $Pd(dppf)Cl_2 \cdot CH_2Cl_2$ (530 mg, 0.65 mmol) was azeotroped with benzene and suspended in 50 mL of dry THF. At room temperature, 4-ethoxy-4-oxobutylzinc bromide (0.5M in THF, 52 mL, 26 mmol) was added dropwise with syringe. The orange suspension became a clear brown solution. The reaction mixture was then refluxed for 1 h. After cooling to room temperature, it was quenched with brine, extracted with EtOAc, washed with 10% HCl and brine, dried over Na$_2$SO$_4$, and evaporated to dryness. Flash chomatography (SiO$_2$, EtOAc/hexane=15:100 to 20:100) gave ethyl 4-(2-(2,2,2-trifluoroacetyl)-1,2,3,4-tetrahydroisoquinolin-5-yl)butanoate as a white solid.

Preparation of 3-(2,2,2-trifluoroacetyl)-1,2,3,4,9,10-hexahydrobenzo[f]isoquinolin-7(8H)-one: A solution of ethyl 4-(2-(2,2,2-trifluoroacetyl)-1,2,3,4-tetrahydro-isoquinolin-5-yl)butanoate (3.98 g, 11.6 mmol) in 10 mL of PPA was stirred at 80° C. for 1 h. After cooling to room temperature, the reaction was quenched with ice-water, extracted with DCM, washed with water, dried over Na$_2$SO$_4$ and evaporated. Flash chomatography (SiO$_2$, hexane/EtOAc=3:1 to 2:1) gave 3-(2,2,2-trifluoroacetyl)-1,2,3,4,9,10-hexahydrobenzo[f]isoquinolin-7(8H)-one as a white solid.

Preparation of (S)-2,2,2-trifluoro-1-(7-hydroxy-1,2,7,8,9,10-hexahydrobenzo[f]-isoquinolin-3(4H)-yl)ethanone: To a solution of (R)-2-methyl-CBS-oxazaborolidine (1M solution in toluene, 0.1 mL, 0.1 mmol) in 3 mL of toluene at −10 ° C. was added BH$_3$.SMe$_2$ (0.23 mL, 2.4 mmol). To this stirred solution was then added 3-(2,2,2-trifluoroacetyl)-1,2,3,4,9,10-hexahydrobenzo[f]isoquinolin-7(8H)-one (594 mg, 2 mmol) in 5 mL of dry THF dropwise while keeping the temperature around −10° C. After stirring at room temperature for 2 h, the reaction mixture was cooled down to −5 ° C. and was quenched with 1 ML of MeOH and was then evaporated to dryness and directly submitted to flash chomatography (SiO$_2$, hexane/EtOAc=2:1 to 1:1) to afford (S)-2,2,2-trifluoro-1-(7-hydroxy-1,2,7,8,9,10-hexahydrobenzo[f]isoquinolin-3(4H)-yl)ethanone as a white solid.

Preparation of (R)-1-(7-azido-1,2,7,8,9,10-hexahydrobenzo[f]isoquinolin-3(4H)-yl)-2,2,2-trifluoroethanone: To a solution of (S)-2,2,2-trifluoro-1-(7-hydroxy-1,2,7,8,9,10-hexahydrobenzo[f]isoquinolin-3(4H)-yl)ethanone (299 mg, 1 mmol) in 3 mL of toluene at −10° C. was added DPPA (0.26 mL, 1.2 mmol). To this stirred solution was then added DBU (0.18 mL, 1.2 mmol) dropwise while keeping the temperature below 0° C. After stirring at room temperature for 3 h, 0.5 mL of 10% HCl was added and the resulting solution was evaporated to dryness and directly submitted to flash chomatography (SiO$_2$, hexane/EtOAc=100:10 to 100:15 to 100:18) to afford (R)-1-(7-azido-1,2,7,8,9,10-hexahydrobenzo[f]-isoquinolin-3(4H)-yl)-2,2,2-trifluoroethanone as a colorless oil which was directly used in the next step.

Preparation of (R)-7-azido-1,2,3,4,7,8,9,10-octahydrobenzo[f]isoquinoline: A solution of (R)-1-(7-azido-1,2,7,8,9,10-hexahydrobenzo[f]isoquinolin-3(4H)-yl)-2,2,2-trifluoroethanone(972 mg, 3.0 mmol) and NaOH (240 mg, 6 mmol) in 21 mL of THF/MeOH/H2O (10/10/1) was stirred at RT for 4 h. The solvent was evaporated and the residue was submitted to flash chomatograph (SiO$_2$, EtOAc/MeOH=100:10 to 100:20 to 100:30) to give (R)-7-azido-1,2,3,4,7,8,9,10-octahydrobenzo[f]isoquinoline as a colorless oil.

Preparation of (R)-7-azido-3-isobutyl-1,2,3,4,7,8,9,10-octahydrobenzo[f]-isoquinoline: To a solution of (R)-7-azido-1,2,3,4,7,8,9,10-octahydrobenzo[f]-isoquinoline (480 mg, 2.0 mmol) and isobutylaldehyde (432 mg, 6 mmol) in 10 mL of dichloroethane was added sodium triacetoxyborohydride (848 mg, 4.0 mmol). After stirring overnight at room temperature, the reaction solution was diluted with EtOAc and washed with sat. NaHCO$_3$ and brine. The organic phase was dried over Na$_2$SO$_4$ and evaporated to dryness in vacuo. Flash chomatography (SiO$_2$, EtOAc) afforded (R)-7-azido-3-isobutyl-1,2,3,4,7,8,9,10-octahydrobenzo[f]isoquinoline as a colorless oil.

Preparation of (R)-3-isobutyl-1,2,3,4,7,8,9,10-octahydrobenzo[f]isoquinolin-7-amine: A suspension of 30 mg of Pd/C (10% w/w) in a solution of (R)-7-azido-3-isobutyl-1,2,3,4,7,8,9,10-octahydrobenzo[f]isoquinoline (296 mg, 1 mmol) in 30 mL of EtOAc was stirred under H2 atmosphere overnight. The reaction mixture was then directly submitted to flash chomatograph (SiO$_2$, EtOAc to EtOAc/2M NH3 in MeOH=100:15 to 100:25 to 100:35) to give (R)-3-isobutyl-1,2,3,4,7,8,9,10-octahydrobenzo[f]isoquinolin-7-amine as a colorless oil.

EXAMPLE 7

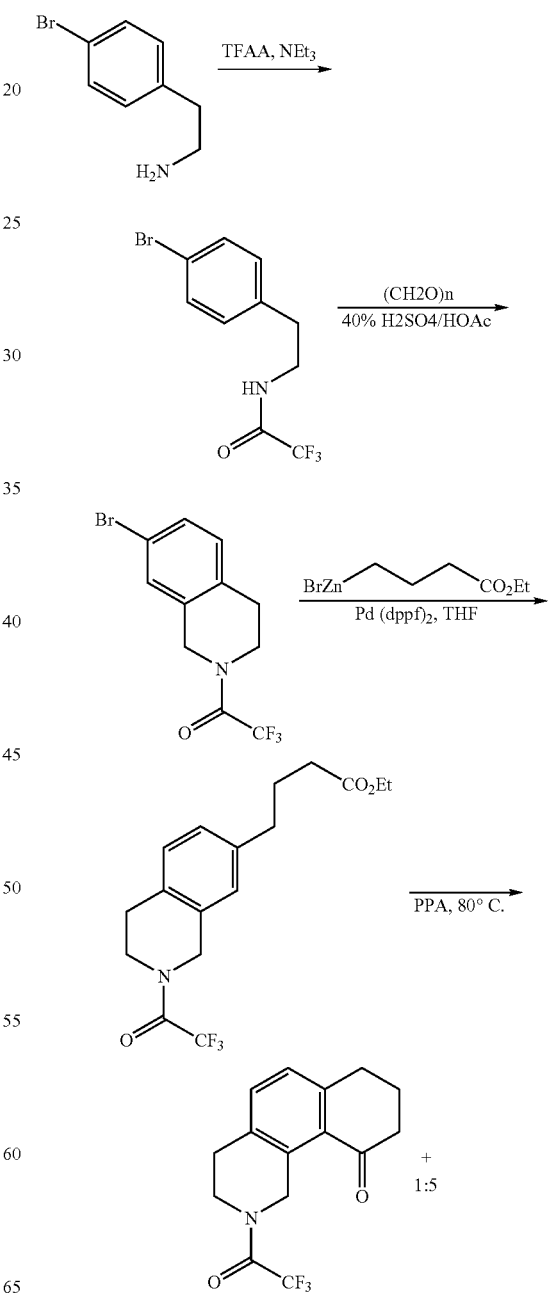

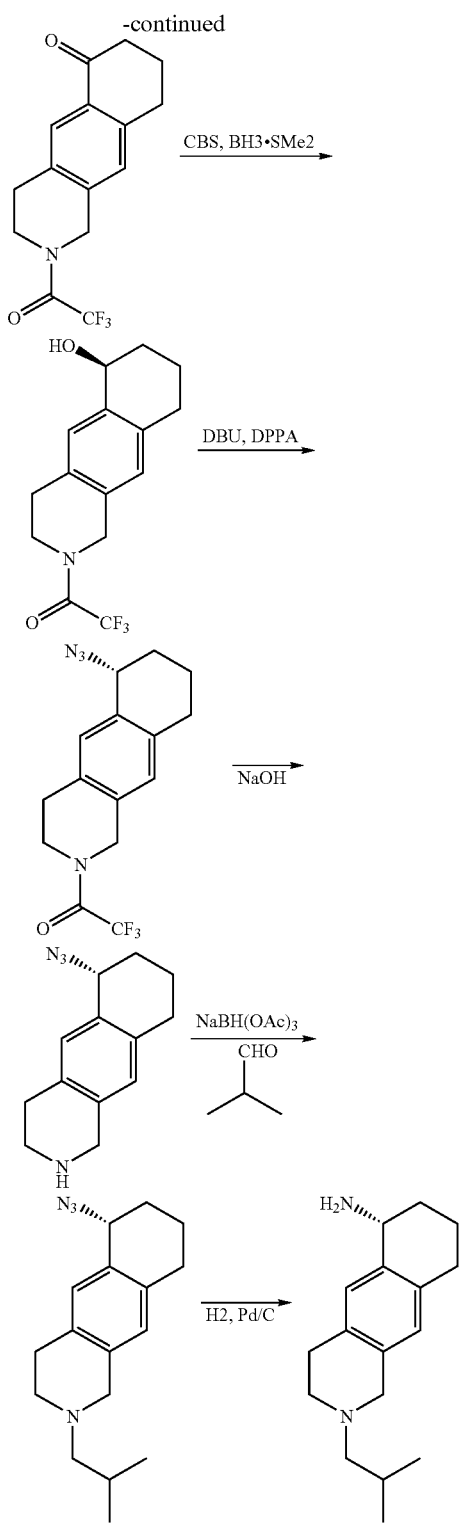

and evaporated in vacuo to give N-(4-bromophenethyl)-2,2,2-trifluoroacetamide as a white solid.

Preparation of 1-(7-bromo-3,4-dihydroisoquinolin-2(1H)-yl)-2,2,2-trifluoro-ethanone: To a suspension of N-(4-bromophenethyl)-2,2,2-trifluoroacetamide (8.88 g, 30 mmol) and paraformaldehyde (13.5 g, 0.45 mol) in 45 mL of glacial acetic acid at room temperature was slowly added 30 mL of sulfuric acid (96.6%). After stirring at room temperature overnight, the reaction mixture was quenched with ice water and extracted with EtOAc, washed with brine and Sat. NaHCO$_3$ and dried over Na$_2$SO$_4$. After concentration, flash chomatography (SiO$_2$, hexane/DCM=1:1) gave 1-(7-bromo-3,4-dihydroisoquinolin-2(1H)-yl)-2,2,2-trifluoroethanone as a white solid.

Preparation of ethyl 4-(2-(2,2,2-trifluoroacetyl)-1,2,3,4-tetrahydroisoquinolin-7-yl)butanoate: A mixture of 1-(7-bromo-3,4-dihydroisoquinolin-2(1H)-yl)-2,2,2-trifluoroethanone (5.34 g, 17.3 mmol) and Pd(dppf)Cl$_2$.CH$_2$Cl$_2$ (708 mg, 0.867 mmol) was azeotroped with benzene and suspended in 50 mL of dry THF. At room temperature, 4-ethoxy-4-oxobutylzinc bromide (0.5M in THF, 52 mL, 26 mmol) was added dropwise with syringe. The orange suspension became a clear brown solution. The reaction mixture was then refluxed for 2 h. After cooling to room temperature, it was quenched with brine, extracted with EtOAc, washed with 10% HCl and brine, dried over Na$_2$SO$_4$, and evaporated to dryness. Flash chomatography (SiO$_2$, EtOAc/hexane=15:100 to 20:100) gave ethyl 4-(2-(2,2,2-trifluoroacetyl)-1,2,3,4-tetrahydroisoquinolin-7-yl)butanoate as a white solid.

Preparation of 2-(2,2,2-trifluoroacetyl)-1,2,3,4,8,9-hexahydrobenzo[h]isoquinolin-10(7H)-one and 2-(2,2,2-trifluoroacetyl)-1,2,3,4,8,9-hexahydrobenzo[g]-isoquinolin-6(7H)-one: A solution of ethyl 4-(2-(2,2,2-trifluoroacetyl)-1,2,3,4-tetrahydroisoquinolin-7-yl)butanoate (5.73 g, 16.7 mmol) in 15 mL of PPA was stirred at 80° C. for 2 h. After cooling to room temperature, the reaction was quenched with ice-water, extracted with DCM, washed with water, dried over Na$_2$SO$_4$ and evaporated. Flash chomatography (SiO$_2$, hexane/EtOAc=5:1 to 4:1 to 3:1 to 2:1) gave 2-(2,2,2-trifluoroacetyl)-1,2,3,4,8,9-hexahydrobenzo[h]-isoquinolin-10(7H)-one (the first fraction from column) as a white solid and 2-(2,2,2-trifluoroacetyl)-1,2,3,4,8,9-hexahydrobenzo[g]isoquinolin-6(7H)-one (the second fraction from column) as a white solid.

Preparation of (S)-2,2,2-trifluoro-1-(6-hydroxy-3,4,6,7,8,9-hexahydrobenzo[g]-isoquinolin-2(1H)-yl)ethanone: To a solution of (R)-2-methyl-CBS-oxazaborolidine (1M solution in toluene, 0.56 mL, 0.56 mmol) in 15 mL of toluene at −10° C. was added BH$_3$.SMe$_2$ (1.27 mL, 13.38 mmol). To this stirred solution was then added 2-(2,2,2-trifluoroacetyl)-1,2,3,4,8,9-hexahydrobenzo[g]-isoquinolin-6(7H)-one(3.31 g, 11.15 mmol)in 5 mL of dry THF dropwise while keeping the temperature around −10° C. After stirring at room temperature for 2 h, the reaction mixture was cooled down to −10° C. and was quenched with 6 mL of MeOH and was then evaporated to dryness and directly submitted to flash chomatography (SiO$_2$, hexane/EtOAc=3:1 to 2:1 to 1:1) to afford (S)-2,2,2-trifluoro-1-(6-hydroxy-3,4,6,7,8,9-hexahydrobenzo[g]isoquinolin-2(1H)-yl)ethanone as a white solid.

Preparation of (R)-1-(6-azido-3,4,6,7,8,9-hexahydrobenzo[g] isoquinolin-2(1H)-yl)-2,2,2-trifluoroethanone: To a solution of (S)-2,2,2-trifluoro-1-(6-hydroxy-3,4,6,7,8,9-hexahydrobenzo[g]isoquinolin-2(1H)-yl)ethanone (3.0 g, 10 mmol) in 30 mL of toluene at −10° C. was added DPPA (2.6 mL, 12 mmol). To this stirred solution was then added DBU (1.8 mL, 12 mmol) dropwise while keeping the temperature below 0° C. After stirring at room temperature overnight, 7

Preparation of N-(4-bromophenethyl)-2,2,2-trifluoroacetamide: To a solution of 2-(4-bromophenyl)ethanamine (10 g, 50 mmol) and NEt3 (13.9 mL, 100 mmol) in 50 mL of dry THF at room temperature was slowly added TFAA (7.76 mL, 55 mmol). After stirring at room temperature for 1 h, the reaction mixture was quenched with Sat. NaHCO$_3$ solution, extracted with EtOAc, washed with brine, dried over Na$_2$SO$_4$, mL of 10% HCl was added and the resulting solution was evaporated to dryness and directly submitted to flash chomatography (SiO$_2$, hexane/EtOAc=100:10 to 100:15 to 100:20) to afford (R)-1-(6-azido-3,4,6,7,8,9-hexahydrobenzo[g]-isoquinolin-2(1H)-yl)-2,2,2-trifluoroethanone as a colorless oil which was directly used in the next step.

Preparation of Preparation of (R)-6-azido-1,2,3,4,6,7,8,9-octahydrobenzo[g]-isoquinoline: A solution of (R)-1-(6-azido-3,4,6,7,8,9-hexahydrobenzo[g]-isoquinolin-2(1H)-yl)-2,2,2-trifluoroethanone (972 mg, 3.0 mmol) and NaOH (240 mg, 6 mmol) in 21 mL of THF/MeOH/H$_2$O (10/10/1) was stirred at RT for 5 h. The solvent was evaporated and the residue was submitted to flash chomatograph (SiO$_2$, EtOAc/MeOH=100:10 to 100:20 to 100:30) to give (R)-6-azido-1,2,3,4,6,7,8,9-octahydrobenzo[g]isoquinoline as a colorless oil.

Preparation of (R)-6-azido-2-isobutyl-1,2,3,4,6,7,8,9-octahydrobenzo[g]isoquinoline: To a solution of (R)-6-azido-1,2,3,4,6,7,8,9-octahydrobenzo[g]-isoquinoline (480 mg, 2.0 mmol) and isobutylaldehyde (432 mg, 6 mmol) in 10 mL of dichloroethane was added sodium triacetoxyborohydride (848 mg, 4.0 mmol). After stirring overnight at room temperature, the reaction solution was diluted with EtOAc and washed with sat. NaHCO$_3$ and brine. The organic phase was dried over Na$_2$SO$_4$ and evaporated to dryness in vacuo. Flash chomatography (SiO$_2$, EtOAc) afforded (R)-6-azido-2-isobutyl-1,2,3,4,6,7,8,9-octahydrobenzo[g]isoquinoline as a colorless oil.

Preparation of (R)-2-isobutyl1,2,3,4,6,7,8,9-octahydrobenzo[g]isoquinolin-6-amine: A suspension of 30 mg of Pd/C (10% w/w) in a solution of (R)-6-azido-2-isobutyl-1,2,3,4,6,7,8,9-octahydrobenzo[g]isoquinoline (296 mg, 1 mmol) in 30 mL of EtOAc was stirred under H2 atmosphere overnight. The reaction mixture was then directly submitted to flash chomatograph (SiO$_2$, EtOAc to EtOAc/2M NH3 in MeOH=100:15 to 100:25 to 100:35) to give (R)-2-isobutyl-1,2,3,4,6,7,8,9-octahydrobenzo[g]isoquinolin-6-amine as a colorless oil.

EXAMPLE 8

Preparation of (R)-4-amino-3,4-dihydronaphthalen-1(2H)-one and (R)-N-(1,2,3,4-tetrahydronaphthalen-1-yl)formamide: To a solution of acetic formic anhydride (0.056 mol) (prepared by stirring acetyl anhydride (7.36 ml, 78.0 mmol) and formic acid (2.94 ml, 78.0 mmol) at 50-60° C. for 2 h then cooling to room temperature) was added (r)-1,2,3,4-tetrahydro-1-naphthylamine (8.20 g, 55.7 mmol) dropwise with stirring at such a rate that the temperature never rose above 40° C. After stirring for 30 min, 300 mL of ether was added, and the solution was stirred at room temperature overnight. The reaction was diluted with ether, washed twice with water, twice with Sat. NaHCO$_3$, with 5% HCl, and finally with water. The organic layer was dried with Na$_2$SO$_4$, filtered, and evaporated to dryness. flash chomatograph (SiO$_2$, hexane/EtOAc=1:1 to pure EtOAc) afforded (R)—N-(1,2,3,4-tetrahydronaphtalen-1-yl)formamide as a white solid.

Preparation of (R)—N-(4-oxo-1,2,3,4-tetrahydronaphthalen-1-yl)formamide: To a solution of (R)—N-(1,2,3,4-tetrahydronaphthalen-1-yl)formamide (4.01 g, 22.9 mmol) in 40 mL of acetic anhydride at 0° C. was added Chomium(VI) oxide (6.00 g, 60.0 mmol). The solution was stirred at 0° C. for 1 h. The solution was filtered, extracted with EtOAc, washed with brine, dried over Na$_2$SO$_4$ and evaporated to dryness. flash chomatograph (SiO$_2$, EtOAc/hexane=1:1 to 2:1 to pure EtOActo EtOAc/MeOH=10:1 to 10:2) afforded (R)—N-(4-oxo-1,2,3,4-tetrahydro-naphthalen-1-yl)formamide as a white solid.

Preparation of (R)-4-amino-3,4-dihydronaphthalen-1(2H)-one: A solution of (R)—N-(4-oxo-1,2,3,4-tetrahydronaphthalen-1-yl)formamide (45 mg, 238 µmol) in 5 mL of HCl and 5 mL of MeOH was refluxed for 2 h and then stirred at RT overnight. The solvent was evaporated and the residue was neutralized with 10N NaOH and was extracted with EtOAc. The extracts was dried over Na$_2$SO$_4$ and evaporated. flash chomatograph (SiO$_2$, EtOAc to EtOAc/2M NH$_3$ in MeOH=100:10 to 100:20) afforded crude (R)-4-amino-3,4-dihydronaphthalen-1(2H)-one as a sticky oil.

EXAMPLE 9

Preparation of 2-(4-(4H-1,2,4-triazol-3-yl)phenyl)ethanamine

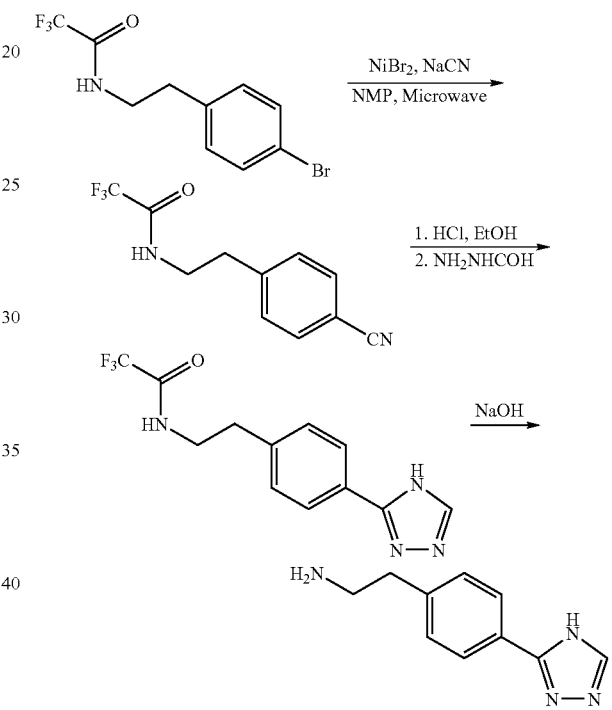

Preparation of N-(4-cyanophenethyl)-2,2,2-trifluoroacetamide: A mixture of N-(4-bromophenethyl)-2,2,2-trifluoroacetamide (2.96 g, 10 mmol), NiBr$_2$ (2.19 g, 10 mmol) and NaCN (0.98 g, 20 mmol) in 2.0 mL of NMP was heated at 200° C. in microwave twice. After cooling down to RT, the mixture was filtered with the help excess of DCM. The filtrate was evaporated to dryness and was submitted to flash chomatography (SiO$_2$, DCM to DCM/EtOAc=3:1) to give (N-(4-cyanophenethyl)-2,2,2-trifluoroacetamide was a white solid, together with 1.1 g for recovered starting material.

Preparation of N-(4-(4H-1,2,4-triazol-3-yl)phenethyl)-2,2,2-trifluoroacetamide: (N-(4-cyanophenethyl)-2,2,2-trifluoroacetamide (0.61 g, 2.52 mmol) was azeotroped with benzene and was dissolved in 10 mL of anhydrous EtOH. To this solution dry HCl was bubbled though for 90 min at 0 C. The solvent was evaporated to dryness under high vacuum to give a yellow solid. This yellow solid and formohydrazide (151 mg, 2.52 mmol) was dissolved in 10 mL of dry pyridine and the resulting solution was refluxed for 2 h. After cooling to RT, pyridine was evaporated and the residue was treated with 5% HCl, extracted with EtOAc, dried over Na$_2$SO$_4$, filtered, and evaporated to dryness. Flash chomatography (SiO₂, EtOAc/DCM=1:1 to Dcm/MeOH=10:1) afforded N-(4-(4H-1,2,4-triazol-3-yl)phenethyl)-2,2,2-trifluoroacetamide as a white solid.

Preparation of 2-(4-(4H-1,2,4-triazol-3-yl)phenyl)ethanamine: A solution of N-(4-(4H-1,2,4-triazol-3-yl)phenethyl)-2,2,2-trifluoroacetamide (83 mg, 0.292 mmol) and NaOH (29 mg, 0.73 mmol) in a mixed solvent (THF/MeOH/H₂O=2 mL/5 mL/1 mL) was stirred at RT for 2 h. The solvent was evaporated to dryness and the residue was submitted to flash chomatography (SiO₂, EtOAc to EtOAc/2M NH₃ in MeOH=100:20 to 100:50) to give 2-(4-(4H-1,2,4-triazol-3-yl)phenyl)-ethanamine as a colorless oil.

EXAMPLE 10

Preparation of (R)-7-nitro-6-(piperidin-1-ylmethyl)-1,2,3,4-tetrahydronaphthalen-1-amine

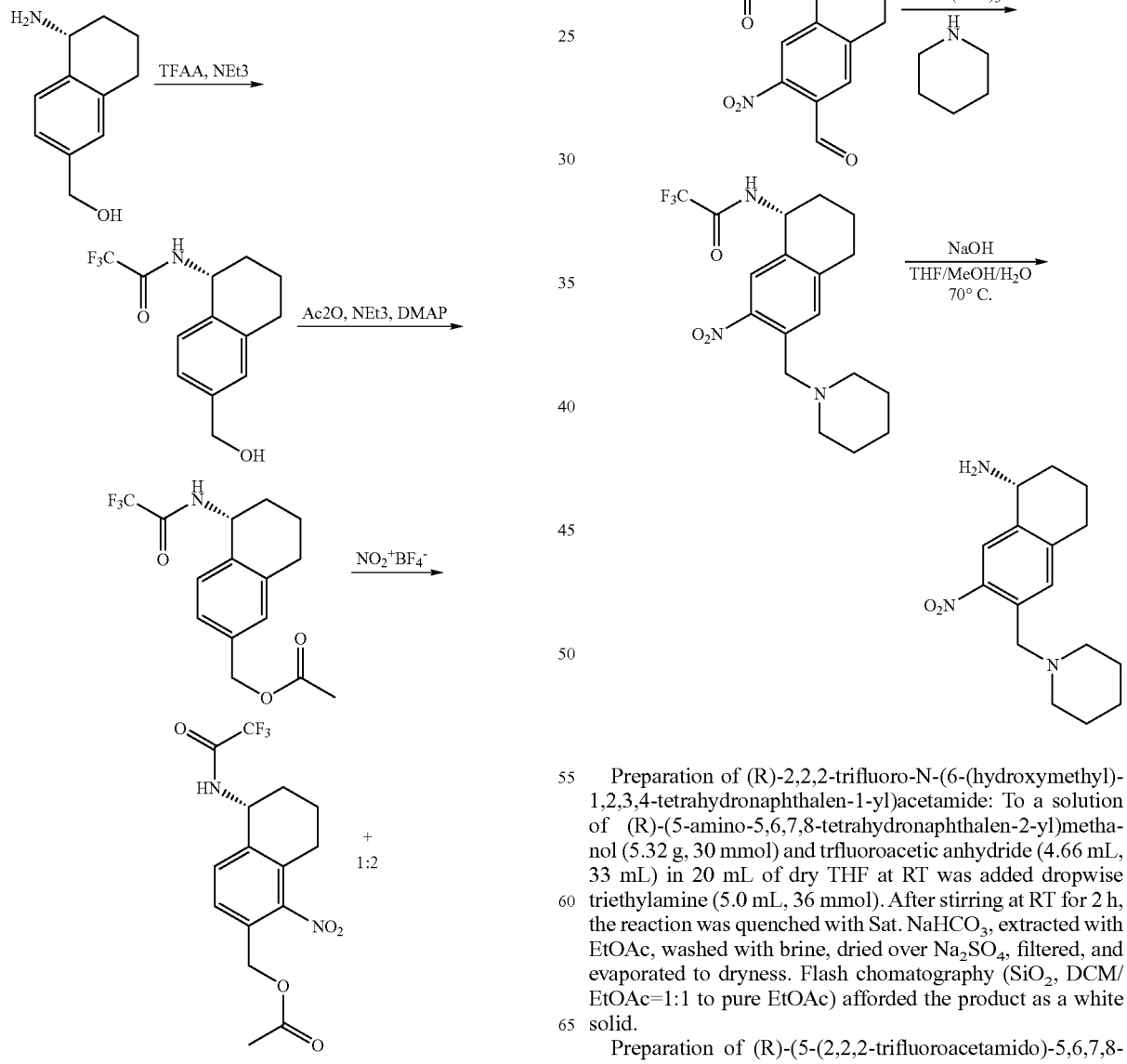

Preparation of (R)-2,2,2-trifluoro-N-(6-(hydroxymethyl)-1,2,3,4-tetrahydronaphthalen-1-yl)acetamide: To a solution of (R)-(5-amino-5,6,7,8-tetrahydronaphthalen-2-yl)methanol (5.32 g, 30 mmol) and trfluoroacetic anhydride (4.66 mL, 33 mL) in 20 mL of dry THF at RT was added dropwise triethylamine (5.0 mL, 36 mmol). After stirring at RT for 2 h, the reaction was quenched with Sat. NaHCO₃, extracted with EtOAc, washed with brine, dried over Na₂SO₄, filtered, and evaporated to dryness. Flash chomatography (SiO₂, DCM/EtOAc=1:1 to pure EtOAc) afforded the product as a white solid.

Preparation of (R)-(5-(2,2,2-trifluoroacetamido)-5,6,7,8-tetrahydronaphthalen-2-yl)methyl acetate: To a solution of (R)-2,2,2-trifluoro-N-(6-(hydroxymethyl)-1,2,3,4-tetrahydronaphthalen-1-yl)acetamide (546 mg, 2 mmol) in 10 mL of dry DCM was added acetic anhydride (0.30 mL, 3 mmol) and triethylamine (0.8 mL, 6 mmol), followed by DMAP (10 mg). After stirring for 2 h at RT, the solution was evaporated to dryness and directly submitted to flash chomatography ($SiO_2$, DCM) to give (R)-(5-(2,2,2-trifluoroacetamido)-5,6,7,8-tetrahydronaphthalen-2-yl)methyl acetate as a white solid.

Preparation of (R)-(1-nitro-5-(2,2,2-trifluoroacetamido)-5,6,7,8-tetrahydronaphthalen-2-yl)methyl acetate and (R)-(3-nitro-5-(2,2,2-trifluoroacetamido)-5,6,7,8-tetrahydronaphthalen-2-yl)methyl acetate: To a solution of (R)-(5-(2,2,2-trifluoroacetamido)-5,6,7,8-tetrahydronaphthalen-2-yl)methyl acetate (160 mg, 0.508 mmol) in 2 mL of MeCN was added $NO_2^+BF_4^-$ (66 mg, 0.508 mmol). After stirring at RT for 20 min, the reaction was quenched with 0.5 mL of Sat. $NaHCO_3$, and the solvent was evaporated to dryness. Flash chomatography ($SiO_2$, DCM/hexane=5:1 to pure DCM) gave (R)-(1-nitro-5-(2,2,2-trifluoroacetamido)-5,6,7,8-tetrahydronaphthalen-2-yl)methyl acetate and (R)-(3-nitro-5-(2,2,2-trifluoroacetamido)-5,6,7,8-tetrahydronaphthalen-2-yl)methyl acetate as white solids.

Preparation of (R)-2,2,2-trifluoro-N-(6-(hydroxymethyl)-7-nitro-1,2,3,4-tetrahydronaphthalen-1-yl)acetamide: To a solution of (R)-(3-nitro-5-(2,2,2-trifluoroacetamido)-5,6,7,8-tetrahydronaphthalen-2-yl)methyl acetate (17 mg) in 10 mL of MeOH was added one drop of 96% $H2SO_4$ and the resulting mixture was stirred at 50° C. for 3 h. After cooling to RT, the reaction was quenched with Sat. $NaHCO_3$ (0.5 mL). The MeOH was evaporated and the residue was directly loaded on column chomatography ($SiO_2$, DCM to DCM/EtOAc=2:1 to 1:1) to give (R)-2,2,2-trifluoro-N-(6-(hydroxymethyl)-7-nitro-1,2,3,4-tetrahydro-naphthalen-1-yl)acetamide as a white solid.

Preparation of (R)-2,2,2-trifluoro-N-(6-formyl-7-nitro-1,2,3,4-tetrahydro-naphthalen-1-yl)acetamide: To a solution of (R)-2,2,2-trifluoro-N-(6-(hydroxymethyl)-7-nitro-1,2,3,4-tetrahydronaphthalen-1-yl)acetamide (350 mg, 1.1 mmol) in 100 mL of DCM was added portion wise $MnO2$ (957 mg, 11 mmol). After stirring at RT for 3 h, the reaction mixture was filtered though silica gel with the help of hexane/EtOAc=1:1 to give ((R)-2,2,2-trifluoro-N-(6-formyl-7-nitro-1,2,3,4-tetrahydronaphthalen-1-yl)acetamide as a white solid.

Preparation of (R)-2,2,2-trifluoro-N-(7-nitro-6-(piperidin-1-ylmethyl)-1,2,3,4-tetrahydronaphthalen-1-yl)acetamide: To a solution of ((R)-2,2,2-trifluoro-N-(6-formyl-7-nitro-1,2,3,4-tetrahydronaphthalen-1-yl)acetamide (350 mg, 1.1 mmol) in 6 mL of 1,2-dichloroethane was added piperidine (187 mg, 2.2 mmol) and $NaBH(OAc)_3$ (350 mg, 1.65 mmol). After stirring at RT overnight, the reaction was quenched with Sat. $NaHCO_3$, extracted with EtOAc, dried over $Na_2SO_4$, filtered, and evaporated to dryness. Flash chomatography ($SiO_2$, EtOAc/hexane=1:1) afforded (R)-2,2,2-trifluoro-N-(7-nitro-6-(piperidin-1-ylmethyl)-1,2,3,4-tetrahydronaphthalen-1-yl)acetamide as a white solid.

Preparation of (R)-7-nitro-6-(piperidin-1-ylmethyl)-1,2,3,4-tetrahydronaphthalen-1-amine: A solution of (R)-2,2,2-trifluoro-N-(7-nitro-6-(piperidin-1-ylmethyl)-1,2,3,4-tetrahydronaphthalen-1-yl)acetamide (230 mg, 0.6 mmol) and NaOH (108 mg, 2.7 mmol) in a mixed solvent (THF/MeOH/$H_2O$=5 mL/5 mL/1 mL) was heated at 70° C. for 3 h. After cooling to RT, the solvent was evaporated to dryness and the residue was directly loaded on column chomatography ($SiO_2$, EtOAc to EtOAc/2M $NH_3$ in MeOH=100:15 to 100:20) to give (R)-7-nitro-6-(piperidin-1-ylmethyl)-1,2,3,4-tetrahydronaphthalen-1-amine (200 mg) as a white solid. Similarly (R)-(1-nitro-5-(2,2,2-trifluoroacetamido)-5,6,7,8-tetrahydronaphthalen-2-yl)methyl acetate was converted to (R)-5-nitro-6-(piperidin-1-ylmethyl)-1,2,3,4-tetrahydronaphthalen-1-amine according to the above sequence of reactions.

EXAMPLE 11

Preparation of (R)-N-methyl-6-(piperidin-1-ylmethyl)-1,2,3,4-tetrahydro-naphthalen-1-amine: (R)-tert-butyl 6-(hydroxymethyl)-1,2,3,4-tetrahydro-naphthalen-1-ylcarbamate. To 30 g (170 mmol) of (R)-(5-amino-5,6,7,8-tetrahydronaphthalen-2-yl)methanol was added 100 mL of ethyl acetate, 100 mL DCM, 100 mL of methanol, and 100 mL of TEA. Next, 62 g of di-t-butyldicarbonate (280 mmol) was slowly added and the mix was stirred under nitrogen overnight. The mix was then concentrated, dissolved in 300 mL of ethyl acetate, and washed with 50 mL of saturated sodium carbonate twice. The ethyl acetate layer was then dried with sodium sulfate and concentrated to give the crude product. Preparation of (R)-tert-butyl 6-formyl-1,2,3,4-tetrahydronaphthalen-1-ylcarbamate: In 200 mL of DCM, 10 g (36 mmol) of (R)-tert-butyl 6-(hydroxymethyl)-1,2,3,4-tetrahydronaphthalen-1-ylcarbamate and 16 g (180 mmol) of manganese oxide were combined and the mix was stirred under nitrogen overnight. The solution was then filtered though celite and the pad was washed with methanol. The filtrate was then concentrated, and the crude was purified on silica using 10 to 40% ethyl acetate in hexane to give the crude product.

Preparation of (R)-tert-butyl 6-(piperidin-1-ylmethyl)-1,2,3,4-tetrahydronaphthalen-1-ylcarbamate: In 100 mL of 1,2-dichloroethane, 5.0 g (18 mmol) of (R)-tert-butyl 6-formyl-1,2,3,4-tetrahydronaphthalen-1-ylcarbamate and 3.1 g (36 mmol) of piperidine were combined. Next, 7.6 g (36 mmol) of sodium triacetoxy borohydride was added and the mix was stirred under nitrogen overnight. The mix was then dissolved in 100 mL of ethyl acetate, washed with 25 mL of saturated sodium bicarbonate, washed with 25 mL of brine, dried with sodium sulfate and concentrated to yield the crude material.

Preparation of (R)-N-methyl-6-(piperidin-1-ylmethyl)-1,2,3,4-tetrahydronaphthalen-1-amine: In 50 mL of dry toluene, 2.0 g (5.8 mmol) of (R)-tert-butyl 6-(piperidin-1-ylmethyl)-1,2,3,4-tetrahydronaphthalen-1-ylcarbamate and 1.5 g (41 mmol) of lithium aluminum hydride were combined and gently refluxed for 24 h. Next the mix was quenched with 5 g of sodium sulfate decahydrate and allowed to stir for 2 h. The mix was then filtered over celite and the pad was washed with ethyl acetate several times. The filtrate was then concentrated and the crude was purified on silica using 0 to 5% MeOH (10% ammonium hydroxide) in ethyl acetate to give the product. MS 259 (ESI, pos. ion).

Similarly, (R)-N-methyl-7-(piperidin-1-ylmethyl)choman-4-amine, (R)-7-((tert-butylamino)methyl)-N-methylchoman-4-amine, and (R)-6-((tert-butylamino)-methyl)-N-methyl-1,2,3,4-tetrahydronaphthalen-1-amine were prepared.

EXAMPLE 12

Preparation of (1R)-6-(1-(piperidin-1-yl)ethyl)-1,2,3,4-tetrahydronaphthalen-1-amine Preparation of tert-butyl(R)-6-(1-(piperidin-1-yl)ethyl)-1,2,3,4-tetrahydro-naphthalen-1-ylcarbamate. Piperidine (3.5 mmol), (R)-tert-butyl 6-acetyl-1,2,3,4-tetrahydronaphthalen-1-ylcarbamate (1.7 mmol), and titanium isopropoxide (2.2 mmol) were combined and stirred for one h. Next the mix was dissolved in 20 mL of methanol and sodium borohydride (1.7 mmol) was added and the mix was stirred for another h.

The methanol was then removed under vacuum. Next, sat. sodium bicarbonate was added (appr. 20 ml), and the mix was extracted with ethyl acetate (2×20 ml). The extracts were washed with brine, dried with sodium sulfate and concentrated. The crude was purified on silica using 0 to 10% MeOH (2M ammonia) in dichloromethane to give the product. MS 359 (ESI, pos. ion) Preparation of (1R)-6-(1-(piperidin-1-yl) ethyl)-1,2,3,4-tetrahydronaphthalen-1-amine: Tert-butyl(R)-6-(1-(piperidin-1-yl)ethyl)-1,2,3,4-tetrahydronaphthalen-1-ylcarbamate (475 mg), was dissolved in 20 ml of DCM, then trifluoroacetic acid (1500 mg) was added and the mix was stirred overnight. The mix was concentrated, dried under vacuum, then quenched with sodium bicarbonate making sure the pH was basic. The solution was then extracted with ethyl acetate, dried with sodium sulfate and concentrated to give the product. MS 259 (ESI, pos. ion).

EXAMPLE 13

Preparation of (1R)-6-(1-(tert-butylamino)ethyl)-1,2,3,4-tetrahydronaphthalen-1-amine Preparation of tert-butyl(R)-6-(1-(tert-butylamino)ethyl)-1,2,3,4-tetrahydro-naphthalen-1-ylcarbamate. T-butyl amine (3.5 mmol), (R)-tert-butyl 6-acetyl-1,2,3,4-tetrahydronaphthalen-1-ylcarbamate (1.7 mmol), and titanium isopropoxide (2.2 mmol) were combined and stirred for one h. Next the mix was dissolved in 20 mL of methanol and sodium borohydride (1.7 mmol) was added and the mix was stirred for another h. The methanol was then removed under vacuum. Next, sat. sodium bicarbonate was added (appr. 20 ml), and the mix was extracted with ethyl acetate (2×20 ml). The extracts were washed with brine, dried with sodium sulfate and concentrated. The crude was purified on silica using 0 to 10% MeOH (2M ammonia) in dichloromethane to give the product. MS 347 (ESI, pos. ion).

Preparation of (1R)-6-(1-(tert-butylamino)ethyl)-1,2,3,4-tetrahydronaphthalen-1-amine: Tert-butyl(R)-6-(1-(tert-butylamino)ethyl)-1,2,3,4-tetrahydronaphthalen-1-ylcarbamate. (275 mg), was dissolved in 20 ml of DCM, then trifluoroacetic acid (900 mg) was added and the mix was stirred overnight. The mix was concentrated, dried under vacuum, then quenched with sodium bicarbonate making sure the pH was basic. The solution was then extracted with ethyl acetate, dried with sodium sulfate and concentrated to give the product. MS 247 (ESI, pos. ion)

EXAMPLE 14

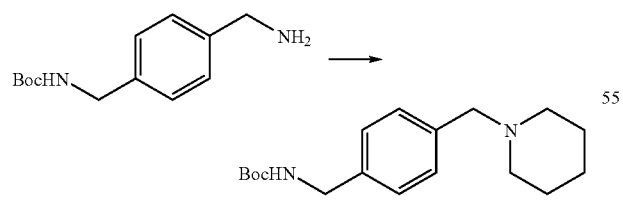

Preparation of (4-Piperidin-1-ylmethyl-benzyl)-carbamic acid tert-butyl ester: The mixture of (4-aminomethyl-benzyl)-carbamic acid tert-butyl ester (4.06 g, 17.2 mmol), 1,5-dibromo-pentane (2.60 mL, 19.1 mmol) and potassium carbonate (8.96 g, 65.1 mmol) in acetonitrile (160 mL) was refluxed overnight under $N_2$. The reaction was cooled to r.t. and filtered. The filtrate was concentrated in vacuo and chomatographed on silica ($CH_2Cl_2 \rightarrow CH_2Cl_2$/MeOH with 2N $NH_3$=25/1) to yield the desired product.

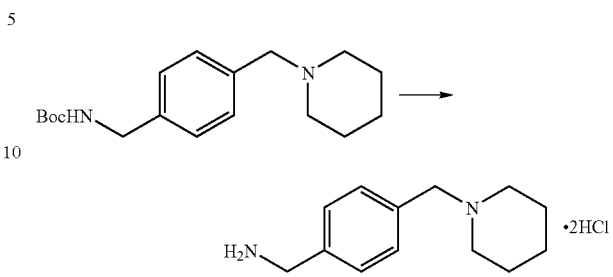

Preparation of 4-Piperidin-1-ylmethyl-benzylamine: The above product (1.32 g, 4.33 mmol) was dissolved in 4M HCl in 1,4-dioxane (40 mL) and methanol (40 mL) and stirred for 2.5 h. The reaction was concentrated in vacuo to yield the desired product (1.20 g, 99%) as dihydrochloride salt.

EXAMPLE 15

N—((R)-6-((cyclopropylamino)methyl)-1,2,3,4-tetrahydronaphthalen-1-yl)-2-((R)-3-oxo-1-tosyl-1,2,3,4-tetrahydropyrazin-2-yl)acetamide

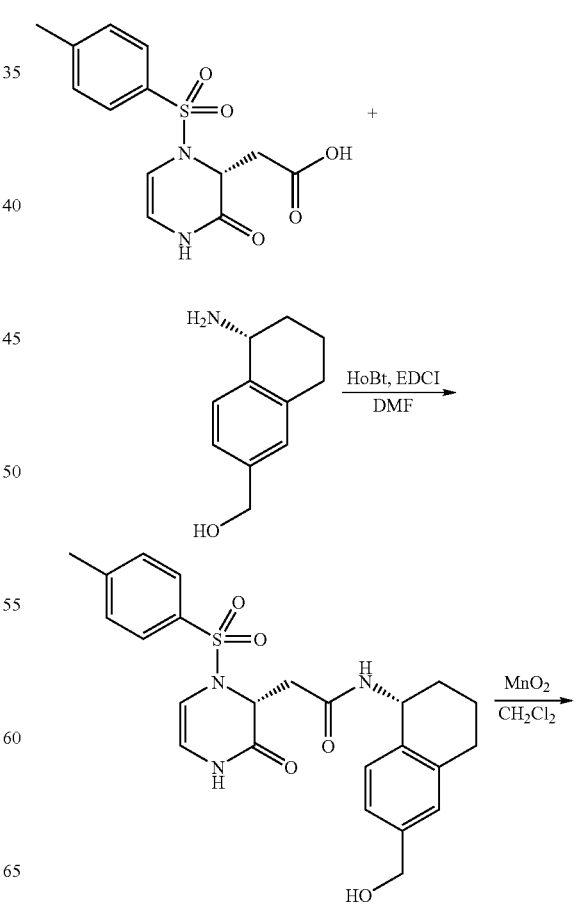

-continued

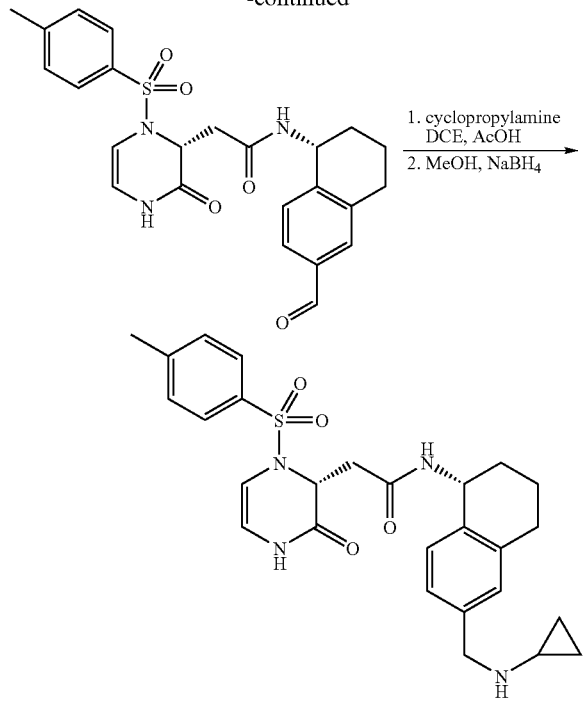

Step 1: (R)-2-(3-oxo-1-tosyl-1,2,3,4-tetrahydropyrazin-2-yl)acetic acid (6 g, 19.33 mmol) was dissolved in anhydrous DMF (100 mL). (R)-(5-Amino-5,6,7,8-tetrahydronaphthalen-2-yl)methanol (3.77 g, 21.27 mmol) and HOBt (Aldrich, 3.14 g, 23.20 mmol) were added followed by EDCI (Aldrich, 4.45 g, 23.20 mmol). The mixture was stirred at RT for 5 h. EtOAc (250 mL) was added and the solution was washed with saturated sodium bicarbonate/brine (2×200 mL), then with 10% HCl/brine (200 mL), then with brine (200 mL). It was concentrated and dried in vacuo to give the desired product.

Step 2: The above compound (7.55 g, 16.08 mmol) was dissolved in 110 mL $CH_2Cl_2$, then manganese dioxide (13.98 g, 160.8 mmol) was added. The mixture was stirred at RT for 7 h. It was filtered though a celite pad and washed with $CH_2Cl_2$, then with MeOH. The filtrate was concentrated and dried in vacuo to give the desired product.

Step 3: To a solution of the above compound (1.00 g, 2.14 mmol) and cyclopropylamine (Aldrich, 0.374 g, 6.42 mmol) in DCE (20 mL) was added glacial acetic acid (0.25 mL) and the solution was stirred for 1 h at RT. MeOH (20 mL) and sodium borohydride (0.405 g, 10.69 mmol) were added and the mixture stirred for 15 min. $CH_2Cl_2$ (100 mL) was added and the solution was rinsed with $H_2O$ (100 mL) and then rinsed with brine (100 mL). It was concentrated and dried in vacuo to give the crude product. It was purified by column chomatography (5% MeOH/$CH_2Cl_2$, silica gel) to give N-(6-((cyclopropylamino)methyl)-1,2,3,4-tetrahydronaphthalen-1-yl)-2-(3-oxo-1-tosyl-1,2,3,4-tetrahydropyrazin-2-yl)acetamide.

Similarly, 2-((R)-4-methyl-3-oxo-1-tosyl-1,2,3,4-tetrahydropyrazin-2-yl)-N—((R)-6-(piperidin-1-ylmethyl)-1,2,3,4-tetrahydronaphthalen-1-yl)acetamide was prepared from (R)-2-(4-methyl-3-oxo-1-tosyl-1,2,3,4-tetrahydropyrazin-2-yl)acetic acid.

The following compounds in Table 1 were prepared similarly.

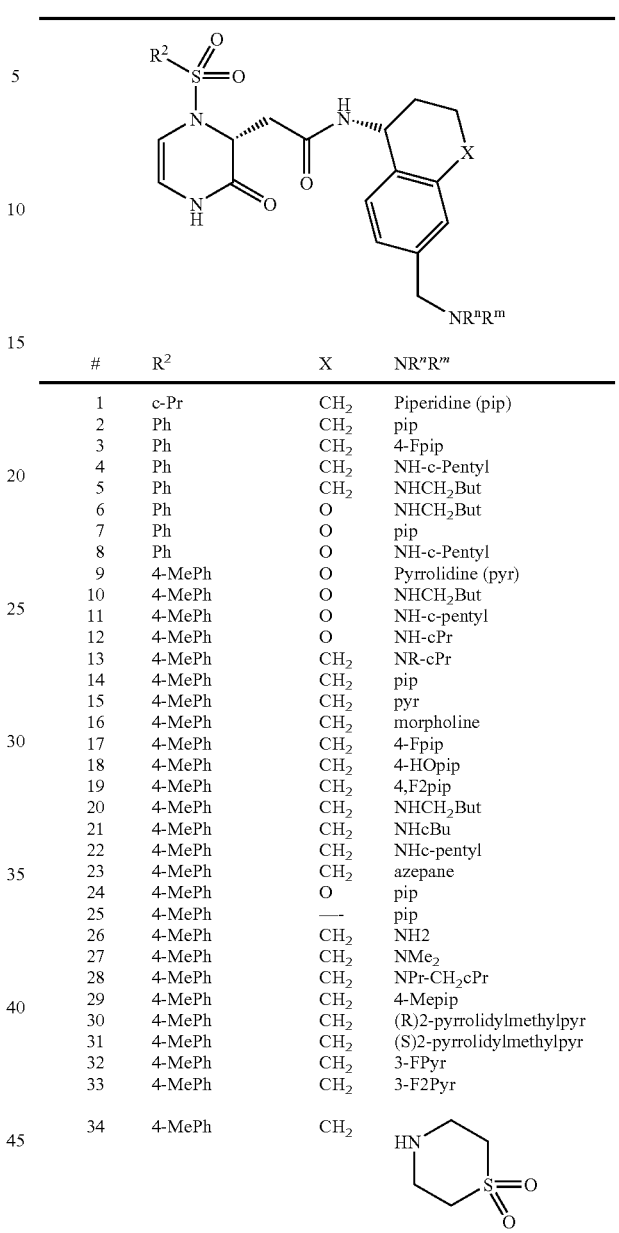

| # | $R^2$ | X | $NR''R'''$ |
|---|---|---|---|
| 1 | c-Pr | $CH_2$ | Piperidine (pip) |
| 2 | Ph | $CH_2$ | pip |
| 3 | Ph | $CH_2$ | 4-Fpip |
| 4 | Ph | $CH_2$ | NH-c-Pentyl |
| 5 | Ph | $CH_2$ | $NHCH_2But$ |
| 6 | Ph | O | $NHCH_2But$ |
| 7 | Ph | O | pip |
| 8 | Ph | O | NH-c-Pentyl |
| 9 | 4-MePh | O | Pyrrolidine (pyr) |
| 10 | 4-MePh | O | $NHCH_2But$ |
| 11 | 4-MePh | O | NH-c-pentyl |
| 12 | 4-MePh | O | NH-cPr |
| 13 | 4-MePh | $CH_2$ | NR-cPr |
| 14 | 4-MePh | $CH_2$ | pip |
| 15 | 4-MePh | $CH_2$ | pyr |
| 16 | 4-MePh | $CH_2$ | morpholine |
| 17 | 4-MePh | $CH_2$ | 4-Fpip |
| 18 | 4-MePh | $CH_2$ | 4-HOpip |
| 19 | 4-MePh | $CH_2$ | 4,F2pip |
| 20 | 4-MePh | $CH_2$ | $NHCH_2But$ |
| 21 | 4-MePh | $CH_2$ | NHcBu |
| 22 | 4-MePh | $CH_2$ | NHc-pentyl |
| 23 | 4-MePh | $CH_2$ | azepane |
| 24 | 4-MePh | O | pip |
| 25 | 4-MePh | — | pip |
| 26 | 4-MePh | $CH_2$ | NH2 |
| 27 | 4-MePh | $CH_2$ | $NMe_2$ |
| 28 | 4-MePh | $CH_2$ | NPr-$CH_2$cPr |
| 29 | 4-MePh | $CH_2$ | 4-Mepip |
| 30 | 4-MePh | $CH_2$ | (R)2-pyrrolidylmethylpyr |
| 31 | 4-MePh | $CH_2$ | (S)2-pyrrolidylmethylpyr |
| 32 | 4-MePh | $CH_2$ | 3-FPyr |
| 33 | 4-MePh | $CH_2$ | 3-F2Pyr |
| 34 | 4-MePh | $CH_2$ | ![thiomorpholine S,S-dioxide] |
| 35 | 4-MePh | $CH_2$ | N-2-Pyridylpiperazine |
| 36 | 3-Cl | $CH_2$ | pip |
| 37 | 4-Cl | $CH_2$ | Pip |
| 38 | 4-Cl | $CH_2$ | NRcPr |
| 39 | 4-Cl | $CH_2$ | azepane |
| 40 | 4-Cl | $CH_2$ | 3-HOPip |
| 41 | 4-Cl | $CH_2$ | $NHCH_2CH_2OMe$ |
| 42 | 4-Cl | $CH_2$ | $NHCH_2CH_2OH$ |
| 43 | 3,4-$Cl_2$ | $CH_2$ | pip |
| 44 | 3,4-$Cl_2$ | $CH_2$ | NHiPr |
| 45 | 3,4-$Cl_2$ | $CH_2$ | NHcPentyl |
| 46 | 3,4-$Cl_2$ | O | NHiPr |
| 47 | 3,4-$Cl_2$ | O | NHcPentyl |
| 48 | 4-MeO | O | pip |
| 49 | 2,3-$Cl_2$ | O | pip |
| 50 | 2,3-$Cl_2$ | $CH_2$ | pip |
| 51 | 2,5-$Me_2$-4-Cl | O | pip |
| 52 | 2,5-$Me_2$-4-Cl | O | NHcPentyl |
| 53 | 2,5-$Me_2$-4-Cl | O | NHBut |
| 54 | 2,5-$Me_2$-4-Cl | O | NH2 |
| 55 | 2,5-$Me_2$-4-Cl | $CH_2$ | NH2 |

-continued

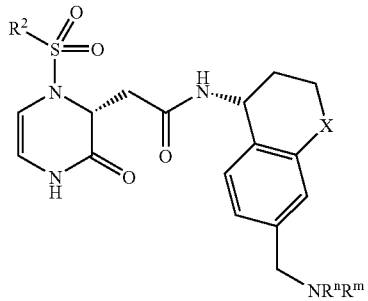

| # | R² | X | NR"R'" |
|---|---|---|---|
| 56 | 2,5-Me₂-4-Cl | CH₂ | NMe₂ |
| 57 | 2,5-Me₂-4-Cl | CH₂ | NHcPentyl |
| 58 | 2,5-Me₂-4-Cl | CH₂ | NHCH₂But |
| 59 | 2,5-Me₂-4-Cl | CH₂ | NITBut |
| 60 | 3-CF3Ph | CH₂ | pip |
| 61 | 3-CF3Ph | O | pip |

EXAMPLE 16

Preparation of N—((R)-6-(1-isobutylamino)ethyl)-1,2,3,4-tetrahydronaphthalen-1-yl)-2-((R)-3-oxo-1-tosyl-1,2,3,4-tetrahydropyrazin-2-yl)acetamide

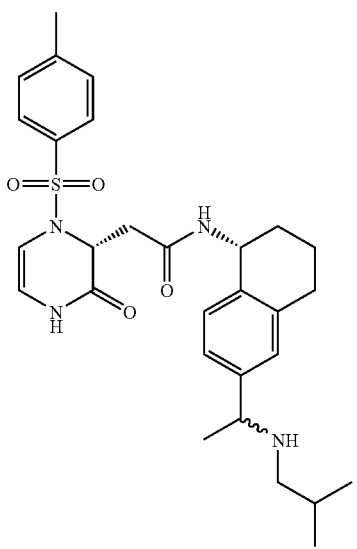

Step A—Preparation of (6-hydroxymethyl-1,2,3,4-tetrahydro-naphthalen-1-yl)-carbamic acid tert-butyl ester: A mixture of (5-amino-5,6,7,8-tetrahydro-naphthalen-2-yl)-methanol (2.50 g, 14.1 mmol, 1.0 eq) and di-tert-butyl dicarbonate (Aldrich, 3.69 g, 16.9 mmol, 1.2 eq) and triethylamine (Aldrich, 2.85 g, 28.2 mmol, 2.0 eq) in CH₂Cl₂ (60 mL) was stirred at room temperature overnight. The reaction was quenched with H₂O (100 mL) and extracted with CH₂Cl₂ (100 mL×3). The extract phase was washed with saturated NaCl, dried over Na₂SO₄, filtered and concentrated. Flash column chomatography (silica gel, 0-35% EtOAc-Hexane) afforded the title compound as a white solid. MS (ESI, pos. ion) m/z: 278 (M+1).

Step B—Preparation of (6-formyl-1,2,3,4-tetrahydro-naphthalen-1-yl)-carbamic acid tert-butyl ester: A mixture of (6-hydroxymethyl-1,2,3,4-tetrahydro-naphthalen-1-yl)-carbamic acid tert-butyl ester (3.16 g, 11.4 mmol, 1.0 eq) and MnO₂ (Aldrich, 12.9 g, 148.3 mmol, 13 eq) in CH₂Cl₂ (110 mL) was stirred at room temperature overnight. The reaction mixture was allowed to pass though a pad of Celite and the pad was washed with CH₂Cl₂ (100 mL×2). The concentration of the filtrate afforded the title compound as a white sticky semisolid. MS (ESI, pos. ion) m/z: 298 (M+Na).

Step C—Preparation of [6-(1-hydroxy-ethyl)-1,2,3,4-tetrahydro-naphthalen-1-yl]-carbamic acid tert-butyl ester: To a sulution of (6-formyl-1,2,3,4-tetrahydro-naphthalen-1-yl)-carbamic acid tert-butyl ester (2.80 g, 10.2 mmol, 1.0 eq) in THF (100 mL) at −78° C. was added a solution of MeMgBr [Aldrich, 1.4M in toluene/THF (3:1), 29 mL, 40.7 mmol, 4.0 eq] slowly. The reaction mixture was stirred at −78° C. for 20 min, warmed up to room temperature and stirred at room temperature for 2 h. The reaction was quenched with saturated NaHCO₃ (120 mL), and the crude product was extracted with EtOAc (100 mL×3). The extract phase was washed with saturated NaCl, dried over Na₂SO₄, filtered and concentrated. The title compound was obtained as a white solid. MS (ESI, pos. ion) m/z: 292 (M+1).

Step D—Preparation of (6-acetyl-1,2,3,4-tetrahydro-naphthalen-1-yl)-carbamic acid tert-butyl ester: A mixture of [6-(1-hydroxy-ethyl)-1,2,3,4-tetrahydro-naphthalen-1-yl]-carbamic acid tert-butyl ester (2.63 g, 9.04 mmol, 1.0 eq) and MnO₂ (Aldrich, 10.2 g, 117.5 mmol, 13 eq) in CH₂Cl₂ (100 mL) was stirred at room temperature overnight. The reaction mixture was allowed to pass though a pad of Celite and the pad was washed with CH₂Cl₂ (100 mL×2). The concentration of the filtrate afforded the title compound as a white sticky semisolid. MS (ESI, pos. ion) m/z: 290 (M+1).

Step E—Preparation of N—((R)-6-acetyl-1,2,3,4-tetrahydronaphthalen-1-yl)-2-((R)-3-oxo-1-tosyl-1,2,3,4-tetrahydropyrazin-2-yl)acetamide: A mixture of (6-acetyl-1,2,3,4-tetrahydro-naphthalen-1-yl)-carbamic acid tert-butyl ester (1.209 g, 4.18 mmol, 1.08 eq) in HCl/EtOAc (4.7 M, 20 mL) was stirred at room temperature for 5 h. The solvent was removed with a rotary evaporator, and the resulting 1-(5-amino-5,6,7,8-tetrahydro-naphthalen-2-yl)-ethanone hydrogen chloride was dried in vacuo. A mixture of 1-(5-amino-5,6,7,8-tetrahydro-naphthalen-2-yl)-ethanone hydrogen chloride, (R)-2-(3-oxo-1-tosyl-1,2,3,4-tetrahydropyrazin-2-yl)acetic acid (1.20 g, 3.87 mmol, 1.0 eq), EDCI (Aldrich, 1.335 g, 7.0 mmol, 1.8 eq), HOBt (Aldrich, 105 mg, 0.774 mmol, 0.2 eq) and diisobutylethylamine (Aldrich, 1.0 g, 7.74 mmol, 2.0 eq) in CH₂Cl₂ (20 mL) was stirred at room temperature overnight. The reaction was quenched with H₂O (100 mL). The crude product was extracted with CH₂Cl₂ (100 mL×3). The extract phase was washed with saturated NaCl, dried over Na₂SO₄, filtered and concentrated. Flash column chomatography (silica gel, 0-5% MeOH—CH₂Cl₂) afforded the title compound as a off-white solid. MS (ESI, pos. ion) m/z: 482 (M+1).

Step F—Preparation of N—((R)-6-(1-(isobutylamino)ethyl)-1,2,3,4-tetrahydro-naphthalen-1-yl)-2-((R)-3-oxo-1- tosyl-1,2,3,4-tetrahydropyrazin-2-yl)acetamide: A mixture of N—((R)-6-acetyl-1,2,3,4-tetrahydronaphthalen-1-yl)-2-((R)-3-oxo-1-tosyl-1,2,3,4-tetrahydropyrazin-2-yl)acetamide (200 mg, 0.415 mmol, 1.0 eq), isobutylamine (Aldrich, 243 mg, 3.33 mmol, 8.0 eq), NaBH(OAc)$_3$ (Aldrich, 264 mg, 1.25 mmol, 3.0 eq) and glacial acetic acid (J, T. Baker, 50 mg, 0.830 mmol, 2.0 eq) in ClCH$_2$CH$_2$Cl (4 mL) was stirred at room temperature for 3 days. The reaction was quenched with saturated NaHCO$_3$ (60 mL). The crude product was extracted with CH$_2$Cl$_2$ (60 mL×3). The extract phase was washed with saturated NaCl, dried over Na$_2$SO$_4$, filtered and concentrated. Flash column chomatography (silica gel, 0-10% MeOH—CH$_2$Cl$_2$) afforded the title compound as a white solid (113 mg, 51%). MS (ESI, pos. ion) m/z: 539 (M+1).

The following compounds were prepared similarly: N—((R)-6-(1-(cyclopentyl-amino)ethyl)-1,2,3,4-tetrahydronaphthalen-1-yl)-2-((R)-3-oxo-1-tosyl-1,2,3,4-tetrahydropyrazin-2-yl)acetamide, N—((R)-6-(1-(cyclopropylamino)ethyl)-1,2,3,4-tetrahydronaphthalen-1-yl)-2-((R)-3-oxo-1-tosyl-1,2,3,4-tetrahydropyrazin-2-yl)acetamide, N—((R)-6-(1-(cyclobutylamino)ethyl)-1,2,3,4-tetrahydronaphthalen-1-yl)-2-((R)-3-oxo-1-tosyl-1,2,3,4-tetrahydropyrazin-2-yl)acetamide, tert-butyl 4-(1-((R)-5-(2-((R)-3-oxo-1-tosyl-1,2,3,4-tetrahydropyrazin-2-yl)acetamido)-5,6,7,8-tetrahydronaphthalen-2-yl)ethyl)piperazine-1-carboxylate, and 2-((R)-3-oxo-1-tosyl-1,2,3,4-tetrahydropyrazin-2-yl)-N—((R)-6-(1-(piperazin-1-yl)ethyl)-1,2,3,4-tetrahydronaphthalen-1-yl)acetamide.

EXAMPLE 17

Preparation of 2-[3-Oxo-1-(toluene-4-sulfonyl)-1,2,3,4-tetrahydro-pyrazin-2(R)-yl]-N-[6-(1-piperidin-1-ylmethyl-vinyl)-1,2,3,4-tetrahydro-naphthalen-1 (R)-yl]-acetamide

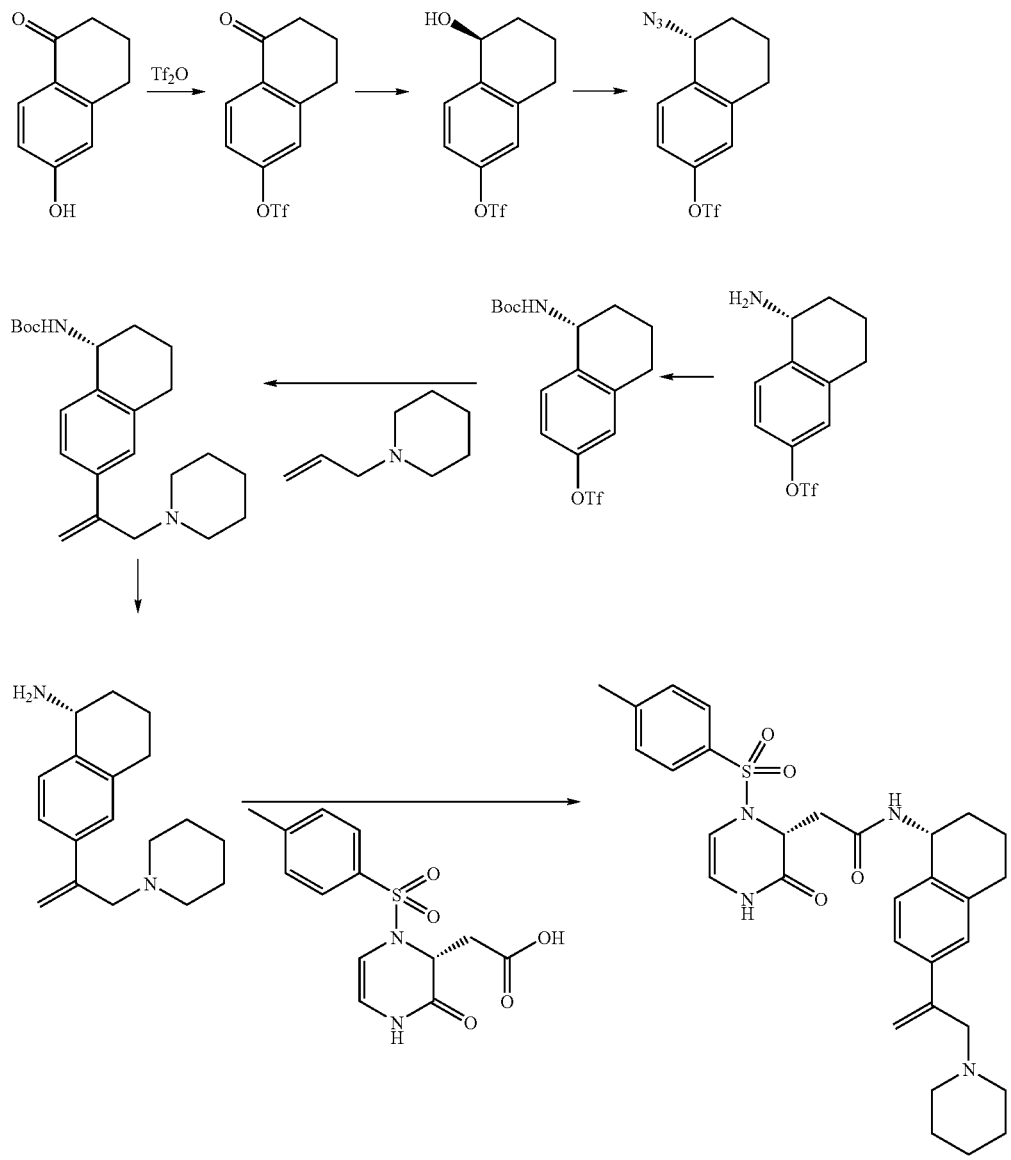

A) Preparation of trifluoro-methanesulfonic acid 5-oxo-5,6,7,8-tetrahydro-naphthalen-2-yl ester: To a 1 L round-bottomed flask charged with 6-hydroxy-1-tetralone (Aldrich, 21.97 g, 0.136 mol) at 0° C. was added $CH_2Cl_2$ (500 mL) and pyridine (Aldrich, 11 mL, 0.136 mmol). Triflic anhydride (Aldrich, 23 mL, 0.136 mmol) was added though an additional funnel over a period of 12 min. The mixture was gradually warmed to RT and stirred at RT overnight. The residue was diluted with water and two phases were separated. The organic phase was washed with 1N HCl (100 mL×2), sat $NaHCO_3$, and brine, dried over $Na_2SO_4$. After filtration and concentration in vacuo, the crude was purified by flash chomatography (5-11% EtOAc-hexane) to provide the title compound as yellow oil. MS (ESI): 295 $(M+H)^+$.

B) Preparation of trifluoro-methanesulfonic acid 5(S)-hydroxy-5,6,7,8-tetrahydro-naphthalen-2-yl ester: To a dry thee-necked flask containing (R)-2-methyl-CBS-oxazaborolidine (Aldrich, 1.94 mL, 1.0M in toluene, 1.93 mmol, 0.05 eq) under $N_2$ was added a solution of $BH_3$-$Me_2S$ (Aldrich, 3.30 mL, 34.80 mmol, 0.9 eq) in toluene (200 mL) though an addition funnel. After the addition, the reaction was cooled to 0° C. A solution of trifluoro-methanesulfonic acid 5-oxo-5,6,7,8-tetrahydro-naphthalen-2-yl ester (step a, 11.37 g, 38.67 mmol, 1.0 eq) in THF (180 mL) was added drop-wise though an addition funnel. Following the addition, the reaction mixture was stirred at RT for 40 min, then quenched with MeOH. The solvent was removed in vacuo and the crude was diluted with $H_2O$ (50 mL). The aqueous phase was extracted with ether (3×150 mL). The combined organic layer was washed with brine, dried over $Na_2SO_4$, filtered and concentrated. The title compound was obtained as an off-white solid by flash chomatography (16-22% EtOAc-hexane).

C) Preparation of trifluoro-methanesulfonic acid 5(R)-azido-5,6,7,8-tetrahydro-naphthalen-2-yl ester: To a solution of trifluoro-methanesulfonic acid 5-hydroxy-5,6,7,8-tetrahydro-naphthalen-2-yl ester (Step b, 11.2 g, 37.9 mmol, 1.0 eq) in THF (150 mL) at RT was added DPPA (Aldrich, 11.1 mL, 51.6 mmol, 1.36 eq). The resulting mixture was cooled to 0° C. and DBU (Aldrich, 7.7 mL, 51.6 mmol, 1.36 eq) was added slowly though a syringe. The mixture was warmed to RT and stirred over the weekend. The reaction was concentrated in vacuo. The crude compound was dissolved in EtOAc (400 mL). The organic layer was washed with $NH_4Cl$ (twice), $H_2O$, and brine, dried over $Na_2SO_4$. After filtration and concentration in vacuo, the crude was purified by flash chomatography (5% EtOAc-hexane) to provide the title compound.

D) Preparation of trifluoro-methanesulfonic acid 5(R)-amino-5,6,7,8-tetrahydro-naphthalen-2-yl ester: To a solution of trifluoro-methanesulfonic acid 5-azido-5,6,7,8-tetrahydro-naphthalen-2-yl ester (step c, 10.3 g, 32.1 mmol, 1.0 eq) in THF (70 mL) was added $PPh_3$ (Aldrich, 8.4 g, 32.1 mmol, 1.0 eq), and $H_2O$ (30 mL) at 0° C. The mixture was warmed to RT and stirred overnight. 2N HCl was added until the mixture was acidic (pH=1-2). The mixture was extracted with toluene (3×100 mL). The aqueous phase was neutralized with 5N NaOH until the pH=12-13, extracted with $Et_2O$ (3×150 mL). The ether solution was dried over $Na_2SO_4$, filtered and concentrated in vacuo. The crude was purified by flash chomatography (6% MeOH—$CH_2Cl_2$) to provide the title compound.

E) Preparation of trifluoro-methanesulfonic acid 5-(R)-tert-butoxycarbonyl-amino-5,6,7,8-tetrahydro-naphthalen-2-yl ester: To a solution of trifluoro-methanesulfonic acid 5(R)-amino-5,6,7,8-tetrahydro-naphthalen-2-yl ester (Step d, 2.0 g, 6.8 mmol, 1.0 eq) in $CH_2Cl_2$ (20 mL) was added $Et_3N$ (1.9 mL, 13.6 mmol, 2.0 eq) and di-tert-butyl carbonate (Aldrich, 1.8 g, 8.1 mmol, 1.2 eq). The mixture was stirred at RT overnight, washed with saturated $NaHCO_3$ (2×20 mL) and brine, and dried over $Na_2SO_4$. After filtration and concentration in vacuo, the crude was purified by flash chomatography (4-10% EtOAc-hexane) to provide the title compound as a white solid.

F) Preparation of [6-(1-piperidin-1-ylmethyl-vinyl)-1,2,3,4-tetrahydro-naphthalen-1(R)-yl]-carbamic acid tert-butyl ester: To a solution of trifluoro-methanesulfonic acid 5-tert-butoxycarbonylamino-5,6,7,8-tetrahydro-naphthalen-2-yl ester (Step e, 1.89 g, 4.79 mmol, 1.0 eq) in $CH_3CN$ (25 mL) purged with $N_2$ was added palladium (II) acetate (Strem Chemicals, 65 mg, 0.29 mmol, 0.06 eq), 1,1'-bis(diphenylphosphino)ferrocene (Aldrich, 0.70 g, 1.26 mmol, 0.26 eq), $K_2CO_3$ (0.99 g, 7.18 mmol, 1.5 eq) and N-allyl piperidine (Lancaster, 3.00 g, 23.96 mmol, 5.0 eq). The vessel was sealed with a septum and heated to 80° C. overnight. After cooling to RT, the mixture was diluted with $H_2O$, and extracted with $Et_2O$ (3×). The ether solution was dried over $Na_2SO_4$, filtered and concentrated in vacuo. The crude was purified by flash chomatography (14-21% EtOAc-Hexane) to provide the title compound. MS (ESI): 371$(M+H)^+$.

G) Preparation of 6-(1-piperidin-1-ylmethyl-vinyl)-1,2,3,4-tetrahydro-naphthalen-1(R)-ylamine: To a solution of [6-(1-piperidin-1-ylmethyl-vinyl)-1,2,3,4-tetrahydro-naphthalen-1(R)-yl]-carbamic acid tert-butyl ester in $CH_2Cl_2$ (3 mL) was added TFA (3 mL). The mixture was stirred at RT for 4 h, concentrated in vacuo. The crude was neutralized with 10% $Na_2CO_3$ until the aqueous phase was basic, then extracted with $CH_2Cl_2$ thee times. The organic solution was washed with brine, dried over $Na_2SO_4$, filtered and concentrated in vacuo to provide the title compound. MS (ESI): 271 $(M+H)^+$.

H) Preparation VIII—2-[3-Oxo-1-(toluene-4-sulfonyl)-1,2,3,4-tetrahydro-pyrazin-2(R)-yl]-N-[6-(1-piperidin-1-ylmethyl-vinyl)-1,2,3,4-tetrahydro-naphthalen-1(R)-yl]-acetamide: To a 20 mL flask equipped with stirring was added [3-oxo-1-(toluene-4-sulfonyl)-1,2,3,4-tetrahydro-pyrazin-2-yl]-acetic acid (82 mg, 0.26 mmol), 6-(1-piperidin-1-ylmethyl-vinyl)-1,2,3,4-tetrahydro-naphthalen-1-ylamine (65 mg, 0.24 mmol), EDC (Aldrich, 69 mg, 0.36 mmol), HOBt (Aldrich, 32 mg, 0.24 mmol), and $CH_2Cl_2$ (2 mL). The reaction mixture was stirred at room temperature overnight and diluted with $CH_2Cl_2$ (40 mL). The organic phase was washed with saturated $NaHCO_3$ and brine, dried over $Na_2SO_4$, filtered and concentrated in vacuo. The crude was purified by preparative TLC in 10% MeOH—$CH_2Cl_2$ to afford the title compound. MS (ESI): 563 $(M+H)^+$.

EXAMPLE 18

Preparation of 2-[3-Oxo-1-(toluene-4-sulfonyl)-1,2,3,4-tetrahydro-pyrazin-2-yl]-N-[4-(3-piperidin-1-yl-propyl)-phenyl]-acetamide

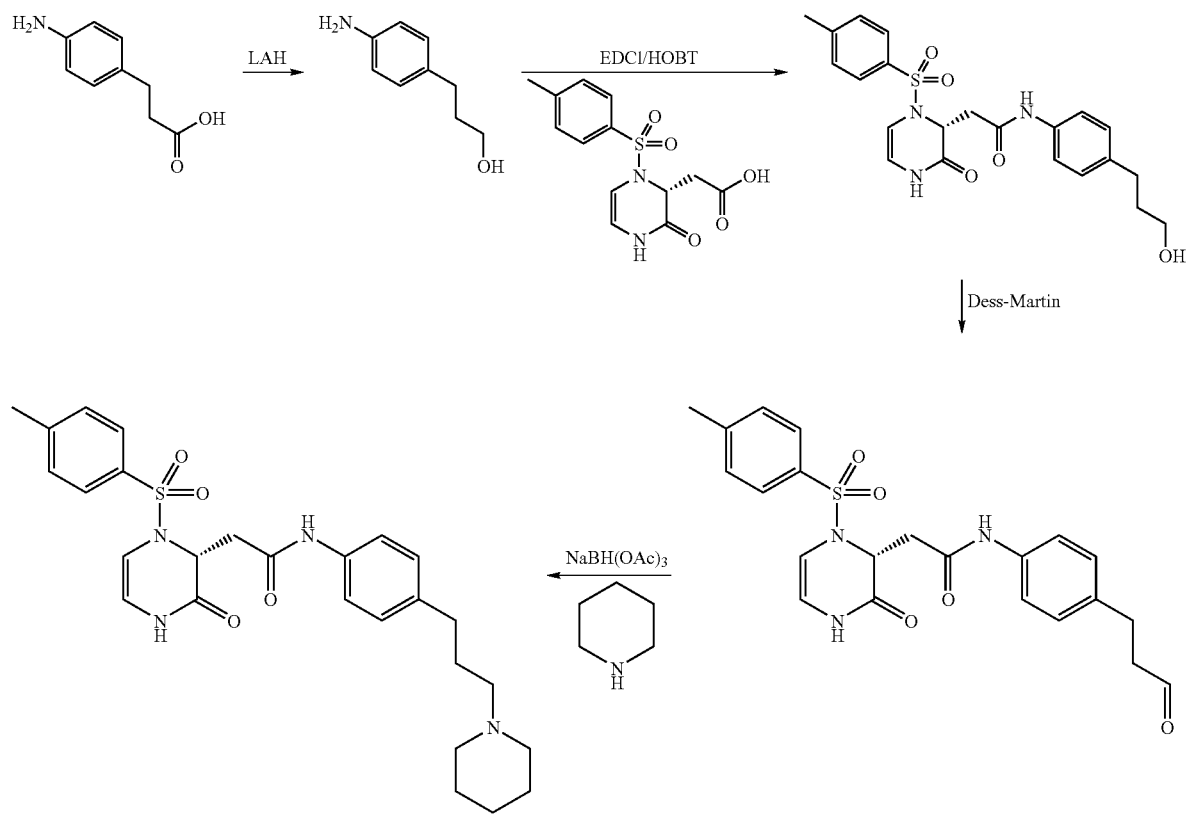

Step 1: Preparation of 3-(4-Amino-phenyl)-propan-1-ol: To an oven-dried 150 mL round-bottomed flask charged with 3-(4-aminophenyl)propionic acid (Aldrich, 3.0 g, 18.16 mmol) was added THF (50 mL) and lithium aluminum hydride (Aldrich, 1.0M THF solution, 37 mL, 36.32 mmol) at 0° C. The reaction mixture was added Na$_2$SO$_4$.10H$_2$O after 3 h until there was no visible bubbles. The liquid was filtered. The solid was washed with THF and CH$_2$Cl$_2$. The filtrate was dried over Na$_2$SO$_4$. After filtration and concentration in vacuo, the crude was purified by flash chomatography (7% MeOH—CH$_2$Cl$_2$) to provide the title product. MS (ESI): 152 (M+H)$^+$.

Step 2: Preparation of N-[4-(3-Hydroxy-propyl)-phenyl]-2-[3-oxo-1-(toluene-4-sulfonyl)-1,2,3,4-tetrahydro-pyrazin-2-yl]-acetamide: To a 20 mL vial was added [3-oxo-1-(toluene-4-sulfonyl)-1,2,3,4-tetrahydro-pyrazin-2-yl]-acetic acid (500 mg, 1.61 mmol), EDC (Aldrich, 464 mg, 2.42 mmol), HOBt (Aldrich, 195 mg, 1.45 mmol), CH$_2$Cl$_2$ (5 mL), 3-(4-amino-phenyl)-propan-1-ol (731 mg, 4.84 mmol) and (iPr)$_2$NEt (Aldrich, 0.56 mL, 3.22 mmol). The reaction mixture was stirred at room temperature overnight and diluted with CH$_2$Cl$_2$ (60 mL). The organic phase was washed with saturated NaHCO$_3$, water and brine, dried over Na$_2$SO$_4$, filtered and concentrated in vacuo. The crude was purified by silica gel chomatography (6%-8% MeOH—CH$_2$Cl$_2$) to afford the title compound. MS (ESI): 444 (M+H)$^+$.

Step 3: Preparation of N-[4-(3-Oxo-propyl)-phenyl]-2-[3-oxo-1-(toluene-4-sulfonyl)-1,2,3,4-tetrahydro-pyrazin-2-yl]-acetamide: The solution of Dess-Martin periodinane (Aldrich, 92 mg, 0.21 mmol) in CH$_2$Cl$_2$ (1 mL) was added N-[4-(3-oxo-propyl)-phenyl]-2-[3-oxo-1-(toluene-4-sulfonyl)-1,2,3,4-tetrahydro-pyrazin-2-yl]-acetamide (73 mg, 0.16 mmol) in CH$_2$Cl$_2$ (1 mL). After the reaction mixture was stirred at rt for 30 min, ether (100 mL) was added, followed by saturated NaHCO$_3$ and 1M Na$_2$S$_2$O$_3$ to dissolve the solid. The ether layer was separated and washed with saturated NaHCO$_3$, water and brine, dried over Na$_2$SO$_4$, filtered and concentrated in vacuo. The crude product was used in next step without purification. MS (ESI): 442 (M+H)$^+$.

Step 4: Preparation of 2-[3-Oxo-1-(toluene-4-sulfonyl)-1,2,3,4-tetrahydro-pyrazin-2-yl]-N-[4-(3-piperidin-1-yl-propyl)-phenyl]-acetamide: To a 20 mL flask equipped with stirring was added N-[4-(3-oxo-propyl)-phenyl]-2-[3-oxo-1-(toluene-4-sulfonyl)-1,2,3,4-tetrahydro-pyrazin-2-yl]-acetamide (45 mg, 0.102 mmol), ClCH$_2$CH$_2$Cl (2 mL), piperidine (Aldrich, 0.02 mL, 0.204 mmol) and one drop of HOAc. NaBH(OAc)$_3$ was added after 5 min. The reaction mixture was stirred at room temperature overnight, then diluted with CH$_2$Cl$_2$ (40 mL). The organic phase was washed with saturated NaHCO$_3$ and brine, dried over Na$_2$SO$_4$, filtered and concentrated in vacuo. Purification by preparative TLC (10% MeOH—CH$_2$Cl$_2$) afforded the title compound. MS (ESI): 511 (M+H)$^+$.

The compounds in the following table were prepared similarly:

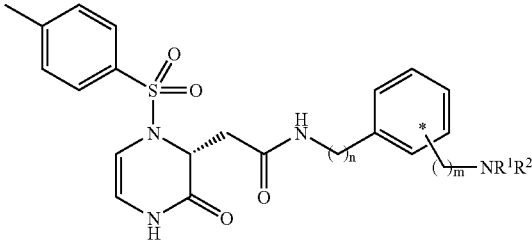

| Cpd # | n | Aryl substitution | m | NR¹R² |
|---|---|---|---|---|
| 62 | 0 | p- | 3 | piperidine |
| 63 | 0 | p- | 3 | N-Mepiperazine |
| 64 | 0 | p- | 3 | NHc-Pr |
| 65 | 0 | m- | 3 | piperidine |
| 66 | 0 | m- | 3 | pyrrolidine |
| 67 | 0 | m- | 3 | NHiBu |
| 68 | 0 | m- | 2 | pyrrolidine |
| 69 | 0 | m- | 2 | piperidine |
| 70 | 0 | m- | 2 | NH-c-$C_5H_9$ |
| 71 | 0 | p- | 2 | pyrrolidine |
| 72 | 0 | p- | 2 | $NMe_2$ |
| 73 | 0 | p- | 1 | piperidine |
| 74 | 1 | p- | 1 | piperidine |
| 75 | 1 | p- | 1 | NHcPr |
| 76 | 1 | m- | 1 | piperidine |
| 77 | 1 | m- | 2 | piperidine |
| 78 | 1 | p- | 2 | piperidine |
| 79 | 1 | p- | 2 | NHiBu |
| 80 | 2 | p- | 1 | piperidine |
| 81 | 2 | p- | 2 | morpholine |
| 82 | 2 | m- | 2 | piperidine |
| 83 | 2 | p- | 3 | NHc-$C_5H_9$ |

EXAMPLE 19

Preparation of 2-[3-Oxo-1-(toluene-4-sulfonyl)-1,2,3,4-tetrahydro-pyrazin-2-yl]-N-[2-(4-piperidin-1-ylmethyl-phenyl)-ethyl]-acetamide: Step 1: Preparation of [4-(2-aminoethyl)-phenyl]-methanol: To an oven-dried 150 mL round-bottomed flask charged with 4-(2-aminoethyl)benzoic acid (Aldrich, 3.1 g, 19 mmol) was added THF (20 mL) and lithium aluminum hydride (Aldrich, 1.0M THF solution, 38 mL, 38 mmol) at 0° C. After the reaction mixture was gradually warmed to rt and stirred overnight, $Na_2SO_4 \cdot 10H_2O$ was added until there was no visible bubbles. The liquid was filtered. The solid was washed with $CH_2Cl_2$. The filtrate was concentration in vacuo to provide the title product. MS (ESI): 152 (M+H)⁺.

Step 2: Preparation of N-[2-(4-hydroxymethyl-phenyl)-ethyl]-2-[3-oxo-1-(toluene-4-sulfonyl)-1,2,3,4-tetrahydro-pyrazin-2-yl]-acetamide: A mixture of [3-oxo-1-(toluene-4-sulfonyl)-1,2,3,4-tetrahydro-pyrazin-2-yl]-acetic acid (620 mg, 2.0 mmol), EDC (Aldrich, 575 mg, 3.0 mmol), HOBt (Aldrich, 270 mg, 2.0 mmol), and [4-(2-amino-ethyl)-phenyl]-methanol (362 mg, 2.4 mmol) was added $CH_2Cl_2$ (15 mL) and DMF (2 mL). The reaction mixture was stirred at room temperature overnight and diluted with $CH_2Cl_2$ (80 mL). The organic phase was washed with saturated $NaHCO_3$, and brine, dried over $Na_2SO_4$, filtered and concentrated in vacuo. The crude was purified by silica gel chomatography (6%-10% MeOH—$CH_2Cl_2$) to afford the title compound. MS (ESI): 444 (M+H)⁺.

Step 3: Preparation of N-[2-(4-chloromethyl-phenyl)-ethyl]-2-[3-oxo-1-(toluene-4-sulfonyl)-1,2,3,4-tetrahydro-pyrazin-2-yl]-acetamide: To a suspension of N-[2-(4-hydroxymethyl-phenyl)-ethyl]-2-[3-oxo-1-(toluene-4-sulfonyl)-1,2,3,4-tetrahydro-pyrazin-2-yl]-acetamide (0.376 g, 0.85 mmol) in 1,4-dioxane (10 mL) was added $SOCl_2$ (Aldrich, 0.25 mL, 3.4 mmol) at rt. The reaction mixture was concentrated in vacuo after 30 min. The crude product was used in next step without purification. MS (ESI): 464 (M+H)⁺.

Step 4: Preparation of 2-[3-oxo-1-(toluene-4-sulfonyl)-1,2,3,4-tetrahydro-pyrazin-2-yl]-N-[2-(4-piperidin-1-ylmethyl-phenyl)-ethyl]-acetamide: To a solution of N-[2-(4-chloromethyl-phenyl)-ethyl]-2-[3-oxo-1-(toluene-4-sulfonyl)-1,2,3,4-tetrahydro-pyrazin-2-yl]-acetamide (195 mg, 0.42 mmol) in $CH_2Cl_2$ (2 mL) was added piperidine (Aldrich, 0.13 mL, 1.3 mmol) at rt. The reaction mixture was stirred at rt overnight and then diluted with $CH_2Cl_2$ (50 mL). The organic solution was washed with saturated $NaHCO_3$, and brine, dried over $Na_2SO_4$, filtered and concentrated in vacuo. Purification by preparative TLC (7% MeOH—$CH_2Cl_2$) afforded the title compound. MS (ESI): 511 (M+H)⁺.

EXAMPLE 20

Preparation of 2-((R)-3-oxo-1-tosyl-1,2,3,4-tetrahydropyrazin-2-yl)-N—((R)-6-(2-(piperidin-1-yl)ethyl)-1,2,3,4-tetrahydronaphthalen-1-yl)acetamide: Step 1; (R)-tert-butyl-6-(hydroxymethyl)-1,2,3,4-tetrahydronaphthalen-1-ylcarbamate: A solution of (t-Boc)₂O (5.5 g, 31.03 mmol) in DMF (10 mL) was added over 1 h to a stirred solution of amine 1 in DMF (15 mL) at 10-15° C. After stirring overnight at room temperature, the reaction solution was diluted with EtOAc/Hexane (1:1), washed with brine, and dried over $Na_2SO_4$ and evaporated to afford the crude product as a white solid. The crude product was directly used in the next step.

Step 2: (R)-tert-butyl 6-(iodomethyl)-1,2,3,4-tetrahydronaphthalen-1-ylcarbamate: To a solution of the compound from step 1 (415.5 mg, 1.5 mmol) in dichloro-methane/ether (1:1, 30 mL) at room temperature were added triphenylphosphine (590 mg, 2.25 mmol) and imidazole (153 mg, 2.25 mmol). To this stirred solution was then added iodine (571 mg, 2.25 mmol). After stirring for 20 min. The reaction was quenched with 10% $Na_2S_2O_3$ (15 mL) until it became a clear two-phase solution. The aqueous phase was extracted with ether. The combined organic phase was dried over $Na_2SO_4$, filtered, and evaporated to dryness. Flash chomatography ($SiO_2$, hexane/$CH_2Cl_2$=3:1 to pure $CH_2Cl_2$) afforded the desired product as a white solid.

Step 3: (R)-tert-butyl 6-((1,3-dithian-2-yl)methyl)-1,2,3,4-tetrahydronaphthylen-1-ylcarbamate: To a solution of 1,3-dithiane (1.01 g, 8.4 mmol) in 10 mL of dry THF at −30° C. was added dropwise 2.5M n-butyllithium in hexane (3.36 mL, 8.4 mmol). After stirring at −20° C. for 1.5 h, a solution of the iodide obtained in Step 2 (542 mg, 1.4 mmole, azeotroped with benzene) in 10 mL of dry THF was added dropwise at −20° C. The reaction was stirred at −5° C. to 0° C. for 1 h. It was then quenched with Sat. $NH_4Cl$ solution, extracted with EtOAc, dried over $Na_2SO_4$, filtered, and evaporated to dryness. Flash chomatography ($SiO_2$, $CH_2Cl_2$/hexane=1:1 to 2:1 to $CH_2Cl_2$/EtOAc=100:3) afforded the desired product as a white solid.

Step 4: (R)-tert-butyl 6-(2-oxoethyl)-1,2,3,4-tetrahydronaphthalen-1-ylcarbamate: The dithiane obtained in Step 3 (6.1 g, 16.1 mmol) and $CaCO_3$ (3.23 g, 32.3 mmol) were suspended in 120 mL of THF/water (5:1). Then $Hg(ClO_4)_2$ (9.65 g, 24.15 mmol) was added portion wise. After stirring at room temperature for 2 h, the reaction mixture was filtered though a celite pad with the help of EtOAc. The filtrate was evaporated to dryness. Flash chomatography (SiO$_2$, DCM to DCM/EtOAc=3:1 to 2:1) gave the desired product as a colorless sticky oil.

Step 5: (R)-tert-butyl 6-(2-(piperidin-1-yl)ethyl)-1,2,3,4-tetrahydronaphthalen-1-ylcarbamate: To a solution of the above product (2.02 g, 7 mmol) and pyperidine (1.79 g, 21 mmol) in 10 mL of dichloroethane was added sodium triacetoxyborohydride (2.97 g, 14 mmol). After stirring overnight at room temperature, the reaction solution was diluted with EtOAc and washed with sat. NaHCO$_3$ and brine. The organic phase was dried over Na$_2$SO$_4$ and evaporated to dryness in vacuo. Flash chomatography (SiO$_2$, DCM to EtOAc to EtOAc/MeOH=100:20) afforded the desired product as a sticky oil.

Step 6 (R)-6-(2-(piperidin-1-yl)ethyl)-1,2,3,4-tetrahydronaphthalen-1-amine: To a solution of the above product (2.0 g, 5.35 mmol) in 25 mL of DCM at room temperature was added TFA (3.66 g, 32 mmol). After stirring at room temperature overnight, the reaction solution was evaporated to dryness. The residue was treated with 2.5 mL of triethylamine and it was evaporated again in vacuo. The crude product was azeotroped with benzene and was directly used in the next step.

Step 7: Preparation of 2-((R)-3-oxo-1-tosyl-1,2,3,4-tetrahydropyrazin-2-yl)-N—((R)-6-(2-(piperidin-1-yl)ethyl)-1,2,3,4-tetrahydronaphthalen-1-yl)acetamide: A solution of (R)-2-(3-oxo-1-tosyl-1,2,3,4-tetrahydropyrazin-2-yl)acetic acid (310 mg, 1.0 mmol), crude (R)-6-(2-(piperidin-1-yl)ethyl)-1,2,3,4-tetrahydronaphthalen-1-amine (310 mg, 1.2 mmol), HOBt (135 mg, 1.0 mmol) and EDCI (191 mg, 1.0 mmol) in 1 mL of DMF was stirred overnight at room temperature. After quenching with sat. NaHCO$_3$ solution, the reaction mixture was extracted with EtOAc. The combined organic phase was washed brine, dried over Na$_2$SO$_4$, and evaporated in vacuo. Flash chomatography (SiO$_2$, EtOAc/MeOH=100:15 to 100:20 to EtOAc/2.0M NH3 in MeOH=100:10 to 100:15 to 100:20) gave the desired product as a white solid. MS: 551.2 (M+1).

Similarly, 2-((R)-1-(4-chlorophenylsulfonyl)-3-oxo-1,2,3,4-tetrahydropyrazin-2-yl)-N—((R)-6-(2-(piperidin-1-yl)ethyl)-1,2,3,4-tetrahydronaphthalen-1-yl)acetamide and 2-((R)-1-(3,4-dichlorophenylsulfonyl)-3-oxo-1,2,3,4-tetrahydropyrazin-2-yl)-N—((R)-6-(2-(piperidin-1-yl)ethyl)-1,2,3,4-tetrahydronaphthalen-1-yl)acetamide were prepared.

EXAMPLE 21

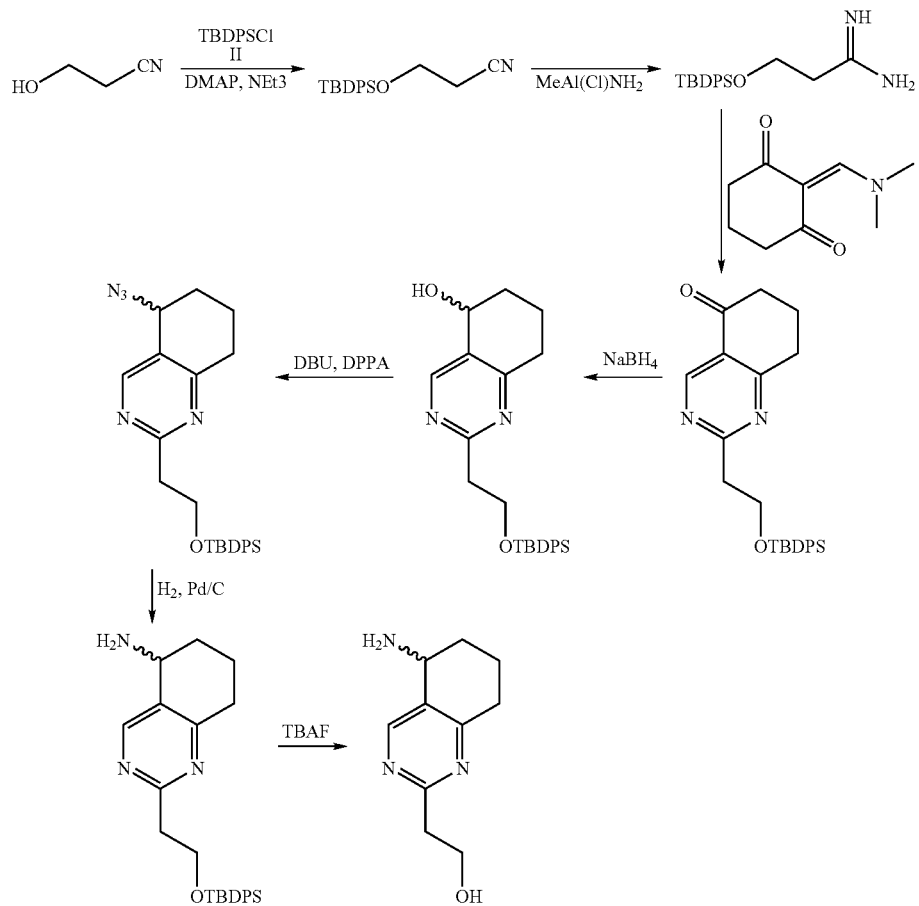

Preparation of 2-(5(R/S)-amino-5,6,7,8-tetrahydroquinazolin-2-yl)ethanol

Step 1: Preparation of 3-(tert-butyldiphenylsilyloxy)-propanenitrile: To a solution of 3-hydroxypropanenitrile (7.1 g, 0.1 mol) and DMAP (1.22 g, 0.01 mmol) in 30 mL of dry DCM at room temperature was added NEt3 (30.3 g, 0.3 mol), followed by TBDPSCl (27.5 g, 0.1 mol). A lot of white solid appeared. After stirring at room temperature overnight, the reaction mixture was quenched with sat. NH₄Cl solution, extracted with DCM, dried over Na₂SO₄, and evaporated in vacuo. Flash chomatography (SiO₂, hexane/EtOAc=100:2 to 100:5 to 100:10) gave of 3-(tert-butyldiphenylsilyloxy)propanenitrile as a white solid.

Step 2: Preparation of 3-(tert-butyldiphenylsilyloxy)-propanamidine: To a suspension of NH₄Cl (5.35 g, 0.1 mol) in 60 mL of dry benzend at 0° C. was slowly added 50 mL of 2M solution of trimethylaluminum in toluene. After the addition was complete, the reaction mixture was allowed to warm up to room temperature and was stirred for 2 h until gas evolution had ceased. A solution of 3-(tert-butyldiphenylsilyloxy)propanenitrile (9.27 g, 0.03 mol) in 20 mL of dry benzene was added to the aluminum amide reagent and the resulting mixture was heated up to 80° C. for 20 h. The reaction mixture was slowly cooled to room temperature and then carefully poured into a slurry of 300 mL of DCM and 200 g of silica gel. It was then filtered and washed thoroughly with MeOH/DCM (1:2). After concentration, flash chomatography (SiO₂, EtOAc to EtOAc/MeOH=100:20 to 100:30 to EtOAc/2M NH₃ in MeOH=100:30) gave the product as a white solid.

Step 3: Preparation of 2-(2-(tert-butyldiphenylsilyloxy)ethyl)-7,8-dihydroquinazolin-5(6H)-one: A solution of 3-(tert-butyldiphenylsilyloxy)-propanamidine (25 g, 77 mmol) and 2-((dimethylamino)methylene)cyclohexane-1,3-dione (12.8 g, 77 mmol) in 400 mL of dry EtOH was heated at 80° C. for 3 h. After cooling to room temperature, the solvent was evaporated. Flash chomatography (SiO₂, EtOAc/hexane=1:1) gave the desired product as a white solid.

Step 4: Preparation of 2-(2-(tert-butyldiphenylsilyloxy)ethyl)-5,6,7,8-tetrahydroquinazolin-5-ol: A solution of 2-(2-(tert-butyldiphenylsilyloxy)ethyl)-7,8-dihydroquinazolin-5(6H)-one (2.16 g, 5 mmol) in 30 mL of dry MeOH was treated with NaBH₄ (189 mg, 5 mmol). After 5 min, the reaction was quenched with 5 mL of sat. NH₄Cl solution. The MeOH was evaporated and the residue was extracted with DCM, dried over Na₂SO₄ and evaporated. Flash chomatography (SiO₂, DCM to EtOAc) gave the desired product as a white solid.

Step 5: Preparation of 5-azido-2-(2-(tert-butyldiphenylsilyloxy)ethyl)-5,6,7,8-tetrahydroquinazoline: To a solution of 2-(2-(tert-butyldiphenylsilyloxy)ethyl)-5,6,7,8-tetrahydroquinazolin-5-ol (2.0 g, 4.63 mmol) in 25 mL of toluene at −10° C. was added DPPA (1.2 mL, 5.56 mmol). To this stirred solution was then added DBU (0.83 mL, 5.56 mmol) dropwise while keeping the temperature below 0° C. After stirring at room temperature for 16 h, the reaction was evaporated to dryness and directly submitted to flash chomatography (SiO₂, hexane/DCM=1:2) to afford the desired product as a white solid.

Step 6: Preparation of 2-(2-(tert-butyldiphenylsilyloxy)ethyl)-5,6,7,8-tetrahydro-quinazolin-5-amine: A suspension of 80 mg of Pd/C (10% w/w) in a solution of 5-azido-2-(2-(tert-butyldiphenylsilyloxy)ethyl)-5,6,7,8-tetrahydroquinazoline (800 mg, 1.75 mmol) in 30 mL of EtOAc was stirred under H₂ atmosphere overnight. The reaction mixture was then directly submitted to flash chomatograph (SiO₂, EtOAc to EtOAc/MeOH=100:15 to EtOAc/2M NH₃ in MeOH=2:1) to give the desired product as a white solid.

Step 6: Preparation of ²-(5-amino-5,6,7,8-tetrahydroquinazolin-2-yl)ethanol: A solution of 2-(2-(tert-butyldiphenylsilyloxy)ethyl)-5,6,7,8-tetrahydroquinazolin-5-amine (570 mg, 1.32 mmol) in 10 mL of THF at 0° C. was treated with a 1M TBAF solution in THF (1.56 mL, 1.56 mmol). After stirring at room temperature overnight, the reaction mixture was directly submitted to flash chomatograph (SiO₂, EtOAc to EtOAc/MeOH=100:15 to EtOAc/2M NH₃ in MeOH=1:1) to give crude product as a white solid.

EXAMPLE 22

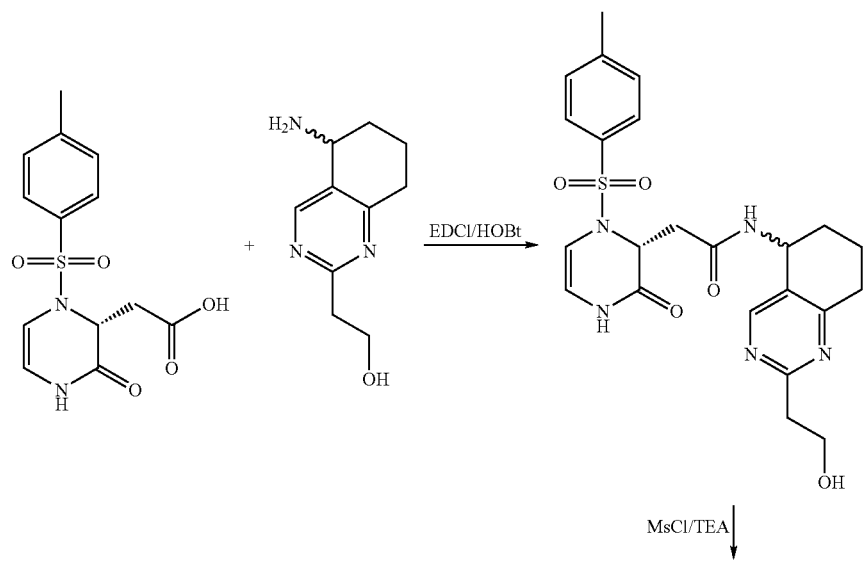

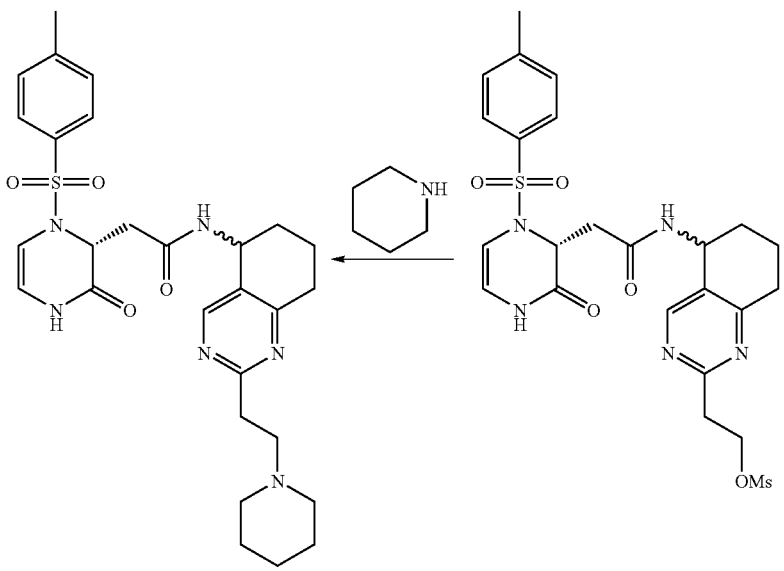

Preparation of (R)-2-(3-oxo-1-tosyl-1,2,3,4-tetrahydropyrazin-2-yl)-N-(2-(2-(piperidin-1-yl)ethyl)-5,6,7,8-tetrahydroquinazolin-5(R/S)-yl)acetamide: A solution of (R)-2-(3-oxo-1-tosyl-1,2,3,4-tetrahydropyrazin-2-yl)acetic acid (1.55 g, 5.0 mmol), crude 2-(5-amino-5,6,7,8-tetrahydroquinazolin-2-yl)ethanol (966 mg, 5.0 mmol), HOBT (676 mg, 5.0 mmol) and EDCI (959 mg, 5.0 mmol) in 2.5 mL of DMF was stirred overnight at room temperature. After quenching with sat. NaHCO₃ solution, the reaction mixture was extracted with EtOAc. The combined organic phase was washed brine, dried over Na₂SO₄, and evaporated in vacuo. Flash chomatography (SiO₂, EtOAc/MeOH=100:15 to 100:20 to 100:25 to 100:30) gave the desired product as a white solid. MS: 486.2 (M+1).

To a solution of the above compound (970 mg, 2.0 mmol) in dry DCM at 0° C. was added MsCl (687 mg, 6.0 mmol), followed by NEt₃ (1.01 g, 10 mmol). After stirring at 0° C. for 20 min, the reaction mixture was quenched with Sat. NaHCO₃ solution, extracted with EtOAc, dried over Na₂SO₄, and evaporated in vacuo. Flash chomatography (SiO₂, EtOAc/MeOH=100:10 to 100:15 to 100:16 to 100:18) gave the desired product as a white solid. MS: 564.2 (M+1).

A solution of the above compound (480 mg, 0.853 mmol) and piperidine (250 mg, 2.94 mmol) in dry DCM at room temperature was stirred overnight. The reaction mixture was quenched with sat. NH₄Cl solution, extracted with EtOAc, wasched with water, dried over Na₂SO₄, and evaporated in vacuo. Flash chomatography (SiO₂, EtOAc/MeOH=100:15 to 100:20 to EtOAc/2M NH₃ in MeOH=100:15 to 100:20 to 100:30) gave the desired product as a white solid. MS: 553.2 (M+1).

EXAMPLE 23

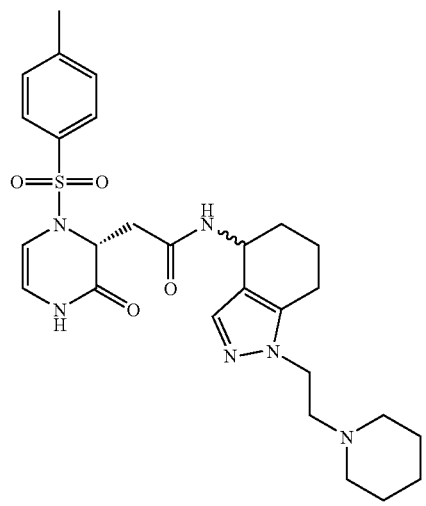

(R)-2-(3-oxo-1-tosyl-1,2,3,4-tetrahydropyrazin-2-yl)-N-(1-(2-(piperidin-1-yl)ethyl)-4,5,6,7-tetrahydro-1H-indazol-4-yl)acetamide A. Preparation of 1-(2-hydroxyethyl)-6,7-dihydro-1H-indazol-4(5H)-one: 2-Hydroxyethyl hydrazine (1.36 mL, 20 mmol) was slowly added to an ice-cooled solution of 2-((dimethylamino)methylene)cyclohexane-1,3-dione (3.34 g) in methanol (50 mL). After stirring at room temperature for 20 min, the solvent was evaporated. Flash chomatography (SiO₂, EtOAc/MeOH=100:5 to 100:7 to 100:10) gave the title compound as a white solid.

B. Preparation of 1-(2-(tert-butyldimethylsilyloxy)ethyl)-6,7-dihydro-1H-indazol-4(5H)-one: To a solution of the product from step A (14 g, 77.8 mmol) in 100 mL of dry DCM was added NEt$_3$ (22 mL, 155.6 mmol), followed by TBSCl (14 g, 93.3 mmol) and DMAP (95 mg, 0.78 mmol). After stirring at room temperature overnight, the reaction was quenched with brine and extracted with EtOAc. Flash chomatography (SiO$_2$, EtOAc/hexane=1:1) gave the title compound as a white solid.

C. Preparation of 1-(2-(tert-butyldimethylsilyloxy)ethyl)-4,5,6,7-tetrahydro-1H-indazol-4-ol: A solution of the product of step B (21 g, 71.4 mmol) in 200 mL of dry MeOH was treated with NaBH$_4$ (2.7 g, 71.4 mmol). After 30 min, the reaction was quenched with 15 mL of Sat. NH$_4$Cl solution. The MeOH was evaporated and the residue was extracted with EtOAc, dried over Na$_2$SO$_4$ and evaporated. Flash chomatography (SiO$_2$, EtOAc/hexane=1:1 to EtOAc) gave the title compound as a white solid.

D. Preparation of 4-azido-1-(2-(tert-butyldimethyl silyloxy)ethyl)-4,5,6,7-tetrahydro-1H-indazole: To a solution of the above alcohol (23 g, 77.7 mmol) in 200 mL of toluene at −10° C. was added DPPA (20 mL, 93.2 mmol). To this stirred solution was then added DBU (13.9 mL, 93.2 mmol) dropwise while keeping the temperature below 0° C. After stirring at room temperature for 18 h, the reaction was evaporated to dryness and directly submitted to flash chomatography (SiO$_2$, hexane/EtOAc=2:1 to EtOAc) to afford the title compound as a colorless liquid, together with 12 g of recovered starting alcohol.

E. Preparation of 1-(2-(tert-butyldimethylsilyloxy)ethyl)-4,5,6,7-tetrahydro-1H-indazol-4-amine: A suspension of 150 mg of Pd/C (10% w/w) in a solution of the product from step D (2.0 g, 6.23 mmol) in 100 mL of EtOAc was stirred under H$_2$ atmosphere overnight. The reaction mixture was then directly submitted to flash chomatograph (SiO$_2$, EtOAc to EtOAc/MeOH=100:20 to EtOAc/2M NH$_3$ in MeOH=100:20 to 100:30 to 100:40) to give the title compound as a white solid.

F. Preparation of (R)—N-(1-(2-(tert-butyldimethylsilyloxy)ethyl)-4,5,6,7-tetrahydro-1H-indazol-4-yl)-2-(3-oxo-1-tosyl-1,2,3,4-tetrahydropiperazin-2-yl)acetamide: A solution of (R)-2-(3-oxo-1-tosyl-1,2,3,4-tetrahydropiperazin-2-yl)acetic acid (750 mg, 2.42 mmol), 1-(2-(tert-butyldimethylsilyloxy)ethyl)-4,5,6,7-tetrahydro-1H-indazol-4-amine (785 mg, 2.66 mmol), HOBt (359 mg, 2.66 mmol) and EDCI (508 mg, 2.66 mmol) in 1.5 mL of DMF was stirred overnight at room temperature.

After quenching with Sat. NaHCO$_3$ solution, the reaction mixture was extracted with EtOAc. The combined organic phase was washed brine, dried over Na$_2$SO$_4$, and evaporated in vacuo. Flash chomatography (SiO$_2$, EtOAc/MeOH=100:2 to 100:4 to 100:6 to 100:8) gave the title compound as a white solid. MS: 588.2 (M+1).

G. Preparation of (R)—N-(1-(2-hydroxyethyl)-4,5,6,7-tetrahydro-1 H-indazol-4-yl)-2-(3-oxo-1-tosyl-1,2,3,4-tetrahydropiperazin-2-yl)acetamide: A solution of the product from step F (1.14 g, 1.94 mmol) in 15 mL of THF at 0° C. was treated with HOAc (1.40 g, 23.3 mmol) followed by a 1.0M solution of TBAF in THF (7.77 mL, 7.77 mmol). After stirring at room temperature overnight, the reaction mixture was evaporated to dryness and was directly submitted to flash chomatograph (SiO$_2$, EtOAc to EtOAc/MeOH=100:15 to 100:18 to 100:20 to 100:25 to 100:30) to give the title compound as a white solid. MS: 474.2 (M+1).

H. Preparation of (R)-2-(4-(2-(3-oxo-1-tosyl-1,2,3,4-tetrahydropiperazin-2-yl)acetamido)-4,5,6,7-tetrahydroindazol-1-yl)ethyl methanesulfonate: To a solution of the product of step G (1.2 g, 2.54 mmol) in dry DCM at 0° C. was added MsCl (0.59 mL, 7.61 mmol), followed by NEt$_3$ (1.77 mL, 12.7 mmol). After stirring at 0° C. for 15 min, the reaction mixture was quenched with sat. NaHCO$_3$ solution, extracted with EtOAc, dried over Na$_2$SO$_4$, and evaporated in vacuo. Flash chomatography (SiO$_2$, EtOAc/MeOH=100:5 to 100:8 to 100:10 to 100:13 to 100:15 to 100:18) gave the product as a white solid. MS: 552.2 (M+1).

I. Preparation of ((R)-2-(3-oxo-1-tosyl-1,2,3,4-tetrahydropiperazin-2-yl)-N-(1-(2-(piperidin-1-yl)ethyl)-4,5,6,7-tetrahydro-1H-indazol-4-yl)acetamide: A solution of the product of step H (220 mg, 0.4 mmol) and piperidine (135 mg, 1.6 mmol) in dry DCM at room temperature was stirred overnight. The reaction mixture was quenched with Sat. NH$_4$Cl solution, extracted with EtOAc, wasched with water, dried over Na$_2$SO$_4$, and evaporated in vacuo. Flash chomatography (SiO$_2$, EtOAc/MeOH=100:15 to 100:20 to EtOAc/2M NH$_3$ in MeOH=100:15 to 100:20 to 100:25) gave the title compound as a white solid. MS: 541.2 (M+1).

EXAMPLE 24

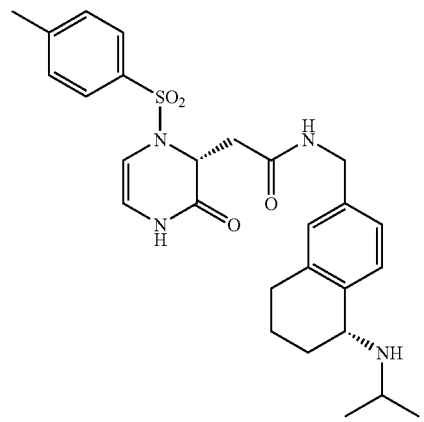

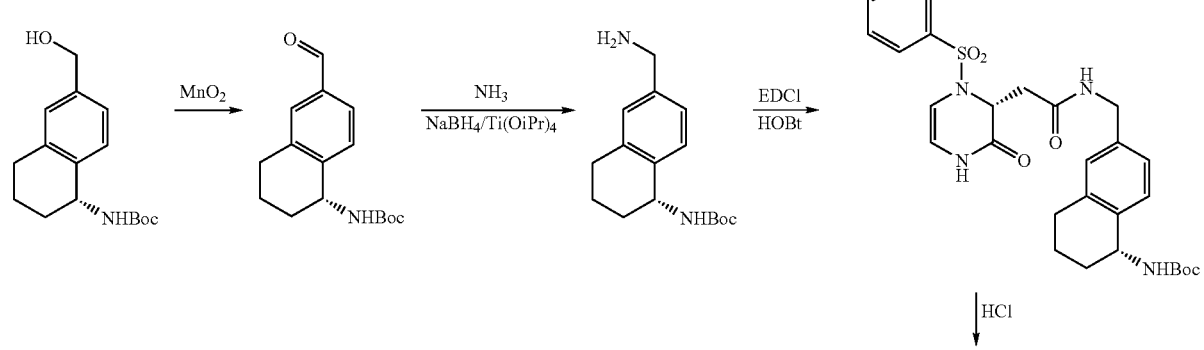

-continued

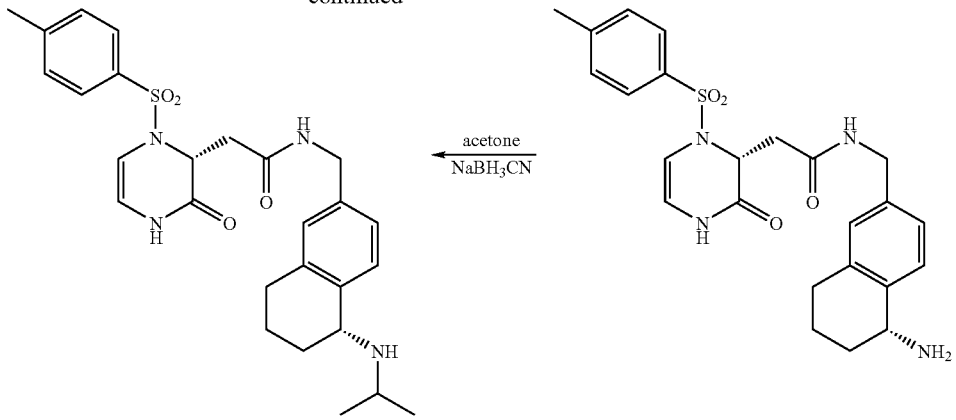

N—(((R)-5-(isopropylamino)-5,6,7,8-tetrahydronaphthalen-2-yl)methyl)-2-((R)-3-oxo-1-tosyl-1,2,3,4-tetrahydropyrazin-2-yl)acetamide A. Preparation of (R)-tert-Butyl 6-formyl-1,2,3,4-tetrahydronaphthalen-1-ylcarbamate: (R)-tert-Butyl 6-(hydroxymethyl)-1,2,3,4-tetrahydronaphthalen-1-ylcarbamate (2.0 g, 7.21 mmol) and Mn(IV) oxide (6.2 g, 72.1 mmol, 10.0 equiv) were stirred in dichloromethane (100 mL) at room temperature for 4 h. The reaction was filtered though celite and concentrated in vacuo to afford (R)-tert-butyl-6-formyl-1,2,3,4-tetrahydronaphthalen-1-ylcarbamate.

B. Preparation of (R)-tert-Butyl 6-(aminomethyl)-1,2,3,4-tetrahydronaphthalen-1-ylcarbamate: A solution of (R)-tert-butyl 6-formyl-1,2,3,4-tetrahydronaphthalen-1-ylcarbamate (1.9 g, 6.90 mmol) in a 2.0M solution of ammonia in MeOH (70 mL) was treated with Ti(IV) isopropoxide (4.1 mL, 13.81 mmol, 2.0 equiv), capped and stirred at room temperature for 14 h. Sodium borohydride (783 mg, 20.7 mmol, 3.0 equiv) was added, and the reaction was stirred for 30 min. Ammonium hydroxide solution (30%, 10 mL) was added, and the suspension was stirred for 1 h to precipitate the titanium salts. The reaction was filtered though celite, the filtrate concentrated and purified on silica gel using 10% 2.0M ammonia/methanol in dichloromethane as eluant, affording (R)-tert-butyl 6-(aminomethyl)-1,2,3,4-tetrahydronaphthalen-1-ylcarbamate.

C. Preparation of tert-Butyl (R)-6-((2-((R)-3-oxo-1-tosyl-1,2,3,4-tetrahydropyrazin-2-yl)acetamido)methyl)-1,2,3,4-tetrahydronaphthalen-1-ylcarbamate. (R)-2-(3-Oxo-1-tosyl-1,2,3,4-tetrahydropyrazin-2-yl)acetic acid (600 mg, 1.93 mmol) and (R)-tert-butyl 6-(aminomethyl)-1,2,3,4-tetrahydronaphthalen-1-ylcarbamate (534 mg, 1.93 mmol, 1.0 equiv) in N,N-dimethylformamide (20 mL) were treated with coupling agents HOBT (391 mg, 2.89 mmol, 1.5 equiv) and EDCI (554 mg, 2.89 mmol, 1.5 equiv). The reaction was stirred at room temperature for 2 h, diluted with saturated sodium bicarbonate solution (25 mL) and extracted with EtOAc (2×25 mL). The combined organic layers were washed with brine (25 mL), dried (MgSO$_4$) and purified on silica gel using 5% methanol in dichloromethane as eluant, affording tert-butyl (R)-6-((2-((R)-3-oxo-1-tosyl-1,2,3,4-tetrahydropyrazin-2-yl)acetamido)methyl)-1,2,3,4-tetrahydronaphthalen-1-ylcarbamate. MS: 567.4 (M−H)$^-$.

D. Preparation of N—(((R)-5-amino-5,6,7,8-tetrahydronaphthalen-2-yl)methyl)-2-((R)-3-oxo-1-tosyl-1,2,3,4-tetrahydropyrazin-2-yl)acetamide: A solution of tert-butyl (R)-6-((2-((R)-3-oxo-1-tosyl-1,2,3,4-tetrahydropyrazin-2-yl)-acetamido)methyl)-1,2,3,4-tetrahydronaphthalen-1-ylcarbamate (875 mg, 1.53 mmol) in methanol (10 mL) was treated with a 1.0M solution of HCl in diethyl ether (10 mL, 10.0 mmol, 6.5 equiv). The reaction was capped and stirred at room temperature for 12 h. The solvents were removed in vacuo, the residue dissolved in dichloromethane (30 mL) and washed with 1.0N solution of sodium hydroxide (25 mL). The aqueous layer was extracted with dichloromethane (3×25 mL). The combined organic layers were dried (MgSO$_4$) and purified on silica gel using 10% 2.0M ammonia/methanol in dichloromethane as eluant, affording of N—(((R)-5-amino-5,6,7,8-tetrahydronaphthalen-2-yl)methyl)-2-((R)-3-oxo-1-tosyl-1,2,3,4-tetrahydropyrazin-2-yl)acetamide. MS: 469.4 (M+H)$^+$.

E. Preparation of N—(((R)-5-(isopropylamino)-5,6,7,8-tetrahydronaphthalen-2-yl)methyl)-2-((R)-3-oxo-1-tosyl-1,2,3,4-tetrahydropyrazin-2-yl)acetamide. A solution of N—(((R)-5-amino-5,6,7,8-tetrahydronaphthalen-2-yl)methyl)-2-((R)-3-oxo-1-tosyl-1,2,3,4-tetrahydropyrazin-2-yl)acetamide (134 mg, 0.28 mmol) and acetone (0.1 mL, 1.43 mmol, 5.0 equiv) in 1,2-dichloroethane (5 mL) were treated with sodium cyanoborohydride (55 mg, 0.84 mmol, 3.0 equiv), and the solution was heated to 50° C. N,N-dimethylformamide (0.1 mL) was added to solubilize the reactants. After 1 h, more acetone (0.2 mL, 2.86 mmol, 10.0 equiv) was added and the reaction was maintained at 50° C. for a further 2 h 30 min. The reaction was cooled to room temperature, diluted with saturated sodium bicarbonate solution (5 mL) and extracted with dichloromethane (3×5 mL). The combined organic layers were dried (MgSO$_4$) and purified on silica gel using 4% 2.0M ammonia/methanol in dichloromethane as eluant, affording 100 mg (71%) of N—(((R)-5-(isopropylamino)-5,6,7,8-tetrahydronaphthalen-2-yl)methyl)-2-((R)-3-oxo-1-tosyl-1,2,3,4-tetrahydropyrazin-2-yl)acetamide. MS: 511.

EXAMPLE 25

N-methyl-2-((R)-3-oxo-1-tosyl-1,2,3,4-tetrahydropyrazin-2-yl)-N—((R)-6-(piperidin-1-ylmethyl)-1,2,3,4-tetrahydronaphthalen-1-yl)acetamide: In 10 ml of dry DCM, 0.5 mmol of (R)-2-(3-oxo-1-tosyl-1,2,3,4-tetrahydropyrazin-2-yl)acetic acid and 0.5 mmol of PyClU were combined. Next, 0.6 mmol of (R)—N-methyl-6-(piperidin-1-ylmethyl)-1,2,3,4-tetrahydronaphthalen-1-amine (prepared in Example 11) and 1.5 mmol of DIEA were added and the mix was stirred at room temperature under nitrogen for 1 h. The reaction was then quenched with 20 ml of saturated sodium bicarbonate, then extracted with EtOAc (2×30 ml), washed with brine (1×20 ml), dried with sodium sulfate, and concentrated. Purification by chomatography over silica gel using 0 to 15% MeOH (2M ammonia) in ethyl acetate gave the title compound. MS 551 (ESI, pos. ion). Similarly, N-methyl-2-((R)-3-oxo-1-(phenylsulfonyl)-1,2,3,4-tetrahydropyrazin-2-yl)-N—((R)-6-(piperidin-1-ylmethyl)-1,2,3,4-tetrahydronaphthalen-1-yl)acetamide, N-methyl-2-((R)-3-oxo-1-tosyl-1,2,3,4-tetrahydropyrazin-2-yl)-N—((R)-7-(piperidin-1-ylmethyl)choman-4-yl)acetamide, N-methyl-2-((R)-3-oxo-1-(phenylsulfonyl)-1,2,3,4-tetrahydropyrazin-2-yl)-N—((R)-7-(piperidin-1-ylmethyl)choman-4-yl)acetamide, N—((R)-7-(((tert-butylamino)methyl)choman-4-yl)-N-methyl-2-((R)-3-oxo-1-tosyl-1,2,3,4-tetrahydropyrazin-2-yl)acetamide, and N—((R)-6-(((tert-butylamino)methyl)-1,2,3,4-tetrahydronaphthalen-1-yl)-N-methyl-2-((R)-3-oxo-1-tosyl-1,2,3,4-tetrahydropyrazin-2-yl)acetamide were prepared.

EXAMPLE 26

Preparation of 2-((R)-3-oxo-1-tosyl-1,2,3,4-tetrahydropyrazin-2-yl)-N—((R)-6-(1-(piperidin-1-yl)ethyl)-1,2,3,4-tetrahydronaphthalen-1-yl)acetamide. (R)-2-(3-Oxo-1-tosyl-1,2,3,4-tetrahydropyrazin-2-yl)acetic acid (140 mg) and (1R)-6-(1-(piperidin-1-yl)ethyl)-1,2,3,4-tetrahydronaphthalen-1-amine (122 mg, prepared in Example 12) are combined in 2 mL of DMF, then EDCI (112 mg) and HOBT (79 mg) are added and the mix is stirred under nitrogen overnight. Next the mix was quenched with sat. sodium bicarb., extracted with ethyl acetate, washed with brine, washed with water, dried with sodium sulfate, and concentrated. The compound was then purified on the varian using 10 to 90% acetonitrile in water to give the product. MS 551 (ESI, pos. ion).

Similarly the following compounds were prepared from the directly coupling of the acid (prepared in Example 1) and amines (either commercially available or prepared according to exampelified in this application).

| Cpd | $R^2$ | Y | X | $R^1/R^4$ | R |
|---|---|---|---|---|---|
| 84 | Ph | CH | $CH_2$ | H/H | H |
| 85 | 4-MePh | CH | $CH_2$ | H/H | H |
| 86 | 4-ClPh | CH | $CH_2$ | H/H | H |
| 87 | 3,4-$Cl_2$Ph | CH | $CH_2$ | H/H | H |
| 88 | 4-MeOPh | CH | $CH_2$ | H/H | H |
| 89 | 3-Cl Ph | CH | $CH_2$ | H/H | H |
| 90 | 2,3-$Cl_2$ Ph | CH | $CH_2$ | H/H | H |
| 91 | 2,5-$Me_2$-4-ClPh | CH | $CH_2$ | H/H | H |
| 92 | 2,4,6-Me3 Ph | CH | $CH_2$ | H/H | H |
| 93 | 4-Me Ph | CH | $CH_2$ | H/H | 5-MeO |
| 94 | 4-Me Ph | CH | $CH_2$ | H/H | 6-MeO |
| 95 | 4-Me Ph | CH | $CH_2$ | H/H | 7-MeO |
| 96 | 4-Me Ph | CH | $CH_2$ | H/H | 5-$NH_2$ |
| 97 | 4-Me Ph | CH | $CH_2$ | H/H | 5-NHAc |
| 98 | 4-Me Ph | CH | $CH_2$ | H/H | 6-$NH_2$ |
| 99 | 4-Me Ph | CH | $CH_2$ | H/H | 5-Me |
| 100 | 4-Me Ph | CH | $CH_2$ | H/H | 5-$CH_2$OH |
| 101 | 4-Me Ph | CH | $CH_2$ | H/H | 5-CN |
| 102 | 4-Me Ph | CH | $CH_2$ | H/H | 5-CO2H |
| 103 | 4-Me Ph | CH | $CH_2$ | H/H | 5-COpiperidine |
| 104 | 4-Me Ph | CH | $CH_2$ | H/H | 6-Me |
| 105 | 4-Me Ph | CH | $CH_2$ | H/H | 5-triazene |
| 106 | 4-Me Ph | CH | $CMe_2$ | H/H | H |
| 107 | 4-Me Ph | CH | $CH_2$ | H/H | 5-tetrazole |
| 108 | 3,4-$Cl_2$ Ph | N | $CH_2$ | H/H | H |
| 109 | 4-Me Ph | CH | NH | H/H | H |
| 110 | 4-Me Ph | CH | NH | CO | H |
| 111 | 4-Me Ph | CH | NAc | H/H | H |
| 112 | 4-Me Ph | CH | SO2 | H/H | H |
| 113 | 4-Me Ph | CH | SO2 | H/H | 6-Cl |
| 114 | 4-Me Ph | CH | CO | H/H | H |
| 115 | 4-Me Ph | CH | CHOH | H/H | H |
| 116 | 4-Me Ph | CH | CMeOH | H/H | H |
| 117 | 4-Me Ph | CH | $C(OCH_2CH_2O)_2$ | H/H | H |

-continued

| | | | | | |
|---|---|---|---|---|---|
| 118 | 4-Me Ph | CH | CH$_2$CH$_2$ | H/H | H |
| 119 | 4-Me Ph | CH | — | H/H | H |
| 120 | 3,4-Cl$_2$ Ph | N | CH$_2$ | H/H | H |
| 121 | 3,4-Cl$_2$ Ph | N | CH$_2$ | H/H | H |
| 122 | 4-Me Ph | CH | CH$_2$ | H/H | 4H-1,2,4-triazol-3-yl |
| 123 | 4-Me Ph | CH | O | Me/Me | H |
| 124 | 4-Me Ph | CH | O | H/H | 6-CH$_2$OH |
| 125 | 4-Me Ph | CH | O | H/H | 6-OSO2CF3 |
| 126 | 4-Me Ph | CH | O | H/H | 6-OMe |
| 127 | 4-Me Ph | CH | O | H/H | 7-OMe |
| 128 | 4-Me Ph | CH | O | H/H | 6-CN |
| 129 | 4-Me Ph | CH | CH$_2$ | H/H | 6-OSO2CF3 |
| 130 | 4-Me Ph | CH | O | H/H | H |
| 131 | 4-Me Ph | CH | O | H/H | 6-Me-7-Cl |
| 132 | 4-Me Ph | CH | O | Me/Me | 6-OMe |
| 133 | 4-Me Ph | CH | O | Me/Me | 5-OMe |
| 134 | 4-Me Ph | CH | O | Me/Me | 7-OMe |
| 135 | 4-Me Ph | CH | O | Me/Me | 8-OMe |
| 136 | 4-Me Ph | CH | O | Me/Me | 7-Cl |
| 137 | 4-Me Ph | CH | O | Me/Me | 6-F |
| 138 | 4-Me Ph | CH | O | Me/Me | 5,7-Cl$_2$ |
| 139 | 4-Me Ph | CH | O | Me/Me | 7-Br |
| 140 | 3,4-Cl$_2$Ph | CH | O | H/H | H |
| 141 | 2,3-Cl$_2$Ph | CH | O | H/H | H |
| 142 | 2,5-Me$_2$-4-ClPh | CH | O | H/H | H |
| 143 | 4-Me Ph | CH | CH$_2$ | H/H | 6-Py-2 |

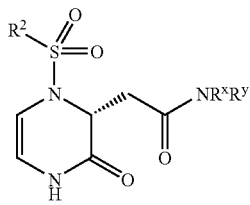

| Cpd # | R$^2$ | NR$^x$R$^y$ |
|---|---|---|
| 144 | 2,3-Cl$_2$Ph | NHCH$_2$Ph |
| 145 | 2,3-Cl$_2$Ph | NHCH$_2$Ph-4-CH$_2$(N)piperidine |
| 146 | 2,3-Cl$_2$Ph | NH(R)CHMePh-4-F |
| 147 | 2,3-Cl$_2$Ph | NHCH$_2$Py-3 |
| 148 | 2,3-Cl$_2$Ph | (2-(thiophen-2-yl)thiazol-4-yl)methylamine |
| 149 | 2,3-Cl$_2$Ph | NH(R)CHMePh |
| 150 | 2,3-Cl$_2$Ph | NHCH$_2$Py-2 |
| 151 | 2,3-Cl$_2$Ph | NHCH$_2$Py-4 |
| 152 | 2,3-Cl$_2$Ph | NHCH$_2$Ph-3-F |
| 153 | 2,3-Cl$_2$Ph | NH-c-C6H11 |
| 154 | 2,3-Cl$_2$Ph | NHPh |
| 155 | 2,3-Cl$_2$Ph | NHCH$_2$CH$_2$Ph |
| 156 | 3,4-Cl$_2$Ph | NH(R)CHMe-c-hexyl |
| 157 | 3,4-Cl$_2$Ph | NH-1-Naph |
| 158 | 3,4-Cl$_2$Ph | NHCH$_2$Ph-4-CH$_2$(N)piperidine |
| 159 | 3,4-Cl$_2$Ph | 3,4-Cl$_2$Ph |
| 160 | 3,4-Cl$_2$Ph | NH-c-C7H13 |
| 161 | 3,4-Cl$_2$Ph | NH-c-C8H15 |
| 162 | 3,4-Cl$_2$Ph | NH-c-C6H11 |
| 163 | 3,4-Cl$_2$Ph | NH-c-C5H9 |
| 164 | 3,4-Cl$_2$Ph | NH-c-C4H7 |
| 165 | 3,4-Cl$_2$Ph | 4-(2-pyridinyl)-1-piperazine |
| 166 | 3,4-Cl$_2$Ph | 2-Phpyrrolidine |
| 167 | 3,4-Cl$_2$Ph | 2-Phpiperidine |
| 168 | 3,4-Cl$_2$Ph | (4-(5,6,7,8-tetrahydro-1,8-naphthyridin-2-yl)butylamine |
| 169 | 3,4-Cl$_2$Ph | (3-(5,6,7,8-tetrahydro-1,8-naphthyridin-2-yl)propylamine |
| 170 | 3,4-Cl$_2$Ph | azocane |
| 171 | 3,4-Cl$_2$Ph | azepane |
| 172 | 3,4-Cl$_2$Ph | 1,2,3,4-tetrahydroisoquinoline |
| 173 | 3,4-Cl$_2$Ph | decahydroisoquinoline |
| 174 | 3,4-Cl$_2$Ph | 1,2,3,4-tetrahydroquinoline |
| 175 | 3,4-Cl$_2$Ph | decahydroquinoline |
| 176 | 3,4-Cl$_2$Ph | indoline |
| 177 | 3,4-Cl$_2$Ph | isoindoline |
| 178 | 3,4-Cl$_2$Ph | 1,5-oxazocane |
| 179 | 3,4-Cl$_2$Ph | 4-Phpiperidine |

-continued

| | | |
|---|---|---|
| 180 | 3,4-Cl$_2$Ph | 4-PhCH$_2$piperidine |
| 181 | 3,4-Cl$_2$Ph | 3-Mepiperidine |
| 182 | 3,4-Cl$_2$Ph | 3-Phpiperidine |
| 183 | 3,4-Cl$_2$Ph | 2-aminoindane |
| 184 | 3,4-Cl$_2$Ph | NHCH$_2$Ph |
| 185 | 3,4-Cl$_2$Ph | NHPh |
| 186 | 3,4-Cl$_2$Ph | NHCH$_2$CH$_2$Ph |
| 187 | 3,4-Cl$_2$Ph | 2-Mepiperidine |
| 188 | 3,4-Cl$_2$Ph | azonane |
| 189 | 3,4-Cl$_2$Ph | 1H-benzo[de]isoquinolin-2(3H)-yl |
| 190 | 3,4-Cl$_2$Ph | 3-Phpyrrolidine |
| 191 | 3,4-Cl$_2$Ph | 3-PhCH$_2$pyrrolidine |
| 192 | 3,4-Cl$_2$Ph | 2-PhCH$_2$pyrrolidine |
| 193 | 3,4-Cl$_2$Ph | 2-PhCH$_2$piperidine |
| 194 | 3,4-Cl$_2$Ph | azepan-4-one |
| 195 | 3,4-Cl$_2$Ph | 3-aza-bicyclo[3.2.2]nonane |
| 196 | 3,4-Cl$_2$Ph | 1,3,3-trimethyl-6-aza-bicyclo[3.2.1]octane |
| 197 | 3,4-Cl$_2$Ph | 3-PhCH$_2$piperidine |
| 198 | 2,5-Me$_2$-4-Cl | NHCH$_2$Ph-4-CH$_2$(N)piperidine |
| 199 | 2,5-Me$_2$-4-Cl | NH(R)CHMePh |
| 200 | 2,5-Me$_2$-4-Cl | NH-2-Me-c-hex |
| 201 | 4-MePh | NHCH$_2$Ph-4-CH$_2$(N)piperidine |
| 202 | 4-MePh | NH(R)CHMePh-4-CH$_2$(N)piperidine |
| 203 | 4-MePh | (4-(5,6,7,8-tetrahydro-1,8-naphthyridin-2-yl)butylamine |
| 204 | 4-MePh | 2-aminotetralin |
| 205 | 4-MePh | methyl 4-(piperidin-2-yl)benzoate |
| 206 | 4-MePh | 4-piperidine-piperidine-4- Ph |
| 207 | 4-MePh | 2-(4-(4H-1,2,4-triazol-3-yl)phenyl)ethanamine |
| 208 | 4-MePh | N-4-pyridinepiperazino-4-Ph |
| 209 | 4-MePh | N-Mepiperazino-4-piperidine |
| 210 | 4-MePh | NHCH$_2$CH$_2$Py-4 |
| 211 | 4-MePh | NH-Ph-4-pic-4 |
| 212 | 4-MePh | N-benzylpiperidine-4-amino |
| 213 | 4-MePh | 4-Me-cyclohexyl amine |
| 214 | 4-MePh | 3- Me-cyclohexyl amine |
| 215 | 4-MePh | 2- Me-cyclohexyl amine |
| 216 | 4-MePh | NH(R)CHMe$_2$-Naph |
| 217 | 4-MePh | NH(R)CHMecyclohexyl |
| 218 | 4-MePh | 4-OH-cyclohexyl amine |
| 219 | 4-MePh | 3-OH-cyclohexyl amine |
| 220 | 4-MePh | NH-1-admantyl |
| 221 | 4-MePh | 2-OH-1-aminoindane |
| 222 | 4-MePh | Ethyl 1-amino-2-cyclohexanecarboxylate |
| 223 | 4-MePh | methyl 2-amino-2-phenylacetate |
| 224 | 4-MePh | 2-HOCJI2-aminocyclohexane |
| 225 | 4-MePh | 1-(2,6-dimethylphenoxy)propan-2-amine |
| 226 | 4-MePh | NHCH$_2$CH$_2$OMe |
| 227 | 4-MePh | N-(2-Py)piperidine-4-ethylamine |
| 228 | 4-MePh | N-(3-Py)piperidine-4-ethylamine |
| 229 | 4-MePh | N-(4-Py)piperidine-4-ethylamine |
| 230 | 4-MePh | N-cyclopopylpiperidine-4-ethylamine |
| 231 | 4-MePh | NHCH$_2$CH$_2$Ph-4-2-Py |
| 232 | 4-MePh | 2-(1H-indol-2-yl)ethanamine |
| 233 | 4-MePh | 5-(aminomethyl)pyridin-2-amine |
| 234 | 4-MePh | 5-(aminomethyl)thiazol-2-amine |
| 235 | 4-MePh | pyrazin-2-ylmethanamine |
| 236 | 4-MePh | 2-(4-(4,5-dihydro-1H-imidazol-2-yl)phenyl)ethanamine |

EXAMPLE 27

(R)-3-(2-(2-(4-(hydroxymethyl)phenyl)piperidin-1-yl)-2-oxoethyl)-4-tosyl-3,4-dihydropyrazin-2(1H)-one: To a solution of (R)-methyl 4-(1-(2-(3-oxo-1-tosyl-1,2,3,4-tetrahydropyrazin-2-yl)acetyl)piperidin-2-yl)benzoate (0.562 g, 1.10 mmol) in CH$_2$Cl$_2$ stirred in dryice-acetone bath under N$_2$ was added DIBAL (1.0M solution in CH$_2$Cl$_2$, 5.50 ml, 5.50 mmol) via syringe over 15 min, and stirred for 30 min. The cold bath was removed and after 2 h MeOH (6.0 ml) was added followed by Na$_2$SO$_4$ (12.0 g) and sat'd NH$_4$Cl aq. (0.30 ml). After 30 min the mixture was filtered and the filtercake was washed with CH$_2$Cl$_2$/MeOH (10/1). The filtrate was concentrated under reduced pressure and the residue was chomatographed on silica (CH$_2$Cl$_2$→CH$_2$Cl$_2$/MeOH=20/1) to yield the product. MS 482.2 (M+H).

(R)-3-(2-oxo-2-(2-(4-(piperidin-1-ylmethyl)phenyl)piperidin-1-yl)ethyl)-4-tosyl-3,4-dihydropyrazin-2(1H)-one: To a solution of R)-3-(2-(2-(4-(hydroxymethyl)phenyl)piperidin-1-yl)-2-oxoethyl)-4-tosyl-3,4-dihydropyrazin-2(1H)-one (0.0949 g, 0.196 mmol) in CH$_2$Cl$_2$ was added MnO$_2$ (0.8569 g, 9.86 mmol) and stirred for 3.5 h. The mixture was filtered with Celite and the filter cake was washed with CH$_2$Cl$_2$MeOH (10/1). The filtrated was concentrated under reduced pressure and dried in vacuo. A portion of the solid obtained (0.0806 g) and piperidine (0.070 ml, 0.71 mmol)

were stirred in 1,2-dichloroethane under N$_2$, and NaBH(OAc)$_3$ (0.0752 g, 0.355 mmol) was added and stirred overnight. The mixture was diluted in AcOEt (80 ml) and washed with sat's NaHCO$_3$ aq. (80 ml×2) and sat'd NaCl aq. (80 ml×2), and dried over Na$_2$SO$_4$. The solvent was removed under reduced pressure and the crude product was chomatographed on silica (CH$_2$Cl$_2$→CH$_2$Cl$_2$/MeOH+2N NH$_3$=20/1) to the product. MS 551.2 (M+H).

EXAMPLE 28

Preparation of (3R)-4-(3,4-dichlorophenylsulfonyl)-3-(2-(4-hydroxy-4-methylazepan-1-yl)-2-oxoethyl)-3,4-dihydropyrazin-2(1H)-one: To a solution of (R)-1-(2-(1-(3,4-dichlorophenylsulfonyl)-3-oxo-1,2,3,4-tetrahydropyrazin-2-yl)acetyl)azepan-4-one (4) (0.0250 g, 0.054 mmol) in THF (8.00 ml, 0.054 mmol) under N$_2$ was added methylmagnesium bromide (1.4M solution in THF/Toluene (75:25), 2.70 ml, 3.78 mmol) in thee times, and stirred overnight. The reaction mixture was cooled in ice-water bath and sodium sulfate dodecahydrate (10.0 g) was added slowly followed by AcOEt (20 ml). After stirring at r.t. for 1 h, the mixture was filtered and the solid was washed with AcOEt. The filtrate was concentrated under reduced pressure and the crude product was chomatographed on silica (CH$_2$Cl$_2$→CH$_2$Cl$_2$/MeOH=20/1) to yield the product. MS 476 (M+H).

The following examples can be made using the above examples and generic schemes.

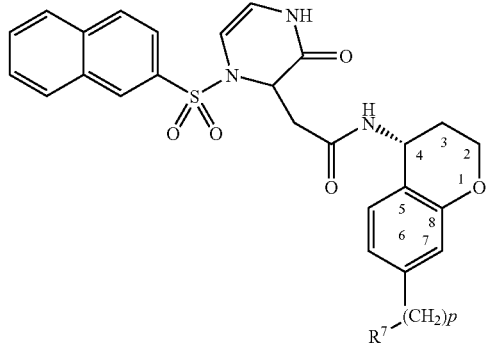

| R$^7$ | p |
|---|---|
| piperidin-1-yl | 2 |
| (CH$_3$)$_2$N— | 1 |
| piperazin-1-yl | 1 |
| 4-CH$_3$-piperazin-1-yl | 1 |
| (Et$_2$)N— | 1 |
| 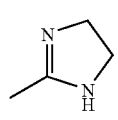 | 1 |
| (CH$_3$)(Et)N— | 2 |
| piperazin-1-yl | 2 |

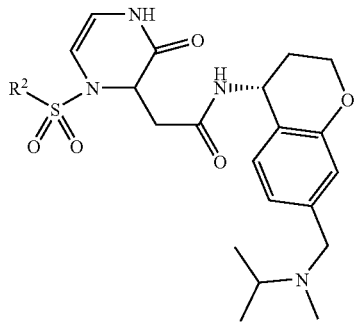

R$^2$ 5,6,7,8-tetrahydronaphth-2-yl
2-quinolyl
phenyl
2-chlorophenyl
3-chlorophenyl
4-chlorophenyl
4-methoxyphenyl
3,5-dichlorophenyl
3-methoxyphenyl
3-fluorophenyl
3-biphenyl
4-biphenyl
3-methylphenyl
3-CF$_3$-phenyl
2,4,6-trichlorophenyl
2,3,4-trichlorophenyl
2,4,5-trichlorophenyl
3,4-dichlorophenyl
4-t-butylphenyl
1-naphthyl
4-methyl-1-naphthyl
phenyl-ethenyl
benzo[1,2,5]oxadiazol-5-yl
5-(dimethylamino)naphth-1-yl
5-chloro-3-methylphenyl
benzothiazol-2-yl
2,3,4,5,6-pentamethylphenyl
6-methoxy-2-naphthyl
3-chloro-4-methylphenyl
5-methoxy-3-methylbenzothien-2-yl
6-methoxy-3-methylbenzothien-2-yl
5-chloro-3-methylbenzothien-2-yl
3-methylbenzothien-2-yl
2,4-dichloro-5-methylpbenyl
3,5-dichloro-4-methylphenyl
2,4-dichloro-3-methylphenyl
7-methoxy-2-naphthyl
6-fluoroethoxy-2-naphthyl
3-methyl-5-trifluoromethoxybenzofur-2-yl
3-methyl-5-methoxybenzofur-2-yl
5-chloro-benzo[1,2,5]oxadiazol-4-yl
3-methyl-5-trifluoromethoxybenzothien-2-yl
6-ethoxy-2-naphthyl
2-Cl-4-CF$_3$-phenyl
6-bromonaphthyl
3-methylbenzofur-2-yl
3-chlorobenzothien-2-yl
5-chloro-benzo[1,2,5]thiadiazol-4-yl
5-chloro-1,3-dimethyl-1H-pyrazol-4-yl
2,3-dichlorothien-5-yl
2,5-dichlorothien-3-yl
5-chloro-2-naphthyl
4-butoxyphenyl
3,5-di(trifluoromethyl)phenyl
5-(isoxazol-3-yl)thien-2-yl
2-chlorothien-5-yl
4-chloro-benzo[1,2,5]oxadiazol-7-yl
2,4-dichloro-6-methylphenyl
2,4,6-trimethylphenyl
2,5-dimethylphenyl

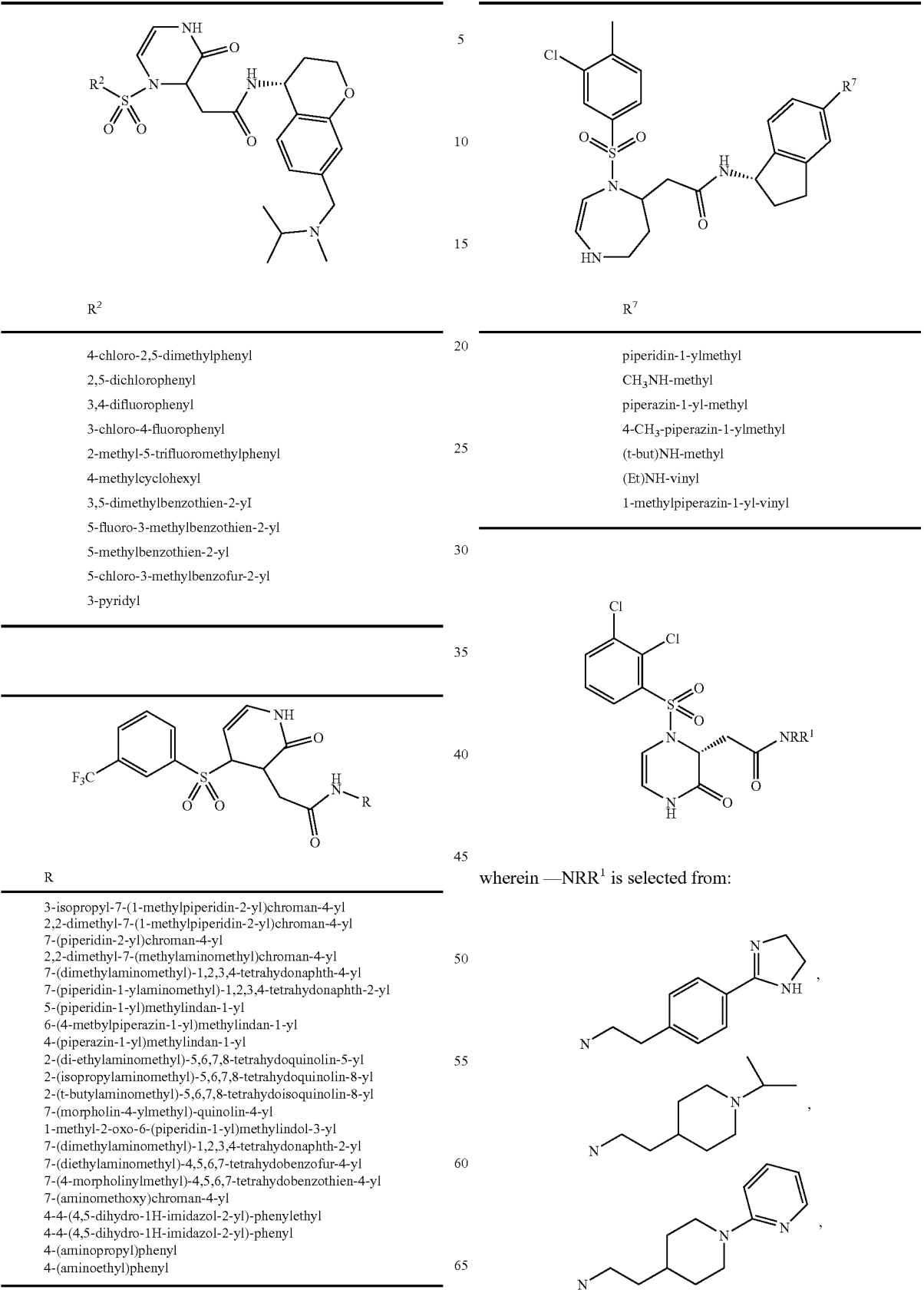

| R² |
|---|
| 4-chloro-2,5-dimethylphenyl |
| 2,5-dichlorophenyl |
| 3,4-difluorophenyl |
| 3-chloro-4-fluorophenyl |
| 2-methyl-5-trifluoromethylphenyl |
| 4-methylcyclohexyl |
| 3,5-dimethylbenzothien-2-yl |
| 5-fluoro-3-methylbenzothien-2-yl |
| 5-methylbenzothien-2-yl |
| 5-chloro-3-methylbenzofur-2-yl |
| 3-pyridyl |

| R⁷ |
|---|
| piperidin-1-ylmethyl |
| $CH_3$NH-methyl |
| piperazin-1-yl-methyl |
| 4-$CH_3$-piperazin-1-ylmethyl |
| (t-but)NH-methyl |
| (Et)NH-vinyl |
| 1-methylpiperazin-1-yl-vinyl |

| R |
|---|
| 3-isopropyl-7-(1-methylpiperidin-2-yl)chroman-4-yl |
| 2,2-dimethyl-7-(1-methylpiperidin-2-yl)chroman-4-yl |
| 7-(piperidin-2-yl)chroman-4-yl |
| 2,2-dimethyl-7-(methylaminomethyl)chroman-4-yl |
| 7-(dimethylaminomethyl)-1,2,3,4-tetrahydonaphth-4-yl |
| 7-(piperidin-1-ylaminomethyl)-1,2,3,4-tetrahydonaphth-2-yl |
| 5-(piperidin-1-yl)methylindan-1-yl |
| 6-(4-metbylpiperazin-1-yl)methylindan-1-yl |
| 4-(piperazin-1-yl)methylindan-1-yl |
| 2-(di-ethylaminomethyl)-5,6,7,8-tetrahydoquinolin-5-yl |
| 2-(isopropylaminomethyl)-5,6,7,8-tetrahydroquinolin-8-yl |
| 2-(t-butylaminomethyl)-5,6,7,8-tetrahydoisoquinolin-8-yl |
| 7-(morpholin-4-ylmethyl)-quinolin-4-yl |
| 1-methyl-2-oxo-6-(piperidin-1-yl)methylindol-3-yl |
| 7-(dimethylaminomethyl)-1,2,3,4-tetrahydonaphth-2-yl |
| 7-(diethylaminomethyl)-4,5,6,7-tetrahydobenzofur-4-yl |
| 7-(4-morpholinylmethyl)-4,5,6,7-tetrahydobenzothien-4-yl |
| 7-(aminomethoxy)chroman-4-yl |
| 4-4-(4,5-dihydro-1H-imidazol-2-yl)-phenylethyl |
| 4-4-(4,5-dihydro-1H-imidazol-2-yl)-phenyl |
| 4-(aminopropyl)phenyl |
| 4-(aminoethyl)phenyl | wherein —NRR¹ is selected from:

-continued

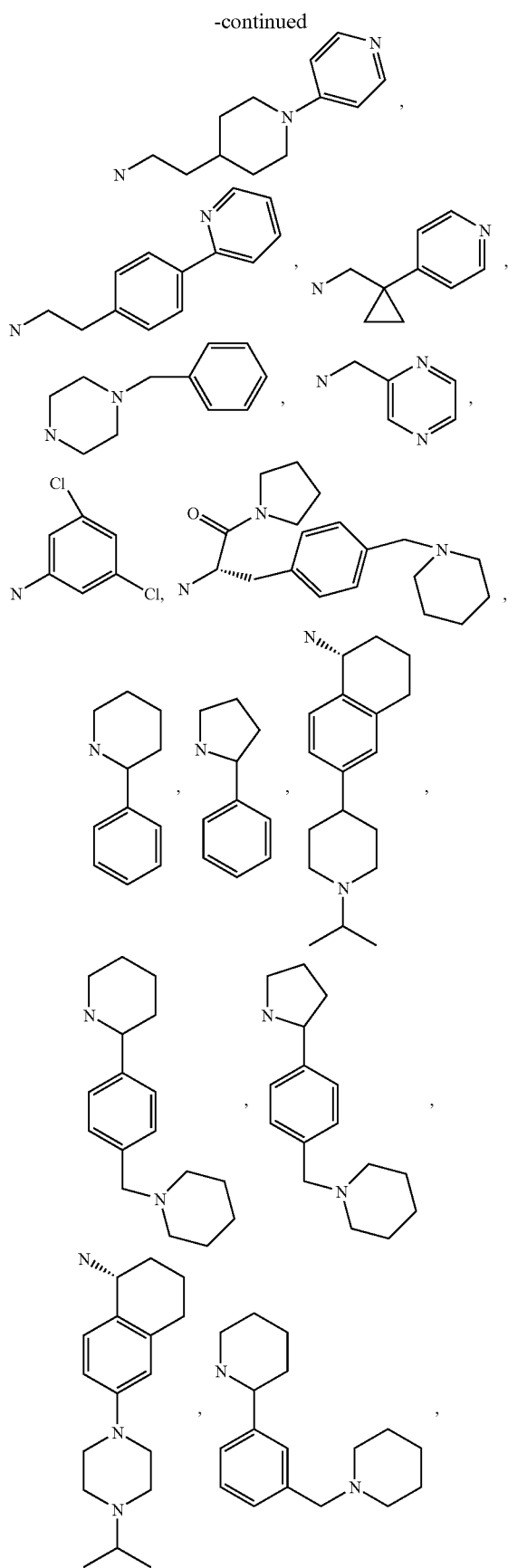

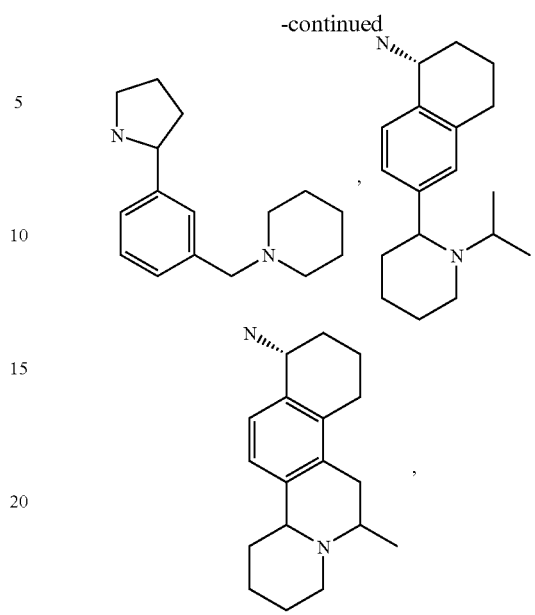

Although the pharmacological properties of the compounds of Formula I-V vary with structural change, in general, activity possessed by compounds of Formula I-V may be demonstrated in vivo. The pharmacological properties of the compounds of this invention may be confirmed by a number of pharmacological in vitro assays. The exemplified pharmacological assays, which follow, have been carried out with the compounds according to the invention and their salts. Compounds of the present invention showed binding $IC_{50}$'s of B1 at doses less than 20 µM.

Biological Testing

Human Bradykinin B1 Receptor and human B2 Receptor In Vitro Binding Assay Supporting Methods Preparation of Membranes Expressing Human B1 and Human B2 Bradykinin Receptor Membranes were prepared from CHO-d⁻AQN cells stably transfected with human bradykinin B1 receptor cDNA. For large-scale production of membranes, cells were grown in 100L suspension culture to 1.0E8 cells/mL then harvested using the Viafuge at continuous centrifugation of 1000 g. For pilot studies, cells were grown in 2 L spinner culture and harvested by centrifugation (1900 g, 10 min, 4° C.). The cell pellet was washed with PBS, centrifuged (1900 g, 10 min, 4° C.), then the cells resuspended in lysis buffer (25 mM HEPES, pH 7.4, 5 mM EDTA, 5 mM EGTA, 3 mM $MgCl_2$, 10% (w/v) sucrose, Complete Protease Inhibitor tablets (EDTA-free)) to a density of 14% w/v for passage through a microfluidizer (Microfluidics 110S, 3 passes, 6,000 psi). The resulting cell lysate was centrifuged (1900 g, 10 min, 4° C.), and the crude particulate fraction isolated by centrifugation (142,000 g, 1 h, 4° C.) of the low-speed supernatant. The resulting pellet was resuspended in ⅓ the original lysis buffer volume, homogenized, and recentrifuged as above. The membrane pellet was resuspended by homogenization in storage buffer (25 mM HEPES, pH 7.4, 3 mM $MgCl_2$, 10% (w/v) sucrose and Complete Protease Inhibitor tablets (EDTA-free)). Single-use aliquots were made and flash-frozen in liquid $N_2$ prior to storage at −80° C.

Membranes containing human bradykinin B2R were purchased from Receptor Biology (now Perkin Elmer Life Sciences). They were derived from a CHO-K1 line stably expressing the human B2 receptor developed by Receptor Biology and subsequently purchased by Amgen. For some studies, membranes were prepared in-house from this same cell line using the method described for human B1 receptor membranes, except cells were grown in roller bottles and harvested using Cellmate.

Radioligand Binding Assay for human B1 and human B2 bradykinin receptor

Human B1 receptor binding assay was performed in 96-well polypropylene plates (Costar 3365) by adding 50 µl [$^3$H] des-arg$^{10}$ kallidin (NET1064; Perkin Elmer Life Sciences) to 10 µl test compound diluted in 90 µl assay buffer (24 mM TES, pH 6.8, 1 mM 1,10 o-phenanthroline, 0.3% BSA, 0.5 mM Pefabloc SC, 2 µg/mL aprotinin, 5 µg/mL leupeptin, and 0.7 µg/mL pepstatin A). Membranes (50 µl) were added last. [$^3$H] des-arg$^{10}$ kallidin was diluted from stock into assay buffer to yield a final concentration of ~0.3 nM in the assay but was adjusted as needed to ensure a concentration at or below the $K_d$ determined for each batch of receptor membranes. Nonspecific binding was defined with 2 µM des-Arg$^{10}$Leu$^9$ kallidin. Membranes were diluted in assay buffer to yield a final concentration of 0.068 nM hB1 receptor in the assay. Compounds were solubilized in either DMSO or ddH$_2$O, plated into polypropylene plates (Costar 3365), then serially diluted in either DMSO or dilution buffer (20 mM Hepes, pH 7.6, 0.1% BSA) to yield a final concentration of either 5% DMSO or no DMSO in the assay. The assay mixture was incubated with shaking for 1 hr at RT and then filtered through GF/C plates presoaked in 0.5% polyethyleneimine (Unifilter; Perkin Elmer Life Sciences) using a Filtermate 96-well harvester (Perkin Elmer Life Sciences). Filter plates were rapidly washed 6 times with 200 µl ice-cold buffer (50 mM Tris, pH 7.4), dried in a vacuum oven at 55° C. for 15-20 min, backed, and 40 µl per well of Microscint 20 was added. The plates were sealed and activity read on Topcount (Perkin Elmer Life Sciences) using a count time of 3 min per channel.

For human B2 bradykinin receptor, the same procedure was followed with the following exceptions: [$^3$H] bradykinin (NET706; Perkin Elmer Life Sciences) was used at a final concentration of ~0.2 nM and non-specific binding was defined with 2 µM bradykinin. Human B2 receptor concentration was 0.068 nM final in the assay.

Data Analysis

Data was analyzed in XLFit with the four-parameter logistic y=A+((B−A)/(1+((C/x)^D))) and fit with the Levenburg-Marquardt algorithm. Raw cpm were converted to percent of control values prior to analysis (POC=((compound cpm−nonspecfic cpm)/(no-compound cpm−nonspecific cpm) *100)). $K_i$ values were determined from the IC$_{50}$ using the Cheng-Prusoff equation and $K_d$ values determined by direct saturation binding of the radioligands.

The compounds of examples 3b-3c, 4, 4b, 5a, 6, 6a, 7, 9-12, and 14 have binding Ki's to the hB1 receptor at a level below 1 µM. The compounds should have binding Ki's to the hB2 receptor at a level above 1 µM.

In vitro B1-Inhibition Activity

In vitro Assay of Human B1 Receptor Function using Calcium Flux

Activation of the G$_q$ linked B1 receptor results in an increase in intracellular calcium. The calcium sensitive photoprotein aequorin can, therefore, be used as an indicator of B1 receptor activation. Aequorin is a 21-kDa photoprotein that forms a bioluminescent complex when linked to the chromophore cofactor coelenterazine. Following the binding of calcium to this complex, an oxidation reaction of coelenterazine results in the production of apoaequorin, coelenteramide, CO$_2$, and light that can be detected by conventional luminometry.

A stable CHO D-/hB1/Aequorin cell line was established and the cells were maintained in suspension in spinner bottles containing a 1:1 ratio of DMEM and HAM F12 (Gibco 11765-047), high glucose (Gibco 11965-084), 10% Heat Inactivated Dialyzed serum (Gibco 26300-061), 1× Non-Essential Amino Acids (Gibco 11140-050), 1× Glutamine-Pen-Strep (Gibco 10378-016), and Hygromycin, 300 µg/mL (Roche 843555). 15-24 h prior to the luminometer assay, 25,000 cells/well (2.5E6 cells/10 mL/plate) were plated in 96-well black-sided clear bottom assay plates (Costar #3904).

Media was removed from the wells and replaced with 60 µl of serum free HAM's F12 with 30 mM HEPES (pH 7.5) and 15 µM coelenterazine (Coelenterazine h Luciferin #90608 from Assay Designs). The plates were incubated for 1.5-2 h. Ten point IC$_{50}$ compound plates containing 1:3 or 1:5 dilutions of antagonist compounds and an agonist activator plate (20 nM des-Arg10-Kallidin final concentration, EC$_{80}$) were prepared using Ham's F12 with 30 mM HEPES, pH 7.5. Following coelenterazine incubation, an automated flash-luminometer platform was used to dispense the B1 antagonist compounds (dissolved in DMSO and diluted with buffer to the desired concentration (final DMSO concentration<1% DMSO)) to the cell plate, a CCD camera situated underneath the cell plate took 12 images of the cell plate at 5 second intervals to determine if there was any agonist activity with the compounds. The hB1 agonist, des-Arg$_{10}$-Kallidin, was added to the cell plate and another 12 images were recorded to determine the IC$_{50}$ of the antagonist(s). The compounds of examples 3c, 7, and 9-12 have binding IC$_{50}$'s to hB1 receptor function at a level below 1 µM.

In vitro Assay of hB2 Receptor Function using Calcium Flux

The intracellular calcium flux induced by hB2 receptor activation was analyzed using an hB2 recombinant cell line (CHO-K1) purchased from PerkinElmer (Catalog Number: RBHB2C000EA) on a fluorometric imaging plate reader (FLIPR). The cells were cultured in T225 flask containing Ham's F12 Nutrient Mixture (Invitrogen Corp., Cat # 11765-047), 10% Fetal Clone II Bovine Serum (HyClone, Cat # SH3006603), 1 mM Sodium pyruvate (100 mM stock, Invitrogen Corp., Cat# 12454-013), and 0.4 mg/mL Geneticin (G418; 50 mg/mL active geneticin, Invitrogen, Cat# 10131-207). Culture medium was changed every other day. 24 h prior to the FLIPR assay, the hB2/CHO cells were washed once with PBS (Invitrogen, Cat.#) and 10 mL of Versene (1:5000, Invitrogen, Cat# 15040-066) was added to each flask. After 5 min incubation at 37° C., Versene was removed and cells were detached from the flask and resuspended in culture medium. Cells were counted and 25,000 cells/well were plated in 96-well black-sided clear bottom assay plates (Costar #3904). Cells were incubated in a 37° C. CO$_2$ incubator overnight.

The media was aspirated from the cells and replaced with 65 µl of dye-loading buffer. The loading buffer was prepared by diluting a stock solution of 0.5 mM Fluo-4 AM (Molecular Probes, dissolved in DMSO containing 10% [w/v] pluronic acid) to a concentration of 1 µM in Clear Dulbecco's Modified Eagle Medium (DMEM) containing 0.1% BSA, 20 mM HEPES, and 2.5 mM probenecid. The cells were dye-loaded for 1 h at RT. The excess dye was removed by washing the cells 2× with assay buffer. The assay buffer consists of Hank's Balanced Salt Solution (HBSS) containing 20 mM HEPES, 0.1% BSA, and 2.5 mM probenecid. After the wash cycles, a volume of 100 μL was left in each well, and the plate was ready to be assayed in the FLIPR System. Single point (10 μM final concentration) POC antagonist compound plates or ten point $IC_{50}$ compound plates containing 1:3 or 1:5 dilutions of antagonist compounds (dissolved in DMSO and diluted with buffer to the desired concentration (final DMSO concentration<1% DMSO)) and an agonist activator plate (0.3 nM bradykinin final concentration, $EC_{80}$) were prepared using assay buffer. The cell plate and the compound plates were loaded onto the FLIPR and during the assay, fluorescence readings are taken simultaneously from all 96 wells of the cell plate. Ten 1-second readings were taken to establish a stable baseline for each well, then 25 μL from the B1 antagonist plate was rapidly (50 μL/sec.) added. The fluorescence signal was measured in 1-second (1 min) followed by 6-second (2 min) intervals for a total of 3 min to determine if there is any agonist activity with the compounds. The B2 agonist, bradykinin, was added to the cell plate and another 3 min were recorded to determine the percent inhibition at 10 μM (POC plates) or the $IC_{50}$ of the antagonist.

Cell and Tissue based In Vitro Assays of hB1 Receptor Binding

These studies established the antagonist activity of several compounds at the bradykinin B1 receptors in vitro cell-based and isolated organ assays.
1. Rabbit endothelial cell B1-specific $PGI_2$ secretion Assay
2. B1 and B2 umblical vein Assay In vitro B1-Inhibition Activity The effectiveness of the compounds as inhibitors of B1 activity (i.e., B1 "neutralization") can be evaluated by measuring the ability of each compound to block B1 stimulated CGRP and substance P release and calcium signaling in Dorsal Root Ganglion (DRG) neuronal cultures.

Dorsal Root Ganglion Neuronal Cultures

Dorsal root ganglia are dissected one by one under aseptic conditions from all spinal segments of embryonic 19-day old (E19) rats that are surgically removed from the uterus of timed-pregnant, terminally anesthetized Sprague-Dawley rats (Charles River, Wilmington, Mass.). DRG are collected in ice-cold L-15 media (GibcoBRL, Grand Island, N.Y.) containing 5% heat inactivated horse serum (GibcoBRL), and any loose connective tissue and blood vessels are removed. The DRG are rinsed twice in $Ca^{2+}$- and $Mg^{2+}$-free Dulbecco's phosphate buffered saline (DPBS), pH 7.4 (GibcoBRL). The DRG are dissociated into single cell suspension using a papain dissociation system (Worthington Biochemical Corp., Freehold, N.J.). Briefly, DRG are incubated in a digestion solution containing 20 U/mL of papain in Earle's Balanced Salt Solution (EBSS) at 37° C. for fifty minutes. Cells are dissociated by trituration through fire-polished Pasteur pipettes in a dissociation medium consisting of MEM/Ham's F12, 1:1, 1 mg/mL ovomucoid inhibitor and 1 mg/mL ovalbumin, and 0.005% deoxyribonuclease I (DNase). The dissociated cells are pelleted at 200×g for 5 min and re-suspended in EBSS containing 1 mg/mL ovomucoid inhibitor, 1 mg/mL ovalbumin and 0.005% DNase. Cell suspension is centrifuged through a gradient solution containing 10 mg/mL ovomucoid inhibitor, 10 mg/mL ovalbumin at 200×g for 6 min to remove cell debris, then filtered through a 88-μM nylon mesh (Fisher Scientific, Pittsburgh, Pa.) to remove any clumps. Cell number is determined with a hemocytometer, and cells are seeded into poly-ornithine 100 μg/mL (Sigma, St. Louis, Mo.) and mouse laminin 1 μg/mL (GibcoBRL)-coated 96-well plates at $10 \times 10^3$ cells/well in complete medium. The complete medium consists of minimal essential medium (MEM) and Ham's F12, 1:1, penicillin (100 U/mL), streptomycin (100 μg/mL), and 10% heat inactivated horse serum (GibcoBRL). The cultures are kept at 37° C., 5% $CO_2$ and 100% humidity. For controlling the growth of non-neuronal cells, 5-fluoro-2'-deoxyuridine (75 μM) and uridine (180 μM) are included in the medium. Two hours after plating, cells are treated with recombinant human β-B1 or recombinant rat β-B1 at a concentration of 10 mg/mL (0.38 nM). Positive controls comprising serial-diluted anti-B1 antibody (R&D Systems, Minneapolis, Minn.) are applied to each culture plate. Compounds are added at ten concentrations using 3.16-fold serial dilutions. All samples are diluted in complete medium before being added to the cultures. Incubation time is generally around 40 h prior to measurement of VR1 expression.

Measurement of VR1 Expression in DRG Neurons.

Cultures are fixed with 4% paraformaldehyde in Hanks' balanced salt solution for 15 min, blocked with Superblock (Pierce, Rockford, Ill.), and permeabilized with 0.25% Nonidet P40 (Sigma) in Tris.HCl (Sigma)-buffered saline (TBS) for 1 h at RT. Cultures are rinsed once with TBS containing 0.1% Tween 20 (Sigma) and incubated with rabbit anti-VR1 IgG (prepared at Amgen) for 1.5 h at RT, followed by incubation of Eu-labeled anti-rabbit second antibody (Wallac Oy, Turku, Finland) for 1 h at RT. Washes with TBS (3× five min with slow shaking) are applied after each antibody incubation. Enhance solution (150 mL/well, Wallac Oy) is added to the cultures. The fluorescence signal is measured in a time-resolved fluorometer (Wallac Oy). VR1 expression in samples treated with the compounds is determined by comparing to a standard curve of B1 titration from 0-1000 ng/mL. Percent inhibition (compared to maximum possible inhibition) of B1 effect on VR1 expression in DRG neurons is determined by comparing to controls that are not B1-treated.

In vivo Antinociceptive Activity in Rat and Monkey Pain Models

Rat Neuropathic Pain Model

Male Sprague-Dawley rats (200 g) are anesthetized with isoflurane inhalant anesthesia and the left lumbar spinal nerves at the level of L5 and L6 are tightly ligated (4-0 silk suture) distal to the dorsal root ganglion and prior to entrance into the sciatic nerve, as first described by Kim and Chung (Kim, S. H.; Chung, J. M. An experimental model for peripheral neuropathy produced by segmental spinal nerve ligation in the rat. Pain 50:355-363, (1992)). The incisions are closed and the rats are allowed to recover. This procedure results in mechanical (tactile) allodynia in the left hind paw as assessed by recording the pressure at which the affected paw (ipsilateral to the site of nerve injury) was withdrawn from graded stimuli (von Frey filaments ranging from 4.0 to 148.1 mN) applied perpendicularly to the plantar surface of the paw (between the footpads) through wire-mesh observation cages. A paw withdrawal threshold (PWT) was determined by sequentially increasing and decreasing the stimulus strength and analyzing withdrawal data using a Dixon non-parametric test, as described by Chaplan et al. (Chaplan, S. R.; Bach, F. W.; Pogrel, J. W.; Chung, J. M.; Yaksh, T. L. Quantitative assessment of tactile allodynia in the rat paw. J. Neurosci. Meth., 53:55-63 (1994)).

Normal rats and sham surgery rats (nerves isolated but not ligated) withstand at least 148.1 mN (equivalent to 15 g) of pressure without responding. Spinal nerve ligated rats respond to as little as 4.0 mN (equivalent to 0.41 g) of pressure on the affected paw. Rats are included in the study only if they did not exhibit motor dysfunction (e.g., paw dragging or dropping) and their PWT was below 39.2 mN (equivalent to 4.0 g). At least seven days after surgery rats are treated with compounds (usually a screening dose of 60 mg/kg) or control diluent (PBS) once by s.c. injection and PWT was determined each day thereafter for 7 days.

Rat CFA Inflammatory Pain Model

Male Sprague-Dawley rats (200 g) are lightly anesthetized with isoflurane inhalant anesthesia and the left hindpaw is injected with complete Freund's adjuvant (CFA), 0.15 mL. This procedure results in mechanical (tactile) allodynia in the left hind paw as assessed by recording the pressure at which the affected paw is withdrawn from graded stimuli (von Frey filaments ranging from 4.0 to 148.1 mN) applied perpendicularly to the plantar surface of the paw (between the footpads) through wire-mesh observation cages. PWT is determined by sequentially increasing and decreasing the stimulus strength and analyzing withdrawal data using a Dixon non-parametric test, as described by Chaplan et al. (1994). Rats are included in the study only if they do not exhibit motor dysfunction (e.g., paw dragging or dropping) or broken skin and their PWT is below 39.2 mN (equivalent to 4.0 g). At least seven days after CFA injection rats are treated with compounds (usually a screening dose of 60 mg/kg) or control solution (PBS) once by s.c. injection and PWT is determined each day thereafter for 7 days. Average paw withdrawal threshold (PWT) is converted to percent of maximum possible effect (%MPE) using the following formula: % MPE=100*(PWT of treated rats−PWT of control rats)/(15-PWT of control rats). Thus, the cutoff value of 15 g (148.1 mN) is equivalent to 100% of the MPE and the control response is equivalent to 0% MPE.

At the screening dose of 60 mg/kg, compounds in vehicle are expected to produce an antinociceptive effect with a PD relationship.

Green Monkey LPS Inflammation Model

The effectiveness of the compounds as inhibitors of B1 activity are evaluated in Male green monkeys (*Cercopithaecus aethiops* St Kitts) challenged locally with B1 agonists essentially as described by deBlois and Horlick (British Journal of Pharmacology, 132:327-335 (2002), which is hereby incorporated by reference in its entirety).

In order to determine whether compounds of the present invention inhibit B1 induced oedema the studies described below are conducted on male green monkeys (*Cercopithaecus aethiops* St Kitts) at the Caribbean Primates Ltd. experimental farm (St Kitts, West Indies). Procedures are reviewed and accepted by the Animal Care Committees of the CR-CHUM (Montreal, Canada) and of Caribbean Primates Ltd. (St Kitts, West Indies). Animals weighing 6.0±0.5 kg (n=67) were anaesthetized (50 mg ketamine kg$^{-1}$) and pretreated with a single intravenous injection of LPS (90 µg kg$^{-1}$) or saline (1 mL) via the saphenous vein.

Inflammation Studies

Kinin-induced oedema is evaluated by the ventral skin fold assay (Sciberras et al., 1987). Briefly, anaesthetized monkeys were injected with captopril (1 mg kg$^{-1}$ 30 min before assay). A single subcutaneous injection of dKD, BK or the vehicle (2 mM amastatin in 100 µl Ringer's lactate) is given in the ventral area and the increase in thickness of skin folds is monitored for 30-45 min using a calibrated caliper. The results are expressed as the difference between the skin fold thickness before and after the subcutaneous injection. Captopril and amastatin are used to reduce degradation of kinins at the carboxyl- and amino-terminus, respectively.

Antagonist Schild Analysis

The dose-response relationship for dKD (1-100 nmol)-induced oedema is determined at 24 h post-LPS in the absence or presence of different concentrations of antagonist. BK (30 nmol) is used as a positive control.

Antagonst Time Course

The time course of inhibition by antagonist is determined at 4, 24 and 48 h, 72 and/or 96 h after single bolus administration. BK (30 nmol) is used as a positive control. DRUGS Ketamine hydrochloride, LPS, amastatin and captopril are from Sigma (MO, U.S.A.). All peptides are from Phoenix Pharmaceuticals (CA, U.S.A.).

Statistics

Values are presented as mean ±standard error of the mean (s.e. mean). In edema studies, the pre-injection thickness of the skin folds was subtracted from the values after subcutaneous challenge. Curve fitting and $EC_{50}$ calculations were obtained using the Delta Graph 4.0 software for Apple Computers. Data were compared by two-way analysis of variance followed by unpaired, one tail Student's t-test with Bonferroni correction. $P<0.05$ was considered statistically significant.

Formulations

Also embraced within this invention is a class of pharmaceutical compositions comprising the active compounds of Formula I-V in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg or 5 to 1000 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.1 and about 50 mg/kg, and more preferably about 0.1 and about 20 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable topological effects are expected when compounds of the present invention are administered in accordance with the present invention.

All mentioned references, patents, applications and publications, are hereby incorporated by reference in their entirety, as if here written.

What is claimed is:

1. A compound of Formula I

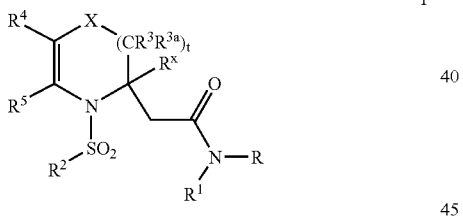

I wherein:
t is 1;
X is selected from NH,
R is selected from
- a) 9-, 10-, or 11-membered fused bicyclic carbocyclic or heterocyclic ring substituted by 1, 2 or 3 basic moieties, and substituted by 0, 1, 2 or 3 groups independently selected from halo, hydroxyl, cyano, oxo, nitro, $(C_1-C_6)$alkoxy, $(C_2-C_6)$alkenyl, $(C_2-C_6)$alkynyl, —C(O)R$^8$, —COOR$^8$, —C(O)NR$^8$R$^8$', —NR$^8$C(O)R$^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
- b) 3-, 4-, 5-, 6- or 7-membered carbocyclic ring substituted by 0, 1, 2 or 3 basic moieties, and substituted by 0, 1, 2 or 3 groups independently selected from halo, hydroxyl, cyano, $(C_1-C_6)$alkoxy, $(C_2-C_6)$alkenyl, $(C_2-C_6)$alkynyl, —C(O)R$^8$, —COOR$^8$, —C(O)NR$^8$R$^{8'}$, —NR$^8$C(O)R$^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
- c) 4-, 5-, 6- or 7-membered heterocyclic ring substituted by 1, 2 or 3 basic moieties, and substituted by 0, 1, 2 or 3 groups independently selected from halo, hydroxyl, cyano, oxo, $(C_1-C_6)$alkoxy, $(C_2-C_6)$alkenyl,$(C_2-C_6)$alkynyl,—C(O)R$^8$, —COOR$^8$, —C(O)NR$^8$R$^{8'}$, —NR$^8$C(O)R$^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
- d) aralkyl substituted by 0, 1, 2 or 3 basic moieties, and substituted by 0, 1, 2 or 3 groups independently selected from halo, hydroxyl, cyano,$(C_1-C_6)$alkoxy, $(C_2-C_6)$alkenyl, $(C_2-C_6)$alkynyl, —C(O)R$^8$, —COOR$^8$, —C(O)NR$^8$R$^{8'}$, —NR$^8$C(O)R$^{8'}$, $(C_1-C_6)$ alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
- e) 5- or 6-membered heterocyclylalkyl substituted by 1, 2 or 3 basic moieties, and substituted by 0, 1, 2 or 3 groups independently selected from halo, hydroxyl, cyano, oxo, $(C_1-C_6)$alkoxy, $(C_2-C_6)$alkenyl, $(C_2-C_6)$alkynyl, —C(O)R$^8$, —COOR$^8$, —C(O)NR$^8$R$^{8'}$, —NR$^8$C(O)R$^{8'}$, $(C_1-C_6)$alkyl, substituted $(C_1-C_6)$ alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
- f) 4-, 5-, 6- or 7-membered carbocyclic or heterocyclic ring substituted by 0,1, 2 or 3 groups independently selected from halo, hydroxyl, cyano, oxo, $(C_1-C_6)$ alkoxy, $(C_2-C_6)$alkenyl, $(C_2-C_6)$alkynyl, —C(O)R$^8$, —COOR$^8$, —C(O)NR$^8$R$^{8'}$, —NR$^8$C(O)R$^{8'}$, $(C_1-C_6)$ alkyl, substituted $(C_1-C_6)$alkyl, aralkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
- g) —$(C_1-C_8)$alkyl-R$^8$, wherein the alkyl is substituted by 0, 1 or 2 groups selected from a basic moiety, phenyl, benzyl, OR$^8$ and NR$^8$R$^{8'}$;
- h) 9-, 10-, or 11-membered fused bicyclic carbocyclic or heterocyclic ring substituted by 0, 1, 2, 3 or 4 groups independently selected from halo, cyano, oxo, $(C_1-C_6)$alkoxy, $(C_2-C_6)$alkenyl, $(C_2-C_6)$alkynyl, —C(O)R$^8$, —COOR$^8$, —C(O)NR$^8$R$^{8'}$, —NR$^8$C(O)R$^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; and
- i) 12-, 13-, 14-, or 15-membered fused tricyclic carbocyclic or heterocyclic ring substituted by 0, 1, 2 or 3 basic moieties, and substituted by 0, 1, 2 or 3 groups independently selected from halo, hydroxyl, cyano, oxo, $(C_1-C_6)$alkoxy, $(C_2-C_6)$alkenyl, $(C_2-C_6)$alkynyl, —C(O)R$^8$, —COOR$^8$, —C(O)NR$^8$R$^{8'}$, —NR$^8$C(O) R$^{8'}$, $(C_1-C_6)$alkyl, substituted $(C_1-C_6)$alkyl, aryl,substituted aryl, heteroaryl, substituted heteroaryl, cycloalkyl, substituted cycloalkyl, substituted saturated or partially saturated heterocyclyl and unsubstituted saturated or partially saturated heterocyclyl;

$R^1$ is selected from H, $C_{1-4}$-alkyl, substituted $C_{1-4}$-alkyl, aryl and substituted aryl; alternatively R and $R^1$ together with the nitrogen atom to which they are attached form a 4-10 membered mono- or bicyclic heterocyclyl ring, optionally containing 1-2 additional heteroatoms, optionally fused with 1 or 2 phenyl or ($C_5$-$C_7$)cycloalkyl groups or optionally substituted with one aryl, heteroaryl or aralkyl group, wherein the heterocyclyl ring and aryl, heteroaryl or aralkyl groups are further optionally substituted with a basic moiety and futher substituted by 0, 1, 2 or 3 groups independently selected from halo, cyano, oxo, ($C_1$-$C_6$)alkoxy, ($C_2$-$C_6$)alkenyl, ($C_2$-$C_6$)alkynyl, —C(O)$R^8$, —COO$R^8$, —C(O)N$R^8R^{8'}$, —N$R^8$C(O)$R^{8'}$, —Oaralkyl, —O$R^8$, ($C_1$-$C_6$)alkyl, and substituted ($C_1$-$C_6$)alkyl;

$R^2$ is selected from aryl, and heterocyclyl selected from thienyl, quinolinyl, isoquinolinyl, 3-pyridyl, thiazol-4-yl, 4-imidazolyl, benzofuryl, benzoxadiazolyl, benzothiadiazolyl, benzothiazolyl, 1H-pyrazolyl, isoxazolthienyl, benzothienyl, thieno[3,2-c]pyridinyl, and tetrahydroisoquinolinyl, wherein $R^2$ is optionally substituted with one to five groups independently selected from halo, —NH$_2$, hydroxyl, cyano, ($C_1$-$C_6$)alkylamino, oxo, ($C_1$-$C_6$)alkoxy, ($C_2$-$C_6$)alkenyl, ($C_2$-$C_6$) alkynyl, di($C_1$-$C_6$)alkylamino, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

$R^4$ and $R^5$ are H;

or $R^3$ and $R^{3a}$ together form oxo;

$R^8$ and $R^{8'}$ independently in each instance are H or selected from lower alkyl, aryl heterocyclyl and heteroaryl, each of which is optionally substituted with one, two or three groups independently selected from lower alkyl, halogen, lower alkoxy, hydroxy, amino, mono- or dialkylamino, and trifluoromethyl;

$R^x$ is selected from H; and wherein each substituted alkyl, substituted aryl, substituted heteroaryl, substituted cycloalkyl and substituted saturated or partially saturated heterocyclyl is substituted by 1, 2 or 3 groups independently selected from halo, —NH$_2$, hydroxyl, cyano, ($C_1$-$C_6$)alkylamino, ($C_1$-$C_6$) haloalkyl, oxo, ($C_1$-$C_6$)alkoxy, ($C_1$-$C_6$)alkoxy($C_1$-$C_6$) alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O) N$R^8R^{8'}$, and —N$R^8$C(O)$R^{8'}$, and wherein the basic moiety is selected from amino, clycloalkylamino($C_1$-$C_6$)alkyl, cycloalkyl ($C_1$-$C_6$alkylamino ($C_1$-$C_6$)alkyl, heterocyclylamino($C_1$-$C_6$) alkyl, heterocyclyl($C_1$-$C_6$)alkylamino($C_1$-$C_6$)alkyl, arylamino($C_1$-$C_6$)alkyl, aryl($C_1$-$C_6$)alkylamino($C_1$-$C_6$) alkyl, ($C_1$-$C_6$)alkylamino($C_1$-$C_6$)alkoxy, ($C_1$-$C_6$)alkylamino($C_1$-$C_6$)alkoxy($C_1$-$C_6$)alkoxy,amino($C_1$-$C_6$) alkoxy, amino($C_1$-$C_6$)alkyl, ($C_1$-$C_6$)alkylalmino($C_1$-$C_6$)alkyl, ($C_1$-$C_4$)alkylamino-($C_2$-$C_6$)alkenyl, 4-8-membered nitrogen-containing heterocyclyl($C_2$-$C_6$)alkenyl, 4-8-membered nitrogen-containing heterocyclyl ($C_1$-$C_6$)alkyl, [4-8-membered nitrogen-containing heterocyclyl]-[4-8-membered nitrogen-containing heterocyclyl], 7-12-membered bicyclic nitrogen-containing heterocyclyl($C_1$-$C_6$)alkyl, heterocyclyl($C_1$-$C_6$)alkylamino($C_2$-$C_6$)alkyl, 5-6 membered heterocyclyoxy, 5-6 membered nitrogen-containing heterocyclyl and 5-7 membered nitrogen-containing heterocyclyl-alkyl; where each basic moiety can be substituted by 0, 1, 2 or 3 groups independently selected from halo, —NH$_2$, —OH, —CN, —CF$_3$, ($C_1$-$C_6$)alkylamino, haloalkyl, oxo, ($C_1$-$C_6$)alkoxy, ($C_1$-$C_6$)alkoxyalkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^8$, —N$R^8$C(O)$R^{8'}$=NCN; and ($C_1$-$C_6$)alkyl, aryl, heteroaryl, cycloalkyl and heterocyclyl, each of which is substituted by 0, 1, 2 or 3 groups independently selected from halo, —NH$_2$, —OH, —CN, —CF$_3$, ($C_1$-$C_6$)alkylamino, haloalkyl, oxo, ($C_1$-$C_6$)alkoxy, ($C_1$-$C_6$)alkoxyalkyl, ($C_1$-$C_6$)alkyl, ($C_2$-$C_6$) alkenyl, ($C_2$-$C_6$)aalkynyl, di($C_1$-$C_6$)alkylamino, 13 C(O)$R^8$, —COO$R^8$, —C(O)N$R^8R^8$, —N$R^8$C(O) $R^{8'}$azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, wherein heteroaryl in the terms heteroaryl and substituted heteroaryl means an unsaturated 5 to 6 membered heteromonocyclyl groups containing 1 to 4 nitrogen atoms, unsaturated 5 to 6 membered heteromonocyclyl group containing a sulfur atom, unsaturated 5- to 6-membered heteromonocyclic group containing 1 to 2 oxygen atoms and 1 to 3 nitrogen atoms, unsaturated 5 to 6-membered heteromonocyclic group containing 1 to 2 sulfur atoms and 1 to 3 nitrogen atoms, unsaturated 9 or 10-membered bicyclic heterocyclic group containing 1 to 5 nitrogen atoms, unsaturated 9 or 10-membered bicyclic heterocyclic group containing 1 to 2 oxygen atoms and 1 to 3 nitrogen atoms, or unsaturated 9 or 10-membered bicyclic heterocyclic group containing 1 to 2 sulfur atoms and 1 to 3 nitrogen atoms; and wherein heterocyclyl in the terms substituted saturated or partially saturated heterocyclyl and unsubstituted saturated or partially saturated heterocyclyl means an saturated 3 to 8-membered heteromonocyclic group containing 1 to 4 nitrogen atoms, saturated 3 to 8-membered heteromonocyclic group containing 1 to 2 oxygen atoms and 1 to 3 nitrogen atom, saturated 3 to 8-membered heteromonocyclic group containing 1 to 2 sulfur atoms and 1 to 3 nitrogen atoms, dihydrothiophene, dihydropyran, dihydrofuran, or dihydrothiazole;

or a pharmaceutically acceptable salt thereof.

2. Compound of claim 1 wherein R is selected from a 9-, 10-, or 11-membered fused bicyclic carbocyclic or heterocyclic ring substituted by 1, 2 or 3 basic moieties, and substituted by 0, 1, 2 or 3 groups independently selected from halo, hydroxyl, cyano, oxo, nitro, ($C_1$-$C_6$)alkoxy, ($C_2$-$C_6$)alkenyl, ($C_2$-$C_6$)alkynyl, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

3. Compound of claim 1 wherein R is selected from a 3-, 4-, 5-, 6- or 7-membered carbocyclic ring substituted by 0, 1, 2 or 3 basic moieties, and substituted by 0, 1, 2 or 3 groups independently selected from halo, hydroxyl, cyano, ($C_1$-$C_6$) alkoxy, ($C_2$-$C_6$)alkenyl, ($C_2$-$C_6$)alkynyl, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

4. Compound of claim 1 wherein R is selected from a 4-, 5-, 6- or 7-membered heterocyclic ring substituted by 1, 2 or 3 basic moieties, and substituted by 0, 1, 2 or 3 groups independently selected from halo, hydroxyl, cyano, oxo, $(C_1-C_6)$ alkoxy, $(C_2-C_6)$alkenyl, $(C_2-C_6)$alkynyl, —C(O)R$^8$, —COOR$^8$, —C(O)NR$^8$R$^{8'}$, —NR$^8$C(O)R$^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

5. Compound of claim 1 wherein R is selected from an aralkyl substituted by 0, 1, 2 or 3 basic moieties, and substituted by 0, 1, 2 or 3 groups independently selected from halo, hydroxyl, cyano, $(C_1-C_6)$alkoxy, $(C_2-C_6)$alkenyl, $(C_2-C_6)$alkynyl, —C(O)R$^8$, —COOR$^8$, —C(O)NR$^8$R$^{8'}$, —NR$^8$C(O)R$^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

6. Compound of claim 1 wherein R is selected from a 5- or 6-membered heterocyclylalkyl substituted by 1, 2 or 3 basic moieties, and substituted by 0, 1, 2 or 3 groups independently selected from halo, hydroxyl, cyano, oxo, $(C_1-C_6)$alkoxy, $(C_2-C_6)$alkenyl, $(C_2-C_6)$alkynyl, —C(O)R$^8$, —COOR$^8$, —C(O)NR$^8$R$^{8'}$, —NR$^8$C(O)R$^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

7. Compound of claim 1 wherein R is selected from a 4-, 5-, 6- or 7-membered carbocyclic or heterocyclic ring substituted by 0, 1, 2 or 3 groups independently selected from halo, hydroxyl, cyano, oxo, $(C_1-C_6)$alkoxy, $(C_2-C_6)$alkenyl, $(C_2-C_6)$alkynyl, —C(O)R$^8$, —COOR$^8$, —C(O)NR$^8$R$^{8'}$, —NR$^8$C(O)R$^{8'}$, $(C_1-C_6)$alkyl, substituted $(C_1-C_6)$alkyl, aralkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

8. Compound of claim 1 wherein R is —$(C_1-C_8)$alkyl-R$^8$, wherein the alkyl is substituted by 0, 1 or 2 groups selected from a basic moiety, phenyl, benzyl, OR$^8$ and NR$^8$R$^{8'}$.

9. Compound of claim 1 wherein R is a 9-, 10-, or 11-membered fused bicyclic carbocyclic or heterocyclic ring substituted by 0, 1, 2, 3 or 4 groups independently selected from halo, cyano, oxo, $(C_1-C_6)$alkoxy, $(C_2-C_6)$alkenyl, $(C_2-C_6)$ alkynyl, —C(O)R$^8$, —COOR$^8$, —C(O)NR$^8$R$^{8'}$, —NR$^8$C(O)R$^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

10. Compound of claim 1 wherein R2 is selected from aryl substituted with 1, 2, 3, 4 or 5 groups independently selected from halo, —NH$_2$, hydroxyl, cyano, $(C_1-C_6)$alkylamino, oxo, $(C_1-C_6)$alkoxy, $(C_2-C_6)$alkenyl, $(C_2-C_6)$alkynyl, di$(C_1-C_6)$ alkylamino, —C(O)R$^8$, —COOR$^8$, —C(O)NR$^8$R$^{8'}$, —NR$^8$C (O)R$^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

11. Compound of claim 1 wherein the compound is selected from
(3R)-3-(2-((2R)-2-(4-(hydroxymethyl)phenyl)-1-piperidinyl)-2-oxoethyl)-4-((4-methylphenyl)sulfonyl)-3,4-dihydro-2(1H)-pyrazinone;
(3R)-3-(2-((2S)-2-(4-(hydroxymethyl)phenyl)-1-piperidinyl)-2-oxoethyl)-4-((4-methylphenyl)sulfonyl)-3,4-dihydro-2(1H)-pyrazinone;
(3R)-3-(2-(1-azepanyl)-2-oxoethyl)-4-((3,4-dichlorophenyl)sulfonyl)-3,4-dihydro-2(1H) -pyrazinone;
(3R)-3-(2-(1-azetidinyl)-2-oxoethyl)-4-((4-methylphenyl)sulfonyl)-3,4-dihydro-2(1H) -pyrazinone;
(3R)-3-(2-(1-azocanyl)-2-oxoethyl)-4-((3,4-dichlorophenyl)sulfonyl)-3,4-dihydro-2(1H) -pyrazinone;
(3R)-3-(2-(1-azonanyl)-2-oxoethyl)-4-((3,4-dichlorophenyl)sulfonyl)-3,4-dihydro-2(1H) -pyrazinone;
(3R)-3-(2-(1H-benzo[de]isoquinolin-2(3H)-yl)-2-oxoethyl)-4-((3,4-dichlorophenyl)sulfonyl)-3,4-dihydro-2 (1H)-pyrazinone;
(3R)-3-(2-(3,4-dihydro-2(1H)-isoquinolinyl)-2-oxoethyl)-4-((4-methylphenyl)sulfonyl) -3,4-dihydro-2(1H)-pyrazinone;
(3R)-3-(2-(3-azabicyclo[3.2.2]non-3-yl)-2-oxoethyl)-4-((3,4-dichlorophenyl)sulfonyl) -3,4-dihydro-2(1H)-pyrazinone;
(3R)-3-(2-(4-(2-hydroxyethyl)-1-piperazinyl)-2-oxoethyl)-4-((4-methylphenyl)sulfonyl) -3,4-dihydro-2(1H)-pyrazinone;
(3R)-4-((3,4-dichlorophenyl)sulfonyl)-3-(2-((2R)-2-(hydroxymethyl)-1-piperidinyl)-2-oxoethyl)-3,4-dihydro-2(1H)-pyrazinone;
(3R)-4-((3,4-dichlorophenyl)sulfonyl)-3-(2-((2R)-2-methyl-1-piperidinyl)-2-oxoethyl) -3,4-dihydro-2(1H)-pyrazinone;
(3R)-4-((3,4-dichlorophenyl)sulfonyl)-3-(2-((2S)-2-(hydroxymethyl)-1-piperidinyl)-2-oxoethyl)-3,4-dihydro-2(1H)-pyrazinone;
(3R)-4-((3,4-dichlorophenyl)sulfonyl)-3-(2-((2S)-2-methyl-1-piperidinyl)-2-oxoethyl) -3,4-dihydro-2(1H)-pyrazinone;
(3R)-4-((3,4-dichlorophenyl)sulfonyl)-3-(2-((3R)-3-(hydroxymethyl)-1-piperidinyl)-2-oxoethyl)-3,4-dihydro-2(1H)-pyrazinone;
(3R)-4-((3,4-dichlorophenyl)sulfonyl)-3-(2-((3R)-3-methyl-1-piperidinyl)-2-oxoethyl) -3,4-dihydro-2(1H)-pyrazinone;
(3R)-4-((3,4-dichlorophenyl)sulfonyl)-3-(2-((3S)-3-(hydroxymethyl)-1-piperidinyl)-2-oxoethyl)-3,4-dihydro-2(1H)-pyrazinone;
(3R)-4-((3,4-dichlorophenyl)sulfonyl)-3-(2-((3S)-3-methyl-1-piperidinyl)-2-oxoethyl) -3,4-dihydro-2(1H)-pyrazinone;
(3R)-4-((3,4-dichlorophenyl)sulfonyl)-3-(2-((4aR,8aR)-octahydro-1 (2H)-quinolinyl)-2-oxoethyl)-3,4-dihydro-2(1H)-pyrazinone;
(3R)-4-((3,4-dichlorophenyl)sulfonyl)-3-(2-((4aR,8aR)-octahydro-2(1H)-isoquinolinyl) -2-oxoethyl)-3,4-dihydro-2(1H)-pyrazinone;
(3R)-4-((3,4-dichlorophenyl)sulfonyl)-3-(2-((4aR,8aS)-octahydro-1(2H)-quinolinyl)-2-oxoethyl)-3,4-dihydro-2(1H)-pyrazinone;
(3R)-4-((3,4-dichlorophenyl)sulfonyl)-3-(2-((4aR,8aS)-octahydro-2(1H)-isoquinolinyl) -2-oxoethyl)-3,4-dihydro-2(1H)-pyrazinone;
(3R)-4-((3,4-dichlorophenyl)sulfonyl)-3-(2-((4aS,8aR)-octahydro-1(2H)-quinolinyl)-2-oxoethyl)-3,4-dihydro-2(1H)-pyrazinone;

(3R)-4-((3,4-dichlorophenyl)sulfonyl)-3-(2-((4aS,8aR)-octahydro-2(1H)-isoquinolinyl)-2-oxoethyl)-3,4-dihydro-2(1H)-pyrazinone;

(3R)-4-((3,4-dichlorophenyl)sulfonyl)-3-(2-((4aS,8aS)-octahydro-1(2H)-quinolinyl)-2-oxoethyl)-3,4-dihydro-2(1H)-pyrazinone;

(3R)-4-((3,4-dichlorophenyl)sulfonyl)-3-(2-((4aS,8aS)-octahydro-2(1H)-isoquinolinyl)-2-oxoethyl)-3,4-dihydro-2(1H)-pyrazinone;

(3R)-4-((3,4-dichlorophenyl)sulfonyl)-3-(2-((4R)-4-hydroxy-1-azepanyl)-2-oxoethyl) -3,4-dihydro-2(1H)-pyrazinone;

(3R)-4-((3,4-dichlorophenyl)sulfonyl)-3-(2-((4R)-4-hydroxy-4-methyl-1-azepanyl)-2-oxoethyl)-3,4-dihydro-2(1H)-pyrazinone;

(3R)-4-((3,4-dichlorophenyl)sulfonyl)-3-(2-((4S)-4-hydroxy-1-azepanyl)-2-oxoethyl) -3,4-dihydro-2(1H)-pyrazinone;

(3R)-4-((3,4-dichlorophenyl)sulfonyl)-3-(2-((4S)-4-hydroxy-4-methyl-1-azepanyl)-2-oxoethyl)-3,4-dihydro-2(1H)-pyrazinone;

(3R)-4-((3,4-dichlorophenyl)sulfonyl)-3-(2-(1,3-dihydro-2H-isoindol-2-yl)-2-oxoethyl) -3,4-dihydro-2(1H)-pyrazinone;

(3R)-4-((3,4-dichlorophenyl)sulfonyl)-3-(2-(1,4-oxazepan-4-yl)-2-oxoethyl)-3,4-dihydro -2(1H)-pyrazinone;

(3R)-4-((3,4-dichlorophenyl)sulfonyl)-3-(2-(2,3-dihydro-1H-indol-1-yl)-2-oxoethyl)-3,4-dihydro-2(1H)-pyrazinone;

(3R)-4-((3,4-dichlorophenyl)sulfonyl)-3-(2-(3,4-dihydro-1(2H)-quinolinyl)-2-oxoethyl) -3,4-dihydro-2(1H)-pyrazinone;

(3R)-4-((3,4-dichlorophenyl)sulfonyl)-3-(2-(3,4-dihydro-2(1H)-isoquinolinyl)-2-oxoethyl)-3,4-dihydro-2(1H)-pyrazinone;

(3R)-4-((3,4-dichlorophenyl)sulfonyl)-3-(2-(4-(hydroxymethyl)-1-piperidinyl)-2-oxoethyl)-3,4-dihydro-2(1H)-pyrazinone;

(3R)-4-((3,4-dichlorophenyl)sulfonyl)-3-(2-(4-methyl-1-piperidinyl)-2-oxoethyl)-3,4-dihydro-2(1H)-pyrazinone;

(3R)-4-((3,4-dichlorophenyl)sulfonyl)-3-(2-oxo-2-((1R,5S)-1,3,3-trimethyl-6-azabicyclo[3.2.1]oct-6-yl)ethyl)-3,4-dihydro-2(1H)-pyrazinone;

(3R)-4-((3,4-dichlorophenyl)sulfonyl)-3-(2-oxo-2-((1S,5R)-1,3,3-trimethyl-6-azabicyclo[3.2.1]oct-6-yl)ethyl)-3,4-dihydro-2(1H)-pyrazinone;

(3R)-4-((3,4-dichlorophenyl)sulfonyl)-3-(2-oxo-2-((2R)-2-(phenylmethyl)-1-pyrrolidinyl)ethyl)-3,4-dihydro-2(1H)-pyrazinone;

(3R)-4-((3,4-dichlorophenyl)sulfonyl)-3-(2-oxo-2-((2R)-2-(phenylmethyl)-1-piperidinyl)ethyl)-3,4-dihydro-2(1H)-pyrazinone;

(3R)-4-((3,4-dichlorophenyl)sulfonyl)-3-(2-oxo-2-((2R)-2-phenyl-1-pyrrolidinyl)ethyl) -3,4-dihydro-2(1H)-pyrazinone;

(3R)-4-((3,4-dichlorophenyl)sulfonyl)-3-(2-oxo-2-((2R)-2-phenyl-1-piperidinyl)ethyl) -3,4-dihydro-2(1H)-pyrazinone;

(3R)-4-((3,4-dichlorophenyl)sulfonyl)-3-(2-oxo-2-((2R)-2-phenyl-1-azepanyl)ethyl)-3,4-dihydro-2(1H)-pyrazinone;

(3R)-4-((3,4-dichlorophenyl)sulfonyl)-3-(2-oxo-2-((2S)-2-(phenylmethyl)-1-pyrrolidinyl)ethyl)-3,4-dihydro-2(1H)-pyrazinone;

(3R)-4-((3,4-dichlorophenyl)sulfonyl)-3-(2-oxo-2-((2S)-2-(phenylmethyl)-1-piperidinyl)ethyl-3,4-dihydro-2(1H)-pyrazinone;

(3R)-4-((3,4-dichlorophenyl)sulfonyl)-3-(2-oxo-2-((2S)-2-phenyl-1-pyrrolidinyl)ethyl) -3,4-dihydro2(1H)-pyrazinone;

(3R)-4-((3,4-dichlorophenyl)sulfonyl)-3-(2-oxo-2-((2S)-2-phenyl-1-piperidinyl)ethyl) -3,4-dihydro-2(1H)-pyrazinone;

(3R)-4-((3,4-dichlorophenyl)sulfonyl)-3-(2-oxo-2-((2S)-2-phenyl-1-azepanyl)ethyl)-3,4-dihydro-2(1H)-pyrazinone;

(3R)-4-((3,4-dichlorophenyl)sulfonyl)-3-(2-oxo-2-((3R)-3-(phenylmethyl)-1-pyrrolidinyl)ethyl)-3,4-dihydro-2(1H)-pyrazinone;

(3R)-4-((3,4-dichlorophenyl)sulfonyl)-3-(2-oxo-2-((3R)-3-phenyl-1-piperidinyl)ethyl) -3,4-dihydro-2(1H)-pyrazinone;

(3R)-4-((3,4-dichlorophenyl)sulfonyl)-3-(2-oxo-2-((3R)-3-phenyl-1-pyrrolidinyl)ethyl) -3,4-dihydro-2(1H)-pyrazinone;

(3R)-4-((3,4-dichlorophenyl)sulfonyl)-3-(2-oxo-2-((3S)-3-(phenylmethyl)-1-pyrrolidinyl)ethyl)-3,4-dihydro-2(1H)-pyrazinone;

(3R)-4-((3,4-dichlorophenyl)sulfonyl)-3-(2-oxo-2-((3S)-3-phenyl-1-piperidinyl)ethyl) -3,4-dihydro-2(1H)-pyrazinone;

(3R)-4-((3,4-dichlorophenyl)sulfonyl)-3-(2-oxo-2-((3S)-3-phenyl-1-pyrrolidinyl)ethyl) -3,4-dihydro-2(1H)-pyrazinone;

(3R)-4-((3,4-dichlorophenyl)sulfonyl)-3-(2-oxo-2-(1-piperidinyl)ethyl)-3,4-dihydro-2(1H)-pyrazinone;

(3R)-4-((3,4-dichlorophenyl)sulfonyl)-3-(2-oxo-2-(1-pyrrolidinyl)ethyl)-3,4-dihydro-2(1H)-pyrazinone;

(3R)-4-((3,4-dichlorophenyl)sulfonyl)-3-(2-oxo-2-(4-(2-pyridinyl)-1-piperazinyl)ethyl) -3,4-dihydro-2(1H)-pyrazinone;

(3R)-4-((3,4-dichlorophenyl)sulfonyl)-3-(2-oxo-2-(4-(phenylmethyl)-1-piperidinyl)ethyl)-3,4-dihydro-2(1H)-pyrazinone;

(3R)-4-((3,4-dichlorophenyl)sulfonyl)-3-(2-oxo-2-(4-phenyl-1-piperidinyl)ethyl)-3,4-dihydro-2(1H)-pyrazinone;

(3R)-4-((4-methylphenyl)sulfonyl)-3-(2-((1R,4R)-2-oxa-5-azabicyclo[2.2.1]hept-5-yl) -2-oxoethyl)-3,4-dihydro-2(1H)-pyrazinone;

(3R)-4-((4-methylphenyl)sulfonyl)-3-(2-((1S,4S)-2-oxa-5-azabicyclo[2.2.1]hept-5-yl) -2-oxoethyl)-3,4-dihydro-2(1H)-pyrazinone;

(3R)-4-((4-methylphenyl)sulfonyl)-3-(2-((4aR,8aS)-octahydro-2(1H)-isoquinolinyl)-2-oxoethyl)-3,4-dihydro-2(1H)-pyrazinone;

(3R)-4-((4-methylphenyl)sulfonyl)-3-(2-((4aS,8aR)-octahydro-2(1H)-isoquinolinyl)-2-oxoethyl)-3,4-dihydro-2(1H)-pyrazinone;

(3R)-4-((4-methylphenyl)sulfonyl)-3-(2-(4-morpholinyl)-2-oxoethyl)-3,4-dihydro-2(1H)-pyrazinone;

(3R)-4-((4-methylphenyl)sulfonyl)-3-(2-oxo-2-((2R)-2-(4-(1-piperidinylmethyl)phenyl)-1-piperidinyl)ethyl)-3,4-dihydro-2(1H)-pyrazinone;

(3R)-4-((4-methylphenyl)sulfonyl)-3-(2-oxo-2-((2S)-2-(4-(1-piperidinylmethyl)phenyl)-1-piperidinyl)ethyl)-3,4-dihydro-2(1H)-pyrazinone;

(4-(((2S)-1-((3,4-dichlorophenyl)sulfonyl)-3-oxo-1,2,3,4-tetrahydro-2-pyrazinyl)acetyl)-1-piperazinyl)acetonitrile;

1-(((2R)-1-((3,4-dichlorophenyl)sulfonyl)-3-oxo-1,2,3,4-tetrahydro-2-pyrazinyl)acetyl)-1,4-diazepan-5-one;

1-(((2R)-1-((3,4-dichlorophenyl)sulfonyl)-3-oxo-1,2,3,4-tetrahydro-2-pyrazinyl)acetyl)-4-azepanone;

1,1-dimethylethyl (1R)-6-(((((2R)-1-((4-methylphenyl)sulfonyl)-3-oxo-1,2,3,4-tetrahydro-2-pyrazinyl)acetyl)amino)methyl)-1,2,3,4-tetrahydro-1-naphthalenylcarbamate;

1,1-dimethylethyl 4-(1-((5R)-5-((((2R)-1-((4-methylphenyl)sulfonyl)-3-oxo-1,2,3,4-tetrahydro-2-pyrazinyl)acetyl)amino)-5,6,7,8-tetrahydro-2-naphthalenyl)ethyl)-1-piperazinecarboxylate;

2-((2R)-1-((2,3-dichlorophenyl)sulfonyl)-3-oxo-1,2,3,4-tetrahydro-2-pyrazinyl)-N-((4-(1-piperidinylmethyl)phenyl)methyl)acetamide;

2-((2R)-1-((2,3-dichlorophenyl)sulfonyl)-3-oxo-1,2,3,4-tetrahydro-2-pyrazinyl)-N-((1R) -1-(4-fluorophenyl)ethyl)acetamide;

2-((2R)-1-((2,3-dichlorophenyl)sulfonyl)-3-oxo-1,2,3,4-tetrahydro-2-pyrazinyl)-N-(3-pyridinylmethyl)acetamide;

2-((2R)-1-((2,3-dichlorophenyl)sulfonyl)-3-oxo-1,2,3,4-tetrahydro-2-pyrazinyl)-N-((2-(2-thienyl)-1,3-thiazol-4-yl)methyl)acetamide;

2-((2R)-1-((2,3-dichlorophenyl)sulfonyl)-3-oxo-1,2,3,4-tetrahydro-2-pyrazinyl)-N-((1R) -1-phenylethyl)acetamide;

2-((2R)-1-((2,3-dichlorophenyl)sulfonyl)-3-oxo-1,2,3,4-tetrahydro-2-pyrazinyl)-N-((1S) -1-(3,3'-difluoro-2'-(3-methyl-1,2,4-oxadiazol-5-yl)-1,1'-biphenyl-4-yl)ethyl)acetamide;

2-((2R)-1-((2,3-dichlorophenyl)sulfonyl)-3-oxo-1,2,3,4-tetrahydro-2-pyrazinyl)-N-(4-pyridinylmethyl)acetamide;

2-((2R)-1-((2,3-dichlorophenyl)sulfonyl)-3-oxo-1,2,3,4-tetrahydro-2-pyrazinyl)-N-(2-pyridinylmethyl)acetamide;

2-((2R)-1-((2,3-dichlorophenyl)sulfonyl)-3-oxo-1,2,3,4-tetrahydro-2-pyrazinyl)-N -(phenylmethyl)acetamide;

2-((2R)-1-((2,3-dichlorophenyl)sulfonyl)-3-oxo-1,2,3,4-tetrahydro-2-pyrazinyl)-N-((1R) -6-(1-piperidinylmethyl)-1,2,3,4-tetrahydro-1-naphthalenyl)acetamide;

2-((2R)-1-((2,3-dichlorophenyl)sulfonyl)-3-oxo-1,2,3,4-tetrahydro-2-pyrazinyl)-N-((3-fluorophenyl)methyl)acetamide;

2-((2R)-1-((3,4-dichlorophenyl)sulfonyl)-3-oxo-1,2,3,4-tetrahydro-2-pyrazinyl)-N-((1R) -1,2,3,4-tetrahydro-1-naphthalenyl)acetamide;

2-((2R)-1-((3,4-dichlorophenyl)sulfonyl)-3-oxo-1,2,3,4-tetrahydro-2-pyrazinyl)-N-((1R) -6-(hydroxymethyl)-1,2,3,4-tetrahydro-1-naphthalenyl)acetamide;

2-((2R)-1-((3,4-dichlorophenyl)sulfonyl)-3-oxo-1,2,3,4-tetrahydro-2-pyrazinyl)-N-((4R) -7-(hydroxymethyl)-3,4-dihydro-2H-chromen-4-yl)acetamide;

2-((2R)-1-((3,4-dichlorophenyl)sulfonyl)-3-oxo-1,2,3,4-tetrahydro-2-pyrazinyl)-N-((1R) -6-(((1-methylethyl)amino)methyl)-1,2,3,4-tetrahydro-1-naphthalenyl)acetamide;

2-((2R)-1-((3,4-dichlorophenyl)sulfonyl)-3-oxo-1,2,3,4-tetrahydro-2-pyrazinyl)-N-((4R) -7-(((1-methylethyl)amino)methyl)-3,4-dihydro-2H-chromen-4-yl)acetamide;

2-((2R)-1-((3,4-dichlorophenyl)sulfonyl)-3-oxo-1,2,3,4-tetrahydro-2-pyrazinyl)-N-((5R) -5,6,7,8-tetrahydro-5-quinolinyl)acetamide;

2-((2R)-1-((3,4-dichlorophenyl)sulfonyl)-3-oxo-1,2,3,4-tetrahydro-2-pyrazinyl)-N-(1-naphthalenyl)acetamide;

2-((2R)-1-((3,4-dichlorophenyl)sulfonyl)-3-oxo-1,2,3,4-tetrahydro-2-pyrazinyl)-N-((4-(1-piperidinylmethyl)phenyl)methyl)acetamide;

2-((2R)-1-((3,4-dichlorophenyl)sulfonyl)-3-oxo-1,2,3,4-tetrahydro-2-pyrazinyl)-N-((1R) -6-(1-piperidinylmethyl)-1,2,3,4-tetrahydro-1-naphthalenyl)acetamide;

2-((2R)-1-((3,4-dichlorophenyl)sulfonyl)-3-oxo-1,2,3,4-tetrahydro-2-pyrazinyl)-N-((1R) -6-(2-(1-piperidinyl)ethyl)-1,2,3,4-tetrahydro-1-naphthalenyl)acetamide;

2-((2R)-1-((3,4-dichlorophenyl)sulfonyl)-3-oxo-1,2,3,4-tetrahydro-2-pyrazinyl)-N-((1R) -6-(((1,1-dimethylethyl)amino)methyl)-1,2,3,4-tetrahydro-1-naphthalenyl)acetamide;

2-((2R)-1-((3,4-dichlorophenyl)sulfonyl)-3-oxo-1,2,3,4-tetrahydro-2-pyrazinyl)-N-((1R) -6-(((1,1-dimethylethyl)amino)methyl)-1,2,3,4-tetrahydro-1-naphthalenyl)acetamide;

2-((2R)-1-((3,4-dichlorophenyl)sulfonyl)-3-oxo-1,2,3,4-tetrahydro-2-pyrazinyl)-N-(2,3-dihydro-1H-inden-2-yl)acetamide;

2-((2R)-1-((3,4-dichlorophenyl)sulfonyl)-3-oxo-1,2,3,4-tetrahydro-2-pyrazinyl)-N -(phenylmethyl)acetamide;

2-((2R)-1-((3,4-dichlorophenyl)sulfonyl)-3-oxo-1,2,3,4-tetrahydro-2-pyrazinyl)-N-(2-phenylethyl)acetamide;

2-((2R)-1-((3,4-dichlorophenyl)sulfonyl)-3-oxo-1,2,3,4-tetrahydro-2-pyrazinyl)-N -phenylacetamide;

2-((2R)-1-((3,4-dichlorophenyl)sulfonyl)-3-oxo-1,2,3,4-tetrahydro-2-pyrazinyl)-N-(4-(5,6,7,8-tetrahydro-1,8-naphthyridin-2-yl)butyl)acetamide;

2-((2R)-1-((3,4-dichlorophenyl)sulfonyl)-3-oxo-1,2,3,4-tetrahydro-2-pyrazinyl)-N-(3 -(5,6,7,8-tetrahydro-1,8-naphthyridin-2-yl)propyl)acetamide;

2-((2R)-1-((3-chlorophenyl)sulfonyl)-3-oxo-1,2,3,4-tetrahydro-2-pyrazinyl)-N-((1 R)-6-(1-piperidinylmethyl)-1,2,3,4-tetrahydro-1-naphthalenyl)acetamide;

2-((2R)-1-((4-(methyloxy)phenyl)sulfonyl)-3-oxo-1,2,3,4-tetrahydro-2-pyrazinyl)-N -((1R)-6-(1-piperidinylmethyl)-1,2,3,4-tetrahydro-1-naphthalenyl)acetamide;

2-((2R)-1-((4-chloro-2,5-dimethylphenyl)sulfonyl)-3-oxo-1,2,3,4-tetrahydro-2-pyrazinyl)-N-((4R)-7-(hydroxymethyl)-3,4-dihydro-2H-chromen-4-yl)acetamide 2-((2R)-1-((4-chloro-2,5-dimethylphenyl)sulfonyl)-3-oxo-1,2,3,4-tetrahydro-2-pyrazinyl)-N-((1R)-6-(hydroxymethyl)-1,2,3,4-tetrahydro-1-naphthalenyl)acetamide;

2-((2R)-1-((4-chloro-2,5-dimethylphenyl)sulfonyl)-3-oxo-1,2,3,4-tetrahydro-2-pyrazinyl)-N-((1R)-1,2,3,4-tetrahydro-1-naphthalenyl)acetamide;

2-((2R)-1-((4-chloro-2,5-dimethylphenyl)sulfonyl)-3-oxo-1,2,3,4-tetrahydro-2-pyrazinyl)-N-((1R)-1-phenylethyl)acetamide;

2-((2R)-1-((4-chloro-2,5-dimethylphenyl)sulfonyl)-3-oxo-1,2,3,4-tetrahydro-2-pyrazinyl)-N-((4R)-7-((cyclopentylamino)methyl)-3,4-dihydro-2H-chromen-4-yl)acetamide;

2-((2R)-1-((4-chloro-2,5-dimethylphenyl)sulfonyl)-3-oxo-1,2,3,4-tetrahydro-2-pyrazinyl)-N-((1R)-6-((cyclopentylamino)methyl)-1,2,3,4-tetrahydro-1-naphthalenyl)acetamide;

2-((2R)-1-((4-chloro-2,5-dimethylphenyl)sulfonyl)-3-oxo-1,2,3,4-tetrahydro-2-pyrazinyl)-N-((1R)-6-(((1,1-dimethylethyl)amino)methyl)-1,2,3,4-tetrahydro-1-naphthalenyl)acetamide;

2-((2R)-1-((4-chloro-2,5-dimethylphenyl)sulfonyl)-3-oxo-1,2,3,4-tetrahydro-2-pyrazinyl)-N-((4R)-7-(((1,1-dimethylethyl)amino)methyl)-3,4-dihydro-2H-chromen-4-yl)acetamide;

2-((2R)-1-((4-chloro-2,5-dimethylphenyl)sulfonyl)-3-oxo-1,2,3,4-tetrahydro-2-pyrazinyl)-N-((1R)-6-(((2,2-dimethylpropyl)amino)methyl)-1,2,3,4-tetrahydro-1-naphthalenyl)acetamide;

2-((2R)-1-((4-chloro-2,5-dimethylphenyl)sulfonyl)-3-oxo-1,2,3,4-tetrahydro-2-pyrazinyl)-N-((4-(1-piperidinylmethyl)phenyl)methyl)acetamide;

2-((2R)-1-((4-chloro-2,5-dimethylphenyl)sulfonyl)-3-oxo-1,2,3,4-tetrahydro-2-pyrazinyl)-N-((3R)-6-(1-piperidinylmethyl)-1,2,3,4-tetrahydro-1-naphthalenyl)acetamide;

2-((2R)-1-((4-chloro-2,5-dimethylphenyl)sulfonyl)-3-oxo-1,2,3,4-tetrahydro-2-pyrazinyl)-N-((4R)-7-(1-piperidinylmethyl)-3,4-dihydro-2H-chromen-4-yl)acetamide;

2-((2R)-1-((4-chlorophenyl)sulfonyl)-3-oxo-1,2,3,4-tetrahydro-2-pyrazinyl)-N-((1R)-6-(2-(1-piperidinyl)ethyl)-1,2,3,4-tetrahydro-1-naphthalenyl)acetamide;

2-((2R)-1-((4-chlorophenyl)sulfonyl)-3-oxo-1,2,3,4-tetrahydro-2-pyrazinyl)-N-((1R)-6-((cyclopropylamino)methyl)-1,2,3,4-tetrahydro-1-naphthalenyl)acetamide;

2-((2R)-1-((4-chlorophenyl)sulfonyl)-3-oxo-1,2,3,4-tetrahydro-2-pyrazinyl)-N-((1R)-6-(((3R)-3-hydroxy-1-piperidinyl)methyl)-1,2,3,4-tetrahydro-1-naphthalenyl)acetamide;

2-((2R)-1-((4-chlorophenyl)sulfonyl)-3-oxo-1,2,3,4-tetrahydro-2-pyrazinyl)-N-((1R)-6-(((2-(methyloxy)ethyl)amino)methyl)-1,2,3,4-tetrahydro-1-naphthalenyl)acetamide;

2-((2R)-1-((4-chlorophenyl)sulfonyl)-3-oxo-1,2,3,4-tetrahydro-2-pyrazinyl)-N-((1R)-6-(((2-hydroxyethyl)amino)methyl)-1,2,3,4-tetrahydro-1-naphthalenyl)acetamide;

2-((2R)-1-((4-chlorophenyl)sulfonyl)-3-oxo-1,2,3,4-tetrahydro-2-pyrazinyl)-N-((1R)-1-phenylethyl)acetamide;

2-((2R)-1-((4-methylphenyl)sulfonyl)-3-oxo-1,2,3,4-tetrahydro-2-pyrazinyl)-N-((1R)-6-(1-(1-piperidinylmethyl)ethenyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((1R)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((1R)-6-(1-piperidinylmethyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((5S)-2-(2-(1-piperidinyl)ethyl)-5,6,7,8-tetrahydro-5-quinazolinyl)acetamide;

2-((2R)-1-((4-methylphenyl)sulfonyl)-3-oxo-1,2,3,4-tetrahydro-2-pyrazinyl)-N-(4-(3-(1-piperidinyl)propyl)phenyl)acetamide;

2-((2R)-1-((4-methylphenyl)sulfonyl)-3-oxo-1,2,3,4-tetrahydro-2-pyrazinyl)-N-(4-(3-(4-methyl-1-piperazinyl)propyl)phenyl)acetamide;

2-((2R)-1-((4-methylphenyl)sulfonyl)-3-oxo-1,2,3,4-tetrahydro-2-pyrazinyl)-N-((1R)-6-((1S)-1-((2-methylpropyl)amino)ethyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((1R)-6-(2-(1-piperidinyl)ethyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((1R)-5-(1-piperidinylmethyl)-2,3-dihydro-1H-inden-1-yl)acetamide;

2-((2R)-1-((4-methylphenyl)sulfonyl)-3-oxo-1,2,3,4-tetrahydro-2-pyrazinyl)-N-(4-(2-(4-morpholinyl)ethyl)phenyl)acetamide;

2-((2R)-1-((4-methylphenyl)sulfonyl)-3-oxo-1,2,3,4-tetrahydro-2-pyrazinyl)-N-(2-(4-(1-piperidinylmethyl)phenyl)ethyl)acetamide;

2-((2R)-1-((4-methylphenyl)sulfonyl)-3-oxo-1,2,3,4-tetrahydro-2-pyrazinyl)-N-(3-(1-pyrrolidinyl)propyl)acetamide;

2-((2R)-1-((4-methylphenyl)sulfonyl)-3-oxo-1,2,3,4-tetrahydro-2-pyrazinyl)-N-(4-(2-(1-pyrrolidinyl)ethyl)phenyl)acetamide;

2-((2R)-1-((4-methylphenyl)sulfonyl)-3-oxo-1,2,3,4-tetrahydro-2-pyrazinyl)-N-((1R)-1-methyl-2-(3-(1-piperidinylmethyl)phenyl)ethyl)acetamide;

2-((2R)-1-((4-methylphenyl)sulfonyl)-3-oxo-1,2,3,4-tetrahydro-2-pyrazinyl)-N-((1R)-1-(4-(1-piperidinylmethyl)phenyl)ethyl)acetamide;

2-((2R)-1-((4-methylphenyl)sulfonyl)-3-oxo-1,2,3,4-tetrahydro-2-pyrazinyl)-N-(4-(1-piperidinyl)butyl)acetamide;

2-((2R)-1-((4-methylphenyl)sulfonyl)-3-oxo-1,2,3,4-tetrahydro-2-pyrazinyl)-N-(4-(1-pyrrolidinyl)butyl)acetamide;

2-((2R)-1-((4-methylphenyl)sulfonyl)-3-oxo-1,2,3,4-tetrahydro-2-pyrazinyl)-N-(5-(1-piperidinyl)pentyl)acetamide;

2-((2R)-1-((4-methylphenyl)sulfonyl)-3-oxo-1,2,3,4-tetrahydro-2-pyrazinyl)-N-(5-(1-pyrrolidinyl)pentyl)acetamide;

2-((2R)-1-((4-methylphenyl)sulfonyl)-3-oxo-1,2,3,4-tetrahydro-2-pyrazinyl)-N-((1R)-1-phenylethyl)acetamide;

2-((2R)-1-((4-methylphenyl)sulfonyl)-3-oxo-1,2,3,4-tetrahydro-2-pyrazinyl)-N-((4S)-1-(2-(1-piperidinyl)ethyl)-4,5,6,7-tetrahydro-1H-indazol-4-yl)acetamide;

2-((2R)-1-((4-methylphenyl)sulfonyl)-3-oxo-1,2,3,4-tetrahydro-2-pyrazinyl)-N-(3-(3-(1-piperidinyl)propyl)phenyl)acetamide;

2-((2R)-1-((4-methylphenyl)sulfonyl)-3-oxo-1,2,3,4-tetrahydro-2-pyrazinyl)-N-(3-(3-(1-pyrrolidinyl)propyl)phenyl)acetamide;

2-((2R)-1-((4-methylphenyl)sulfonyl)-3-oxo-1,2,3,4-tetrahydro-2-pyrazinyl)-N-(3-(3-((2-methylpropyl)amino)propyl)phenyl)acetamide;

2-((2R)-1-((4-methylphenyl)sulfonyl)-3-oxo-1,2,3,4-tetrahydro-2-pyrazinyl)-N-((1R)-6-((4-(2-pyridinyl)-1-piperazinyl)methyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-(2-(4-((4-methyl-1-piperazinyl)methyl)phenyl)ethyl)acetamide;

2-((2R)-1-((4-methylphenyl)sulfonyl)-3-oxo-1,2,3,4-tetrahydro-2-pyrazinyl)-N-(2-(4-(((2-methylpropyl)amino)methyl)phenyl)ethyl)acetamide;

2-((2R)-1-((4-methylphenyl)sulfonyl)-3-oxo-1,2,3,4-tetrahydro-2-pyrazinyl)-N-((4R)-7-(1-pyrrolidinylmethyl)-3,4-dihydro-2H-chromen-4-yl)acetamide;

2-((2R)-1-((4-methylphenyl)sulfonyl)-3-oxo-1,2,3,4-tetrahydro-2-pyrazinyl)-N-((4-(1-piperidinylmethyl)phenyl)methyl)acetamide;

2-((2R)-1-((4-methylphenyl)sulfonyl)-3-oxo-1,2,3,4-tetrahydro-2-pyrazinyl)-N-((1R)-6-(1-pyrrolidinylmethyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((1R)-6-(1-piperidinylmethyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((4-(1-piperidinylmethyl)phenyl)methyl)acetamide;

2-((2R)-1-((4-methylphenyl)sulfonyl)-3-oxo-1,2,3,4-tetrahydro-2-pyrazinyl)-N-(4-(4-pyridinylmethyl)phenyl)acetamide;

2-((2R)-1-((4-methylphenyl)sulfonyl)-3-oxo-1,2,3,4-tetrahydro-2-pyrazinyl)-N-((8R) -2,6,6-trimethyl-3-oxo-2,3,5,6,7,8-hexahydro-8-isoquinolinyl)acetamide;

2-((2R)-1-((4-methylphenyl)sulfonyl)-3-oxo-1,2,3,4-tetrahydro-2-pyrazinyl)-N-((8S) -2,6,6-trimethyl-3-oxo-2,3,5,6,7,8-hexahydro-8-isoquinolinyl)acetamide;

2-((2R)-1-((4-methylphenyl)sulfonyl)-3-oxo-1,2,3,4-tetrahydro-2-pyrazinyl)-N-((1R)-6-(4-morpholinylmethyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((1R)-6-(((2S)-2-(1-pyrrolidinylmethyl)-1-pyrrolidinyl)methyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-(4-(5,6,7,8-tetrahydro-1,8-naphthyridin-2-yl)butyl)acetamide;

2-((2R)-1-((4-methylphenyl)sulfonyl)-3-oxo-1,2,3,4-tetrahydro-2-pyrazinyl)-N-((1R)-6-(2-pyridinyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((1S)-1-(2-naphthalenyl)ethyl)acetamide;

2-((2R)-1-((4-methylphenyl)sulfonyl)-3-oxo-1,2,3,4-tetrahydro-2-pyrazinyl)-N-((1R)-1-(2-naphthalenyl)ethyl)acetamide;

2-((2R)-1-((4-methylphenyl)sulfonyl)-3-oxo-1,2,3,4-tetrahydro-2-pyrazinyl)-N-((3S)-2-oxo-3-azepanyl)acetamide;

2-((2R)-1-((4-methylphenyl)sulfonyl)-3-oxo-1,2,3,4-tetrahydro-2-pyrazinyl)-N-((1R)-6-(1-(1-piperazinyl)ethyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((1R)-6-((4-methyl-1-piperidinyl)methyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-(1-(phenylmethyl)-4-piperidinyl)acetamide;

2-((2R)-1-((4-methylphenyl)sulfonyl)-3-oxo-1,2,3,4-tetrahydro-2-pyrazinyl)-N-((3S)-2-oxo-3-azepanyl)acetamide;

2-((2R)-1-((4-methylphenyl)sulfonyl)-3-oxo-1,2,3,4-tetrahydro-2-pyrazinyl)-N-((3R)-2-oxo-3-azepanyl)acetamide;

2-((2R)-1-((4-methylphenyl)sulfonyl)-3-oxo-1,2,3,4-tetrahydro-2-pyrazinyl)-N -tricyclo[3.3.1.1~3,7~]dec-1-ylacetamide;

2-((2R)-1-((4-methylphenyl)sulfonyl)-3-oxo-1,2,3,4-tetrahydro-2-pyrazinyl)-N-((1R,2R) -2-((phenylmethyl)oxy)cyclohexyl)acetamide;

2-((2R)-1-((4-methylphenyl)sulfonyl)-3-oxo-1,2,3,4-tetrahydro-2-pyrazinyl)-N-((1S,2S) -2-((phenylmethyl)oxy)cyclohexyl)acetamide;

2-((2R)-1-((4-methylphenyl)sulfonyl)-3-oxo-1,2,3,4-tetrahydro-2-pyrazinyl)-N-((4R)-7-(1-pyrrolidinylmethyl)-3,4-dihydro-2H-chromen-4-yl)acetamide;

2-((2R)-1-((4-methylphenyl)sulfonyl)-3-oxo-1,2,3,4-tetrahydro-2-pyrazinyl)-N-((1R)-6-(1-pyrrolidinylmethyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((1R)-7-nitro-6-(1-piperidinylmethyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-((1R)-5-nitro-6-(1-piperidinylmethyl)-1,2,3,4-tetrahydro-1-naphthalenyl)acetamide;

2-((2R)-1-((4-methylphenyl)sulfonyl)-3-oxo-1,2,3,4-tetrahydro-2-pyrazinyl)-N-(2-(4-(4H-1,2,4-triazol-3-yl)phenyl)ethyl)acetamide;

2-((2R)-1-((4-methylphenyl)sulfonyl)-3-oxo-1,2,3,4-tetrahydro-2-pyrazinyl)-N-((7R)-3-(2-methylpropyl)-1,2,3,4,7,8,9,10-octahydrobenzo[f]isoquinolin-7-yl)acetamide;

2-((2R)-1-((4-methylphenyl)sulfonyl)-3-oxo-1,2,3,4-tetrahydro-2-pyrazinyl)-N-((1R)-4-oxo-1,2,3,4-tetrahydro-1-naphthalenyl)acetamide;

2-((2R)-1-(cyclopropylsulfonyl)-3-oxo-1,2,3,4-tetrahydro-2-pyrazinyl)-N-((1R)-6-(1-piperidinylmethyl)-1,2,3,4-tetrahydro-1-naphthalenyl)acetamide;

2-((2R)-3-oxo-1-(phenylsulfonyl)-1,2,3,4-tetrahydro-2-pyrazinyl)-N-((1R)-6-(1-piperidinylmethyl)-1,2,3,4-tetrahydro-1-naphthalenyl)acetamide;

2-((2R)-3-oxo-1-(phenylsulfonyl)-1,2,3,4-tetrahydro-2-pyrazinyl)-N -(phenylmethyl)acetamide;

2-((2R)-3-oxo-1-(phenylsulfonyl)-1,2,3,4-tetrahydro-2-pyrazinyl)-N-((4R)-7-(1-piperidinylmethyl)-3,4-dihydro-2H-chromen-4-yl)acetamide;

2-((2R)-3-oxo-1-(phenylsulfonyl)-1,2,3,4-tetrahydro-2-pyrazinyl)-N-((1R)-1-phenylethyl)acetamide;

2-((2R)-3-oxo-1-(phenylsulfonyl)-1,2,3,4-tetrahydro-2-pyrazinyl)-N-((1S)-1-phenylethyl)acetamide;

2-((2R)-3-oxo-1-(phenylsulfonyl)-1,2,3,4-tetrahydro-2-pyrazinyl)-N-((1R)-1,2,3,4-tetrahydro-1-naphthalenyl)acetamide;

2-((2R)-4-methyl-1-((4-methylphenyl)sulfonyl)-3-oxo-1,2,3,4-tetrahydro-2-pyrazinyl)-N -((1R)-1,2,3,4-tetrahydro-1-naphthalenyl)acetamide;

2-((2S)-1-((4-methylphenyl)sulfonyl)-3-oxo-1,2,3,4-tetrahydro-2-pyrazinyl)-N-((1R)-6-(1-piperidinylmethyl)-1,2,3,4-tetrahydro-1-naphthalenyl)acetamide;

2-((2S)-1-((4-methylphenyl)sulfonyl)-3-oxo-1,2,3,4-tetrahydro-2-pyrazinyl)-N-((6R)-2-(2-methylpropyl)-1,2,3,4,6,7,8,9-octahydrobenzo[g]isoquinolin-6-yl)acetamide;

2-((2S)-1-((4-methylphenyl)sulfonyl)-3-oxo-1,2,3,4-tetrahydro-2-pyrazinyl)-N-((7R)-3-(2-methylpropyl)-1,2,3,4,7,8,9,10-octahydrobenzo[f]isoquinolin-7-yl)acetamide;

2-((4S)-4-((2-((2R)-1-((4-methylphenyl)sulfonyl)-3-oxo-1,2,3,4-tetrahydro-2-pyrazinyl)acetyl)amino)-4,5,6,7-tetrahydro-1H-indazol-1-yl)ethyl methanesulfonate;

2-((5R)-5-((2-((2S)-1-((4-methylphenyl)sulfonyl)-3-oxo-1,2,3,4-tetrahydro-2-pyrazinyl)acetyl)amino)-5,6,7,8-tetrahydro-2-quinazolinyl)ethyl methanesulfonate;

2-(1-((4-methylphenyl)sulfonyl)-3-oxo-1,2,3,4-tetrahydro-2-pyrazinyl)-N-((2R)-1,2,3,4-tetrahydro-2-naphthalenyl)acetamide;

2-(1-((4-methylphenyl)sulfonyl)-3-oxo-1,2,3,4-tetrahydro-2-pyrazinyl)-N-((2S)-1,2,3,4-tetrahydro-2-naphthalenyl)acetamide;

ethyl (1R,2R)-2-((((2R)-1-((4-methylphenyl)sulfonyl)-3-oxo-1,2,3,4-tetrahydro-2-pyrazinyl)acetyl)amino)cyclohexanecarboxylate;

ethyl (1R,2S)-2-(((((2R)-1-((4-methylphenyl)sulfonyl)-3-oxo-1,2,3,4-tetrahydro-2-pyrazinyl)acetyl)amino)cyclohexanecarboxylate;

ethyl (1S,2R)-2-(((((2R)-1-((4-methylphenyl)sulfonyl)-3-oxo-1,2,3,4-tetrahydro-2-pyrazinyl)acetyl)amino)cyclohexanecarboxylate;

ethyl (1S,2S)-2-(((((2R)-1-((4-methylphenyl)sulfonyl)-3-oxo-1,2,3,4-tetrahydro-2-pyrazinyl)acetyl)amino)cyclohexanecarboxylate;

methyl (2S)-((((2R)-1-((4-methylphenyl)sulfonyl)-3-oxo-1,2,3,4-tetrahydro-2-pyrazinyl)acetyl)amino)(phenyl)ethanoate;

methyl 2-((1R)-1-((((2R)-1-((4-methylphenyl)sulfonyl)-3-oxo-1,2,3,4-tetrahydro-2-pyrazinyl)acetyl)amino)-2,3-dihydro-1H-inden-5-yl)benzoate;

methyl 4-((2R)-1-(((2R)-1-((4-methylphenyl)sulfonyl)-3-oxo-1,2,3,4-tetrahydro-2-pyrazinyl)acetyl)-2-piperidinyl)benzoate;

methyl 4-((2S)-1-(((2R)-1-((4-methylphenyl)sulfonyl)-3-oxo-1,2,3,4-tetrahydro-2-pyrazinyl)acetyl)-2-piperidinyl)benzoate;

N-(((5R)-5-((1-methylethyl)amino)-5,6,7,8-tetrahydro-2-naphthalenyl)methyl)-2-((2R)-1-((4-methylphenyl)sulfonyl)-3-oxo-1,2,3,4-tetrahydro-2-pyrazinyl)acetamide;

N-(((5R)-5-amino-5,6,7,8-tetrahydro-2-naphthalenyl)methyl)-2-((2R)-1-((4-methylphenyl)sulfonyl)-3-oxo-1,2,3,4-tetrahydro-2-pyrazinyl)acetamide;

N-((1R)-1-(3,3'-difluoro-2'-(3-methyl-1,2,4-oxadiazol-5-yl)-1,1'-biphenyl-4-yl)ethyl)-2-((2R)-1-((4-methylphenyl)sulfonyl)-3-oxo-1,2,3,4-tetrahydro-2-pyrazinyl)acetamide;

N-((1R)-1-(4-(hydroxymethyl)phenyl)ethyl)-2-((2R)-1-((4-methylphenyl)sulfonyl)-3-oxo-1,2,3,4-tetrahydro-2-pyrazinyl)acetamide;

N-((1R)-1-cyclohexylethyl)-2-((2R)-1-((4-methylphenyl)sulfonyl)-3-oxo-1,2,3,4-tetrahydro-2-pyrazinyl)acetamide;

N-((1R)-2-((2,6-dimethylphenyl)oxy)-1-methylethyl)-2-((2R)-1-((4-methylphenyl)sulfonyl)-3-oxo-1,2,3,4-tetrahydro-2-pyrazinyl)acetamide;

N-((1R)-2,3-dihydro-1H-inden-1-yl)-2-((2R)-1-((4-methylphenyl)sulfonyl)-3-oxo-1,2,3,4-tetrahydro-2-pyrazinyl)acetamide;

N-((1R)-5-(hydroxymethyl)-2,3-dihydro-1H-inden-1-yl)-2-((2R)-1-((4-methylphenyl)sulfonyl)-3-oxo-1,2,3,4-tetrahydro-2-pyrazinyl)acetamide;

N-((1R)-6-(((2,2-dimethylpropyl)amino)methyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-(((2,2-dimethylpropyl)amino)methyl)-1,2,3,4-tetrahydro-1-naphthalenyl)-2-((2R)-3-oxo-1-(phenylsulfonyl)-1,2,3,4-tetrahydro-2-pyrazinyl)acetamide;

N-((1R)-6-(((2,2-dimethylpropyl)amino)methyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-(((2R)-2-(hydroxymethyl)-1-pyrrolidinyl)methyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-(((2S)-2-(hydroxymethyl)-1-pyrrolidinyl)methyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-(((cyclopropylmethyl)(propyl)amino)methyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-(((cyclopropylmethyl)(propyl)amino)methyl)-1,2,3,4-tetrahydro-1-naphthalenyl)-2-((2R) -1-((4-methylphenyl)sulfonyl)-3-oxo-1,2,3,4-tetrahydro-2-pyrazinyl)acetamide;

N-((1R)-6-((1S)-1-(cyclobutylamino)ethyl)-1,2,3,4-tetrahydro-1-naphthalenyl)-2-((2R) -1-((4-methylphenyl)sulfonyl)-3-oxo-1,2,3,4-tetrahydro-2-pyrazinyl)acetamide;

N-((1R)-6-((1S)-1-(cyclopentylamino)ethyl)-1,2,3,4-tetrahydro-1-naphthalenyl)-2-((2R) -1-((4-methylphenyl)sulfonyl)-3-oxo-1,2,3,4-tetrahydro-2-pyrazinyl)acetamide;

N-((1R)-6-((1S)-1-(cyclopropylamino)ethyl)-1,2,3,4-tetrahydro-1-naphthalenyl)-2-((2R) -1-((4-methylphenyl)sulfonyl)-3-oxo-1,2,3,4-tetrahydro-2-pyrazinyl)acetamide;

N-((1R)-6-((4-fluoro-1-piperidinyl)methyl)-1,2,3,4-tetrahydro-1-naphthalenyl)-2-((2R) -3-oxo-1-(phenylsulfonyl)-1,2,3,4-tetrahydro-2-pyrazinyl)acetamide;

N-((1R)-6-((cyclopentylamino)methyl)-1,2,3,4-tetrahydro-1-naphthalenyl)-2-((2R)-1-((3,4-dichlorophenyl)sulfonyl)-3-oxo-1,2,3,4-tetrahydro-2-pyrazinyl)acetamide;

N-((1R)-6-((cyclopentylamino)methyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-((cyclopentylamino)methyl)-1,2,3,4-tetrahydro-1-naphthalenyl)-2-((2R)-3-oxo-1-(phenylsulfonyl)-1,2,3,4-tetrahydro-2-pyrazinyl)acetamide;

N-((1R)-6-((cyclopropylamino)methyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-((dimethylamino)methyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-(1-azepanylmethyl)-1,2,3,4-tetrahydro-1-naphthalenyl)-2-((2R)-1-((4-chlorophenyl)sulfonyl)-3-oxo-1,2,3,4-tetrahydro-2-pyrazinyl)acetamide;

N-((1R)-6-(aminomethyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-(hydroxymethyl)-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-acetyl-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R)-6-acetyl-1,2,3,4-tetrahydro-1-naphthalenyl)-2-((2R)-1-((4-methylphenyl)sulfonyl)-3-oxo-1,2,3,4-tetrahydro-2-pyrazinyl)acetamide;

N-((1R,2R)-2-hydroxycyclohexyl)-2-((2R)-1-((4-methylphenyl)sulfonyl)-3-oxo-1,2,3,4-tetrahydro-2-pyrazinyl)acetamide;

N-((1R,2R)-2-methylcyclohexyl)-2-((2R)-1-((4-methylphenyl)sulfonyl)-3-oxo-1,2,3,4-tetrahydro-2-pyrazinyl)acetamide;

N-((1R,5R,7S)-3-hydroxytricyclo[3.3.1.1~3,7~]dec-1-yl)-2-((2R)-1-((4-methylphenyl)sulfonyl)-3-oxo-1,2,3,4-tetrahydro-2-pyrazinyl)acetamide;

N-((1S)-2-((2,6-dimethylphenyl)oxy)-1-methylethyl)-2-((2R)-1-((4-methylphenyl)sulfonyl)-3-oxo-1,2,3,4-tetrahydro-2-pyrazinyl)acetamide;

N-((1S)-2-(3-(hydroxymethyl)phenyl)-1-methylethyl)-2-((2R)-1-((4-methylphenyl)sulfonyl)-3-oxo-1,2,3,4-tetrahydro-2-pyrazinyl)acetamide;

N-((1S)-2,3-dihydro-1H-inden-1-yl)-2-((2R)-1-((4-methylphenyl)sulfonyl)-3-oxo -1,2,3,4-tetrahydro-2-pyrazinyl)acetamide;

N-((1S)-2-cyclohexyl-1-(hydroxymethyl)ethyl)-2-((2R)-1-((4-methylphenyl)sulfonyl)-3-oxo-1,2,3,4-tetrahydro-2-pyrazinyl)acetamide;

N-((1S)-2-hydroxy-1-phenylethyl)-2-((2R)-1-((4-methylphenyl)sulfonyl)-3-oxo-1,2,3,4-tetrahydro-2-pyrazinyl)acetamide;

N-((1S)-3-methylcyclohexyl)-2-(1-((4-methylphenyl)sulfonyl)-3-oxo-1,2,3,4-tetrahydro -2-pyrazinyl)acetamide;

N-((1S,2R)-2-hydroxy-2,3-dihydro-1H-inden-1-yl)-2-((2R)-1-((4-methylphenyl)sulfonyl)-3-oxo-1,2,3,4-tetrahydro-2-pyrazinyl)acetamide;

N-((1S,2R)-2-methylcyclohexyl)-2-((2R)-1-((4-methylphenyl)sulfonyl)-3-oxo-1,2,3,4-tetrahydro-2-pyrazinyl)acetamide;

N-((1S,2S)-2-hydroxycyclohexyl)-2-((2R)-1-((4-methylphenyl)sulfonyl)-3-oxo-1,2,3,4-tetrahydro-2-pyrazinyl)acetamide;

N-((1S,2S)-2-methylcyclohexyl)-2-((2R)-1-((4-methylphenyl)sulfonyl)-3-oxo-1,2,3,4-tetrahydro-2-pyrazinyl)acetamide;

N-(2-fluorophenyl)methyl)-2-((2R)-3-oxo-1-(phenylsulfonyl)-1,2,3,4-tetrahydro-2-pyrazinyl)acetamide;

N-((2R)-5-(methyloxy)-1,2,3,4-tetrahydro-2-naphthalenyl)-2-(1-((4-methylphenyl)sulfonyl)-3-oxo-1,2,3,4-tetrahydro-2-pyrazinyl)acetamide;

N-((2R)-6-(methyloxy)-1,2,3,4-tetrahydro-2-naphthalenyl)-2-(1-((4-methylphenyl)sulfonyl)-3-oxo-1,2,3,4-tetrahydro-2-pyrazinyl)acetamide;

N-((2R)-6-bromo-1,2,3,4-tetrahydro-2-naphthalenyl)-2-((2R)-1-((4-methylphenyl)sulfonyl)-3-oxo-1,2,3,4-tetrahydro-2-pyrazinyl)acetamide;

N-((2R)-7-(methyloxy)-1,2,3,4-tetrahydro-2-naphthalenyl)-2-(1-((4-methylphenyl)sulfonyl)-3-oxo-1,2,3,4-tetrahydro-2-pyrazinyl)acetamide;

N-((2R)-8-bromo-1,2,3,4-tetrahydro-2-naphthalenyl)-2-(1-((4-methylphenyl)sulfonyl)-3-oxo-1,2,3,4-tetrahydro-2-pyrazinyl)acetamide;

N-((2S)-6-bromo-1,2,3,4-tetrahydro-2-naphthalenyl)-2-((2R)-1-((4-methylphenyl)sulfonyl)-3-oxo-1,2,3,4-tetrahydro-2-pyrazinyl)acetamide;

N-(3-fluorophenyl)methyl)-2-((2R)-3-oxo-1-(phenylsulfonyl)-1,2,3,4-tetrahydro-2-pyrazinyl)acetamide;

N-(4-cyanophenyl)methyl)-2-((2R)-1-((4-methylphenyl)sulfonyl)-3-oxo-1,2,3,4-tetrahydro-2-pyrazinyl)acetamide;

N-(4-fluorophenyl)methyl)-2-((2R)-3-oxo-1-(phenylsulfonyl)-1,2,3,4-tetrahydro-2-pyrazinyl)acetamide;

N-((4R)-1,1-dioxido-3,4-dihydro-2H-1-benzothiopyran-4-yl)-2-((2R)-1-((4-methylphenyl)sulfonyl)-3-oxo-1,2,3,4-tetrahydro-2-pyrazinyl)acetamide;

N-((4R)-2,2-dimethyl-3,4-dihydro-2H-chromen-4-yl)-2-((2R)-1-((4-methylphenyl)sulfonyl)-3-oxo-1,2,3,4-tetrahydro-2-pyrazinyl)acetamide;

N-((4R)-3,4-dihydro-2H-chromen-4-yl)-2-((2R)-1-((4-(methyloxy)phenyl)sulfonyl)-3-oxo-1,2,3,4-tetrahydro-2-pyrazinyl)acetamide;

N-((4R)-6-chloro-1,1-dioxido-3,4-dihydro-2H-1-benzothiopyran-4-yl)-2-((2R)-1-((4-methylphenyl)sulfonyl)-3-oxo-1,2,3,4-tetrahydro-2-pyrazinyl)acetamide;

N-((4R)-6-chloro-7-methyl-3,4-dihydro-2H-chromen-4-yl)-2-((2R)-1-((3,4-dichlorophenyl)sulfonyl)-3-oxo-1,2,3,4-tetrahydro-2-pyrazinyl)acetamide;

N-((4R)-7-(((2,2-dimethylpropyl)amino)methyl)-3,4-dihydro-2H-chromen-4-yl)-2-((2R) -1-((4-methylphenyl)sulfonyl)-3-oxo-1,2,3,4-tetrahydro-2-pyrazinyl)acetamide;

N-((4R)-7-(((2,2-dimethylpropyl)amino)methyl)-3,4-dihydro-2H-chromen-4-yl)-2-((2R) -3-oxo-1-(phenylsulfonyl)-1,2,3,4-tetrahydro-2-pyrazinyl)acetamide;

N-((4R)-7-(((2,2-dimethylpropyl)amino)methyl)-3,4-dihydro-2H-chromen-4-yl)-2-((2R) -1-((4-methylphenyl)sulfonyl)-3-oxo-1,2,3,4-tetrahydro-2-pyrazinyl)acetamide;

N-((4R)-7-((cyclopentylamino)methyl)-3,4-dihydro-2H-chromen-4-yl)-2-((2R)-1-((4-methylphenyl)sulfonyl)-3-oxo-1,2,3,4-tetrahydro-2-pyrazinyl)acetamide;

N-((4R)-7-((cyclopentylamino)methyl)-3,4-dihydro-2H-chromen-4-yl)-2-((2R)-1-((3,4-dichlorophenyl)sulfonyl)-3-oxo-1,2,3,4-tetrahydro-2-pyrazinyl)acetamide;

N-((4R)-7-((cyclopentylamino)methyl)-3,4-dihydro-2H-chromen-4-yl)-2-((2R)-3-oxo-1-(phenylsulfonyl)-1,2,3,4-tetrahydro-2-pyrazinyl)acetamide;

N-((4R)-7-((cyclopropylamino)methyl)-3,4-dihydro-2H-chromen-4-yl)-2-((2R)-1-((4-methylphenyl)sulfonyl)-3-oxo-1,2,3,4-tetrahydro-2-pyrazinyl)acetamide;

N-((4R)-7-(hydroxymethyl)-3,4-dihydro-2H-chromen-4-yl)-2-((2R)-1-((4-methylphenyl)sulfonyl)-3-oxo-1,2,3,4-tetrahydro-2-pyrazinyl)acetamide;

N-((4R)-7-cyano-3,4-dihydro-2H-chromen-4-yl)-2-((2R)-1-((4-methylphenyl)sulfonyl) -3-oxo-1,2,3,4-tetrahydro-2-pyrazinyl)acetamide;

N-((4S)-1-(2-(((1,1-dimethylethyl)(dimethyl)silyl)oxy)ethyl)-4,5,6,7-tetrahydro-1H -indazol-4-yl)-2-((2R)-1-((4-methylphenyl)sulfonyl)-3-oxo-1,2,3,4-tetrahydro-2-pyrazinyl)acetamide;

N-((4S)-1-(2-((2,2-dimethylpropyl)amino)ethyl)-4,5,6,7-tetrahydro-1H-indazol-4-yl)-2-((2R)-1-((4-methylphenyl)sulfonyl)-3-oxo-1,2,3,4-tetrahydro-2-pyrazinyl)acetamide;

N-((4S)-1-(2-(cyclopropylamino)ethyl)-4,5,6,7-tetrahydro-1H-indazol-4-yl)-2-((2R)-1-((4-methylphenyl)sulfonyl)-3-oxo-1,2,3,4-tetrahydro-2-pyrazinyl)acetamide;

N-((4S)-1-(2-hydroxyethyl)-4,5,6,7-tetrahydro-1H-indazol-4-yl)-2-((2R)-1-((4-methylphenyl)sulfonyl)-3-oxo-1,2,3,4-tetrahydro-2-pyrazinyl)acetamide;

N-((4S)-2,2-dimethyl-3,4-dihydro-2H-chromen-4-yl)-2-((2R)-1-((4-methylphenyl)sulfonyl)-3-oxo-1,2,3,4-tetrahydro-2-pyrazinyl)acetamide;

N-((4S)-3,4-dihydro-2H-chromen-4-yl)-2-((2R)-1-((4-(methyloxy)phenyl)sulfonyl)-3-oxo-1,2,3,4-tetrahydro-2-pyrazinyl)acetamide;

N-((5S)-2-(2-hydroxyethyl)-5,6,7,8-tetrahydro-5-quinazolinyl)-2-((2R)-1-((4-methylphenyl)sulfonyl)-3-oxo-1,2,3,4-tetrahydro-2-pyrazinyl)acetamide;

N-(1,1-dimethylethyl)-2-((2R)-1-((4-methylphenyl)sulfonyl)-3-oxo-1,2,3,4-tetrahydro-2-pyrazinyl)acetamide;

N-(2-(3-formylphenyl)propyl)-2-((2R)-1-((4-methylphenyl)sulfonyl)-3-oxo-1,2,3,4-tetrahydro-2-pyrazinyl)acetamide;

N-(2-(4-((cyclopentylamino)methyl)phenyl)ethyl)-2-((2R)-1-((4-methylphenyl)sulfonyl) -3-oxo-1,2,3,4-tetrahydro-2-pyrazinyl)acetamide;

N-(2-(4-((cyclopropylamino)methyl)phenyl)ethyl)-2-((2R)-1-((4-methylphenyl)sulfonyl) -3-oxo-1,2,3,4-tetrahydro-2-pyrazinyl)acetamide;

N-(2-(4-(hydroxymethyl)phenyl)ethyl)-2-((2R)-1-((4-methylphenyl)sulfonyl)-3-oxo -1,2,3,4-tetrahydro-2-pyrazinyl)acetamide;

N-(2-(4-(hydroxymethyl)phenyl)ethyl)-2-((2R)-1-((4-methylphenyl)sulfonyl)-3-oxo -1,2,3,4-tetrahydro-2-pyrazinyl)acetamide;

N-(2-(4-aminophenyl)ethyl)-2-((2R)-1-((4-methylphenyl)sulfonyl)-3-oxo-1,2,3,4-tetrahydro-2-pyrazinyl)acetamide;

N-(2-(4-cyanophenyl)ethyl)-2-((2R)-1-((4-methylphenyl)sulfonyl)-3-oxo-1,2,3,4-tetrahydro-2-pyrazinyl)acetamide;

N-(2,3-dihydro-1H-inden-2-yl)-2-((2R)-1-((4-methylphenyl)sulfonyl)-3-oxo-1,2,3,4-tetrahydro-2-pyrazinyl)acetamide;

N-(3-(3-hydroxypropyl)phenyl)-2-((2R)-1-((4-methyl-2,4-cyclohexadien-1-yl)sulfonyl) -3-oxo-1,2,3,4-tetrahydro-2-pyrazinyl)acetamide;

N-(3-(cyclohexylamino)propyl)-2-((2R)-1-((4-methylphenyl)sulfonyl)-3-oxo-1,2,3,4-tetrahydro-2-pyrazinyl)acetamide;

N-(4-(1,4'-bipiperidin-1'-yl)phenyl)-2-((2R)-1-((4-methylphenyl)sulfonyl)-3-oxo-1,2,3,4-tetrahydro-2-pyrazinyl)acetamide;

N-(4-(2-(dimethylamino)ethyl)phenyl)-2-((2R)-1-((4-methylphenyl)sulfonyl)-3-oxo -1,2,3,4-tetrahydro-2-pyrazinyl)acetamide;

N-(4-(3-hydroxypropyl)phenyl)-2-((2R)-1-((4-methylphenyl)sulfonyl)-3-oxo-1,2,3,4-tetrahydro-2-pyrazinyl)acetamide;

N-(4-hydroxybutyl)-2-((2R)-1-((4-methylphenyl)sulfonyl)-3-oxo-1,2,3,4-tetrahydro-2-pyrazinyl)acetamide;

N-(5-hydroxypentyl)-2-((2R)-1-((4-methylphenyl)sulfonyl)-3-oxo-1,2,3,4-tetrahydro-2-pyrazinyl)acetamide;

N-(cis-4-methylcyclohexyl)-2-((2R)-1-((4-methylphenyl)sulfonyl)-3-oxo-1,2,3,4-tetrahydro-2-pyrazinyl)acetamide;

N-(trans-4-methylcyclohexyl)-2-((2R)-1-((4-methylphenyl)sulfonyl)-3-oxo-1,2,3,4-tetrahydro-2-pyrazinyl)acetamide;

N-cyclobutyl-2-((2R)-1-((3,4-dichlorophenyl)sulfonyl)-3-oxo-1,2,3,4-tetrahydro-2-pyrazinyl)acetamide;

N-cycloheptyl-2-((2R)-1-((3,4-dichlorophenyl)sulfonyl)-3-oxo-1,2,3,4-tetrahydro-2-pyrazinyl)acetamide;

N-cyclohexyl-2-((2R)-1-((3,4-dichlorophenyl)sulfonyl)-3-oxo-1,2,3,4-tetrahydro-2-pyrazinyl)acetamide;

N-cyclooctyl-2-((2R)-1-((3,4-dichlorophenyl)sulfonyl)-3-oxo-1,2,3,4-tetrahydro-2-pyrazinyl)acetamide;

N-cyclopentyl-2-((2R)-1-((3,4-dichlorophenyl)sulfonyl)-3-oxo-1,2,3,4-tetrahydro-2-pyrazinyl)acetamide;

N-cyclopropyl-2-((2R)-1-((3,4-dichlorophenyl)sulfonyl)-3-oxo-1,2,3,4-tetrahydro-2-pyrazinyl)acetamide;

N-methyl-2-((2R)-1-((4-methylphenyl)sulfonyl)-3-oxo-1,2,3,4-tetrahydro-2-pyrazinyl) -N-((1R)-6-(1-piperidinylmethyl)-1,2,3,4-tetrahydro-1-naphthalenyl)acetamide; and N-methyl-2-((2R)-1-((4-methylphenyl)sulfonyl)-3-oxo-1,2,3,4-tetrahydro-2-pyrazinyl) -N-((4R)-7-(1-piperidinylmethyl)-3,4-dihydro-2H-chromen-4-yl)acetamide.

12. A pharmaceutical composition comprising a pharmaceutically acceptable carrier and a compound according to claim 1.

13. A method of treating pain comprising administering an effective amount a compound according to claim 1.

* * * * *

UNITED STATES PATENT AND TRADEMARK OFFICE
CERTIFICATE OF CORRECTION

PATENT NO. : 7,662,811 B2 Page 1 of 1
APPLICATION NO. : 11/182216
DATED : February 16, 2010
INVENTOR(S) : Askew, Jr. et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 768 days.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,662,811 B2 | Page 1 of 1 |
| APPLICATION NO. | : 11/182216 | |
| DATED | : February 16, 2010 | |
| INVENTOR(S) | : Benny C. Askew, Jr. et al. | |

It is certified that error appears in the above-identified patent and that said Letters Patent is hereby corrected as shown below:

Column 129, line 14, "futher" should be --further--.
Column 129, lines 54 and 55, "clycloalkylamino" should be --cycloalkylamino--.
Column 129, line 61, "alkylalmino" should be --alkylamino--.
Column 130, line 16, "aalkynyl" should be --alkynyl--; delete "13".
Column 130, line 17, after "–C(O)NR$^8$R$^8$," insert --and--.
Column 130, lines 22 and 23, "heteromonocyclyl" should be --heteromonocyclic--.
Column 130, line 24, "heteromonocyclyl" should be --heteromonocyclic--.

Signed and Sealed this
First Day of March, 2011

David J. Kappos
*Director of the United States Patent and Trademark Office*